(12) United States Patent
Kelner

(10) Patent No.: US 12,269,793 B2
(45) Date of Patent: *Apr. 8, 2025

(54) AFFINITY ILLUDOFULVENE CONJUGATES

(71) Applicant: AF Chemicals, LLC, San Diego, CA (US)

(72) Inventor: Michael Kelner, San Diego, CA (US)

(73) Assignee: AF CHEMICALS, LLC, San Diego, CA (US)

( * ) Notice: Subject to any disclaimer, the term of this patent is extended or adjusted under 35 U.S.C. 154(b) by 38 days.

This patent is subject to a terminal disclaimer.

(21) Appl. No.: 18/175,495

(22) Filed: Feb. 27, 2023

(65) Prior Publication Data

US 2023/0212113 A1    Jul. 6, 2023

Related U.S. Application Data

(63) Continuation of application No. 17/103,780, filed on Nov. 24, 2020, now Pat. No. 11,591,295.

(60) Provisional application No. 63/116,772, filed on Nov. 20, 2020, provisional application No. 62/940,096, filed on Nov. 25, 2019.

(30) Foreign Application Priority Data

Nov. 24, 2020   (EP) .................... 20 209 541

(51) Int. Cl.
| | |
|---|---|
| C07C 317/44 | (2006.01) |
| A61K 31/215 | (2006.01) |
| A61K 31/255 | (2006.01) |
| A61K 31/265 | (2006.01) |
| A61K 31/27 | (2006.01) |
| A61K 31/4015 | (2006.01) |
| A61K 38/05 | (2006.01) |
| A61K 38/06 | (2006.01) |
| A61K 47/54 | (2017.01) |
| C07C 205/42 | (2006.01) |
| C07C 225/14 | (2006.01) |
| C07C 271/34 | (2006.01) |
| C07C 309/72 | (2006.01) |
| C07C 311/16 | (2006.01) |
| C07D 207/444 | (2006.01) |
| C07K 5/062 | (2006.01) |
| C07K 5/083 | (2006.01) |

(52) U.S. Cl.
CPC .......... *C07C 317/44* (2013.01); *A61K 31/215* (2013.01); *A61K 31/255* (2013.01); *A61K 31/265* (2013.01); *A61K 31/27* (2013.01); *A61K 31/4015* (2013.01); *A61K 38/05* (2013.01); *A61K 38/06* (2013.01); *A61K 47/554* (2017.08); *C07C 205/42* (2013.01); *C07C 225/14* (2013.01); *C07C 271/34* (2013.01); *C07C 309/72* (2013.01); *C07C 311/16* (2013.01); *C07D 207/444* (2013.01); *C07K 5/06026* (2013.01); *C07K 5/06052* (2013.01); *C07K 5/0806* (2013.01); *C07C 2603/94* (2017.05)

(58) Field of Classification Search
None
See application file for complete search history.

(56) References Cited

U.S. PATENT DOCUMENTS

| | | | | |
|---|---|---|---|---|
| 2015/0290152 A1* | 10/2015 | Kelner | ............... | A61K 47/554 552/641 |
| 2016/0015658 A1* | 1/2016 | Kelner | ............... | A61K 31/122 514/249 |

* cited by examiner

*Primary Examiner* — Bethany P Barham
*Assistant Examiner* — Peter Anthopolos
(74) *Attorney, Agent, or Firm* — SCI-LAW STRATEGIES, PC

(57) ABSTRACT

In an embodiment of the invention, a composition for treating a cell population comprises a medicant. The medicant moiety can be an illudofulvene analog. In an embodiment of the invention, a composition for treating a cell population comprises an Affinity Medicant Conjugate (AMC). The affinity moiety can be an antibody, an antibody fragment, a receptor protein, a peptidic growth factor, an anti-angiogenic protein, a specific binding peptide, protease cleavable peptide, a glycopeptide, a peptide, a peptidic toxin, a protein toxin and an oligonucleotide. The affinity moiety can be covalently bound to the medicant via a linker.

20 Claims, 8 Drawing Sheets
Specification includes a Sequence Listing.

FIG. 1A
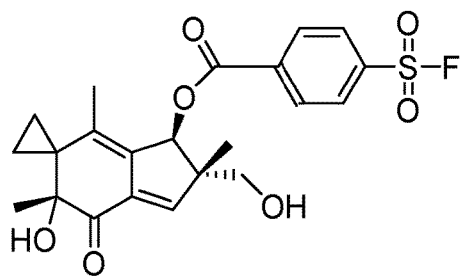
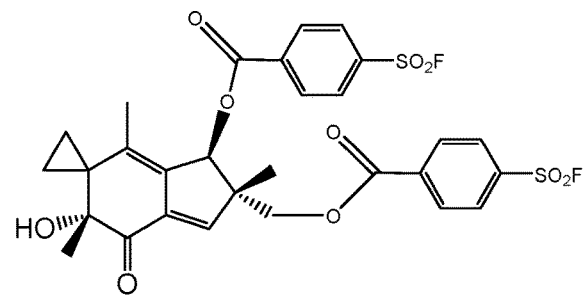
FIG. 1B
FIG. 1C
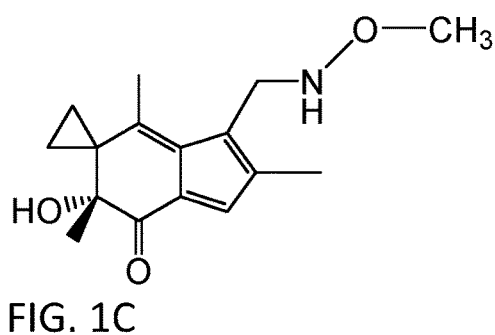
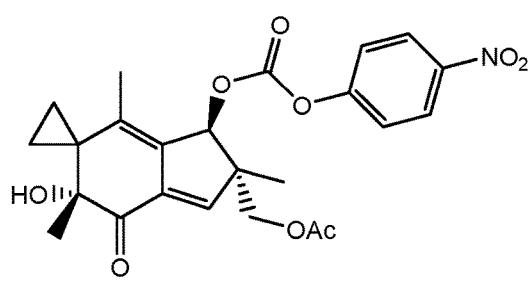
FIG. 1D
FIG. 1E
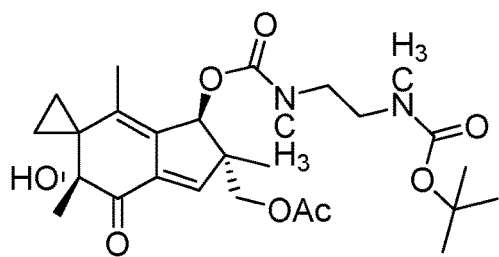
FIG. 1F
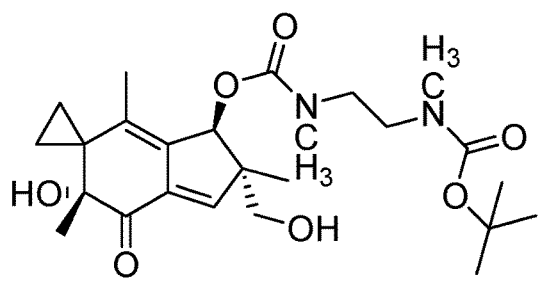
FIG. 1G
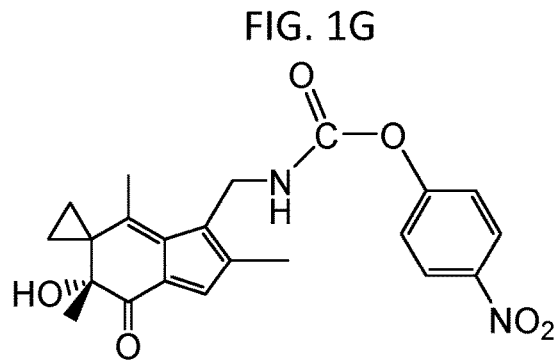
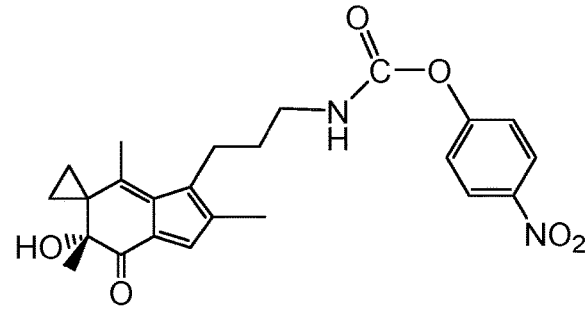
FIG. 1H

AFFINITY ILLUDOFULVENE CONJUGATES

PRIORITY CLAIM

This application claims priority to (i) U.S. Utility application Ser. No. 17/103,780 entitled "AFFINITY ILLUDOFULVENE CONJUGATES", inventor: Michael Kelner et al. filed Nov. 24, 2020, which claims priority to (ii) U.S. Provisional Application No. 62/940,096 entitled "AFFINITY ILLUDOFULVENE CONJUGATES", inventor: Michael Kelner et al. filed Nov. 25, 2019, (iii) U.S. Provisional Application No. 63/116,772 entitled "AFFINITY ILLUDOFULVENE CONJUGATES", inventor: Michael Kelner et al. filed Nov. 20, 2020, and (iv) EP Patent Application No. 20209541.0 entitled "AFFINITY ILLUDOFULVENE CONJUGATES", inventor: Michael Kelner et al. filed Nov. 24, 2020, which applications (i)-(iv) are herein expressly incorporated by reference in their entireties and for all purposes.

REFERENCE TO A "SEQUENCE LISTING," A TABLE, OR A COMPUTER PROGRAM LISTING APPENDIX SUBMITTED AS AN ASCII TEXT FILE

The Sequence Listing written in file MKEL-01049U53_ST26.XML, created Mar. 2, 2023, 441,324 bytes, machine format IBM-PC, MS-Windows operating system, is hereby incorporated by reference in its entirety and for all purposes.

TECHNICAL FIELD

The present invention relates to compositions and methods for treating target molecules including cell populations with either a medicant or an affinity medicant conjugate including an antibody drug conjugate or a small molecule medicant conjugate.

BACKGROUND ART

The present invention is directed to a medicant or an Affinity Medicant Conjugate (AMC) including illudofulvene based medicants, illudofulvene based Affinity Medicant Linker Conjugates (AMLC), illudofulvene based antibody-drug conjugates (ADC) and illudofulvene based medicant-linker (ML) compounds, as well as to compositions of the same, and to methods for their use in treating cancer, an autoimmune to methods of using illudofulvene based Ligand Linker Medicant (LLM) conjugates and illudofulvene based ML compounds in vitro, in situ, and in vivo for the detection, diagnosis or treatment of cells and associated pathological conditions.

SUMMARY OF INVENTION

There exists a continuing need for chemotherapeutic agents for treating cancer. In particular there is a need for chemotherapeutic agents that have activity against cancers with resistant phenotypes and which can inhibit tumor growth and which have an adequate therapeutic index to be effective for in vivo treatment. In an embodiment of the invention, the chemotherapeutic agents can be delivered to tumors as a stand alone treatment. In an alternative embodiment of the invention, the chemotherapeutic agents can be delivered to a specific patient population having a specific tumors as a stand alone treatment. In another embodiment of the invention, the chemotherapeutic agents can be conjugated with an antibody to form an effective treatment. In another embodiment of the invention, the chemotherapeutic agents can be conjugated with an antibody, an antibody fragment, a receptor protein, a peptidic growth factor, an anti-angiogenic protein, a specific binding peptide, protease cleavable peptide, a glycopeptide, a peptide, a peptidic toxin, a protein toxin and an oligonucleotide and delivered to a specific patient population having a specific tumors to form an effective treatment. In various embodiments of the invention, the therapeutic treatment can be delivered in humans as well as in animals. For example, such therapeutic applications can include: cancer, adenocarcinoma, carcinoma, breast cancer, prostate cancer, ovarian cancer, endometrial cancer, neuroendocrine tumors, infertility, polycystic ovary syndrome, endometriosis, and precocious puberty. For example, veterinary and agricultural applications can include treatment of cancer, adenocarcinoma, carcinoma, ovarian cancer, endometrial cancer, neuroendocrine tumors, and endometriosis in farmyard and/or companion animals.

BRIEF DESCRIPTION OF THE DRAWINGS

This invention is described with respect to specific embodiments thereof. Additional features can be appreciated from the FIG. s in which:

FIG. 1A shows analog 317; FIG. 1B shows analog 318; FIG. 1C shows analog 332; FIG. 1D shows analog 333; FIG. 1E shows analog 334; FIG. 1F shows analog 335; FIG. 1G shows analog 337; FIG. 1H shows analog 338.

DETAILED DESCRIPTION OF THE INVENTION

Definitions

Figure 1I:
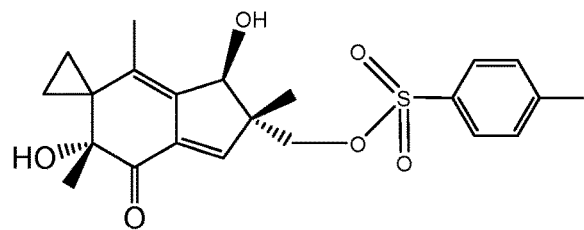
FIG. 1I shows analog 339.

As used herein, the term "receptor for a biologically active polypeptide" means a receptor which can bind a biologically active peptide conjugate.

As used herein, the term "cell population" is used to describe a set or subset of cells expressing a molecule such as a receptor.

The phrase 'Other Drugs' means docetaxel, cabazitaxel, mitoxantrone, estramustine, prednisone, carboplatin, bevacizumab, paclitaxel, gemcitabine, doxorubicin, topotecan, etoposide, tamoxifen, letrozole, sorafenib, fluorouracil, capecitabine, oxaliplatin, interferon-alpha, 5-fluorouracil (5-FU), a histone deacetylase (HDAC) inhibitor, ipilimumab, bortezomib, carfilzomib, thalidomide, lenalidomide, pomalidomide, dexamethasone, cyclophosphamide, vincristine, melphalan, tegafur, irinotecan, cetuximab, leucovorin, SN-38, everolimus, temsirolimus, bleomycin, lomustine, depsipeptide, erlotinib, cisplatin, busulfan, epirubicin, arsenic trioxide, bendamustine, fulvestrant, teniposide, adriamycin, decitabine, estramustine, azaguanine, aclarubicin, mitomycin, paclitaxel, taxotere, APO010, ara-c, methylprednisolone, methotrexate, methyl-gag, belinostat, idarubicin, IL4-PR38, valproic acid, all-trans retinoic acid (ATRA), cytoxan, suberoylanilide hydroxamic acid, leukeran, fludarabine, vinblastine, dacarbazine, hydroxyurea, tegafur, daunorubicin, mechlorethamine, streptozocin, carmustine, mercaptopurine, dactinomycin, tretinoin, ifosfamide, floxuridine, thioguanine, PSC 833, herceptin, celecoxib, iressa, anastrozole, and rituximab.

'Acylfulvene' means an Illudofulvene subgroup with the following structural molecular formula:

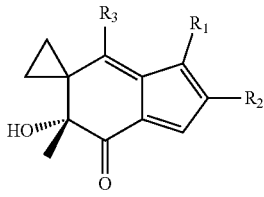

where $R_1$, $R_2$, $R_3$, $R_8$, $R_9$, $R_{10}$, $R_{11}$, are as set forth in Formula P1, as given herein.

'Formula P1' means $R_1$ represents —H, —$CR_9R_8OH$, —$CHR_9CHR_8OH$, —$CHR_{10}CHR_9CHR_8OH$, —$CH_2CHR_{10}CHR_9CHR_8OH$, —$CR_9R_8OH$, —$CHR_9CHR_8OH$, —$CHR_{10}CHR_9CHR_8OH$, —$CH_2CHR_{10}CHR_9CHR_8OH$, —C(=O)H, —$CH_2$(C=O)H, —$CH_2CH_2$(C=O)H, —$CH_2CH_2CH_2$(C=O)H, —$CH_2CH_2CH_2CH_2$(C=O)H, —$CR_9R_8$(C=O)H, —$CHR_9CHR_8$(C=O)H, —$CH_2CHR_9CHR_8$(C=O)H, —$CR_9R_8$(C=O)$R_{10}$, —$CHR_9CHR_8$(C=O)$R_{10}$, —$CH_2CHR_9CHR_8$(C=O)$R_{10}$, —$CH_2CH_2CHR_9CHR_8$(C=O)$R_{10}$, —$CO_2H$, —$CHR_9CO_2H$, —$CHR_8CHR_9CO_2H$, —$CHR_{10}CHR_8CHR_9CO_2H$, —$CO_2R_{10}$, —$CHR_9CO_2R_{10}$, —$CHR_8CHR_9CO_2R_{10}$, —$CH_2CHR_8CHR_9CO_2R_{10}$, —$CHR_9CH_2CH_2CHR_8CO_2H$, —$CHR_9CH_2CH_2CHR_8CO_2R_{10}$, —$CR_8$=$CH_2$, —$CHR_8CH$=$CH_2$, —$CH_2CHR_8CH$=$CH_2$, —$CH_2CH_2CHR_8CH$=$CH_2$, —$CR_8$=$CHR_9$, —$CHR_8CR_9$=$CH_2$, —$CH_2CHR_8CR_9$=$CH_2$, —$CH_2CH_2CHR_8CR_9$=$CH_2$, —$CR_8$=$CR_9R_{10}$, —$CHR_8CH$=$CR_9R_{10}$, —$CH_2CHR_8CH$=$CHR_9R_{10}$, —$CH_2CH_2CHR_8CH$=$CHR_9R_{10}$, —Cl, —Br, —I, —F, —$NO_2$, —$NR_8R_9$, —$CH_2Cl$, —$CH_2Br$, —$CH_2I$, —$CH_2F$, —$CR_8Cl_2$, —$CR_8Br_2$, —$CR_8I_2$, —$CR_8F_2$, —$CCl_3$, —$CBr_3$, —$CI_3$, —$CF_3$, —$CHR_8Cl$, —$CR_8R_9Cl$, —$CHR_8CHR_9Cl$, —$CHR_{10}CHR_8CHR_9Cl$, —$CH_2CHR_{10}CHR_8CHR_9Cl$, —$CHR_8Br$, —$CR_8R_9Br$, —$CHR_8CHR_9Br$, —$CHR_{10}CHR_8CHR_9Br$, —$CH_2CHR_{10}CHR_8CHR_9Br$, —$CHR_8I$, —$CR_8R_9I$, —$CHR_8CHR_9I$, —$CHR_{10}CHR_8CHR_9I$, —$CH_2CHR_{10}CHR_8CHR_9I$, —$CR_8R_9NH_2$, —$CHR_8CHR_9NH_2$, —$CHR_{10}CHR_8CHR_9NH_2$, —$CH_2CHR_{10}CHR_8CHR_9NH_2$, —$CR_9R_{10}NHR_8$, —$CHR_9CHR_{10}NHR_8$, —$CH_2CHR_9CHR_{10}NHR_8$, —$CH_2CH_2CHR_9CHR_{10}NHR_8$, —$CHR_9NHR_8R_{10}$, —$CHR_9CH_2NHR_8R_{10}$, —$CH_2CHR_9CHR_9NR_{10}R_8$, —$CH_2CH_2CH_2NHR_8$, —$CR_9R_8OR_{10}$, —$CH_2CR_8R_9OR_{10}$, —$CH_2CH_2CR_8R_9OR_{10}$, —$CH_2CH_2CH_2R_8R_9OR_{10}$, —$CH_2CH_2CH_2CH_2R_8R_9OR_{10}$, —$CHR_8OC$(=O)$CHR_9R_{10}$, —$CHR_8OC$(=O)$CHR_9R_{10}$, —$CH_2CH_2OC$(=O)$CHR_9R_{10}$, —$CH_2CH_2CHR_8OC$(=O)$CHR_9R_{10}$, —$CH_2CH_2CH_2CH_2OC$(=O)$CHR_9R_{10}$, —$CHR_8$(=O)$OCHR_9R_{10}$, —$CHR_8$(=O)$OCHR_9R_{10}$, —$CH_2CHR_8$(=O)$OCHR_9R_{10}$, —$CH_2CH_2CHR_8$(=O)$OCHR_9R_{10}$, —$CH_2CH_2CH_2CHR_8$(=O)$OCHR_9R_{10}$, —$R_{12}C$=$CR_9CH_2OH$, —$R_{12}C$=$CR_9C$(=O)H, —$R_{12}C$=$CR_9CH_2OR_{10}$, —$R_{12}C$=$CR_9C$(=O) $R_{10}$, —$CH_3$, —$CH_2CH_2$, —$CHR_8CH_2$, —$CHR_8CH_2CH_2$, —$CHR_8CHR_9CH_3$, —$OCH_3$, —$OCR_8R_9R_{10}$, —$OCH_2CR_8R_9R_{10}$, —$OCR_9R_8CHR_{10}$, —$OCHR_8CH_2CH_3$, —$OCHR_8CHR_9CH_3$, —$NR_8CH_3$, —$NR_8CH_2CH_3$, —$NR_9CHR_8CH_3$, —$NR_9CHR_8CH_2CH_3$, —$NR_{10}CHR_8CHR_9CH_3$, —$OCH_2OR_8$, —$OCHR_8OR_9$, —$OCHR_8CH_2OR_9$, —$OCHR_8CHR_9OR_{10}$, —OC(=O)$OR_8$, —$OCH_2C$(=O)$OR_8$, —$OCHR_9C$(=O)$OR_8$, —$CR_8$(=N)H, —$CH_2CR_8$(=N)H, —$CH_2CR_8$(=N)H, —$CH_2CH_2CR_8$ (=N)H, —$CH_2CH_2CR_8$(=N)H, —$CH_2CH_2CH_2CR_8$(=N)H, —$CR_8$(=N)OH, —$CH_2CR_8$(=N)OH, —$CH_2CR_8$(=N)OH, —$CH_2CH_2CR_8$ (=N)OH, —$CH_2CH_2CH_2CR_8$(=N)OH, —$CH_2CH_2CH_2CH_2CR_8$ (=N)OH, —$CR_8$(=N)$R_9$, —$CH_2CR_8$(=N) $R_9$, —$CH_2CR_8$(=N) $R_9$, —$CH_2CH_2CR_8$ (=N) $R_9$, —$CH_2CH_2CH_2CR_8$(=N)$R_9$, —$CH_2CH_2CH_2CH_2CR_8$(=N)$R_9$, —$CR_8$(=N)$OR_9$, —$CH_2CR_8$(=N)$OR_9$, —$CH_2CR_8$(=N)O $R_9$, —$CH_2CH_2CR_8$ (=N)$OR_9$, —$CH_2CH_2CHR_8$(=N)$OR_9$, —$CH_2CH_2CH_2CR_8$ (=N)$OR_9$, —$CR_8$(=N)$NR_9$, —$CH_2CR_8$(=N)$NR_9$, —$CH_2CR_8$(=N)$NR_9$, —$CH_2CH_2CR_8$ (=N)$NR_9$, $CH_2CH_2CH_2$—$CR_8$ (=N)$NR_9$, —$CH_2CH_2CH_2CH_2CR_8$ (=N)$NR_9$, —$CR_8$(=N)$NR_9S$ (=O)$_2R_{10}$, —$CH_2C(R_8)$(=N)$NR_9S$(=O)$_2R_{10}$, —$CH_2CH_2C(R_8)$(=N)$NR_9S$(=O)$_2R_{10}$, —$CH_2CH_2CH_2C$ ($R_8$)(=N)$NR_9S$(=O)$_2R_{10}$, —$CH_2CH_2CH_2CH_2$, —C($R_8$) (=N)$NR_9S$(=O)$_2R_{10}$, —$R_{12}N(R_8)C$(=O)$NR_9R_{10}$, —$R_{12}N(R_8)C$(=S)$NR_9R_{10}$, —$R_{12}N(OR_8)C$(=O)$NR_9R_{10}$, —$R_{12}N(OR_8)C$(=S)$NR_9R_{10}$, —$R_{12}OS(O_2)NH_2$, —$R_{12}NHS(O_2)NH_2$, —$R_{12}OS(O_2)NR_8R_9$, —$R_{12}NHS(O_2)NR_8R_9$, —$CH_2N(R_8)S(O_2)NR_9R_{10}$, —$CH_2CH_2N(R_8)S(O_2)NR_9R_{10}$, —$CH_2CH_2CH_2N(R_8)S(O_2)NR_9R_{10}$, —$CH_2N(R_8)S(O_2)CR_9R_{10}R_{11}$, —$CH_2CH_2N(R_8)S(O_2)$ $CR_9R_{10}R_{11}$, —$CH_2CH_2CH_2N(R_8)S(O_2)CR_9R_{10}R_{11}$, —$N(R_8)C$(=O)$R_9$, —$CH_2N(R_8)C$(=O)$R_9$, —$CH_2CH_2N(R_8)C$(=O)$R_9$, —$CH_2CH_2CH_2N(R_8)C$(=O)$R_9$, —$CH_2N(R_8)(C$=O) $NR_9R_{10}$, —$CH_2CH_2N(R_8)(C$=O)$NR_9R_{10}$, —$CH_2CH_2N$ ($R_8$)(C=O)$NR_9R_{10}$, —$CH_2N(R_8)(C$=O)$CR_9R_{10}R_{11}$, —$CH_2CH_2N(R_8)(C$=O) $CR_9R_{10}R_{11}$, —$CH_2CH_2N(R_8)$ (C=O) $CR_9R_{10}R_{11}$, —$R_{12}N(OH)C$(=O)NHOH, —$R_{12}N$ (OH)C(=S)NHOH, —$R_{12}N(OR_8)C$(=O)$NHOR_9$, —$R_{12}N$ ($OR_8$)C(=S)$NHOR_9$, —$R_{12}OS(O_2)NHOH$, —$R_{12}NHS$ ($O_2$)NHOH, —$R_{12}OS(O_2)NHOR_9$, —$R_{12}OS(O_2)N(R_8)$ $OR_9$, —$R_{12}NR_8S(O_2)NHOR_9$, —$CR_9$(=N)$OR_8$, —NH ($OR_8$), —C(C=O)$NHR_8$, —C(C=O)$NR_9R_8$, —$NR_{10}$ ($OR_8$)C(=O)$R_9$, —N($OR_8$)C(=O)$NR_9$, —$NR_8(R_9)SR_{10}$, —N($R_8$)S(=O)$R_9$, —N($R_8$)S(=O)$_2R_9$, —OC(=O)$NR_8$, —N($OR_8$)C(=O)$OR_9$, —N($R_8$)C(=S)$R_9$, —O(S(=O)$_2R_8$, —$R_{12}O(S(=O)_2R_8$, —O(S(=O)$_2NR_8$, —$R_{12}O(S(=O)_2$ $NR_8$, —S(=O)$R_8$, —$R_{12}O(S(=O)R_8$, —S(=O)$_2R_8$, —$R_{12}S$ (=O)$_2R_8$, —$NR_{10}(R_9)S(=O)_2NHR_8$, —$NR_9(C$=O)$R_8$, —NR₉(C=O)OR₈, —NR₉O(C=O)OR₈, —NR₉(C=O)NR₈R₁₀, —R₁₂N(R₉)S(=O)₂NHR₈, —R₁₂N(R₉)(C=O)R₈, —R₁₂N(R₉)(C=O)OR₈, —R₁₂N(R₉)(C=O)NR₈, —N(=NR₁₀)R₈, —R₉—N(=NR₁₀)R₈, —C(R₁₀)(=N—N=)CR₈R₉; —N₃, —CH₂N₃, —CH₂CH₂N₃, —CH₂CH₂CH₂N₃, —CH₂CH₂CH₂CH₂N₃, —CHR₈N₃, —CR₉R₈N₃, —CHR₉CHR₈N₃, —CH₂CHR₉CHR₈N₃, —CH₂CH₂CH₂CHR₈N₃, —C(R₈)=N—R₉, —CH₂C(R₈)=N—R₉, —CH₂CH₂C(R₈)=N—R₉, —CH₂CH₂CH₂C(R₈)=N—R₉, —N₃, —CH₂CH₂N₃, —CH₂CH₂CH₂N₃, —CH₂CH₂CH₂CH₂N₃; —CH₂NHC(=O)OC(CH₃)₃, —CH₂NOHC(=O)OC(CH₃)₃, —CH₂CH₂NHC(=O)OC(CH₃)₃, —CH₂CH₂NOHC(=O)OC(CH₃)₃, —CH₂CH₂CH₂NHC(=O)OC(CH₃)₃, —CH₂CH₂CH₂NOHC(=O)OC(CH₃)₃, —CH₂NHFmoc; —CH₂NOHFmoc; —CH₂CH₂NHFmoc; —CH₂CH₂NOHFmoc; —CH₂CH₂CH₂NH—Fmoc; —CH₂CH₂CH₂NOH-Fmoc, and R₂ and R₃ each independently represent —H, —OH, —CH₃, —OCH₃, —C(=O)CH₃, —OC(=O)CH₃, —C(=O)OCH₃, —C(=O)CH₂CH₃, —OC(=O)CH₂CH₃, —C(=O)OCH₂CH₃, —CH₂CH₃, —CH(CH₃)₂, —C(CH₃) 3, —CH₂CH₂CH₃, —CH₂CH(CH₃)₂, —CHC(CH₃)₃, —CH₂OH, —NH₂, —NHOH, —CH₂NH₂, —CH₂NHOH, —N₃, and (C₁-C₄)alkyl; where R₈, R₉, R₁₀, R₁₁ each independently represent —H, —OH, —CH₃, —CH₂CH₃, —CH₂=CH₂, —CH₂CH₂=CH₂, —CH₂CH₂CH₂=CH₂, —C(H)=O, —CH₂C(H)=O, —CH₂CH₂C(H)=O, —CH(CH₃)CH₃, —CH₂CH₂CH₃, —CH₂CH(CH₃)CH₃, —CHC(CH₃)₂CH₃, —C(=O)CH₃, —C(=O)CH₂CH₃, —C(=O)NH₂, —CH₂OH, —CH₂CH₂OH, —C(H)(OH)C(H₂)(OH), —OCH₃, —OC(CH₃)₃, —OCH₂CH₃, —OCH(CH₃)₂, —CO₂H, —C(=O)OCH₃, —C(=O)OCH₂CH₃, —OC(=O)CH₃, —OC(=O)CH₂CH₃, —OC(=O)OCH₃, —OC(=O)OCH₂CH₃, —C(CH₃)₃, —CH₂CH₂(CH₃)₂, —CHC(CH₃)₃, —CH₂CH₂OH, CH₂CH₂CH₂OH, —Cl, —Br, —I, —F, —CH₂Cl, —CH₂Br, —CH₂I, —CH₂F, —CHCl₂, —CHBr₂, —CHI₂, —CHF₂, —CCl₃, —CBr₃, —Cl₃, —CF₃, —NH₂, —CH₂NH₂, —NH(OH), —CH₂N(OH), —NH(OCH₃), —N(OCH₂CH₃), —CH₂NH(OCH₃), —CH₂N(OCH₂CH₃), —N₃, —CH₂N₃, —CH₂CH₂N₃, —CH=NH, —CH=NOH, —CH=NOCH₃, —SH, —SCH₃, —SCH₂CH₃, —NO₂, —CN, cyclopropane ring, saturated or unsaturated cyclobutane ring, saturated or unsaturated cyclopentane ring, saturated or unsaturated cyclohexane ring, benzene ring, phenolic ring, xylene ring, an amino acid(s), and (C₁-C₄)alkyl, and R12 represents —CH₂—, —CH₂CH₂—, —CH(CH₃)CH₂—, —C(CH₃)CH₂—, —CH=CH—, —O—, —S—, —O(C=O)—, —(C=O)O—, —NH—, —N(R₈)—, —N(OH)—, —CH2-O—, —O—CH₂—, —CH₂CH₂—O—, —O—CH₂CH₂—, —S(=O)—, —(S=O)₂—, —NH(S=O)₂—, —N(OH)S(=O)₂—, —S(=O)₂NH—, —S(=O)₂N(OH)—, —NHS(=O)₂—, —N(OH)S(=O)₂—, —CH₂NH—, —CH₂N(R₈)—, —CH₂N(OH)—, —NHCH₂—, —N(R₈)CH₂—, —N(OH)CH₂—, —OC(C=O)O—, —OC(=O)NR₈—, —NR₈C(=O)O—.

'Illudin' means an Illudofulvene subgroup with the following structural molecular formula:

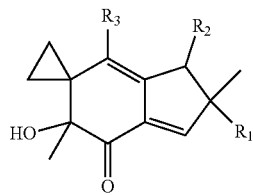

where R₁, R₂, R₃, are as set forth in Formula P2, as given herein.

'Formula P2' means where R₁, R₂, and R₃ each independently represent —H, —OH, —CH₃, —OCH₃, —C(=O)CH₃, —OC(=O)CH₃, —C(=O)OCH₃, —C(=O)CH₂CH₃, —OC(=O)CH₂CH₃, —C(=O)OCH₂CH₃, —CH₂CH₃, —CH(CH₃)₂, —C(CH₃)₃, —CH₂CH₂CH₃, —CH₂CH(CH₃)₂, —CHC(CH₃)₃, —CH₂OH, —NH₂, —CH₂NH₂, —N₃, —CH₂NHOH, —NHOH, —CH₂NHC(=O)OC(CH₃)₃, —CH₂NOHC(=O)OC(CH₃)₃, —C(=O)H, —C(=O)OH, —CH₂OSi(CH₃)₂C(CH₃)₃, —OS(=O)₂CH₃, —CH₂OS(=O)₂(C₄H₆)CH₃, —OC(=O)O(C₆H₄)NO₂, —OC(=O)N(CH₃)CH₂CH₂N(CH₃)C(=O)OC(CH₃)₃, —OC(C=O)N(CH₃)CH₂CH₂N(CH₃)H, —OC(=O)NHCH₂CH₂NH₂, —NH(FMOC), —NOH(FMOC), —CH₂NH(FMOC), —CH₂NOH(FMOC), —OSi(CH₂CH₂CH₃)₃, —OSi(CH₃)₂C(CH₃)₃, and (C1-C4) alkyl.

Figure 1J:
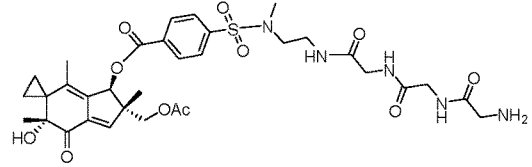
FIG. 1J shows analog 345.
Figure 1K:
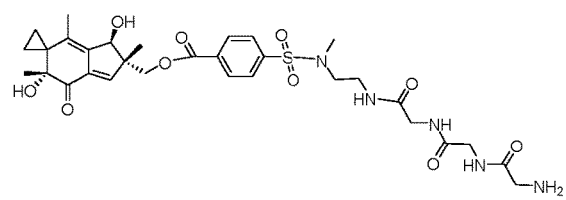
FIG. 1K shows analog 346.
Figure 1L:
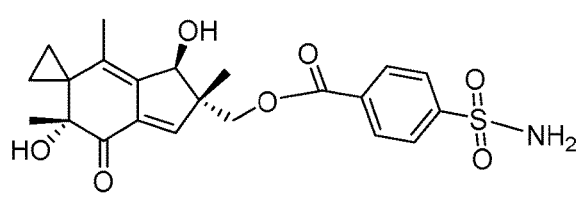
FIG. 1L shows analog 347.
Figure 1M:
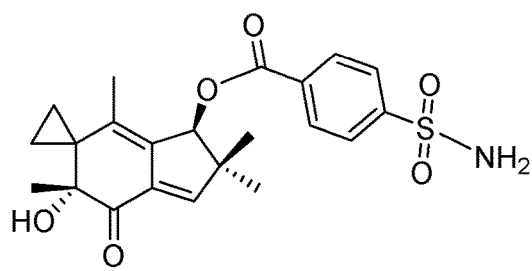
FIG. 1M shows analog 348.
Figure 1N:
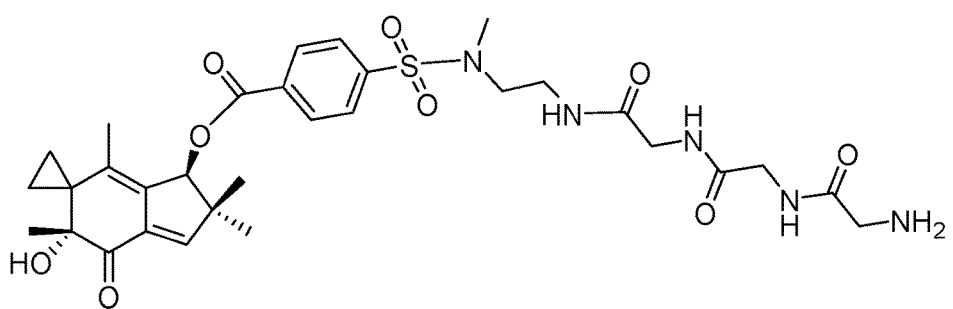
FIG. 1N shows analog 351.
Figure 1O:
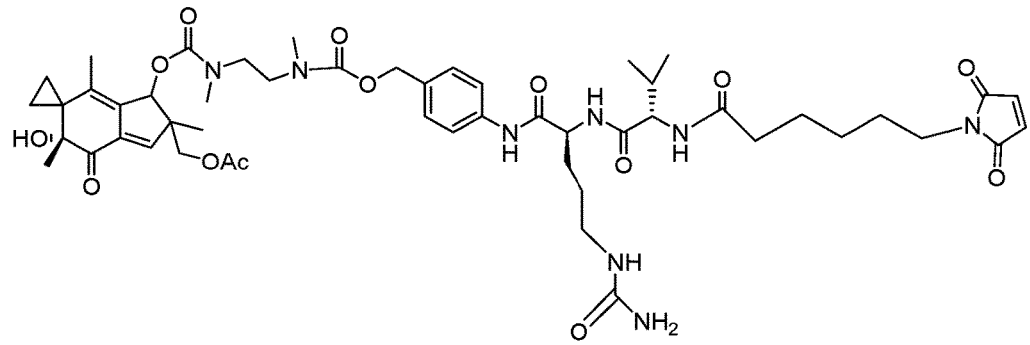
FIG. 1O shows analog 353.
Figure 1P:
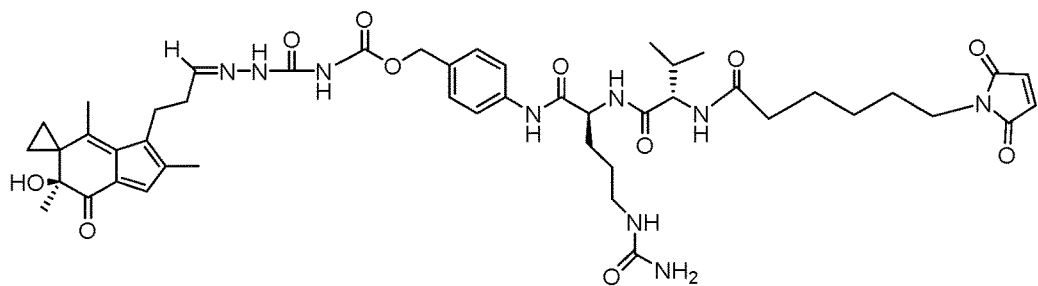
FIG. 1P shows analog 354.
Figure 1Q:
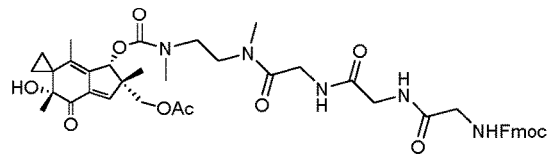
FIG. 1Q shows analog 356.
Figure 1R:
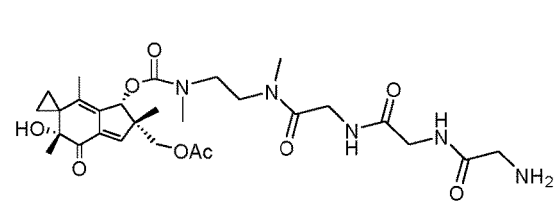
FIG. 1R shows analog 357.
Figure 1S:
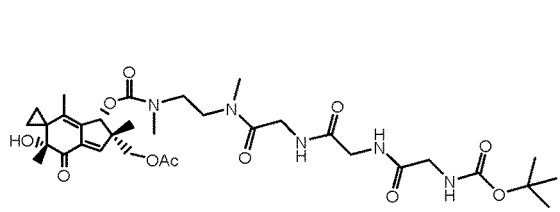
FIG. 1S shows analog 359.
Figure 1T:
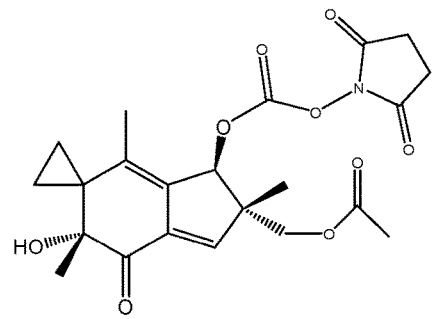
FIG. 1T shows analog 361.
Figure 1U:
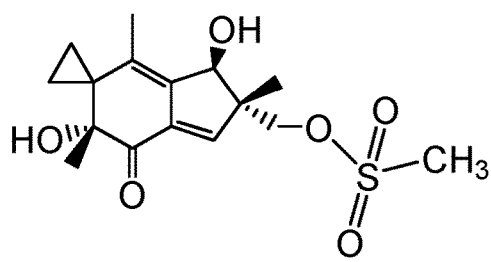
FIG. 1U shows analog 362.
Figure 1V:
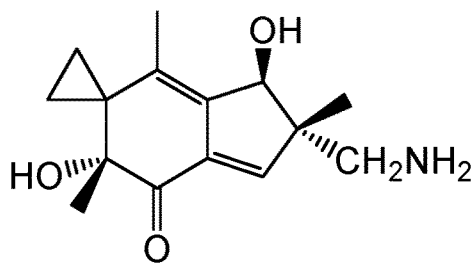
FIG. 1V shows analog 363.
Figure 1W:
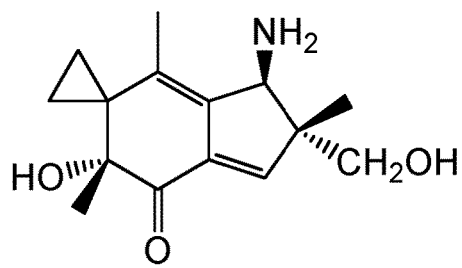
FIG. 1W shows analog 364.
Figure 1X:
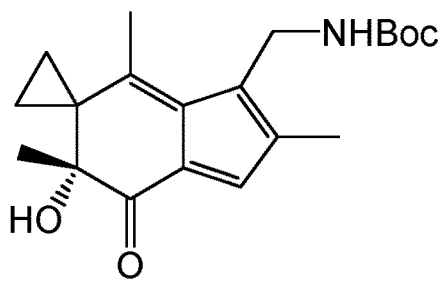
FIG. 1X shows analog 366.
Figure 1Y:
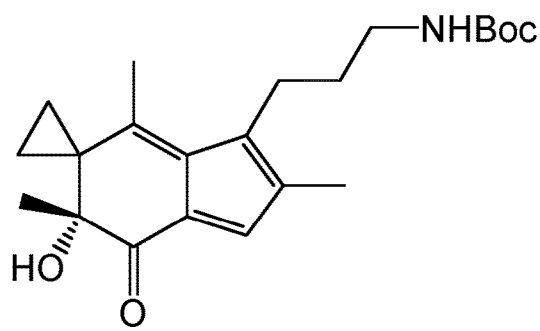
FIG. 1Y shows analog 367.
Figure 1Z:
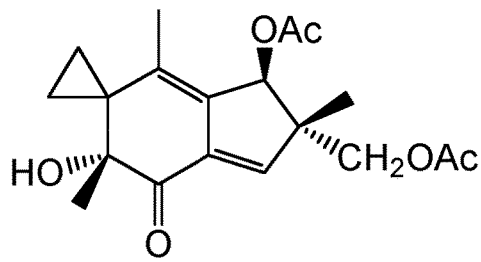
FIG. 1Z shows analog 368.
Figure 2A:
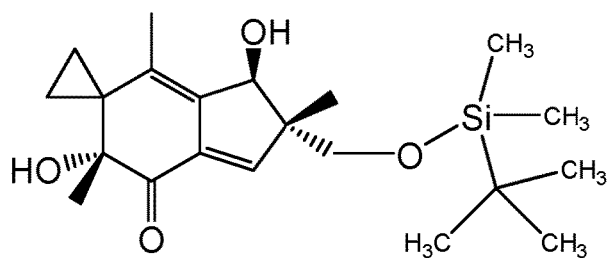
FIG. 2A shows analog 369.
Figure 2B:
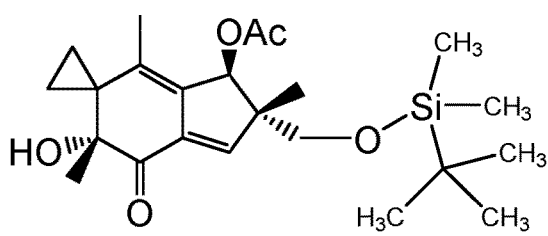
FIG. 2B shows analog 370.
Figure 2C:
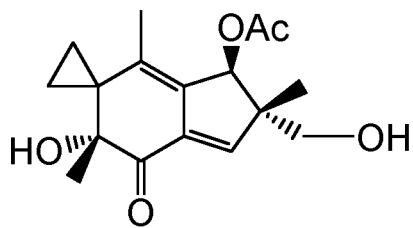
FIG. 2C shows analog 371.
Figure 2D:
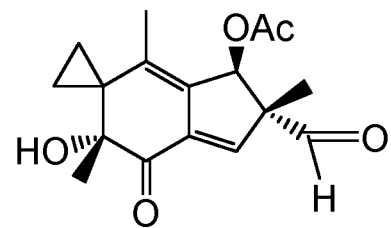
FIG. 2D shows analog 372.
Figure 2E:
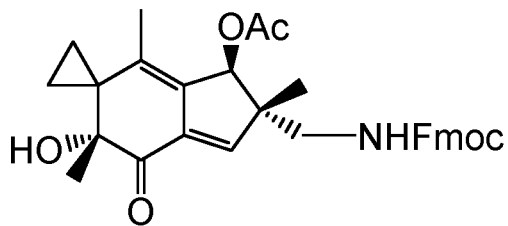
FIG. 2E shows analog 373.
Figure 2F:
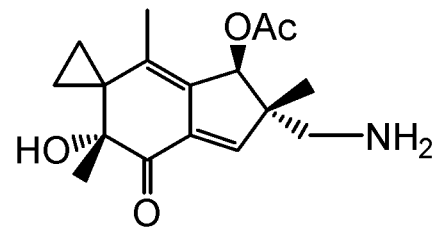
FIG. 2F shows analog 374.
Figure 2G:
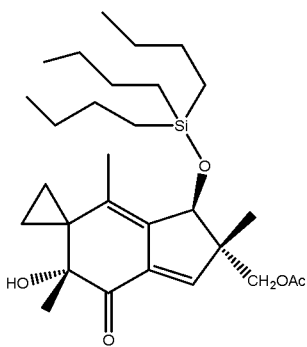
FIG. 2G shows analog 377.
Figure 2H:
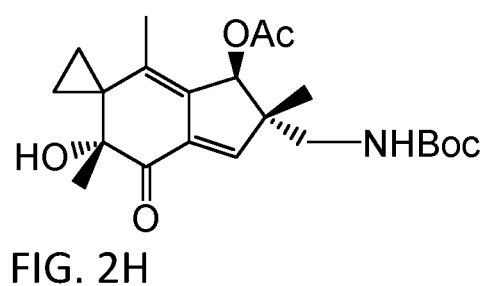
FIG. 2H shows analog 378.
Figure 2I:
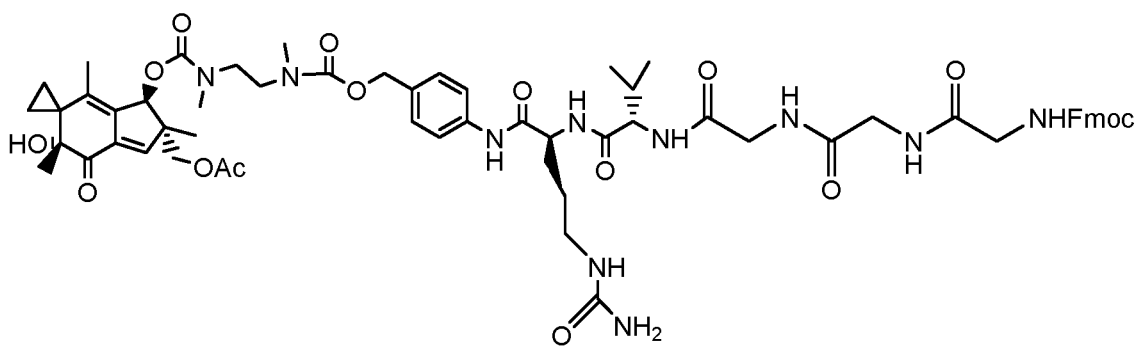
FIG. 2I shows analog 379.
Figure 2J:
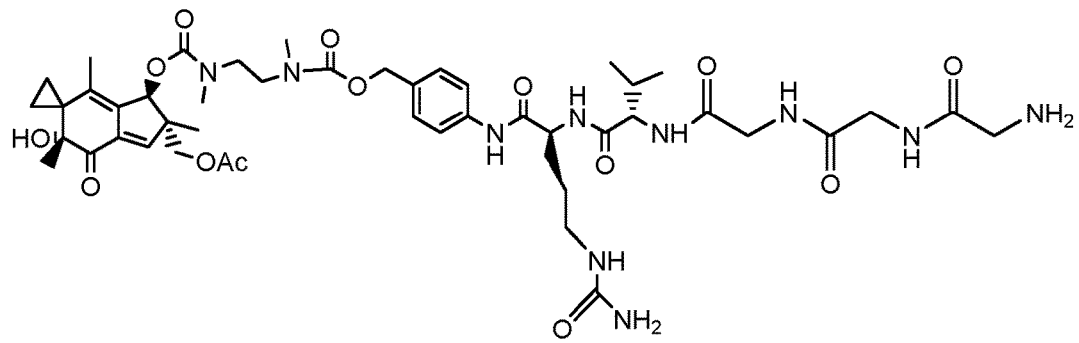
FIG. 2J shows analog 380.
Figure 2K:
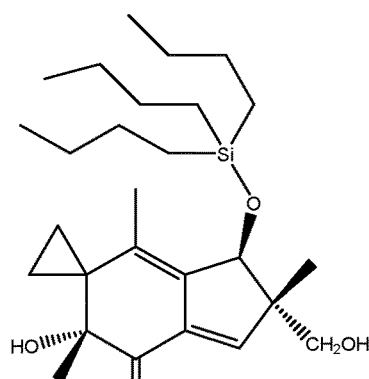
FIG. 2K shows analog 381.
Figure 2L:
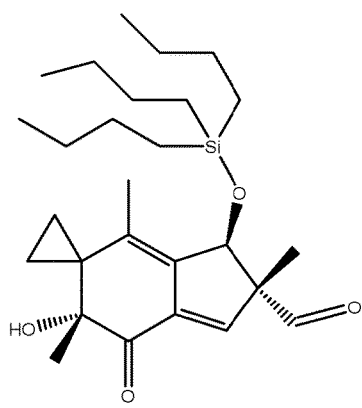
FIG. 2L shows analog 382.
Figure 2M:
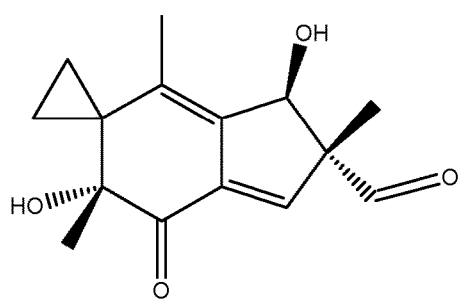
FIG. 2M shows analog 383.
Figure 2N:
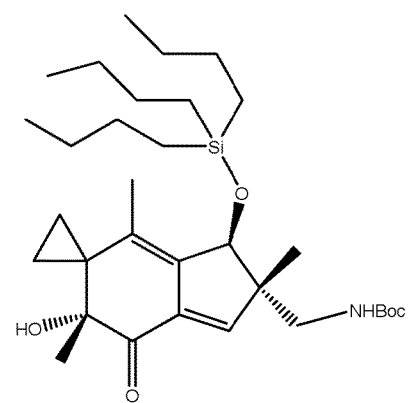
FIG. 2N shows analog 384.
Figure 2O:
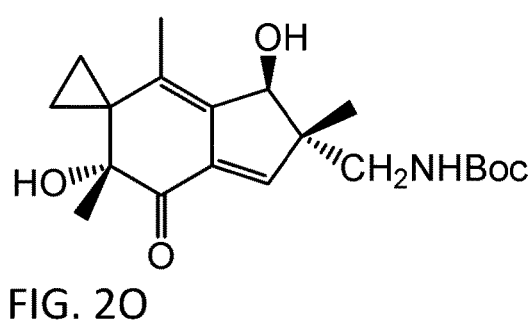
FIG. 2O shows analog 389.
Figure 2P:
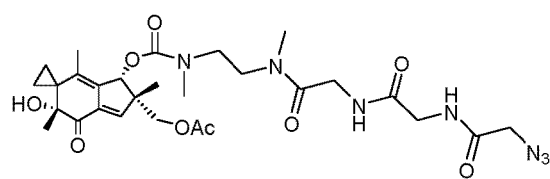
FIG. 2P shows analog 392.
Figure 2Q:
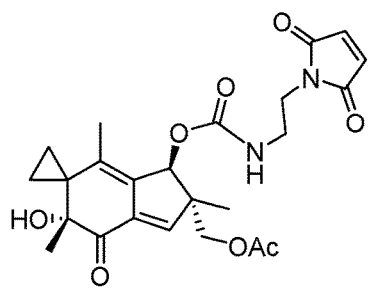
FIG. 2Q shows analog 393.
Figure 2R:
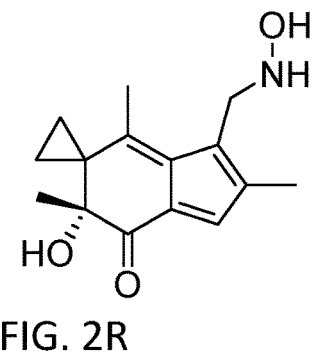
FIG. 2R shows analog 394.
Figure 2S:
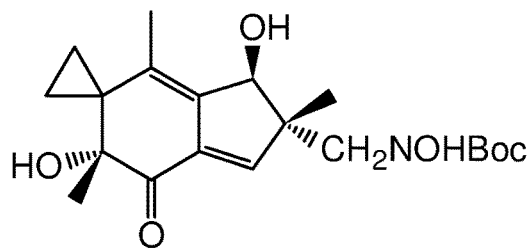
FIG. 2S shows analog 397.
Figure 2T:
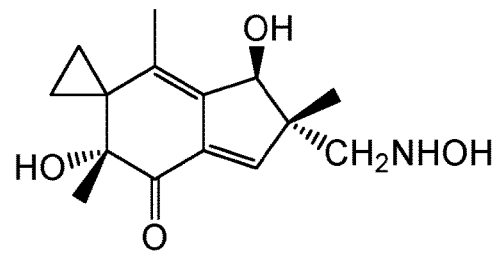
FIG. 2T shows analog 398.
Figure 2U:
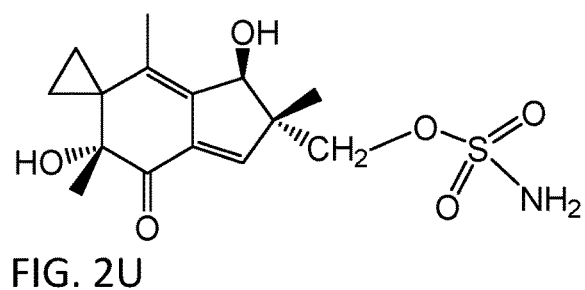
FIG. 2U shows analog 399.
Figure 2V:
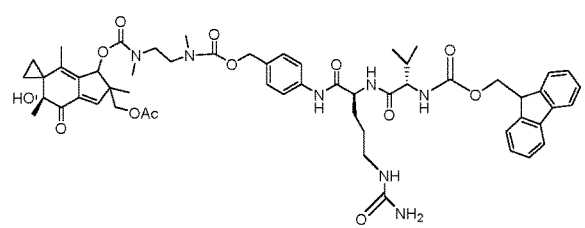
FIG. 2V shows analog 401.
Figure 2W:
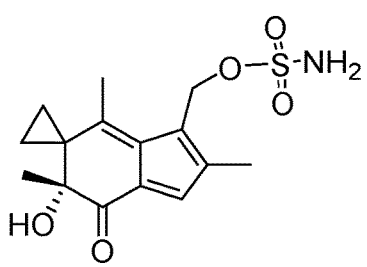
FIG. 2W shows analog 402.
Figure 2X:
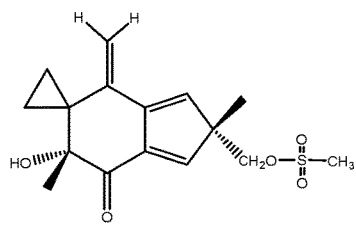
FIG. 2X shows analog 403.
Figure 2Y:
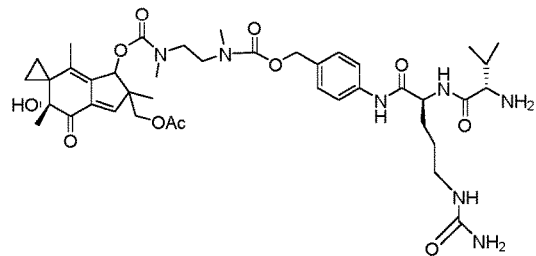
FIG. 2Y shows analog 404.
Figure 3A:
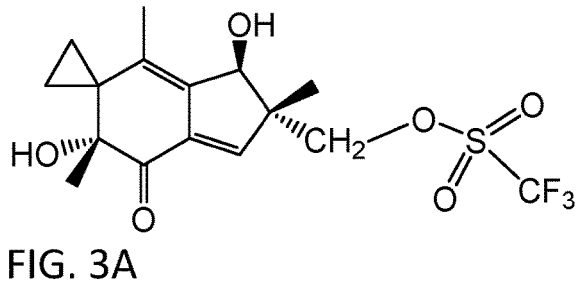
FIG. 3A shows analog 407.
Figure 2Z:
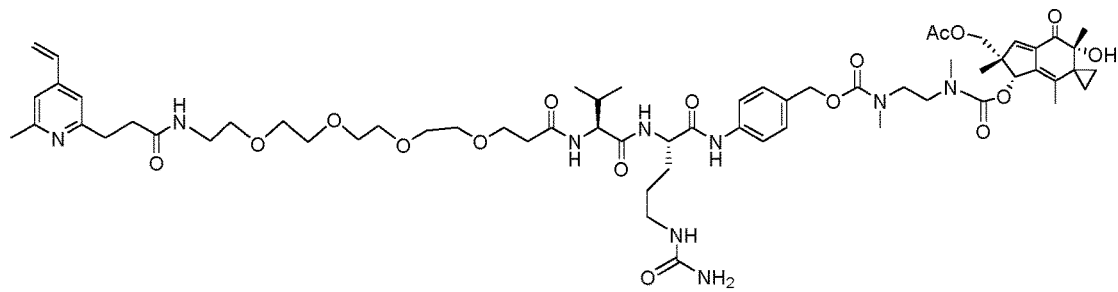
FIG. 2Z shows analog 405.
Figure 3B:
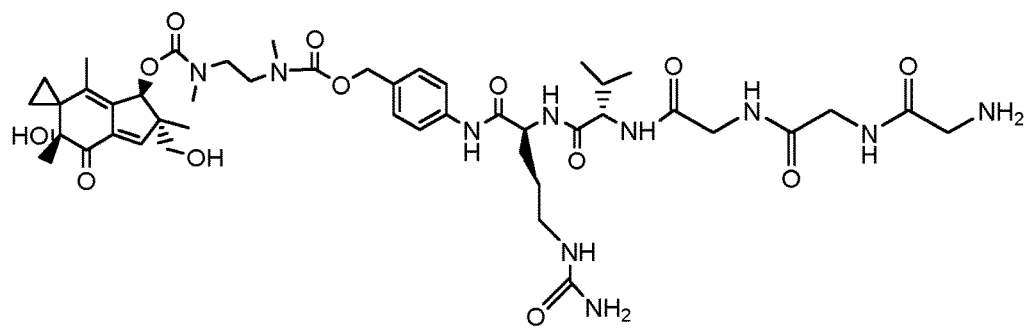
FIG. 3B shows analog 408.
Figure 3C:
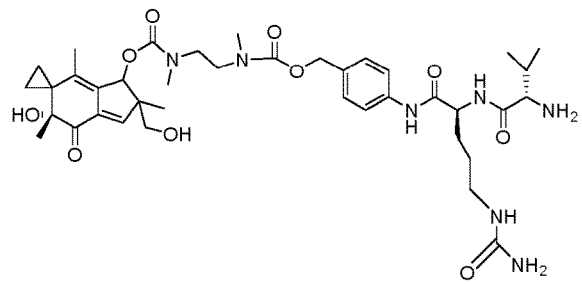
FIG. 3C shows analog 409 and FIG. 3D shows analog 410, according to various embodiments of the invention.
Figure 3D:
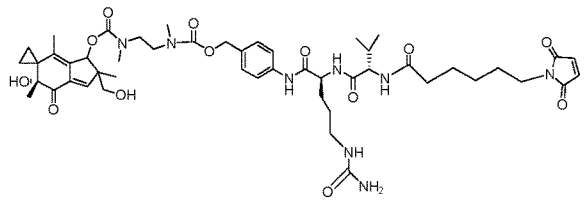

Table V is a listing of IUPAC names of the Illudofulvene Analog according to various embodiments of the present invention. FIGS. 1A-3D show the structure of analogs 317, 318, 332, 333, 334, 335, 337, 338, 339, 345, 346, 347, 348, 351, 353, 354, 356, 357, 359, 361, 362, 363, 364, 366, 367, 368, 369, 370, 371, 372, 373, 374, 377, 378, 379, 380, 381, 382, 383, 384, 389, 392, 393, 394, 397, 398, 399, 401, 402, 403, 404, 405, 407, 408, 409, and 410 respectively.

As used herein, the terms "analog", "medicant" and "medicant moiety" are used interchangeably and comprise synthetic and naturally occurring drugs, toxins, nutraceuticals and other cytoactive, anti-inflammatory and bioactive molecules including Doxorubicin (Immunomedics), auristatins E (Seattle Genetics), auristatins F (Celdex), monomethyl auristatin E (MMAE) (Amgen), monomethyl auristatin F (MMAF) (Astelles), maytanasines (Immunogen), DM1 (Biotest), DM4 (Amgen), calicheamicin (CellTech), irinotecan, folate, SN38 (Immunomedics), Pyrrolobenzodiazepines (Seattle Genetics), MGBA a duocarmycin derivative (Medarex), thalidomides, taxanes, penicillins, Trastuzumab emtansine (Genentech for Breast cancer uses maytanasine derive DM-1). Some of the above analogs are stand alone drugs, but can be used as a medicant moiety in an affinity drug conjugate according to various embodiments of the invention.

As used herein, the phrase "peptide receptor" includes peptide hormone receptors, protein hormone receptors, chemotactic receptors and chemokine receptors.

As used herein, the term "receptor" includes growth factor receptors, peptide hormone receptors, peptide receptors, steroid hormone receptors, steroid receptors and lipid receptors.

As used herein, phrase "affinity medicant conjugate" is an Affinity Moiety covalently bound to a medicant moiety, and includes antibody medicant conjugates, where the antibody is directed to a specific receptor. As used herein the phrase 'Affinity Moiety' includes antibodies, antibody fragments, peptides, proteins, growth factors, steroids, and lipids, where the antibodies, antibody fragments, peptides, proteins, growth factors, steroids, folate or lipids have an affinity for a specific receptor, receptors, is processed by an enzyme to produce a ligand that has an affinity for a specific receptor or otherwise directs the Affinity Moiety to a specific subset of cells. A 'medicant moiety' includes a group bound to an Affinity Moiety, which when released acts as a medicant.

As used herein, the term "Affinity Moiety" (AM) is used to describe a chemical group or molecule that can bind a receptor or proteins. An AM is understood to have a minimum binding affinity greater than approximately $1\times10^{-3}$ M affinity. As used herein, the term AM includes "ligands", "ligand moieties", "affinity unit" and an AM modified to include a linker. As used herein, the phrase "an affinity moiety directed to a peptide receptor" is used to describe a molecule or a portion of a molecule which has a binding affinity to the peptide receptor greater than approximately $1\times10^{-10}$ M. In this range approximately means $1\times10^{-9}$ M to $1\times10^{-11}$ M. In an embodiment of the invention, an AM directed to a peptide receptor has a binding affinity to the peptide receptor greater than approximately $1\times10^{-12}$ M. In this range approximately means $1\times10^{-11}$ M to $1\times10^{-13}$ M.

As used herein, the term "cytoactive" (which is abbreviated as "CA") is used to describe a small molecule that disrupts a cellular process, modulates a cellular process or otherwise affects the normal function of the cell. As used herein, the term "toxin" or "toxic" is used to describe a small molecule which interferes with RNA or DNA synthesis, causes RNA or DNA strand scission, blocks cell cycling, division, replication or is otherwise cytotoxic to the cell. As used herein, the term "toxin moiety" is used to describe a toxin modified to include a linker. As used herein, the phrase "a moiety possessing cell cytotoxicity" is used to describe a toxin moiety which when given in the concentration range of approximately $1\times10^{-3}$ M to approximately $1\times10^{-9}$ M results in inhibition of DNA synthesis or proliferation in an appropriate cultured cell line and/or when administered intravenously to an animal in the dosage approximately $1\times10^{-4}$ g to approximately $1\times10^{-9}$ g of the compound per kilogram of body weight of the animal results in in vivo cell death. As used herein, the term "ablated" is used to describe a reduction in the cell population of between approximately 50% and approximately 95%. In this range approximately means plus or minus five (5) percent. In an embodiment of the invention, a toxin moiety ablating a cell population reduces the cell population by approximately 100 percent. As used herein, the term "impaired" is used to describe a reduction in the cell population of between approximately 30% and approximately 50%. In this range approximately means plus or minus ten (10) percent.

As used herein, the term "linker" is used to describe one or more covalently bonded groups of atoms that are covalently bonded to a medicant moiety and an AM. For example a linker can be covalently bound to both an illudofulvene moiety and to an antibody or other ligand moiety with an affinity for a receptor.

As used herein, the term "non releasable linker" is used to describe a linker covalently bound to an AM and a medicant moiety in which the AM and the medicant moiety remain covalently bound to the linker after internalization and exposure to both reducing and acidic environments of vesicles within the cell. As used herein, the term "membrane permeability" is used to describe a compound comprising a linker covalently bound to an AM and an illudofulvene moiety, where the compound can diffuse across membranes within the cell.

As used herein, the term "transmembrane receptor" means a protein that spans the plasma membrane of a cell with the extracellular domain of the protein having the ability to bind an AM and the intracellular domain having an activity such as activation of G protein signaling which is induced upon the AM binding.

As used herein, the term "seven transmembrane receptor" is a transmembrane receptor including a transmembrane domain where the protein spans the cell membrane in seven (7) regions.

As used herein, the term "G-protein coupled receptor" means a seven transmembrane domain receptor which transduces a biological signal via G-protein coupling.

As used herein, the term "conjugated" or "conjugate" means a chemical compound that is formed by joining two or more compounds with one or more chemical bonds or linkers. In an embodiment of the invention, an antibody and a medicant form a conjugate.

As used herein, the term "antibody" herein is used in the broadest sense and specifically covers intact antibodies, monoclonal antibodies, polyclonal antibodies, mono-specific antibodies, multi-specific antibodies (e.g., bi-specific antibodies), and antibody fragments that exhibit the desired biological activity, including those antibodies directed against Alk, Alk fusion proteins, CD 2 (SEQ. ID. 001), CD3epsilon (SEQ. ID. 002), CD5 (SEQ. ID. 003), CD7 (SEQ. ID. 004), CD19 (SEQ. ID. 005), CD20 (SEQ. ID. 006), CD22 (SEQ. ID. 007), CD25 (SEQ. ID. 008), CD30 (SEQ. ID. 009), CD33 (SEQ. ID. 010), CD37 (SEQ. ID. 011), CD44 (SEQ. ID. 012), CD44v6 (SEQ. ID. 013), CD56 (SEQ. ID. 014), CD70 (SEQ. ID. 015), CD74 (SEQ. ID. 016), CD79 (SEQ. ID. 017), CD79b (SEQ. ID. 018), CD 80 (SEQ. ID. 019), CD 86 (SEQ. ID. 020), CD138 (syndecan 1) (SEQ. ID. 021), CAIX (SEQ. ID. 022), Integrin alphaV-beta 3 (SEQ. ID. 023), EphA2 (SEQ. ID. 024), Cripto1 (SEQ. ID. 025), CanAg (SEQ. ID. 026), ENPP3 (SEQ. ID. 027), Nectin-4 (SEQ. ID. 028), Mesothelin (SEQ. ID. 029), Lewis Y (SEQ. ID. 030), EGFRvIII (SEQ. ID. 031), SLC44A4 (SEQ. ID. 032), EBTR (endothelin) (SEQ. ID. 033), erbB2/neu/HER2 (SEQ. ID. 034), Transferrin receptor (SEQ. ID. 035), 55 kDa breast cancer antigen, 72 kDa TAA, GPNMB (osteoactivin) (SEQ. ID. 038), CA-IX (SEQ. ID. 039), CEA (CD66e) (SEQ. ID. 040), CEACAMS (SEQ. ID. 041), PSMA (SEQ. ID. 042), CA125 (MUC16) (SEQ. ID. 043), Mud 1 (CA6) (SEQ. ID. 044), Melanoma glycoprotein NMB (SEQ. ID. 045), IL-2R (SEQ. ID. 166 and 046), IL13R (SEQ. ID. 047), TACSTD2 (TROP2 or EGP1) (SEQ. ID. 048), Folate receptor 1 (SEQ. ID. 049), Mucin 16 (SEQ. ID. 050), Endothelin receptor ETB (SEQ. ID. 051), STEAP1 (SEQ. ID. 052), SLC44A4 (AGS-5) (SEQ. ID. 053), AGS-16 (SEQ. ID. 054), and Guanylyl cyclase C (SEQ. ID. 055). An intact antibody has primarily two regions: a variable region and a constant region. The variable region binds to and interacts with a target antigen. The variable region includes a complementary determing region (CDR) that recognizes and binds to a specific binding site on a particular antigen. The constant region may be recognized by and interact with the immune system. An antibody can be of any type or class (e.g., IgG, IgE, IgM, IgD, and IgA) or subclass (e.g., IgG1, IgG2, IgG3, IgG4, IgA1 and IgA2). The antibody can be derived from any suitable species. In some embodiments, the antibody is of human or murine origin. An antibody can be, for example, human, humanized or chimeric.

As used herein, the terms "specifically binds" and "specific binding" refer to antibody binding to a predetermined antigen. Typically, the antibody binds with an affinity of at least about $1\times10^7$ M, and binds to the predetermined antigen with an affinity that is at least two-fold greater than its affinity for binding to a non-specific antigen (e.g., Bovine Serum Albumin, casein) other than the predetermined antigen or a closely-related antigen.

As used herein, the term "monoclonal antibody" as used herein refers to an antibody obtained from a population of substantially homogeneous antibodies, i.e., the individual antibodies comprising the population are identical except for possible naturally-occurring mutations that may be present in minor amounts and includes "chimeric" antibodies in which a portion of the heavy and/or light chain is identical to or homologous with the corresponding sequence of antibodies derived from a particular species or belonging to a particular antibody class or subclass, while the remainder of the chain(s) is identical to or homologous with the corresponding sequences of antibodies derived from another species or belonging to another antibody class or subclass, as well as fragments of such antibodies, so long as they exhibit the desired biological activity. Monoclonal antibodies are highly specific, being directed against a single antigenic site. The modifier "monoclonal" indicates the character of the antibody as being obtained from a substantially homogeneous population of antibodies, and is not to be construed as requiring production of the antibody by any particular method.

As used herein, an "intact antibody" is one which comprises an antigen-binding variable region as well as a light chain constant domain ($C_L$) and heavy chain constant domains, $C_{H1}$, $C_{H2}$, $C_{H3}$ and $C_{H4}$, as appropriate for the antibody class. The constant domains may be native sequence constant domains (e.g., human native sequence constant domains) or amino acid sequence variants thereof.

As used herein, the term an "intact antibody" may have one or more "effector functions", which refers to those biological activities attributable to the Fc region (e.g., a native sequence Fc region or amino acid sequence variant Fc region) of an antibody. Examples of antibody effector functions include complement dependent cytotoxicity, antibody-dependent cell-mediated cytotoxicity (AMCC) and antibody-dependent cell-mediated phagocytosis.

As used herein, the term an "antibody fragment" comprises a portion of an intact antibody, preferably comprising the antigen-binding or variable region thereof. Examples of antibody fragments include Fab, Fab', F(ab')$_2$, and Fv fragments, di-abodies, tri-abodies, tetrabodies, linear antibodies, single-chain antibody molecules, scFv, scFv-Fc, multi-specific antibody fragments formed from antibody fragment(s), a fragment(s) produced by a Fab expression library, or an epitope-binding fragments of any of the above which immuno specifically bind to a target antigen (e.g., a cancer cell antigen, a viral antigen or a microbial antigen).

As used herein, the term "variable" in the context of an antibody refers to certain portions of the variable domains of the antibody that differ extensively in sequence and are used in the binding and specificity of each particular antibody for its particular antigen. This variability is concentrated in three segments called "hypervariable regions" in the light chain and the heavy chain variable domains. The more highly conserved portions of variable domains are called the Framework Regions (FRs). The variable domains of native heavy and light chains each comprise four FRs connected by three hypervariable regions.

As used herein, "isolated" means separated from other components of (a) a natural source, such as a plant or animal cell or cell culture, or (b) a synthetic organic chemical reaction mixture. As used herein, "purified" means that when isolated, the isolate contains at least 95%, and in another aspect at least 98%, of a compound (e.g., a conjugate) by weight of the isolate.

As used herein, an "isolated" antibody is one which has been identified and separated and/or recovered from a component of its natural environment. Contaminant components of its natural environment are materials which would interfere with diagnostic or therapeutic uses for the antibody, and may include enzymes, hormones, and other proteinaceous or non-proteinaceous solutes. In preferred embodiments, the antibody will be purified (1) to greater than 95% by weight of antibody as determined by the Lowry method, and most preferably more than 99% by weight, (2) to a degree sufficient to obtain at least 15 residues of N-terminal or internal amino acid sequence by use of a spinning cup sequenator, or (3) to homogeneity by SDS-PAGE under reducing or non-reducing conditions using Coomassie blue or, preferably, silver stain. Isolated antibody includes the antibody in situ within recombinant cells since at least one component of the antibody's natural environment will not be present. Ordinarily, however, isolated antibody will be prepared by at least one purification step.

As used herein, an antibody which "induces apoptosis" is one which induces programmed cell death as determined by binding of annexin V, fragmentation of DNA, cell shrinkage, dilation of endoplasmic reticulum, cell fragmentation, and/or formation of membrane vesicles (called apoptotic bodies). The cell is a tumor cell, e.g., a breast, ovarian, stomach, endometrial, salivary gland, lung, kidney, colon, thyroid, pancreatic or bladder cell. Various methods are available for evaluating the cellular events associated with apoptosis. For example, phosphatidyl serine (PS) translocation can be measured by annexin binding; DNA fragmentation can be evaluated through DNA laddering; and nuclear/chromatin condensation along with DNA fragmentation can be evaluated by any increase in hypodiploid cells.

As used herein, the term "therapeutically effective amount" refers to an amount of a medicant effective to treat a disease or disorder in a mammal. In the case of cancer, the therapeutically effective amount of the medicant may reduce the number of cancer cells; reduce the tumor size; inhibit (i.e., slow to some extent and preferably stop) cancer cell infiltration into peripheral organs; inhibit (i.e., slow to some extent and preferably stop) tumor metastasis; inhibit, to some extent, tumor growth; and/or relieve to some extent one or more of the symptoms associated with the cancer. To the extent the medicant may inhibit the growth of and/or kill existing cancer cells, it may be cytostatic and/or cytotoxic. For cancer therapy, efficacy can, for example, be measured by assessing the time to disease progression (TTP) and/or determining the response rate (RR).

As used herein, the term "substantial amount" refers to a majority, i.e. greater than approximately fifty percent (50%) of a population, of a mixture or a sample. In this range approximately means plus or minus ten percent (10%).

As used herein, the term "intracellular metabolite" refers to a compound resulting from a metabolic process or reaction inside a cell on an Affinity Medicant Linker conjugate (e.g., an Antibody Drug Conjugate (AMC)). The metabolic process or reaction may be an enzymatic process such as proteolytic cleavage of a peptide linker of the AMC. Intracellular metabolites include, but are not limited to, antibodies and free medicant which have undergone intracellular cleavage after entry, diffusion, uptake or transport into a cell.

As used herein, the terms "intracellularly cleaved" and "intracellular cleavage" refer to a metabolic process or reaction inside a cell on an Affinity Medicant Linker conjugate (e.g., an Antibody Medicant conjugate (AMC) or the like), whereby the covalent attachment, e.g., the linker, between the Medicant moiety (M) and the Affinity unit (e.g., an antibody (Ab)) is broken, resulting in the free Medicant, or other metabolite of the conjugate dissociated from the antibody inside the cell. The cleaved moieties of the Affinity Medicant Linker conjugate are thus intracellular metabolites.

As used herein, the term "bioavailability" refers to the systemic availability (i.e., blood/plasma levels) of a given amount of a medicant administered to a patient. Bioavailability is an absolute term that indicates measurement of both the time (rate) and total amount (extent) of medicant that reaches the general circulation from an administered dosage form.

As used herein, the term "cytotoxic activity" refers to a cell-killing, a cytostatic or an anti-proliferative effect of an Affinity Medicant Linker conjugate or an intracellular metabolite of an Affinity Medicant Linker conjugate. Cytotoxic activity may be expressed as the $IC_{50}$ value, which is the concentration (molar or mass) per unit volume at which half the cells survive.

As used herein, the term "cytotoxic agent" as used herein refers to a substance that inhibits or inhibits the function of cells and/or causes destruction of cells. The term is intended to include radioactive isotopes (e.g., $^{211}At$, $^{131}I$, $^{125}I$, $^{90}Y$, $^{186}Re$, $^{188}Re$, $^{153}Sm$, $^{212}Bi$, $^{32}P$, $^{60}C$, and radioactive isotopes of Lu), chemotherapeutic agents, and toxins such as small molecule toxins or enzymatically active toxins of bacterial, fungal, plant or animal origin, including synthetic analogs and derivatives thereof. In one aspect, the term does not include a radioactive isotope(s).

As used herein, a "disorder" is any condition that would benefit from treatment with an Affinity Medicant Linker Conjugate. This includes chronic and acute disorders or diseases including those pathological conditions which predispose a mammal to the disorder in question. Non-limiting examples of disorders to be treated herein include benign and malignant cancers; leukemia and lymphoid malignancies, neuronal, glial, astrocytal, hypothalamic and other glandular, macrophagal, epithelial, stromal and blastocoelic disorders; and inflammatory, angiogenic and immunologic disorders.

As used herein, the terms "cancer" and "cancerous" refer to or describe the physiological condition or disorder in mammals that is typically characterized by unregulated cell growth. A "tumor" comprises one or more cancerous cells.

As used herein, an "autoimmune disease" herein is a disease or disorder arising from and directed against an individual's own tissues or a co-segregate or manifestation thereof or resulting condition therefrom.

As used herein, an example of a "patient" includes, but is not limited to, a human, rat, mouse, guinea pig, monkey, pig, goat, cow, horse, dog, cat, bird and fowl. In an exemplary embodiment, the patient is a human.

As used herein, the terms "treat" or "treatment," unless otherwise indicated by context, refer to therapeutic treatment and prophylactic measures to prevent relapse, wherein the object is to inhibit or slow down (lessen) an undesired physiological change or disorder, such as the development or spread of cancer. For purposes of this invention, beneficial or desired clinical results include, but are not limited to, alleviation of symptoms, diminishment of extent of disease, stabilized (i.e., not worsening) state of disease, delay or slowing of disease progression, amelioration or palliation of the disease state, and remission (whether partial or total), whether detectable or undetectable. "Treatment" can also mean prolonging survival as compared to expected survival if not receiving treatment. Those in need of treatment include those already having the condition or disorder as well as those prone to have the condition or disorder.

As used herein, in the context of cancer, the term "treating" includes any or all of inhibiting growth of tumor cells, cancer cells, or of a tumor; inhibiting replication of tumor cells or cancer cells, lessening of overall tumor burden or decreasing the number of cancerous cells, and ameliorating one or more symptoms associated with the disease.

As used herein, in the context of an autoimmune disease, the term "treating" includes any or all of inhibiting replication of cells associated with an autoimmune disease state including, but not limited to, cells that produce an autoimmune antibody, lessening the autoimmune-antibody burden and ameliorating one or more symptoms of an autoimmune disease.

As used herein, in the context of an infectious disease, the term "treating" includes any or all of: inhibiting the growth, multiplication or replication of the pathogen that causes the infectious disease and ameliorating one or more symptoms of an infectious disease.

As used herein, the term "package insert" is used to refer to instructions customarily included in commercial packages of therapeutic products, that contain information about the indication(s), usage, dosage, administration, contraindications and/or warnings concerning the use of such therapeutic products.

As used herein, a "native sequence" polypeptide is one which has the same amino acid sequence as a polypeptide, e.g., a tumor-associated antigen receptor, derived from nature. Such native sequence polypeptides can be isolated from nature or can be produced by recombinant or synthetic means. Thus, a native sequence polypeptide can have the amino acid sequence of a naturally-occurring human polypeptide, a murine polypeptide, or a polypeptide from any other mammalian species.

As used herein, an "isolated" nucleic acid molecule is a nucleic acid molecule that is identified and separated from at least one contaminant nucleic acid molecule with which it is ordinarily associated in the natural source of the nucleic acid. An isolated nucleic acid molecule is other than in the form or setting in which it is found in nature. Isolated nucleic acid molecules therefore are distinguished from the nucleic acid molecule as it exists in natural cells. However, an isolated nucleic acid molecule includes a nucleic acid molecule contained in cells that ordinarily express the nucleic acid where, for example, the nucleic acid molecule is in a chromosomal location different from that of natural cells.

As used herein, the expression "control sequences" refers to nucleic acid sequences necessary for the expression of an operably linked coding sequence in a particular host organism. The control sequences that are suitable for prokaryotes, for example, include a promoter, optionally an operator sequence, and a ribosome binding site. Eukaryotic cells are known to utilize promoters, polyadenylation signals, and enhancers.

As used herein, a nucleic acid is "operably linked" when it is placed into a functional relationship with another nucleic acid sequence. For example, DNA for a pre-sequence or secretory leader is operably linked to DNA encoding a polypeptide if it is expressed as a pre-protein that participates in the secretion of the polypeptide; a promoter or enhancer is operably linked to a coding sequence, for example, if it affects the transcription of the sequence; or a ribosome binding site is operably linked to a coding sequence if it is positioned so as to facilitate translation. Generally, "operably linked" means that the DNA sequences being linked are contiguous, and, in the case of a secretory leader, contiguous and in reading phase. However, enhancers do not have to be contiguous. Linking can be accomplished by ligation at convenient restriction sites. If such sites do not exist, the synthetic oligonucleotide adaptors or linkers can be used in accordance with conventional practice.

As used herein, the terms "cell," "cell line," and "cell culture" are used interchangeably and all such designations include progeny. The words "transformants" and "transformed cells" include the primary subject cell and cultures or progeny derived therefrom without regard for the number of transfers. It is also understood that all progeny may not be precisely identical in DNA content, due to deliberate or inadvertent mutations. Mutant progeny that have the same function or biological activity as screened for in the originally transformed cell are included. Where distinct designations are intended, it will be clear from the context.

As used herein, the term "chiral" refers to molecules which have the property of non-superimposability of the mirror image partner, while the term "achiral" refers to molecules which are superimposable on their mirror image partner.

As used herein, the term "stereoisomers" refers to compounds which have identical chemical constitution, but differ with regard to the arrangement of the atoms or groups in space.

As used herein, "diastereomer" refers to a stereoisomer with two or more centers of chirality and whose molecules are not mirror images of one another. Diastereomers have different physical properties, e.g., melting points, boiling points, spectral properties, and reactivities. Mixtures of diastereomers may separate under high resolution analytical procedures such as electrophoresis and chromatography.

The abbreviations used herein have their conventional meaning within the chemical and biological arts. The chemical structures and formulae set forth herein are constructed according to the standard rules of chemical valency known in the chemical arts.

Where substituent groups are specified by their conventional chemical formulae, written from left to right, they equally encompass the chemically identical substituents that would result from writing the structure from right to left, e.g., —CH$_2$O— is equivalent to —OCH$_2$—.

The term "alkyl," by itself or as part of another substituent, means, unless otherwise stated, a straight (i.e., unbranched) or branched chain, or combination thereof, which may be fully saturated, mono- or polyunsaturated and can include di- and multivalent radicals, having the number of carbon atoms designated (i.e., C$_1$-C$_{10}$ means one to ten carbons). Examples of saturated hydrocarbon radicals include, but are not limited to, groups such as methyl, ethyl, n-propyl, isopropyl, n-butyl, t-butyl, isobutyl, sec-butyl, (cyclohexyl)methyl, homologs and isomers of, for example, n-pentyl, n-hexyl, n-heptyl, n-octyl, and the like. An unsaturated alkyl group is one having one or more double bonds or triple bonds. Examples of unsaturated alkyl groups include, but are not limited to, vinyl, 2-propenyl, crotyl, 2-isopentenyl, 2-(butadienyl), 2,4-pentadienyl, 3-(1,4-pentadienyl), ethynyl, 1- and 3-propynyl, 3-butynyl, and the higher homologs and isomers. An alkoxy is an alkyl attached to the remainder of the molecule via an oxygen linker (—O—).

The term "alkylene," by itself or as part of another substituent, means, unless otherwise stated, a divalent radical derived from an alkyl, as exemplified, but not limited by, —CH$_2$CH$_2$CH$_2$CH$_2$—. Typically, an alkyl (or alkylene) group will have from 1 to 24 carbon atoms, with those groups having 10 or fewer carbon atoms being preferred in the present invention. A "lower alkyl" or "lower alkylene" is a shorter chain alkyl or alkylene group, generally having eight or fewer carbon atoms.

The term "heteroalkyl," by itself or in combination with another term, means, unless otherwise stated, a stable straight or branched chain, or combinations thereof, consisting of at least one carbon atom and at least one heteroatom selected from the group consisting of O, N, P, Si, and S, and wherein the nitrogen and sulfur atoms may optionally be oxidized, and the nitrogen heteroatom may optionally be quaternized. The heteroatom(s) O, N, P, S, and Si may be placed at any interior position of the heteroalkyl group or at the position at which the alkyl group is attached to the remainder of the molecule. Examples include, but are not limited to: —CH$_2$—CH$_2$—O—CH$_3$, —CH$_2$—CH$_2$—NH—CH$_3$, —CH$_2$—CH$_2$—N(CH$_3$)—CH$_3$, —CH$_2$—S—CH$_2$—CH$_3$, —CH$_2$—CH$_2$, —S(O)—CH$_3$, —CH$_2$—CH$_2$—S(O)$_2$—CH$_3$, —CH=CH—O—CH$_3$, —Si(CH$_3$)$_3$, —CH$_2$—CH=N—OCH$_3$, —CH=CH—N(CH$_3$)—CH$_3$, —O—CH$_3$, —O—CH$_2$—CH$_3$, and —CN. Up to two heteroatoms may be consecutive, such as, for example, —CH$_2$—NH—OCH$_3$.

Similarly, the term "heteroalkylene," by itself or as part of another substituent, means, unless otherwise stated, a divalent radical derived from heteroalkyl, as exemplified, but not limited by, —CH$_2$—CH$_2$—S—CH$_2$—CH$_2$— and —CH$_2$—S—CH$_2$—CH$_2$—NH—CH$_2$—. For heteroalkylene groups, heteroatoms can also occupy either or both of the chain termini (e.g., alkyleneoxy, alkylenedioxy, alkyleneamino, alkylenediamino, and the like). Still further, for alkylene and heteroalkylene linking groups, no orientation of the linking group is implied by the direction in which the formula of the linking group is written. For example, the formula —C(O)$_2$R'— represents both —C(O)$_2$R'— and —R'C(O)$_2$—. As described above, heteroalkyl groups, as used herein, include those groups that are attached to the remainder of the molecule through a heteroatom, such as —C(O)R', —C(O)NR', —NR'R", —OR', —SR', and/or —SO$_2$R'. Where "heteroalkyl" is recited, followed by recitations of specific heteroalkyl groups, such as —NR'R" or the like, it will be understood that the terms heteroalkyl and —NR'R" are not redundant or mutually exclusive. Rather, the specific heteroalkyl groups are recited to add clarity. Thus, the term "heteroalkyl" should not be interpreted herein as excluding specific heteroalkyl groups, such as —NR'R" or the like.

The terms "cycloalkyl" and "heterocycloalkyl," by themselves or in combination with other terms, mean, unless otherwise stated, cyclic versions of "alkyl" and "heteroalkyl," respectively. Additionally, for heterocycloalkyl, a heteroatom can occupy the position at which the heterocycle is attached to the remainder of the molecule. Examples of cycloalkyl include, but are not limited to, cyclopropyl, cyclobutyl, cyclopentyl, cyclohexyl, 1-cyclohexenyl, 3-cyclohexenyl, cycloheptyl, and the like. Examples of heterocycloalkyl include, but are not limited to, 1-(1,2,5,6-tetrahydropridyl), 1-piperidinyl, 2-piperidinyl, 3-piperidinyl, 4-morpholinyl, 3-morpholinyl, tetrahydrofuran-2-yl, tetrahydrofuran-3-yl, tetrahydrothien-2-yl, tetrahydrothien-3-yl, 1-piperazinyl, 2-piperazinyl, and the like. A "cycloalkylene" and a "heterocycloalkylene," alone or as part of another substituent, means a divalent radical derived from a cycloalkyl and heterocycloalkyl, respectively.

The terms "halo" or "halogen," by themselves or as part of another substituent, mean, unless otherwise stated, a fluorine, chlorine, bromine, or iodine atom. Additionally, terms such as "haloalkyl" are meant to include monohaloalkyl and polyhaloalkyl. For example, the term "halo(C$_1$-C$_4$)

alkyl" includes, but is not limited to, fluoromethyl, difluoromethyl, trifluoromethyl, 2,2,2-trifluoroethyl, 4-chlorobutyl, and 3-bromopropyl.

The term "acyl" means, unless otherwise stated, —C(O)R where R is a substituted or unsubstituted alkyl, substituted or unsubstituted cycloalkyl, substituted or unsubstituted heteroalkyl, substituted or unsubstituted heterocycloalkyl, substituted or unsubstituted aryl, or substituted or unsubstituted heteroaryl.

The term "aryl" means, unless otherwise stated, a polyunsaturated, aromatic, hydrocarbon substituent, which can be a single ring or multiple rings (preferably from 1 to 3 rings) that are fused together (i.e., a fused ring aryl) or linked covalently. A fused ring awl refers to multiple rings fused together wherein at least one of the fused rings is an awl ring. The term "heteroaryl" refers to awl groups (or rings) that contain from one to four heteroatoms selected from N, O, and S, wherein the nitrogen and sulfur atoms are optionally oxidized, and the nitrogen atom(s) are optionally quaternized. Thus, the term "heteroaryl" includes fused ring heteroaryl groups (i.e., multiple rings fused together wherein at least one of the fused rings is a heteroaromatic ring). A 5,6-fused ring heteroarylene refers to two rings fused together, wherein one ring has 5 members and the other ring has 6 members, and wherein at least one ring is a heteroaryl ring. Likewise, a 6,6-fused ring heteroarylene refers to two rings fused together, wherein one ring has 6 members and the other ring has 6 members, and wherein at least one ring is a heteroaryl ring. And a 6,5-fused ring heteroarylene refers to two rings fused together, wherein one ring has 6 members and the other ring has 5 members, and wherein at least one ring is a heteroaryl ring. A heteroaryl group can be attached to the remainder of the molecule through a carbon or heteroatom. Non-limiting examples of aryl and heteroaryl groups include phenyl, 1-naphthyl, 2-naphthyl, 4-biphenyl, 1-pyrrolyl, 2-pyrrolyl, 3-pyrrolyl, 3-pyrazolyl, 2-imidazolyl, 4-imidazolyl, pyrazinyl, 2-oxazolyl, 4-oxazolyl, 2-phenyl-4-oxazolyl, 5-oxazolyl, 3-isoxazolyl, 4-isoxazolyl, 5-isoxazolyl, 2-thiazolyl, 4-thiazolyl, 5-thiazolyl, 2-furyl, 3-furyl, 2-thienyl, 3-thienyl, 2-pyridyl, 3-pyridyl, 4-pyridyl, 2-pyrimidyl, 4-pyrimidyl, 5-benzothiazolyl, purinyl, 2-benzimidazolyl, 5-indolyl, 1-isoquinolyl, 5-isoquinolyl, 2-quinoxalinyl, 5-quinoxalinyl, 3-quinolyl, and 6-quinolyl. Substituents for each of the above noted awl and heteroaryl ring systems are selected from the group of acceptable substituents described below. An "arylene" and a "heteroarylene," alone or as part of another substituent, mean a divalent radical derived from an awl and heteroaryl, respectively.

For brevity, the term "awl" when used in combination with other terms (e.g., aryloxy, arylthioxy, arylalkyl) includes both awl and heteroaryl rings as defined above. Thus, the term "arylalkyl" is meant to include those radicals in which an awl group is attached to an alkyl group (e.g., benzyl, phenethyl, pyridylmethyl, and the like) including those alkyl groups in which a carbon atom (e.g., a methylene group) has been replaced by, for example, an oxygen atom (e.g., phenoxymethyl, 2-pyridyloxymethyl, 3-(1-naphthyloxy)propyl, and the like).

The term "oxo," as used herein, means an oxygen that is double bonded to a carbon atom.

The term "alkylsulfoxide" as used herein, means a moiety having the formula R—S(O)—R', where R and R' are alkyl groups as defined above. R and R' may have a specified number of carbons (e.g., "$C_1$-$C_4$ alkylsulfoxide").

Each of the above terms (e.g., "alkyl," "heteroalkyl," "aryl," and "heteroaryl") includes both substituted and unsubstituted forms of the indicated radical. Preferred substituents for each type of radical are provided below.

Substituents for the alkyl and heteroalkyl radicals (including those groups often referred to as alkylene, alkenyl, heteroalkylene, heteroalkenyl, alkynyl, cycloalkyl, heterocycloalkyl, cycloalkenyl, and heterocycloalkenyl) can be one or more of a variety of groups selected from, but not limited to, —OR', =O, =NR', =N—OR', —NR'R", —SR', -halogen, —SiR'R"R''', —OC(O)R', —C(O)R', —CO$_2$R', —CONR'R", —OC(O)NR'R", —NR"C(O)R', —NR'—C(O)NR"R''', —NR"C(O)$_2$R', —NR—C(NR'R"R''')=NR"", —NR—C(NR'R")=NR''', —S(O)R', —S(O)$_2$R', —S(O)$_2$NR'R", —NRSO$_2$R', —OS(O)$_2$NR'R", —NRS(O)$_2$NR'R", —CN, and —NO$_2$ in a number ranging from zero to (2 m'+1), where m' is the total number of carbon atoms in such radical. R', R", R''', and R"" each preferably independently refer to hydrogen, substituted or unsubstituted heteroalkyl, substituted or unsubstituted cycloalkyl, substituted or unsubstituted heterocycloalkyl, substituted or unsubstituted awl (e.g., awl substituted with 1-3 halogens), substituted or unsubstituted alkyl, alkoxy, or thioalkoxy groups, or arylalkyl groups. When a compound of the invention includes more than one R group, for example, each of the R groups is independently selected as are each R', R", R''', and R"" group when more than one of these groups is present. When R' and R" are attached to the same nitrogen atom, they can be combined with the nitrogen atom to form a 4-, 5-, 6-, or 7-membered ring. For example, —NR'R" includes, but is not limited to, 1-pyrrolidinyl and 4-morpholinyl. From the above discussion of substituents, one of skill in the art will understand that the term "alkyl" is meant to include groups including carbon atoms bound to groups other than hydrogen groups, such as haloalkyl (e.g., —CF$_3$ and —CH$_2$CF$_3$) and acyl (e.g., —C(O)CH$_3$, —C(O)CF$_3$, —C(O)CH$_2$OCH$_3$, and the like).

Similar to the substituents described for the alkyl radical, substituents for the awl and heteroaryl groups are varied and are selected from, for example: —OR', —NR'R", —SR', -halogen, —SiR'R"R''', —OC(O)R', —C(O)R', —CO$_2$R', —CONR'R", —OC(O)NR'R", —NR"C(O)R', —NR'—C(O)NR"R''', —NR"C(O)$_2$R', —NR—C(NR'R"R''')=NR"", —NR—C(NR'R")=NR''', —S(O)R', —S(O)$_2$R', —S(O)$_2$NR'R", —NRSO$_2$R', —OS(O)$_2$NR'R", —NRS(O)$_2$NR'R", —CN, —NO$_2$, —R', —N$_3$, —CH(Ph)$_2$, fluoro($C_1$-$C_4$)alkoxy, and fluoro($C_1$-$C_4$)alkyl, in a number ranging from zero to the total number of open valences on the aromatic ring system; and where R', R", R''', and R"" are preferably independently selected from hydrogen, substituted or unsubstituted alkyl, substituted or unsubstituted heteroalkyl, substituted or unsubstituted cycloalkyl, substituted or unsubstituted heterocycloalkyl, substituted or unsubstituted awl, and substituted or unsubstituted heteroaryl. When a compound of the invention includes more than one R group, for example, each of the R groups is independently selected as are each R', R", R''', and R"" groups when more than one of these groups is present.

Two or more substituents may optionally be joined to form aryl, heteroaryl, cycloalkyl, or heterocycloalkyl groups. Such so-called ring-forming substituents are typically, though not necessarily, found attached to a cyclic base structure. In one embodiment, the ring-forming substituents are attached to adjacent members of the base structure. For example, two ring-forming substituents attached to adjacent members of a cyclic base structure create a fused ring structure. In another embodiment, the ring-forming substituents are attached to a single member of the base structure. For example, two ring-forming substituents attached to a single member of a cyclic base structure create a spirocyclic structure. In yet another embodiment, the ring-forming substituents are attached to non-adjacent members of the base structure.

Two of the substituents on adjacent atoms of the awl or heteroaryl ring may optionally form a ring of the formula -T-C(O)—(CRR')$_q$—U—, wherein T and U are independently —NR—, —O—, —CRR'—, or a single bond, and q is an integer of from 0 to 3. Alternatively, two of the substituents on adjacent atoms of the aryl or heteroaryl ring may optionally be replaced with a substituent of the formula -A-(CH$_2$)$_r$—B—, wherein A and B are independently —CRR'—, —O—, —NR—, —S—, —S(O)—, —S(O)$_2$—, —S(O)$_2$NR'—, —OS(O)$_2$NR'—, —NRS(O)$_2$NR'—, or a single bond, and r is an integer of from 1 to 4. One of the single bonds of the new ring so formed may optionally be replaced with a double bond. Alternatively, two of the substituents on adjacent atoms of the awl or heteroaryl ring may optionally be replaced with a substituent of the formula —(CRR')$_s$—X'—(C"R'")$_d$—, where s and d are independently integers of from 0 to 3, and X' is —O—, —NR'—, —S—, —S(O)—, —S(O)$_2$—, —OS(O)$_2$NR'—, —NRS(O)$_2$NR'—, or —S(O)$_2$NR'—. The substituents R, R', R", and R'" are preferably independently selected from hydrogen, substituted or unsubstituted alkyl, substituted or unsubstituted cycloalkyl, substituted or unsubstituted heterocycloalkyl, substituted or unsubstituted awl, and substituted or unsubstituted heteroaryl.

As used herein, the terms "heteroatom" or "ring heteroatom" are meant to include oxygen (O), nitrogen (N), sulfur (S), phosphorus (P), and silicon (Si).

A "substituent group," as used herein, means a group selected from the following moieties: (A) —OH, —NH$_2$, —SH, —CN, —CF$_3$, —NO$_2$, oxo, halogen, unsubstituted alkyl, unsubstituted heteroalkyl, unsubstituted cycloalkyl, unsubstituted heterocycloalkyl, unsubstituted awl, unsubstituted heteroaryl, and (B) alkyl, heteroalkyl, cycloalkyl, heterocycloalkyl, awl, and heteroaryl, substituted with at least one substituent selected from: (i) oxo, —OH, —NH$_2$, —SH, —CN, —CF$_3$, —NO$_2$, halogen, unsubstituted alkyl, unsubstituted heteroalkyl, unsubstituted cycloalkyl, unsubstituted heterocycloalkyl, unsubstituted aryl, unsubstituted heteroaryl, and (ii) alkyl, heteroalkyl, cycloalkyl, heterocycloalkyl, awl, and heteroaryl, substituted with at least one substituent selected from: (a) oxo, —OH, —NH$_2$, —SH, —CN, —CF$_3$, —NO$_2$, halogen, unsubstituted alkyl, unsubstituted heteroalkyl, unsubstituted cycloalkyl, unsubstituted heterocycloalkyl, unsubstituted aryl, unsubstituted heteroaryl, and (b) alkyl, heteroalkyl, cycloalkyl, heterocycloalkyl, awl, or heteroaryl, substituted with at least one substituent selected from: oxo, —OH, —NH$_2$, —SH, —CN, —CF$_3$, —NO$_2$, halogen, unsubstituted alkyl, unsubstituted heteroalkyl, unsubstituted cycloalkyl, unsubstituted heterocycloalkyl, unsubstituted aryl, and unsubstituted heteroaryl.

A "size-limited substituent" or "size-limited substituent group," as used herein, means a group selected from all of the substituents described above for a "substituent group," wherein each substituted or unsubstituted alkyl is a substituted or unsubstituted $C_1$-$C_{20}$ alkyl, each substituted or unsubstituted heteroalkyl is a substituted or unsubstituted 2 to 20 membered heteroalkyl, each substituted or unsubstituted cycloalkyl is a substituted or unsubstituted $C_4$-$C_8$ cycloalkyl, and each substituted or unsubstituted heterocycloalkyl is a substituted or unsubstituted 4 to 8 membered heterocycloalkyl.

A "lower substituent" or "lower substituent group," as used herein, means a group selected from all of the substituents described above for a "substituent group," wherein each substituted or unsubstituted alkyl is a substituted or unsubstituted $C_1$-$C_8$ alkyl, each substituted or unsubstituted heteroalkyl is a substituted or unsubstituted 2 to 8 membered heteroalkyl, each substituted or unsubstituted cycloalkyl is a substituted or unsubstituted $C_5$-$C_7$ cycloalkyl, and each substituted or unsubstituted heterocycloalkyl is a substituted or unsubstituted 5 to 7 membered heterocycloalkyl.

The term "pharmaceutically acceptable salts" is meant to include salts of the active compounds that are prepared with relatively nontoxic acids or bases, depending on the particular substituents found on the compounds described herein. When compounds of the present invention contain relatively acidic functionalities, base addition salts can be obtained by contacting the neutral form of such compounds with a sufficient amount of the desired base, either neat or in a suitable inert solvent. Examples of pharmaceutically acceptable base addition salts include sodium, potassium, calcium, ammonium, organic amino, or magnesium salt, or a similar salt. When compounds of the present invention contain relatively basic functionalities, acid addition salts can be obtained by contacting the neutral form of such compounds with a sufficient amount of the desired acid, either neat or in a suitable inert solvent. Examples of pharmaceutically acceptable acid addition salts include those derived from inorganic acids like hydrochloric, hydrobromic, nitric, carbonic, monohydrogencarbonic, phosphoric, monohydrogenphosphoric, dihydrogenphosphoric, sulfuric, monohydrogensulfuric, hydriodic, or phosphorous acids and the like, as well as the salts derived from relatively nontoxic organic acids like acetic, propionic, isobutyric, maleic, malonic, benzoic, succinic, suberic, fumaric, lactic, mandelic, phthalic, benzenesulfonic, p-tolylsulfonic, citric, tartaric, oxalic, methanesulfonic, and the like. Also included are salts of amino acids such as arginate, and salts of organic acids like glucuronic or galacturonic acids. Certain specific compounds of the present invention contain both basic and acidic functionalities that allow the compounds to be converted into either base or acid addition salts.

Thus, the compounds of the present invention may exist as salts, such as with pharmaceutically acceptable acids. The present invention includes such salts. Examples of such salts include hydrochlorides, hydrobromides, sulfates, methanesulfonates, nitrates, maleates, acetates, citrates, fumarates, tartrates (e.g., (+)-tartrates, (−)-tartrates, or mixtures thereof including racemic mixtures), succinates, benzoates, and salts with amino acids such as glutamic acid. These salts may be prepared by methods known to those skilled in the art.

The neutral forms of the compounds are preferably regenerated by contacting the salt with a base or acid and isolating the parent compound in the conventional manner. The parent form of the compound differs from the various salt forms in certain physical properties, such as solubility in polar solvents.

In addition to salt forms, the present invention provides compounds in a prodrug form. Prodrugs of the compounds described herein are those compounds that readily undergo chemical changes under physiological conditions to provide the compounds of the present invention. Additionally, prodrugs can be converted to the compounds of the present invention by chemical or biochemical methods in an ex vivo environment. For example, prodrugs can be slowly converted to the compounds of the present invention when placed in a transdermal patch reservoir with a suitable enzyme or chemical reagent.

Certain compounds of the present invention can exist in unsolvated forms as well as solvated forms, including hydrated forms. In general, the solvated forms are equivalent to unsolvated forms and are encompassed within the scope of the present invention. Certain compounds of the present invention may exist in multiple crystalline or amorphous forms. In general, all physical forms are equivalent for the uses contemplated by the present invention and are intended to be within the scope of the present invention.

Certain compounds of the present invention possess asymmetric carbon atoms (optical centers) or double bonds; the racemates, diastereomers, tautomers, geometric isomers, and individual isomers are encompassed within the scope of the present invention. The compounds of the present invention do not include those that are known in the art to be too unstable to synthesize and/or isolate.

The compounds of the present invention may also contain unnatural proportions of atomic isotopes at one or more of the atoms that constitute such compounds. For example, the compounds may be radiolabeled with radioactive isotopes, such as for example tritium ($^3$H), iodine-125 ($^{125}$I), carbon-13 ($^{13}$C), or carbon-14 ($^{14}$C). All isotopic variations of the compounds of the present invention, whether radioactive or not, are encompassed within the scope of the present invention.

Many organic compounds exist in optically active forms, i.e., they have the ability to rotate the plane of plane-polarized light. In describing an optically active compound, the prefixes D and L, or R and S, are used to denote the absolute configuration of the molecule about its chiral center(s). The prefixes d and l or (+) and (−) are employed to designate the sign of rotation of plane-polarized light by the compound, with (−) or l meaning that the compound is levorotatory. A compound prefixed with (+) or d is dextrorotatory. For a given chemical structure, these stereoisomers are identical except that they are mirror images of one another. A specific stereoisomer may also be referred to as an enantiomer, and a mixture of such isomers is often called an enantiomeric mixture. A 50:50 mixture of enantiomers is referred to as a racemic mixture or a racemate, which may occur where there has been no stereoselection or stereospecificity in a chemical reaction or process. The terms "racemic mixture" and "racemate" refer to an equimolar mixture of two enantiomeric species, devoid of optical activity.

As used herein, an amino acid "derivative" includes an amino acid having substitutions or modifications by covalent attachment of a parent amino acid, such as, e.g., by alkylation, glycosylation, acetylation, phosphorylation, and the like. Further included within the definition of "derivative" is, for example, one or more analogs$_1$ of an amino acid with substituted linkages, as well as other modifications known in the art.

As used herein, a "natural amino acid" refers to arginine, glutamine, phenylalanine, tyrosine, tryptophan, lysine, glycine, alanine, histidine, serine, proline, glutamic acid, aspartic acid, threonine, cysteine, methionine, leucine, asparagine, isoleucine, and valine, unless otherwise indicated by context.

As used herein, a "protecting group" refers to a moiety that when attached to a reactive group in a molecule masks, reduces or prevents that reactivity. Representative hydroxy protecting groups include acyl groups, benzyl and trityl ethers, tetrahydropyranyl ethers, trialkylsilyl ethers and allyl ethers. Representative amino protecting groups include formyl, acetyl, trifluoroacetyl, benzyl, benzyloxycarbonyl (CBZ), tert-butoxycarbonyl (Boc), trimethyl silyl (TMS), 2-trimethylsilyl-ethanesulfonyl (SES), trityl and substituted trityl groups, allyloxycarbonyl, 9-fluorenylmethyloxycarbonyl (FMOC), nitro-veratryloxycarbonyl (NVOC), and the like. Examples of a "hydroxyl protecting group" include, but are not limited to, methoxymethyl ether, 2-methoxyethoxymethyl ether, tetrahydropyranyl ether, benzyl ether, p-methoxybenzyl ether, trimethylsilyl ether, triethylsilyl ether, triisopropyl silyl ether, t-butyldimethyl silyl ether, triphenylmethyl silyl ether, acetate ester, substituted acetate esters, pivaloate, benzoate, methanesulfonate and p-toluenesulfonate.

As used herein, a "leaving group" refers to a functional group that can be substituted by another functional group. Such leaving groups are well known in the art, and examples include, but are not limited to, a halide (e.g., chloride, bromide, and iodide), methanesulfonyl (mesyl), p-toluenesulfonyl (tosyl), trifluoromethylsulfonyl (triflate), and trifluoromethylsulfonate.

The phrase "pharmaceutically acceptable salt," as used herein, refers to pharmaceutically acceptable organic or inorganic salts of a compound (e.g., a Medicant Linker compound, or an Affinity Medicant Linker conjugate). The compound typically contains at least one amino group, and accordingly acid addition salts can be formed with this amino group. Exemplary salts include, but are not limited to, sulfate, citrate, acetate, oxalate, chloride, bromide, iodide, nitrate, bisulfate, phosphate, acid phosphate, isonicotinate, lactate, salicylate, acid citrate, tartrate, oleate, tannate, pantothenate, bitartrate, ascorbate, succinate, maleate, gentisinate, fumarate, gluconate, glucuronate, saccharate, formate, benzoate, glutamate, methanesulfonate, ethanesulfonate, benzenesulfonate, p-toluenesulfonate, and palmoate (i.e., 1,1'-methylene-bis-(2-hydroxy-3-naphthoate)) salts. A pharmaceutically acceptable salt may involve the inclusion of another molecule such as an acetate ion, a succinate ion or other counter ion. The counter ion may be any organic or inorganic moiety that stabilizes the charge on the parent compound. Furthermore, a pharmaceutically acceptable salt may have more than one charged atom in its structure. Instances where multiple charged atoms are part of the pharmaceutically acceptable salt can have multiple counter ions. Hence, a pharmaceutically acceptable salt can have one or more charged atoms and/or one or more counter ion.

As used herein, a "pharmaceutically acceptable solvate" or "solvate" refer to an association of one or more solvent molecules and a compound of the invention, e.g., an Affinity Medicant Linker conjugate or a Medicant Linker compound. Examples of solvents that form pharmaceutically acceptable solvates include, but are not limited to, water, isopropanol, ethanol, methanol, DMSO, ethyl acetate, acetic acid, and ethanolamine.

The following abbreviations are used herein and have the indicated definitions: Boc is N-(t-butoxycarbonyl), cit is citrulline, clap is dolaproine, DCM is dichloromethane, DIEA is N,N-diisopropylethylamine, dil is dolaisoleuine, DMF is N,N-dimethylformamide, DMSO is dimethylsulfoxide, doe is dolaphenine, dov is N,N-dimethylvaline, DTNB is 5,5'-dithiobis(2-nitrobenzoic acid), DTPA is diethylenetriaminepentaacetic acid, DTT is dithiothreitol, Fmoc is N-(9-fluorenylmethoxycarbonyl), gly is glycine, HATU is O-(7-azabenzotriazol-1-yl)-N,N,N',N-tetramethyluronium hexafluorophosphate, HBTU is 2-[1H-benzotriazole-1-yl]-1,1,3,3-tetramethylaminium hexafluorophosphate; HOBt is 1-hydroxybenzotriazole, HPLC is high pressure liquid chromatography, ile is isoleucine, lys is lysine, MeOH is methanol, MeVal is N-methyl-valine, PAB is p-aminobenzyl, PBS is phosphate-buffered saline (pH 7.4), Ph is phenyl, phe is L-phenylalanine, PyBrop is bromo tris-pyrrolidino phosphonium hexafluorophosphate, TFA is trifluoroacetic acid, UV is ultraviolet, and val is valine.

The following LU abbreviations are used herein and have the indicated definitions: Val Cit or vc is a valine-citrulline dipeptide site in protease cleavable linker; PABC is p-aminobenzylcarbamoyl; (Me)vc is N-methyl-valine citrulline, where the linker peptide bond has been modified to prevent its cleavage by cathepsin B; and $MC(PEG)_6$-OH is maleimidocaproyl-polyethylene glycol.

As used herein, a "pegylated compound" refers to a compound conjugated with two or more polyethylene glycol moieties or two or more polypropylene glycol moieties or a combination thereof.

As used herein, a "pro-peptide" includes pro-peptide, pre-peptide, pro-protein and pre-protein amino acid sequences including those amino acid sequences cleaved by enzymes disclosed in Table III.

Malignant neoplasia is the second most common cause of death in the United States behind cardiovascular disease. Chemotherapy has exerted a predominant role in increasing life spans for patients with a variety of tumors including Burkitt's lymphoma, acute lymphocytic leukemia and Hodgkin's disease. Further, new cancer chemotherapeutic agents and methods of care combined with early detection and treatment have resulted in decreases in the overall incidence of cancer and decreases in the death rates from all cancers combined. Responsive tumors represent only a small fraction of the various types of cancer. Further, agents such as cyclophosphamide, adriamycin, 5-fluorouracil and hexamethylmelamine, which are highly active against clinical solid tumors, are limited. Thus, patients with many types of malignancies remain at significant risk for relapse and mortality. After relapse, some patients can be re-induced into remission with their initial treatment regimen. However, higher doses of the initial chemotherapeutic agent or the use of additional agents are frequently required, indicating the development of at least partial medicant resistance. Evidence indicates medicant resistance can develop simultaneously to several agents, including medicant resistance to treatments to which the patient was not exposed. The development of multiple-medicant resistant tumors may be a function of tumor mass and constitutes a major cause of treatment failure. To overcome this medicant resistance, high-dose chemotherapy with or without radiation and allogenic or autologous bone marrow transplantation can be employed. The high-dose chemotherapy may employ the original medicant(s) or be altered to include additional agents. As a result, there remain many cancer patients for whom no or minimally effective therapy exists. Accordingly, there is a need for the development of novel chemotherapeutics with greater efficacy or safety, either as monotherapy or in combination with other chemotherapeutic agents, and such agents with the potential to overcome medicant resistance in cancer cells.

Illudins are toxic natural products produced by mushrooms of the genus *Omphalotus*. Syn-Illudins are semisynthetic derivatives of Illudins. Acylfulvenes are also semisynthetic derivatives of Illudins. Syn-Illudins and Acylfulvenes have each been chemically modified at select sites to allow their use as medicants. The modifications in the Syn-Illudins do not alter any of the cyclic rings (cyclopropane, cyclopentane, cyclohexane) of the basic Illudin chemical structure. The modifications of Acylfulvenes differ from Syn-Illudins in that an additional double bond (an unsaturated bond) has been created in the 5 membered (cyclopentane) ring.

Illudins function as alkylating agents that damage DNA and thereby block transcription. The blockage can be repaired through nucleotide excision. The toxicity of the illudins has prevented any applications in human tumor therapy. Acylfulvenes have been developed which exhibit promising antitumor activity with a better safety profile, as described in U.S. Pat. Nos. 5,439,936; 5,523,490 and 6,380,403 which are each herein expressly incorporated by reference in their entireties. (6'R)-6'-hydroxy-3'-(hydroxymethyl)-2',4',6'-trimethylspiro[cyclopropane-1,5'-inden]-7'(6'H)-one (analog 002, Table V) is an illudofulvene analog of illudin S which has demonstrated clinical activity with an acceptable safety profile in hormone-refractory prostate cancer. Most relevant to clinical applications, irofulven activity is independent of common resistance mechanisms such as the multi-medicant resistance phenotype, anti-apoptotic B-cell lymphoma 2 (Bcl-2) (SEQ. ID. 056) over expression, as well as tumor protein 53 (p53) (SEQ. ID. 057) and cyclin dependent kinase inhibitor 1 (p21/WAF1) (SEQ. ID. 058) mutations.

Growth factors, including peptides and proteins are critical mediators of a wide range of cell-cell communication. They are important endocrine, paracrine and autocrine messengers. Growth factors function as neurotransmitters and neuromodulators, regulate chemotaxis, immune function, development, cell growth, and can influence tumor cells. The receptors that recognize growth factors are highly selective and define specific cell populations. As a result, growth factor receptors are a large and important class of medicant (including drug) targets. In addition to physiologic noncancerous cell populations, these receptors can also be expressed in various cancer cell populations.

A polypeptide is a long, continuous, and unbranched chain of amino acids. A glycol-peptide is a peptide that contains one or more carbohydrate moieties covalently attached to the side chains of specific amino acids. A pro-peptide, is an inactive peptide that can be turned into an active form through a post translational modification that enzymatically cleaves the pro-peptide. Examples include pro-insulin (SEQ. ID. 059) and pro-opiomelanocortin (SEQ. ID. 060). Enzymatically cleaving the pro-peptide, allows for the peptide to be available on short notice and/or in large quantities. Some pro-peptides are secreted from the cell. Many of these are synthesized with an N-terminal signal peptide that targets the pro-peptide for secretion.

Cytokines are small proteins (approximately 5 to 20 kDa) that affect the behavior of other cells, and sometimes the releasing cell itself and are thereby important in cell signaling. Many specific cytokines can be released by a variety of different kinds of cells, e.g., macrophages, B lymphocytes, T lymphocytes, mast cells, endothelial cells, fibroblasts, and various stromal cells. Cytokines act through specific receptors, and are important in the humoral and cell-based immune responses. Cytokines also regulate the maturation, growth, and responsiveness of specific cell populations. Cytokines circulate in much higher concentrations than hormones and in contrast with hormones are made by a variety of different kinds of cells. Cytokines are important in host responses to infection, immune responses, inflammation, trauma, sepsis, cancer, and reproduction. As a result, cytokine receptors are upregulated in many forms of cancers.

A steroid is an organic compound that contains four cycloalkane rings joined to each other. Examples of steroids include the dietary lipid cholesterol and the sex hormones estradiol and testosterone. The core of a steroid molecule is composed of seventeen carbon atoms bonded together that take the form of four fused rings: three six-carbon atom rings and one five-carbon atom ring. A variety of functional groups can be attached to the four-ring core. Steroids can also vary depending on the oxidation state of the rings. A steroid hormone is a steroid that acts as a hormone. Steroid hormones can be grouped into five groups (glucocorticoids, mineralocorticoids, androgens, estrogens, and progesterones) based on the receptors to which they bind. Steroid hormones, particularly androgens, are essential not only for growth and development but also in the progression of many forms of cancer. As a result, steroid hormone receptors are upregulated in many forms of cancers.

The retinoic acid receptor (RAR) is a nuclear receptor which can also act as a transcription factor. The RAR can be activated by either all-trans retinoic acid or 9-cis retinoic acid. There are three RAR isoforms (alpha (SEQ. ID. 061), beta (SEQ. ID. 062), and gamma (SEQ. ID. 063)), each encoded by separate genes, where splice variants generate still further diversity in the expressed receptor. The retinoid X receptor (RXR) is a nuclear receptor activated by 9-cis retinoic acid. There are also three RXR isoforms (alpha (SEQ. ID. 064), beta (SEQ. ID. 065), and gamma (SEQ. ID. 066)), each encoded by separate genes. RXR hetero-dimerizes with subfamily 1 nuclear receptors including RAR. In the absence of ligand, the RAR/RXR dimer binds to retinoic acid response elements complexes with a co-repressor protein. Binding of agonist ligands to RAR results in dissociation of the co-repressor and recruitment of a co-activator protein that, in turn, promotes transcription of the downstream target gene into mRNA and thereby protein or other RNA signaling mechanisms.

Lipid metabolism is altered in many forms of cancer, including upregulation of de novo lipid synthesis. Cancer cells can also use alternative enzymes and pathways to facilitate the production of fatty acids. These newly synthesized lipids may support a number of cellular processes to promote cancer cell proliferation and survival. Elaidic acid or (E)-octadec-9-enoic acid is the trans isomer of oleic acid and is found in small quantities in caprine milk, bovine milk and some meats. It increases Cholesteryl Ester Transfer Protein (CETP) (SEQ. ID. 067) activity, which in turn raises levels of very low density lipoprotein and lowers levels of high density lipoprotein (HDL) cholesterol. CETP is found in plasma, where it is involved in the transfer of cholesteryl ester from HDL to other lipoproteins. Defects in the CETP gene are a cause of hyperalphalipoproteinemia 1.

An antibody is a protein made up of four peptide chains disulfide linked together to form a "Y"-shape. Antibodies are produced by plasma cells and are used by the immune system to identify and neutralize foreign antigens such as bacteria and viruses. The antibody recognizes a unique part of the antigen using each FAB portion of the protein (i.e., the tip of the "Y" portion of the antibody), allowing a specific high affinity binding interaction to occur. The binding interaction of different antibodies can target specific antigen epitopes. An antibody fragment containing one or both FAB portions can also target specific antigen epitopes.

The ability of the Illudofulvene analogs to inhibit tumor cell growth is shown in Table VII and Table VIII. Table VII shows the ability of Illudofulvene analogs to inhibit tumor cell growth. Table VIII shows screening data with the National Cancer Institute (NCI) Developmental Therapeutics Program (DTP) NCI 60 cell line screen assay comparing conventional anti cancer drugs Epothilone A, MMA, DM1 with the previously reported illudofulvene analogs (analog 002, analog 142, analog 159, analog 176) and with the illudofulvene analogs (analog 334 (FIG. 1AE), analog 362 (FIG. 1AU), analog 371 (FIG. 1BC), analog 383 (FIG. 1BM), and analog 394 (FIG. 1AE)). In Table VIII, 'Cytotoxicity' is defined as the ability to actually kill tumor cells was detected versus only inhibiting growth of tumor cells, while 'MDR activity' is the ability to equally kill a drug resistant daughter cell as compared to the non-drug resistant parent cell. The conventional anticancer drugs, Epothilone A, MMA and DM1 were able to inhibit the growth of cells in the NCI 60 cell line screen but were not able to actually kill timor cells. That is they were not cytotoxic. Further, they were not MDR active. All of the illudofulvene analogs in Table VIII (analog 334, analog 362, analog 371, analog 383 and analog 394) were cytotoxic in the NCI 60 cell line assay. The illudofulvene analog 371 is the most potent compound at lysing the NCI 60 tumor cell line. The MV522 cell line is a lung-derived adenocarcinoma cell line, in various embodiments of the invention, the MV522 cell line represents a "target" cell line. That is an illudofulvene analog that exhibits toxicity against this solid tumor cell line shows a desirable result. The 8392B cell line represents a hematopoietic (non-solid) cell line. In various embodiments of the invention, the 8392B cell line is considered a "nontarget" cell line. The two hour toxicity data represents the concentration of a given analog for which a two hour exposure will inhibit 50% of the DNA synthesis activity in a given cell line. The 48 hour exposure data represents the concentration at which a given analog with a 48 hour exposure will inhibit the growth or viability in a given cell line as defined by the standard Trypan Blue Exclusion assay. As an example, analog 002 will inhibit the target MV522 cell line at 110 nM with only a 2 hour exposure but has no inhibitory effect on the nontarget 8392B cell line at 26,000 nM (26 µM). Analog 002 with a prolonged exposure period (e.g. 48 hours) can eventually inhibit the nontarget cell line. In contrast, Analog 201 will inhibit the target MV522 cell line with only a 2 hour exposure (IC50=360 nM) but has minimal effect on the 8392B cell nontarget line with even a 48 hour exposure (IC50=26,000 nM) indicating superior anticancer activity as a monotherapeutic agent. In contrast to these two analogs, analog 224 displayed minimal toxicity as well as no differential toxicity between the target and nontarget cell line indicating it would have minimal properties as a monotherapeutic anticancer agent.

As used herein, a "growth factor" or an "anti-angiogenic protein" includes Adrenomedullin (SEQ. ID. 068), Angiopoietin (Ang) (SEQ. ID. 069, 106, 111, and 145), Autocrine motility factor (SEQ. ID. 070), Bone morphogenetic proteins (BMPs) (SEQ. ID. 071), Brain-derived neurotrophic factor (BDNF) (SEQ. ID. 072), Endostatin (SEQ. ID. 073), Endostar (SEQ. ID. 074), Epidermal growth factor (EGF) (SEQ. ID. 075), Erythropoietin (EPO) (SEQ. ID. 076), Fibroblast growth factor (FGF) (SEQ. ID. 077), Glial cell line-derived neurotrophic factor (GDNF) (SEQ. ID. 078), Granulocyte colony-stimulating factor (G-CSF) (SEQ. ID. 079), Granulocyte macrophage colony-stimulating factor (GM-CSF) (SEQ. ID. 080), Growth differentiation factor-9 (GDF9) (SEQ. ID. 081), Hepatocyte growth factor (HGF) (SEQ. ID. 082), Hepatoma-derived growth factor (HDGF) (SEQ. ID. 083), Insulin-like growth factor (IGF) (SEQ. ID. 084), Migration-stimulating factor (SEQ. ID. 085), Myostatin (GDF-8) (SEQ. ID. 086), Nerve growth factor (NGF) (SEQ. ID. 087) and other neurotrophins (SEQ. ID. 144), Platelet-derived growth factor (PDGF A) (SEQ. ID. 088), PDGF B (SEQ. ID 168), PDGF C (SEQ. ID. 036), PDGF D (SEQ. ID. 037), Thrombopoietin (TPO) (SEQ. ID. 089), Transforming growth factor alpha(TGF-α) (SEQ. ID. 090), Transforming growth factor beta(TGF-β) (SEQ. ID.

091), Tumor necrosis factor-alpha(TNF-α) (SEQ. ID. 092), Vascular endothelial growth factor (VEGF) (SEQ. ID. 093), and placental growth factor (P1GF) (SEQ. ID. 094).

As used herein, a "protein toxin" includes ricin A chain (SEQ. ID. 095), ricin B chain (SEQ. ID. 096), diphtheria toxin (SEQ. ID. 097), *Pseudomonas aeurginosa* exotoxin A (SEQ. ID. 098), r-gelonin (SEQ. ID. 099), saporin (SEQ. ID. 100), glycosylated protein toxins, deglcosylated protein toxins and protein toxin fragments which includes deglycosylated ricin A, deglycosylated ricin B, *Pseudomonas aeurginosa* exotoxin A PE40 fragment (SEQ. ID. 101) and *Pseudomonas aeurginosa* exotoxin A PE38 fragment (SEQ. ID. 102).

As used herein, a "steroid" includes cholesterol (5-cholesten-3beta-ol), pregnenolone (3beta-hydroxy-5-pregnen-20-one), 17-hydroxyprenenolone (3-beta,17-dihydroxy-5-pregnen one), progesterone (4-pregnene-3,20-dione), 17-hydroxyprogesterone (17-hydroxy-4-pregnene-3,20-dione), androstenedione (4-androstene-3,17-dione), 4-hydroxyandrostenedione (4-hydroxy-4-androstene-3,17-dione), 11-beta-hydroxyandostenedione (11beta-4-androstene-3,17-dione), androstanediol (3-beta,17-beta-Androstanediol), androsterone (3-alpha-hydroxy-5alpha-androstan-17-one), epiandrosterone (3-beta-hydroxy-5alpha-androstan-17-one), adrenosterone (4-androstene-3,11,17-trione), dehydroepiandrosterone (3beta-hydroxy-5-androsten-17-one), dehydroepiandrosterone sulfate (3-beta-sulfooxy-5-androsten-17-one), testosterone (17beta-hydroxy-4-androsten-3-one), epitestosterone (17-alpha-hydroxy-4-androsten-3-one), 5-alpha-dihydrotesterone (17-beta-hydroxy-5alpha-androstan-3-one), 5-beta-dihydrotestosterone (17-beta-hydroxy-5beta-androstan-3-one), 11-beta-hydroxytesosterone (11-beta,17beta-dihydroxy-4-androsten-3-one), 11-ketotesosterone (17-beta-hydroxy-4-androsten-3,17-dione), estrogen (including: estrone (3-hydroxy-1,3,5(10)-estratrien-17-one), estradiol (1,3,5(10)-estratriene-3,17beta-diol), and estriol (1,3,5(10)-estratriene-3,16alpha,17beta-triol)), corticosterone (11-beta,21-dihydroxy-4-pregnene-3,20-dione), deoxycorticosterone (21-hydroxy-4-pregnene-3,20-dione), cortisol (11-beta,17,21-trihydroxy-4-pregnene-3,20-dione), 11-deoxycortisol (17,21-dihydroxy-4-pregnene-3,20-dione), cortisone (17,21-dihydroxy-4-pregnene-3,11,20-trione), 18-hydroxycorticosterone (11-beta,18,21-trihydroxy-4-pregnene-3,20-dione), 1-alpha-hydroxycorticosterone (1-alpha,11-beta,21-trihydroxy-4-pregnene-3,20-dione), and aldosterone (18,11-hemiacetal of 11beta,21-dihydroxy-3,20-dioxo-4-pregnen-18-al).

As used herein, a "Specific Binding Peptide" includes an "anti-angiogenic peptide" (SEQ. ID. 146) and an "integrin binding peptide" (SEQ. ID. 147). A "Specific Binding Peptide" includes integrin binding peptide RGD4C=CDCRGDFC (SEQ. D. 147), integrin binding peptide RGD10 (SEQ. ID. 148), c(RGDyK) (SEQ. D. 149), integrin binding peptide c(RGDfK) (SEQ. D. 150), integrin binding peptide [c(RGDyK)]2 (SEQ. D. 151), integrin binding peptide CAGKNFFWKTFTSC (SEQ. D. 152), cilengitide (cyclic RGD pentapeptide) (SEQ. D. 153), ATN-161 (peptide antagonist of integrin alpha5beta1) (SEQ. ID. 154), ATN-454 (Ac—PHSCN—NH$_2$) (peptide antagonist of integrin alpha5beta1) (SEQ. ID. 155), tumstatin T7 peptide TMPFLFCNVNDVCNFASRNDYSYWL (SEQ. ID. 156), tumstatin sequence 1 YSNS (SEQ. ID. 157), tumstatin sequence 2 YSNSG (SEQ. ID. 158), endostatin motif FLSSRLQDLYSIVRRADRAA (SEQ. ID. 159), endostatin motif IVRRADRAAVP (SEQ. ID. 160), laminin peptide A13 (RQVFQVAYIIIKA) (SEQ. ID. 161), laminin peptide C16 (KAFDITYVRLKF) (SEQ. ID. 162), laminin peptide C16S (DFKLFAVTIKYR) (SEQ. ID. 163), and VEGFR1 peptide (CPQPRPLC) (SEQ. ID. 164).

As used herein, a traditional linker includes linkers that can be formed from those reagents disclosed in Tables IA-ID, IIA-IIID, IIIA-IIIC, IVA-IVC, VA-VB, and VIA-VID of U.S. Pat. No. 9,381,178.

As used herein, a "FSB linker" includes those linkers selected from the group consisting of 4-fluorosulfonyl benzoyl, 3-fluorosulfonyl benzoyl and 2-fluorosulfonyl benzoyl as depicted in FIG. 15 of U.S. Pat. No. 9,381,178.

As used herein, a "Mall" linker includes a malonic linker and a maleimide linker covalently attached to an illudofulvene analog.

As used herein, a "protease" includes those enzymes disclosed in Table III.

As used herein, a "cytokine" includes chemokines, interferons, interleukins, lymphokines, tumor necrosis factor, neutrophil activating protein-2, monocyte chemotactic protein-1 and the like.

Despite recent advances in therapy, many patients with cancer invariably relapse and require additional treatments. Most of these patient's cancers become refractory to standard chemotherapy and/or radiation treatment regimens. The prognosis for these patients is poor and long term survival rates for metastatic solid tumor cancers remain very low. Thus, there is a need for the development of novel agents and treatment regimens that specifically target these recurring tumor cells and also produce less systemic toxicity. Target therapies, such as monoclonal antibodies, now provide a promising alternative to the conventional cytotoxic chemotherapy approach.

Monoclonal antibody based therapy has recently achieved considerable success in oncology and there are currently nine monoclonal antibodies (without a medicant attached) approved by the FDA as cancer therapeutics. As an example, HERCEPTIN® and RITUXAN® (both produced by Genentech, South San Francisco, California), are used to successfully treat breast cancer and non-Hodgkin's lymphoma, respectively. HERCEPTIN® is a recombinant DNA-derived humanized monoclonal antibody selectively binding to the extracellular domain of the Human Epidermal growth factor Receptor 2 (HER2) proto-oncogene whereas RITUXAN® is a genetically engineered chimeric murine/human monoclonal antibody directed against the CD20 antigen overexpressed on the surface of normal and malignant B lymphocytes.

Recent clinical evidence indicates that while the monoclonal antibody based therapies are effective at inducing remission, they do not always produce a complete cure, and relapses eventually occur in most patients. There is now a tremendous interest in the use of antibody medicant conjugates as a class of therapeutics that utilize the antigen-selectivity of monoclonal antibodies to deliver potent cytotoxic medicants to specific tumor cells. Antibody medicant conjugates are produced by attaching a cytotoxic agent to an antibody that binds specifically to a tumor-associated antigen.

In theory, antibody medicant conjugates can confer an increased therapeutic index to highly potent medicants by improving therapeutic efficacy and reducing systemic toxicity (by minimizing damage to normal tissues), although this goal has been elusive in achieving. The basis for the efficacy of antibody medicant conjugates is that they target tumor cells that preferentially express an antigen that is recognized by the associated antibody. In contrast, non-tumor cells either fail to express this antigen, or express the antigen at a very low level. In theory, only the tumor cells expressing the associated antibody are recognized and destroyed by the AMC, and other cells are left untouched and undamaged.

While different medicant classes have been tried for delivery via antibodies, only a few have proved efficacious for use as antibody medicant conjugates. The two main medicant classes used to date to produce antibody medicant conjugates are the auristatins (MMAE/N-methylvaline-valine-dolaisoleuine-dolaproine-norephedrine or MMAF/N-methylvaline-valine-dolaisoleuine-dolaproine-phenylalanine) and the maytansines (DM1 or DM4). Currently only two antibody medicant conjugates are approved by the U.S.F.D.A. and marketed; brentuximab vedotin (auristatin based) and ado-trastuzumab emtansine (maytansine based).

Illudofulvenes have several unique properties over agents traditional used to make medicants and/or antibody drug conjugates (ADCs). Firstly, these are the only agents known to function by inhibition of the DNA transcription-coupled repair pathway, see e.g., U.S. Pat. No. 10,285,955 entitled AFFINITY MEDICANT CONJUGATES, issued May 14, 2019, which is herein incorporated by reference inits entirety and for all purposes. No other toxin, drug or medicant inhibits this pathway. The result is that illudofulvenes are true cytotoxic agents whereas other agents traditionally used to produce ADCs (pyrrolobenzodiazepines, maytansines, fumagillols, dolstatins, auristatins, enadiynes, halichondrins, and tubulysins) are only cytostatic. In the NCI-DTP 60 cell line panel these other agents were capable of inhibiting tumor cell growth ($IC_{50}$ value), had some ability to block tumor cell growth (TGI value) but none were capable of actually causing tumor cell death or cytotoxicity (Table VI). The illudin derivatives, however, are capable of killing tumor cells at nanomolar concentrations (Table VI). This means that while ADCs developed using other toxins can stall tumor cell growth, they cannot actually kill the tumor cell. Once the effect of the drug has worn off the tumor cells will again grow and kill the patient. In contrast, the illudofulvenes actually kill the tumor cell with as little as a 2 hour exposure. Secondly, whereas tumor cells will undergo apoptosis or cell death with hours once the DNA transcription-coupled repair pathway is blocked, normal diploid non-tumor cells can survive for hours. This translates into a wide therapeutic window for ADCs developed with illudofulvenes. The two ADC agents currently FDA approved for administration deliver a dose of the associated toxin that is 300% higher than a lethal dose which is why these agents have severe systemic toxicity. In contrast, the comparable ADC developed with illudofulvenes will deliver a dose of the associated toxin that is 40% of a known non-toxic dose (estimated at 28% of a toxic dose and only 12% of a lethal dose). Thus, ADCs developed with illudofulvenes will have minimal systemic toxicity as compared to current agents. Thirdly, these agents are stable down to a pH of 2.0. An ADC is engulfed by a tumor cell, transported to the endosomes (pH<6.0) and then into the lysozomes (pH<4). Many agents used for ADCs will degrade in these low pH environment, whereas illudofulvenes are stable. 4). Cancer cells can become resistant to various toxins and drugs through the development of what is termed multi-drug resistance. This process is known to occur through several different mechanisms. Whereas other toxins and drugs are substrates for the most common MDR mechanisms (MDR1/gp170 and MRP/gp180), and cancer cells can become resistant to these agents, the illudofulvenes remain active against all MDR phenotypes regardless of the mechanism (see Table IV). Hence, if tumor cells have already developed multi-drug resistance prior to ADC with a conventional toxin, or during the administration of a course of the ADC, the ADC will have no efficacy. In contrast, ADCs developed with illudofulvenes will continue to kill cancer cells. Illudofulvenes as stand alone treatments or in ADCs can be coupled with a screen to select a patient population that will respond to the illudofulvenes, see e.g., U.S. patent application Ser. No. 16/708,005 entitled METHODS, COMPOSITIONS AND DEVICES FOR TREATING CANCER WITH ILLUDOFULVENES, filed Dec. 9, 2020, which is herein incorporated by reference inits entirety and for all purposes The present invention is based on the discovery that illudofulvene are active as medicant delivery agents in vitro and in vivo and can be conjugated directly to a linker, via a variety of peptide or non-peptide bonds, and are active as medicant delivery agents in vitro and in vivo. Similar to other medicant classes used to produce antibody medicant conjugates, the illudofulvenes can be conjugated to a linker that allows subsequent coupling to a monoclonal antibody. Unlike previous medicant classes such as the auristatins (MMAE, MMAF, dolstatin-10), the maytansines (DM1 or DM4), the irinotecans and their metabolites (SN38), the calicheamicins (17-DMAG), the pyrrolobenzodiazepines (SJG-136), the duocarmycins (CC-1065), many of the illudofulvenes compounds do not require a linker and can be directly attached to a monoclonal antibody or fragment thereof by a variety of simple chemical reactions. In this sense, the lack of requirement for a linker or a spacer, the illudofulvenes compounds are unique. They will directly form covalent bonds with reactive groups on an AM such as a monoclonal antibody. In addition, because of their very small size and extreme cytotoxicity the illudofulvenes can be coupled directly to very small molecular weight entities (or affinity moieties) that allow tumor specific cytotoxicity without the concomitant requirement of use of a monoclonal antibody. Examples include the ability to link illudofulvenes directly to steroids which allow the medicant-affinity complex to kill cells overexpressing a specific steroid receptor (such as estrogen- or progesterone-positive breast cancer cells) or even to be chemically coupled to various lipids. The small size and extreme cytotoxicity illudofulvenes allows direct coupling to peptides which can preferentially bind to tumor cells (integrin binding peptides) or display anti-angiogenic properties to hinder tumor invasion. The illudofulvenes can also be coupled to specific peptides which actually renders the medicant-affinity complex non-toxic until the peptide is cleaved by a protease secreted by tumor cells. An example includes PSA (prostate specific antigen) secreted by prostate adenocarcinoma cells. Again, unlike previous medicant classes such as the auristatins (MMAE, MMAF, dolstatin-10), the maytansines (DM1 or DM4), the irinotecans and their metabolites (SN38), the calicheamicins (17-DMAG), the pyrrolobenzodiazepines (SJG-136), the duocarmycins (CC-1065), the illudofulvenes compounds do not require a linker and can be directly attached to a steroid or a peptide that will subsequently function as an AM and direct the associated complex to specific tumor cells. In an embodiment of the invention, an illudofulvenes is attached to either a Specific Binding Peptide or a peptide which when cleaved by a specific protease (see Table III) such as PSA generates an entity which is cytotoxic (see Table II).

Trastuzumab emtansine (Genentech for Breast cancer) uses maytanasine derive DM-1, a stable non-cleavable linker. Brentuximab vedotin (Seattle Genetics/Takeda for Hodgkin's Lymphoma) uses auristatin MMAE to anti-CD30, an enzyme sensitive cleavable linker.

The malonic linker, maleimide linker and SMCC [succinimidyl 4-(N-maleimidomethyl)-cyclohexane-1-carboxylate] linker can form active intermediates that react with sulfhydryl groups on an antibody. SMCC has been used to bind maytansine derivative DM1 to the monoclonal antibody Herceptin. The AMC was internalized where the Herceptin was degraded by proteases and DM1 was released into the cytosol. Further, Sulfo-SMCC [sulfosuccinimidyloxycarbonyl-α-methyl-α-(2-pyridyldithio)toluene] forms an active intermediate that reacts with sulfhydryl groups on an antibody. The resulting Sulfo-SMCC AMC is more water soluble than the SMCC AMC.

Compounds and Conjugates. The present invention is drawn to a series of compounds and conjugates containing a Medicant moiety (M) linked via its C terminus to a LU (LU). The LU can operate to provide a suitable release of M.

In one group of embodiments, the invention provides Medicant Linker compounds having Formula I: LU-M (I) or a pharmaceutically acceptable salt or solvate thereof where the medicant loading is represented by p, the average number of medicant molecules per affinity (e.g., an antibody) (e.g. of Formula II, IIa, IIa'). Medicant loading may range from 1 to 20 Medicant units (M) per Affinity unit (e.g., Ab or in Ab). Compositions of Formula IIa and Formula IIa' include mixtures of antibodies conjugated with a range of medicants, from 1 to 20.

In some embodiments, p is from about 1 to about 8 Medicant units per Affinity unit. In some embodiments, p is 1. In some embodiments, p is from about 2 to about 8 Medicant units per Affinity unit. In some embodiments, p is from about 2 to about 6, 2 to about 5, or 2 to about 4 Medicant units per LU. In some embodiments, p is about 2, about 4, about 6 or about 8 Medicant units per Affinity unit.

The average number of Medicants units per Affinity unit in a preparation from a conjugation reaction may be characterized by conventional means such as mass spectroscopy, ELISA assay, and HPLC. The quantitative distribution of Affinity Medicant Linker conjugates in terms of p may also be determined. In some instances, separation, purification, and characterization of homogeneous Affinity Medicant Linker conjugates, where p is a certain value from Affinity Medicant Linker conjugates with other medicant loadings may be achieved by means such as reverse phase HPLC or electrophoresis.

Returning to Formula IIa', the conjugates comprise an antibody covalently attached to one or more Medicant units (moieties) via a LU: A, a, W and w are as described above. The antibody medicant conjugate include pharmaceutically acceptable salts or solvates thereof.

The medicant loading is represented by p, the average number of Medicant units per antibody in a molecule of Formula II. Medicant loading may range from 1 to 20 medicants (M) per Ab or mAb. Compositions of the AMC of Formula IIa' include mixtures of antibodies conjugated with a range of medicants, from 1 to 20. In some embodiments, p is from about 1 to about 8 Medicant units per antibody. In some embodiments, p is 1. In some embodiments, p is from about 2 to about 8 Medicant units per antibody. In some embodiments, p is from about 2 to about 6, 2 to about 5, or 2 to about 4 Medicant units per antibody. In some embodiments, p is about 2, about 4, about 6 or about 8 Medicant units per antibody.

The average number of medicants per antibody in preparations of AMCs from conjugation reactions may be characterized by conventional means such as UV/visible spectroscopy, mass spectrometry, ELISA assay, and HPLC. The quantitative distribution of AMCs in terms of p may also be determined. In some instances, separation, purification, and characterization of homogeneous AMCs where p is a certain value from AMC with other medicant loadings may be achieved by means such as reverse phase HPLC or electrophoresis.

For some antibody medicant conjugates, p may be limited by the number of attachment sites on the antibody. For example, where the attachment is a cysteine thiol, an antibody may have only one or several cysteine thiol groups, or may have only one or several sufficiently reactive thiol groups through which a LU may be attached. In some embodiments, the cysteine thiol is a thiol group of a cysteine residue that forms an interchain disulfide bond. In some embodiments, the cysteine thiol is a thiol group of a cysteine residue that does not form an interchain disulfide bond.

Typically, less than the theoretical maximums of medicant moieties are conjugated to an antibody during a conjugation reaction. An antibody may contain, for example, many lysine residues that do not react with the Medicant Linker compound intermediate or LU reagent. Only the most reactive lysine groups may react with an amine-reactive LU reagent. Generally, antibodies do not contain many, if any, free and reactive cysteine thiol groups which may be linked to a Medicant moiety via a LU. Most cysteine thiol residues in the antibodies exist as disulfide bridges and must be reduced with a reducing agent such as dithiothreitol (DTT). The antibody may be subjected to denaturing conditions to reveal reactive nucleophilic groups such as lysine or cysteine. The loading (medicant/antibody ratio) of an AMC may be controlled in several different manners, including: (i) limiting the molar excess of Medicant Linker compound intermediate or LU reagent relative to antibody, (ii) limiting the conjugation reaction time or temperature, and (iii) partial or limiting reductive conditions for cysteine thiol modification.

Where more than one nucleophilic group reacts with a Medicant Linker compound intermediate, or LU reagent followed by Medicant moiety reagent, then the resulting product is a mixture of Affinity Medicant Linker Conjugates (e.g., AMCs) with a distribution of one or more Medicant moieties per Affinity unit (e.g., an antibody). The average number of medicants per Affinity unit (e.g., antibody) may be calculated from the mixture by, for example, dual enzyme linked immune serum assay (ELISA) antibody assay, specific for antibody and specific for the medicant. Individual Affinity Medicant Linker Conjugate molecules may be identified in the mixture by mass spectroscopy, and separated by high performance liquid chromatography (HPLC), e.g., hydrophobic interaction chromatography. Thus, a homogeneous conjugate with a single loading value may be isolated from the conjugation mixture by electrophoresis or chromatography.

A "Linker Unit" (LU) is a bifunctional compound which can be used to link a Medicant unit and/or an Affinity unit to form an Affinity Medicant Linker conjugate. Such conjugates are useful, for example, in the formation of immunoconjugates directed against tumor associated antigens. Such conjugates allow the selective delivery of cytotoxic drugs to tumor cells. A LU includes a traditional linker, a 4-fluorosulfonyl benzoyl (4-FSB) linker, a 3-fluorosulfonyl benzoyl (3-FSB) linker a 2-fluorosulfonyl benzoyl (2-FSB) linker, a maleimide (Mall) linker, an azlactone linker and a bridging amino acid.

A traditional linker is as defined in U.S. Pat. No. 9,381,178. A Stretcher Unit includes two or more Linker Units.

A bridging amino acid means —NH—C(R')H—CO— or —N(R")—C(R')H—CO— including glycine, L-alanine, L-serine, L-threonine, L-cysteine, L-valine, L-leucine, L-isoleucine, L-methionine, L-proline, L-phenylalanine, L-tyrosine, L-tryptophan, L-aspartic acid, L-glutamic acid, L-asparagine, L-glutamine, L-histidine, L-lysine, L-arginine, L-homocysteine, L-selenocysteine, L-pyrrolysine, L-carnitine, L-hypusine, 2-aminoisobutyric acid, dehydroalanine, L-gamma-aminobutyric acid, L-ornithine, L-citrulline, L-α-Amino-n-butyric acid, L-Norvaline, L-Norleucine, L-Pipecolic acid, L-Alloisoleucine, L-α,β-diaminopropionic acid, L-α,γ-diaminobutyric acid, L-Allothreonine, L-α-Amino-n-heptanoic acid, L-Homoserine, β-Amino-n-butyric acid, β-Aminoisobutyric acid, γ-Aminobutyric acid, L-isovaline, L-Sarcosine, N-ethyl glycine, N-propyl glycine, N-isopropyl glycine, L-N-methyl alanine, L-N-ethyl alanine, N-methyl β-alanine, N-ethyl β-alanine, Isoserine, L-α-hydroxy-γ-aminobutyric acid, L-diaminopimelic acid, cystathione, L-aminoisobutyric acid, dehydroalanine, delta-aminolevulinic acid, 4-aminobenzoic acid, L-Hydroxyproline, Formylmethioinine, L-lanthionine, djenkolic acid, L-Pyroglutamic acid, Hypusine, L-carboxyglutamic acid, penicillamine, L-thialysine, quisqualic acid, L-canavine, L-azetidine-2-carboxylic acid, D-alanine, D-serine, D-threonine, D-cysteine, D-valine, D-leucine, D-isoleucine, D-methionine, D-proline, D-phenylalanine, D-tyrosine, D-tryptophan, D-aspartic acid, D-glutamic acid, D-asparagine, D-glutamine, D-histidine, D-lysine, D-arginine, D-homocysteine, D-selenocysteine, D-pyrrolysine, D-carnitine, D-hypusine, D-gamma-aminobutyric acid, D-ornithine, D-citrulline, D-α-Amino-n-butyric acid, D-Norvaline, D-Norleucine, D-Pipecolic acid, D-Alloisoleucine, D-α,β-diaminopropionic acid, D-α,γ-diaminobutyric acid, D-Allothreonine, D-α-Amino-n-heptanoic acid, D-Homoserine, D-isovaline, D-Sarcosine, D-N-methyl alanine, D-N-ethyl alanine, D-α-hydroxy-γ-aminobutyric acid, D-diaminopimelic acid, D-aminoisobutyric acid, D-Hydroxyproline, D-lanthionine, D-Pyroglutamic acid, D-carboxyglutamic acid, D-thialysine, quisqualic acid, D-canavine, D-azetidine-2-carboxylic acid. A 'modified bridging amino acid' means a bridging amino acid with R' including a hydroxyl group that has been esterified, a bridging amino acid with R' including a sulphur atom where the sulphur atom has been reacted with an alkyl or other organic group and/or a bridging amino acid with R' including a primary amino group that has been converted into a secondary or tertiary amino group.

In one embodiment, the LU of the Medicant Linker compound and Affinity Medicant Linker conjugate has the formula: —$W_w$-$A_a$ wherein -A- is a Stretcher Unit; a is 1 or 2; each —W— is independently an Amino Acid unit; w is independently an integer ranging from 1 to 20. In the Affinity Medicant Linker conjugate, the LU serves to attach the Medicant moiety and the AM.

The Affinity Moiety (AM) includes within its scope an Affinity Unit (AU) that specifically binds or reactively associates or complexes with a receptor, antigen or other receptive moiety associated with a given target-cell population. An AU is a molecule that binds to, complexes with, or reacts with a receptor, antigen or other receptive moiety of a cell population sought to be therapeutically or otherwise biologically modified. In one aspect, the AM acts to deliver the Medicant unit to the particular target cell population with which the AM interacts. Such AM's include, but are not limited to, proteins, polypeptides and peptides and include, antibodies, binding proteins, smaller molecular weight proteins, polypeptides, peptides, lectins, glycoproteins, non-peptides, vitamins, nutrient-transport molecules (such as, but not limited to, transferrin), or any other cell binding molecule or substance.

In an embodiment of the invention, an AM can form a bond to a Stretcher Unit. In an alternative embodiment of the invention, an AM can form a bond to the Stretcher Unit of the LU via a heteroatom of the AM. Heteroatoms that may be present on an AM include sulfur (in one embodiment, from a sulfhydryl group of an AM), oxygen (in one embodiment, from a carbonyl, carboxyl or hydroxyl group of an AM) and nitrogen (in one embodiment, from a primary or secondary amino group of an AM). These hetero atoms can be present on the AM in the AM's natural state, for example a naturally-occurring antibody, or can be introduced into the AM via chemical modification.

In one embodiment, an AM unit has a sulfhydryl group and the AM bonds to the LU via the sulfhydryl group's sulfur atom. In another embodiment, the AM has lysine residues that can react with activated esters (such esters include, but are not limited to, N-hydroxysuccinimide, pentafluorophenyl, and p-nitrophenyl esters) of the Stretcher Unit of the AM and thus form an amide bond consisting of the primary nitrogen atom of the AM and the carboxyl group of the AM. In yet another aspect, the AM has one or more lysine residues that can be chemically modified to introduce one or more sulfhydryl groups. The AM bonds to the LU via the sulfhydryl group's sulfur atom. The reagents that can be used to modify lysines include, but are not limited to, N-succinimidyl S-acetylthioacetate (SATA) and 2-Iminothiolane hydrochloride (Traut's Reagent).

In another embodiment, the AM can have one or more carbohydrate groups that can be chemically modified to have one or more sulfhydryl groups. The AM bonds to the LU (or a Stretcher Unit) via the sulfhydryl group's sulfur atom. In yet another embodiment, the AM can have one or more carbohydrate groups that can be oxidized to provide an aldehyde (—CHO) group. The corresponding aldehyde can form a bond with a reactive site on a Stretcher Unit. Reactive sites on a Stretcher Unit that can react with a carbonyl group on an AM include, but are not limited to, hydrazine and hydroxylamine.

Useful non-immunoreactive protein, polypeptide, or peptide affinity moieties include, but are not limited to, transferrin, epidermal growth factors ("EGF"), bombesin, gastrin, gastrin-releasing peptide, platelet-derived growth factor, IL-2, IL-6, transforming growth factors ("TOP"), such as TGF-.alpha. and TGF-.beta., vaccinia growth factor ("VGF"), insulin and insulin-like growth factors I and II, somatostatin, lectins and apoprotein from low density lipoprotein.

Useful polyclonal antibodies are heterogeneous populations of antibody molecules derived from the sera of immunized animals. Useful monoclonal antibodies are homogeneous populations of antibodies to a particular antigenic determinant (e.g., a cancer cell antigen, a viral antigen, a microbial antigen, a protein, a peptide, a carbohydrate, a chemical, nucleic acid, or fragments thereof). A monoclonal antibody (mAb) to an antigen-of-interest can be prepared by using any technique known in the art which provides for the production of antibody molecules by continuous cell lines in culture.

Useful monoclonal antibodies include, but are not limited to, human monoclonal antibodies, humanized monoclonal antibodies, antibody fragments, or chimeric monoclonal antibodies. Human monoclonal antibodies may be made by any of numerous techniques known in the art.

The antibody can also be a bispecific antibody. Methods for making bispecific antibodies are known in the art and are discussed infra.

The antibody can be a functionally active fragment, derivative or analog of an antibody that immunospecifically binds to target cells (e.g., cancer cell antigens, viral antigens, or microbial antigens) or other antibodies that bind to tumor cells or matrix. In this regard, "functionally active" means that the fragment, derivative or analog is able to elicit anti-anti-idiotype antibodies that recognize the same antigen that the antibody from which the fragment, derivative or analog is derived recognized. Specifically, in an exemplary embodiment the antigenicity of the idiotype of the immunoglobulin molecule can be enhanced by deletion of framework and CDR sequences that are C-terminal to the CDR sequence that specifically recognizes the antigen. To determine which CDR sequences bind the antigen, synthetic peptides containing the CDR sequences can be used in binding assays with the antigen by any binding assay method known in the art (e.g., the BIA core assay).

Other useful antibodies include fragments of antibodies such as, but not limited to, F(ab')$_2$ fragments, Fab fragments, Fvs, single chain antibodies, diabodies, tiabodies, tetrabodies, scFv, scFv-FV, or any other molecule with the same specificity as the antibody.

Additionally, recombinant antibodies, such as chimeric and humanized monoclonal antibodies, comprising both human and non-human portions, which can be made using standard recombinant DNA techniques, are useful antibodies. A chimeric antibody is a molecule in which different portions are derived from different animal species, such as for example, those having a variable region derived from a murine monoclonal and human immunoglobulin constant regions. Humanized antibodies are antibody molecules from non-human species having one or more complementarity determining regions (CDRs) from the non-human species and a framework region from a human immunoglobulin molecule. Such chimeric and humanized monoclonal antibodies can be produced by recombinant DNA techniques known in the art.

Completely human antibodies are particularly desirable and can be produced using transgenic mice that are incapable of expressing endogenous immunoglobulin heavy and light chains genes, but which can express human heavy and light chain genes. The transgenic mice are immunized in the normal fashion with a selected antigen, e.g., all or a portion of a polypeptide of the invention. Monoclonal antibodies directed against the antigen can be obtained using conventional hybridoma technology. The human immunoglobulin transgenes harbored by the transgenic mice rearrange during B cell differentiation, and subsequently undergo class switching and somatic mutation. Thus, using such a technique, it is possible to produce therapeutically useful IgG, IgA, IgM and IgE antibodies. Other human antibodies can be obtained commercially from, for example, Abgenix, Inc. (now Amgen, Freemont, Calif.) and Medarex (Princeton, N.J.).

Completely human antibodies that recognize a selected epitope can be generated using a technique referred to as "guided selection." In this approach a selected non-human monoclonal antibody, e.g., a mouse antibody, is used to guide the selection of a completely human antibody recognizing the same epitope. Human antibodies can also be produced using various techniques known in the art, including phage display libraries.

In other embodiments, the antibody is a fusion protein of an antibody, or a functionally active fragment thereof, for example in which the antibody is fused via a covalent bond (e.g., a peptide bond), at either the N-terminus or the C-terminus to an amino acid sequence of another protein (or portion thereof, preferably at least 10, 20 or 50 amino acid portion of the protein) that is not from an antibody. Preferably, the antibody or fragment thereof is covalently linked to the other protein at the N-terminus of the constant domain.

Antibodies include analogs and derivatives that are either modified, i.e., by the covalent attachment of any type of molecule as long as such covalent attachment permits the antibody to retain its antigen binding immunospecificity. For example, but not by way of limitation, derivatives and analogs of the antibodies include those that have been further modified, e.g., by glycosylation, acetylation, pegylation, phosphorylation, amidation, derivatization by known protecting/blocking groups, proteolytic cleavage, linkage to a cellular antibody unit or other protein, etc. Any of numerous chemical modifications can be carried out by known techniques including, but not limited to, specific chemical cleavage, acetylation, formylation, metabolic synthesis in the presence of tunicamycin, etc. Additionally, the analog or derivative can contain one or more unnatural amino acids.

Antibodies can have modifications (e.g., substitutions, deletions or additions) in amino acid residues that interact with Fc receptors. In particular, antibodies can have modifications in amino acid residues identified as involved in the interaction between the anti-Fc domain and the FcRn receptor.

Antibodies immunospecific for a cancer cell antigen can be obtained commercially or produced by any method known to one of skill in the art such as, e.g., chemical synthesis or recombinant expression techniques. The nucleotide sequence encoding antibodies immunospecific for a cancer cell antigen can be obtained, e.g., from the GenBank database or a database like it, literature publications, or by routine cloning and sequencing.

In a specific embodiment, known antibodies for the treatment of cancer can be used. Antibodies immunospecific for a cancer cell antigen can be obtained commercially or produced by any method known to one of skill in the art such as, e.g., recombinant expression techniques. The nucleotide sequence encoding antibodies immunospecific for a cancer cell antigen can be obtained, e.g., from the GenBank database or a database like it, the literature publications, or by routine cloning and sequencing. Examples of antibodies available for the treatment of cancer include, but are not limited to, RITUXAN® (rituximab; Genentech) which is a chimeric anti-CD20 monoclonal antibody for the treatment of patients with non-Hodgkin's lymphoma; OVAREX which is a murine antibody for the treatment of ovarian cancer; PANOREX (Glaxo Wellcome, N.C.) which is a murine IgG$_{2a}$ antibody for the treatment of colorectal cancer; Cetuximab ERBITUX (Imclone Systems Inc., NY) which is an anti-EGFR IgG chimeric antibody for the treatment of epidermal growth factor positive cancers, such as head and neck cancer; Vitaxin (MedImmune, Inc., MD) which is a humanized antibody for the treatment of sarcoma; CAMPATH I/H (Leukosite, MA) which is a humanized IgG$_1$ antibody for the treatment of chronic lymphocytic leukemia (CLL); SMART MI95 (Protein Design Labs, Inc., CA) and SGN-33 (Seattle Genetics, Inc., WA) which is a humanized anti-CD33 IgG antibody for the treatment of acute myeloid leukemia (AML); LYMPHOCIDE (Immunomedics, Inc., NJ) which is a humanized anti-CD22 IgG antibody for the treatment of non-Hodgkin's lymphoma; SMART ID10 (Protein Design Labs, Inc., CA) which is a humanized anti-HLA-DR antibody for the treatment of non-Hodgkin's lymphoma; ONCOLYM (Techniclone, Inc., CA) which is a radiolabeled murine anti-HLA-Dr10 antibody for the treatment of non-Hodgkin's lymphoma; ALLOMUNE (BioTransplant, CA) which is a humanized anti-CD2 mAb for the treatment of Hodgkin's Disease or non-Hodgkin's lymphoma; AVASTIN (Genentech, Inc., CA) which is an anti-VEGF humanized antibody for the treatment of lung and colorectal cancers; Epratuzamab (Immunomedics, Inc., NJ and Amgen, Calif.) which is an anti-CD22 antibody for the treatment of non-Hodgkin's lymphoma; and CEACIDE (Immunomedics, N.J.) which is a humanized anti-CEA antibody for the treatment of colorectal cancer.

Other antibodies useful in the treatment of cancer include, but are not limited to, antibodies against the following antigens (where exemplary cancers that can be treated with the antibody are in parentheses): Alk (adrenocarcinomas) (SEQ. ID. 103), CA125 (ovarian) (SEQ. ID. 104), CA15-3 (carcinomas) (SEQ. ID. 105), CA19-9 (carcinomas), L6 (carcinomas) (SEQ. ID. 107), Lewis Y (carcinomas) (SEQ. ID. 108), Lewis X (carcinomas) (SEQ. ID. 109), alpha fetoprotein (carcinomas) (SEQ. ID. 110), CA 242 (colorectal), placental alkaline phosphatase (carcinomas) (SEQ. ID. 112), prostate specific antigen (prostate) (SEQ. ID. 113), prostate specific membrane antigen (prostate) (SEQ. ID. 114), prostatic acid phosphatase (prostate) (SEQ. ID. 115), epidermal growth factor (carcinomas), MAGE-1 (carcinomas) (SEQ. ID. 117), MAGE-2 (carcinomas) (SEQ. ID. 118), MAGE-3 (carcinomas) (SEQ. ID. 119), MAGE-4 (carcinomas) (SEQ. ID. 120), anti-transferrin receptor (carcinomas) (SEQ. ID. 121), p97 (melanoma) (SEQ. ID. 122), MUC1 (breast cancer) (SEQ. ID. 123), CEA (colorectal) (SEQ. ID. 124), gp100 (melanoma) (SEQ. ID. 125), MART-1 (melanoma) (SEQ. ID. 126), IL-2 receptor (T-cell leukemia and lymphomas), CD2 (buccal mucosa) (SEQ. ID. 128), CD20 (non-Hodgkin's lymphoma) (SEQ. ID. 129), CD52 (leukemia) (SEQ. ID. 130), CD33 (leukemia), CD22 (lymphoma), beta human chorionic gonadotropin (carcinoma) (SEQ. ID. 133), CD38 (multiple myeloma) (SEQ. ID. 134), CD40 (lymphoma) (SEQ. ID. 135), CD80 (colorectal), CD86 (colorectal), mucin (carcinomas), P21 (carcinomas), MPG (melanoma) (SEQ. ID. 140), Neu oncogene product (carcinomas) and STEAP-1 (prostate).

Compositions and Methods of Administration. In other embodiments, described is a pharmaceutical composition including an effective amount of an Affinity Medicant Linker conjugate and/or a Medicant Linker compound and a pharmaceutically acceptable carrier or vehicle. The compositions are suitable for veterinary or human administration.

The present pharmaceutical compositions can be in any form that allows for the composition to be administered to a patient. For example, the composition can be in the form of a solid or liquid. Typical routes of administration include, without limitation, parenteral, ocular and intra-tumor. Parenteral administration includes subcutaneous injections, intravenous, intramuscular or intrasternal injection or infusion techniques. In one aspect, the compositions are administered parenterally. In a specific embodiment, the compositions are administered intravenously.

Pharmaceutical compositions can be formulated so as to allow an Affinity Medicant Linker conjugate and/or a Medicant Linker compound to be bioavailable upon administration of the composition to a patient. Compositions can take the form of one or more dosage units, where for example, a tablet can be a single dosage unit, and a container of an Affinity Medicant Linker conjugate and/or a Medicant Linker compound in liquid form can hold a plurality of dosage units.

Materials used in preparing the pharmaceutical compositions can be non-toxic in the amounts used. It will be evident to those of ordinary skill in the art that the optimal dosage of the active ingredient(s) in the pharmaceutical composition will depend on a variety of factors. Relevant factors include, without limitation, the type of animal (e.g., human), the particular form of the Affinity Medicant Linker conjugate and/or a Medicant Linker compound, the manner of administration, and the composition employed.

The pharmaceutically acceptable carrier or vehicle can be solid or particulate, so that the compositions are, for example, in tablet or powder form. The carrier(s) can be liquid. In addition, the carrier(s) can be particulate.

The composition can be in the form of a liquid, e.g., a solution, emulsion or suspension. In a composition for administration by injection, one or more of a surfactant, preservative, wetting agent, dispersing agent, suspending agent, buffer, stabilizer and isotonic agent can also be included.

The liquid compositions, whether they are solutions, suspensions or other like form, can also include one or more of the following: sterile diluents such as water for injection, saline solution, preferably physiological saline, Ringer's solution, isotonic sodium chloride, fixed oils such as synthetic mono or digylcerides which can serve as the solvent or suspending medium, polyethylene glycols, glycerin, cyclodextrin, propylene glycol or other solvents; antibacterial agents such as benzyl alcohol or methyl paraben; antioxidants such as ascorbic acid or sodium bisulfite; chelating agents such as ethylenediaminetetraacetic acid; buffers such as acetates, citrates, phosphates or amino acids and agents for the adjustment of tonicity such as sodium chloride or dextrose. A parenteral composition can be enclosed in ampoule, a disposable syringe or a multiple-dose vial made of glass, plastic or other material. Physiological saline is an exemplary adjuvant. An injectable composition is preferably sterile.

The amount of the Affinity Medicant Linker conjugate and/or a Medicant Linker compound that is effective in the treatment of a particular disorder or condition will depend on the nature of the disorder or condition, and can be determined by standard clinical techniques. In addition, in vitro or in vivo assays can optionally be employed to help identify optimal dosage ranges. The precise dose to be employed in the compositions will also depend on the route of administration, and the seriousness of the disease or disorder, and should be decided according to the judgment of the practitioner and each patient's circumstances.

The compositions comprise an effective amount of an Affinity Medicant Linker conjugate and/or a Medicant Linker compound such that a suitable dosage will be obtained. Typically, this amount is at least about 0.01% of an Affinity Medicant Linker conjugate and/or a Medicant Linker compound by weight of the composition. In an exemplary embodiment, pharmaceutical compositions are prepared so that a parenteral dosage unit contains from about 0.01% to about 2% by weight of the Affinity Medicant Linker conjugate and/or a Medicant Linker compound.

For intravenous administration, the composition can comprise from about 0.01 to about 100 mg of an Affinity Medicant Linker conjugate and/or a Medicant Linker compound per kg of the patient's body weight. In one aspect, the composition can include from about 1 to about 100 mg of an Affinity Medicant Linker conjugate and/or a Medicant Linker compound per kg of the patient's body weight. In another aspect, the amount administered will be in the range from about 0.1 to about 25 mg/kg of body weight of the Affinity Medicant Linker conjugate and/or a Medicant Linker compound.

Prior art ADC's such as Kadcyla or Adcetris deliver a dose of the associated toxin (auristatins MMAE or emtansine DM-1) that is three or more times the lethal dose (for that toxin) which results in severe systemic (or non-target) toxicity. In contrast, illudofulvenes ADC's (such as analog 189, analog 190, analog 217, analog 218, analog 219, analog 222, or analog 316 deliver less than one third (i.e., <⅓) of a lethal dose, minimizing the risk and severity of systemic toxicity. Illudofulvenes are true cytotoxic agents whereas other toxic agents used in prior art ADC's (e.g., pyrrolobenzodiazepines, maytansines, fumagillols, dolstatins, auristatins, enadiynes, halichondrins, and tubulysins) are only cytostatic. See Table VI (based on the NCI-DTP 60 cell line). Hence, other payloads, such as those used in Herceptin, Adcetris or Rituxin only stall tumor cell growth and do not actually kill the tumor cells. Other payloads (e.g., pyrrolobenzodiazepines, maytansines, fumagillols, dolstatins, auristatins, enadiynes, halichondrins, and tubulysins) are not active against multidrug phenotypes, notably the MDR1/GP170 and MRP/GP180 transport mechanisms (see Table IV). Illudofulvenes show the excellent effect of remaining active against all MDR phenotypes known regardless of the mechanism of resistance (see Table IV). Hence, if tumor cells have already developed multi-drug resistance to a prior art ADC with a prior art toxin, or develop multi-drug resistance during the administration of a course of the prior art ADC with a prior art toxin, then the ADC will have no efficacy. In contrast, ADCs developed with illudofulvenes have the advantageous effect that they will continue to kill cancer cells.

Generally, the dosage of an Affinity Medicant Linker conjugate and/or a Medicant Linker compound administered to a patient is typically about 0.01 mg/kg to about 20 mg/kg of the patient's body weight. In one aspect, the dosage administered to a patient is between about 0.01 mg/kg to about 10 mg/kg of the patient's body weight. In another aspect, the dosage administered to a patient is between about 0.1 mg/kg and about 10 mg/kg of the patient's body weight. In yet another aspect, the dosage administered to a patient is between about 0.1 mg/kg and about 5 mg/kg of the patient's body weight. In yet another aspect the dosage administered is between about 0.1 mg/kg to about 3 mg/kg of the patient's body weight. In yet another aspect, the dosage administered is between about 1 mg/kg to about 3 mg/kg of the patient's body weight.

The Affinity Medicant Linker conjugate and/or a Medicant Linker compound can be administered by any convenient route, for example by infusion or bolus injection. Administration can be systemic or local. Various delivery systems are known, e.g., encapsulation in liposomes, microparticles, microcapsules, capsules, etc., and can be used to administer an Affinity Medicant Linker conjugate and/or a Medicant Linker compound. In certain embodiments, more than one Affinity Medicant Linker conjugate and/or a Medicant Linker compound is administered to a patient.

In specific embodiments, it can be desirable to administer one or more Affinity Medicant Linker conjugates and/or a Medicant Linker compound locally to the area in need of treatment. This can be achieved, for example, and not by way of limitation, by local infusion during surgery; topical application, e.g., in conjunction with a wound dressing after surgery; by injection; by means of a catheter; or by means of an implant, the implant being of a porous, non-porous, or gelatinous material, including membranes, such as sialastic membranes, or fibers. In one embodiment, administration can be by direct injection at the site (or former site) of a cancer, tumor or neoplastic or pre-neoplastic tissue. In another embodiment, administration can be by direct injection at the site (or former site) of a manifestation of an autoimmune disease.

In yet another embodiment, the Affinity Medicant Linker conjugate and/or a Medicant Linker compound can be delivered in a controlled release system, such as but not limited to, a pump or various polymeric materials can be used. In yet another embodiment, a controlled-release system can be placed in proximity of the target of the Linker Affinity conjugate and/or a Medicant Linker compound, e.g., the liver, thus requiring only a fraction of the systemic dose.

The term "carrier" refers to a diluent, adjuvant or excipient, with which an Affinity Medicant Linker conjugate and/or a Medicant Linker compound is administered. Such pharmaceutical carriers can be liquids, such as water and oils, including those of petroleum, animal, vegetable or synthetic origin. The carriers can be saline, and the like. In addition, auxiliary, stabilizing and other agents can be used. In one embodiment, when administered to a patient, the Affinity Medicant Linker conjugate and/or the Medicant Linker compound and pharmaceutically acceptable carriers are sterile. Water is an exemplary carrier when the Affinity Medicant Linker conjugate and/or a Medicant Linker compound are administered intravenously. Saline solutions and aqueous dextrose and glycerol solutions can also be employed as liquid carriers, particularly for injectable solutions. The present compositions, if desired, can also contain minor amounts of wetting or emulsifying agents, or pH buffering agents.

The present compositions can take the form of solutions, pellets, powders, sustained-release formulations, or any other form suitable for use.

In an embodiment, the Affinity Medicant Linker conjugates and/or Medicant Linker compounds are formulated in accordance with routine procedures as a pharmaceutical composition adapted for intravenous administration to animals, particularly human beings. Typically, the carriers or vehicles for intravenous administration are sterile isotonic aqueous buffer solutions. Where necessary, the compositions can also include a solubilizing agent. Compositions for intravenous administration can optionally comprise a local anesthetic such as lignocaine to ease pain at the site of the injection. Generally, the ingredients are supplied either separately or mixed together in unit dosage form, for example, as a dry lyophilized powder or water free concentrate in a hermetically sealed container such as an ampoule or sachette indicating the quantity of active agent. Where an Affinity Medicant Linker conjugate and/or Medicant Linker compound is to be administered by infusion, it can be dispensed, for example, with an infusion bottle containing sterile pharmaceutical grade water or saline. Where the Affinity Medicant Linker conjugate and/or Medicant Linker compound is administered by injection, an ampoule of sterile water for injection or saline can be provided so that the ingredients can be mixed prior to administration.

The composition can include various materials that modify the physical form of a solid or liquid dosage unit. For example, the composition can include materials that form a coating shell around the active ingredients. The materials that form the coating shell are typically inert, and can be selected from, for example, sugar, shellac, and other enteric coating agents. Alternatively, the active ingredients can be encased in a gelatin capsule.

Whether in solid or liquid form, the present compositions can include a pharmacological agent used in the treatment of cancer, an autoimmune disease or an infectious disease.

Treatment of Cancer. The Affinity Medicant Linker conjugates and Medicant Linker compounds are useful for inhibiting the multiplication of a tumor cell or cancer cell, causing apoptosis in a tumor or cancer cell, or for treating cancer in a patient. The Affinity Medicant Linker conjugates and/or Medicant Linker compounds can be used accordingly in a variety of settings for the treatment of animal cancers. The Affinity Medicant Linker Conjugates can be used to deliver a Medicant or Medicant unit to a tumor cell or cancer cell. Without being bound by theory, in one embodiment, the AM of an Affinity Medicant Linker conjugate binds to or associates with a cancer-cell or a tumor-cell-associated antigen, and the Affinity Medicant Linker conjugate can be taken up (internalized) inside a tumor cell or cancer cell through receptor-mediated endocytosis or other internalization mechanism. The antigen can be attached to a tumor cell or cancer cell or can be an extracellular matrix protein associated with the tumor cell or cancer cell. Once inside the cell, one or more specific peptide sequences within or at the Medicant unit's proximal end of the LU are hydrolytically cleaved by one or more tumor cell or cancer cell-associated proteases, resulting in release of the Medicant unit. The released Medicant unit is then free to migrate within the cell and induce cytotoxic or cytostatic activities. The Affinity Medicant Linker conjugate also can be cleaved by an intracellular protease to release the Medicant moiety. In an alternative embodiment, the Medicant or Medicant unit is cleaved from the Affinity Medicant Linker conjugate outside the tumor cell or cancer cell, and the Medicant or Medicant unit subsequently penetrates the cell.

The Affinity Medicant Linker conjugates provide conjugation-specific tumor or cancer medicant targeting, thus reducing general toxicity of the Medicant. The LUs stabilize the Affinity Medicant Conjugates in blood, yet are cleavable by tumor-specific proteases within the cell, liberating a Medicant unit.

In one embodiment, the AM binds to the tumor cell or cancer cell. In another embodiment, the AM binds to a tumor cell or cancer cell antigen which is on the surface of the tumor cell or cancer cell. In another embodiment, the AM binds to a tumor cell or cancer cell antigen which is an extracellular matrix protein associated with the tumor cell or cancer cell.

The specificity of the AM for a particular tumor cell or cancer cell can be important for determining those tumors or cancers that are most effectively treated. For example, an Affinity Medicant Linker conjugate and/or Medicant Linker compound having a BR96 AM can be useful for treating antigen positive carcinomas including those of the lung, breast, colon, ovaries, and pancreas Affinity Medicant Linker conjugates having an anti-CD30 or an anti-CD70 binding affinity moiety can be useful for treating hematologic malignancies.

Other particular types of cancers that can be treated with an Affinity Medicant Linker conjugate and/or a Medicant Linker compound include, but are not limited to fibrosarcoma, myxosarcoma, liposarcoma, chondrosarcoma, osteogenic sarcoma, chordoma, angiosarcoma, endotheliosarcoma, lymphangiosarcoma, lymphangioendotheliosarcoma, synovioma, mesothelioma, Ewing's tumor, leiomyosarcoma, rhabdomyo sarcoma, colon cancer, colorectal cancer, kidney cancer, pancreatic cancer, bone cancer, breast cancer, ovarian cancer, prostate cancer, esophageal cancer, stomach cancer, oral cancer, nasal cancer, throat cancer, squamous cell carcinoma, basal cell carcinoma, adenocarcinoma, sweat gland carcinoma, sebaceous gland carcinoma, papillary carcinoma, papillary adenocarcinomas, cystadenocarcinoma, medullary carcinoma, bronchogenic carcinoma, renal cell carcinoma, hepatoma, bile duct carcinoma, choriocarcinoma, seminoma, embryonal carcinoma, Wilms' tumor, cervical cancer, uterine cancer, testicular cancer, small cell lung carcinoma, bladder carcinoma, lung cancer, epithelial carcinoma, glioma, glioblastoma multiforme, astrocytoma, medulloblastoma, craniopharyngioma, ependymoma, pinealoma, hemangioblastoma, acoustic neuroma, oligodendroglioma, meningioma, skin cancer, melanoma, neuroblastoma, retinoblastoma blood-borne cancers, including but not limited to: acute lymphoblastic leukemia "ALL", acute lymphoblastic B-cell leukemia, acute lymphoblastic T-cell leukemia, acute myeloblastic leukemia "AML", acute promyelocytic leukemia "APL", acute monoblastic leukemia, acute erythroleukemic leukemia, acute megakaryoblastic leukemia, acute myelomonocytic leukemia, acute nonlymphocyctic leukemia, acute undifferentiated leukemia, chronic myelocytic leukemia "CML", chronic lymphocytic leukemia "CLL", hairy cell leukemia, multiple myeloma acute and chronic leukemias: lymphoblastic, myelogenous, lymphocytic, myelocytic leukemias Lymphomas: Hodgkin's disease, non-Hodgkin's Lymphoma, Multiple myeloma, Waldenstrom's macroglobulinemia, Heavy chain disease, Polycythemia vera.

Multi-Modality Therapy for Cancer. Cancers, including, but not limited to, a tumor, metastasis, or other disease or disorder characterized by uncontrolled cell growth, can be treated or inhibited by administration of an Affinity Medicant Linker conjugate or Medicant Linker compound.

In other embodiments, methods for treating cancer are provided, including administering to a patient in need thereof an effective amount of an Affinity Medicant Linker conjugate and a chemotherapeutic agent. In one embodiment the chemotherapeutic agent is that with which treatment of the cancer has not been found to be refractory. In another embodiment, the chemotherapeutic agent is that with which the treatment of cancer has been found to be refractory. The Affinity Medicant Linker conjugates can be administered to a patient that has also undergone surgery as treatment for the cancer.

In some embodiments, the patient also receives an additional treatment, such as radiation therapy. In a specific embodiment, the Affinity Medicant Linker conjugate is administered concurrently with the chemotherapeutic agent or with radiation therapy. In another specific embodiment, the chemotherapeutic agent or radiation therapy is administered prior or subsequent to administration of an Affinity Medicant Linker conjugate.

A chemotherapeutic agent can be administered over a series of sessions. Any one or a combination of the chemotherapeutic agents, such a standard of care chemotherapeutic agent(s), can be administered.

Additionally, methods of treatment of cancer with an Affinity Medicant Linker conjugate and/or a Medicant Linker compound are provided as an alternative to chemotherapy or radiation therapy where the chemotherapy or the radiation therapy has proven or can prove too toxic, e.g., results in unacceptable or unbearable side effects, for the subject being treated. The patient being treated can, optionally, be treated with another cancer treatment such as surgery, radiation therapy or chemotherapy, depending on which treatment is found to be acceptable or bearable.

Example 1. Synthesis of Medicant 113. The Wittig reaction was performed on analog 010. First 65 mg $CH_3PPh_3Br$ (0.185 mmol) in anhydrous THF was cooled to −75° C. and stirred for 1 hour. Then 200 μL of n-butyl lithium (0.183 mmol) was added very slowly to the flask while maintaining temperature at −75° C., and a yellow precipitate formed. It was stirred for another 1.5 hours then analog 010 (50 mg, 0.183 mmol) was slowly added while maintaining temperature at −75° C., followed by stirring for 2.0 hours. The reaction was quenched with ammonium chloride, extracted with $CH_2Cl_2$, washed with water, $NaHCO_3$, and saline. Dried over $Na_2SO_4$ and concentrated. The residue was eluted through a column (10% ethyl acetate in hexane) to give analog 113 as a solid.

Example 2. Synthesis of Medicant-Estrone 107. Analog 106 (see Example 13) (139 mg 0.384 mmol, 1 equiv.), DMAP (4 mg, 0.03 mmol, 0.08 equiv.) and estrone (104.4 mg, 0.384 mmol, 1 equiv.) were dissolved in $CH_2Cl_2$ (14 mL) at 0° C. To this solution was added $CH_2Cl_2$ solution of DCC (460 μL, 1 M, 0.46 mmol, 1.2 equiv.) through a syringe. After 0.5 hours the solution was raised to RT. After 2 hours the mixture was filtered and the filtrate was washed with dilute HCl (1.5%), saturated $NaHCO_3$ and brine in sequence. The organic phase was then dried and evaporated. The residue was eluted through a column ($CH_2Cl_2$/Methanol, 10:0.25) to give analog 107 (100 mg, 42%) as semisolid. Analog 107 can be subsequently linked to estrone.

Example 3. Preparation of Medicant-Estradiol 108. Analog 038 (58.5 mg, 0.2035 mmol), beta-estradiol (58.0 mg, 0.2150 mmol) and DMAP (5 mg. 0.048 mmol) were dissolved in $CH_2Cl_2$ (5.6 mL) at 0° C. To this solution was added $CH_2Cl_2$ solution of DCC (250 μL, 1 M, 0.244 mmol), stirred for 30 minutes, allowed to warm to RT then stirred for 1.5 hours. The filtrate was washed with dilute HCl (1.5%), saturated $NaHCO_3$ and brine in sequence. The organic phase was dried over $Na_2SO_4$, and evaporated. The residue was eluted through a column (100% $CH_2Cl_2$), fractions collected then eluted through a second column ($CH_2Cl_2$ plus 0.5% methanol), to give analog 108 (45 mg) as a solid.

Table I shows the cytotoxic data $IC_{50}$ values (micromolar, 2 hour exposure, N=3, mean±SD) for 108. MCF7 over express estrogen alpha-receptors. MCF7 cells are preferentially killed by 110 the acylfulvene-estrone analog and to a lesser extent 108 the acylfulvene-estradiol analog because estrone preferentially binds to alpha-receptor.

Example 4. Preparation of Medicant-Estradiol 109. Analog 106 (54.5 mg, 0.15 mmol, 1 equiv.), β-estradiol (40.5 mg, 0.15 mmol), and DMAP (1.8 mg, 0.015 mmol, 0.1 equiv.) were dissolved in $CH_2Cl_2$ (5 mL) at 0° C. To this solution was added $CH_2Cl_2$ solution of DCC (165 μL, 1 M, 0.165 mmol, 1.1 equiv.). The mixture was raised to RT after 0.5 h. After another 2 h, the mixture was filtered. The filtrate was washed with dilute HCl (1.5%), saturated $NaHCO_3$ and brine in sequence. The organic phase was dried and evaporated. The residue was eluted through a column ($CH_2Cl_2$/Methanol 10:0.25) to give analog 109 (55 mg, 60%) as semisolid.

Example 5. Preparation of Medicant-Estrone 110. Analog 038 (68 mg, 0.2365 mmol), estrone (68.0 mg, 0.2160 mmol) and DMAP (5 mg. 0.048 mmol) were dissolved in $CH_2Cl_2$ (8.0 mL) at 0° C. To this solution was added $CH_2Cl_2$ solution of DCC (300 μL, 1 M, 0.283 mmol), stirred for 30 minutes, allowed to warm to RT then stirred for 0.5 hours. The filtrate was washed with dilute HCl (1.5%), saturated $NaHCO_3$ and brine in sequence. The organic phase was dried over $Na_2SO_4$, and evaporated. The residue was eluted through a column (100% $CH_2Cl_2$), fractions collected then eluted through a second column ($CH_2Cl_2$ plus 0.5% methanol), to give analog 110 (40 mg) as a solid.

Table I shows the cytotoxic data $IC_{50}$ values (micromolar, 2 hour exposure, N=3, mean+SD) for 110. MCF7 cells over express estrogen alpha-receptors. MCF7 cells are preferentially killed by the acylfulvene-estrone analog 110 and to a lesser extent by the acylfulvene-estradiol analog 108 because estrone preferentially binds to alpha-receptor. In contrast, illudin M killed both ER negative and ER positive cells to the same extent. The data in Table I demonstrates that analog 108 and analog 110 are preferentially cytotoxic to cells expressing large numbers of estrogen receptors on their surface.

Example 6. Preparation of Medicant-Testosterone 111. Analog 038 (52.5 mg, 0.182 mmol), testosterone (50.0 mg, 0.173 mmol) and DMAP (5 mg. 0.048 mmol) were dissolved in $CH_2Cl_2$ (8.0 mL) at 0° C. To this solution was added $CH_2Cl_2$ solution of DCC (250 μL, 1 M), stirred for 30 minutes, allowed to warm to RT then stirred for 2 hours. The filtrate was washed with dilute HCl (1.5%), saturated $NaHCO_3$ and brine in sequence. The organic phase was dried over $Na_2SO_4$, and evaporated. The residue was eluted through a column (100% $CH_2Cl_2$ plus 0.5% methanol), to give analog 111 (15 mg) as a solid.

Example 7. Preparation of Medicant-Androsterone 112. Analog 038 (29 mg), androsterone (25.0 mg) and DMAP (5 mg. 0.048 mmol) were dissolved in $CH_2Cl_2$ (5.0 mL) at 0° C. To this solution was added $CH_2Cl_2$ solution of DCC (150 μL, 1 M), stirred for 30 minutes, allowed to warm to RT then stirred for 2 hours. The filtrate was washed with dilute HCl (1.5%), saturated $NaHCO_3$ and brine in sequence. The organic phase was dried over $Na_2SO_4$, and evaporated. The residue was eluted through a column (2:3 ethyl acetate: hexane) to give analog 112 (15 mg) as a solid.

In an embodiment of the present invention, an illudin2 moiety 1302 linked via a traditional linker 1240 to a steroid 1140 bind to receptors for the steroid and directs the illudin2 moiety 1302 to cell populations expressing the receptor. In an embodiment of the present invention, a steroid 1140 linked via a traditional linker 1240 to an illudin2 moiety 1302 acts as an AM for the steroid hormone receptor and directs the illudin2 moiety 1302 to tissues containing cells expressing the receptor. In an embodiment of the present invention, a steroid 1140 linked via a traditional linker 1240 to an illudin2 moiety 1302 acts as an AM for the steroid hormone receptor and directs the illudin2 moiety 1302 to tumors containing cells over-expressing the receptor compared to non tumor cells.

Example 4. Preparation of Medicant-Estradiol 109. Analog 106 (54.5 mg, 0.15 mmol, 1 equiv.), β-estradiol (40.5 mg, 0.15 mmol), and DMAP (1.8 mg, 0.015 mmol, 0.1 equiv.) were dissolved in $CH_2Cl_2$ (5 mL) at 0° C. To this solution was added $CH_2Cl_2$ solution of DCC (165 μL, 1 M, 0.165 mmol, 1.1 equiv.). The mixture was raised to RT after 0.5 h. After another 2 h, the mixture was filtered. The filtrate was washed with dilute HCl (1.5%), saturated $NaHCO_3$ and brine in sequence. The organic phase was dried and evaporated. The residue was eluted through a column ($CH_2Cl_2$/Methanol 10:0.25) to give analog 109 (55 mg, 60%) as semisolid.

Example 5. Preparation of Medicant-Estrone 110. Analog 038 (68 mg, 0.2365 mmol), estrone (68.0 mg, 0.2160 mmol) and DMAP (5 mg. 0.048 mmol) were dissolved in $CH_2Cl_2$ (8.0 mL) at 0° C. To this solution was added $CH_2Cl_2$ solution of DCC (300 μL, 1 M, 0.283 mmol), stirred for 30 minutes, allowed to warm to RT then stirred for 0.5 hours. The filtrate was washed with dilute HCl (1.5%), saturated $NaHCO_3$ and brine in sequence. The organic phase was dried over $Na_2SO_4$, and evaporated. The residue was eluted through a column (100% CH$_2$Cl$_2$), fractions collected then eluted through a second column (CH$_2$Cl$_2$ plus 0.5% methanol), to give analog 110 (40 mg) as a solid.

Table I shows the cytotoxic data IC$_{50}$ values (micromolar, 2 hour exposure, N=3, mean+SD) for 110. MCF7 cells over express estrogen alpha-receptors. MCF7 cells are preferentially killed by the acylfulvene-estrone analog 110 and to a lesser extent by the acylfulvene-estradiol analog 108 because estrone preferentially binds to alpha-receptor. In contrast, illudin M killed both ER negative and ER positive cells to the same extent. The data in Table I demonstrates that compounds 108 and 110 are preferentially cytotoxic to cells expressing large numbers of estrogen receptors on their surface.

Example 6. Preparation of Medicant-Testosterone 111. Analog 038 (52.5 mg, 0.182 mmol), testosterone (50.0 mg, 0.173 mmol) and DMAP (5 mg. 0.048 mmol) were dissolved in CH$_2$Cl$_2$ (8.0 mL) at 0° C. To this solution was added CH$_2$Cl$_2$ solution of DCC (250 µL, 1 M), stirred for 30 minutes, allowed to warm to RT then stirred for 2 hours. The filtrate was washed with dilute HCl (1.5%), saturated NaHCO$_3$ and brine in sequence. The organic phase was dried over Na$_2$SO$_4$, and evaporated. The residue was eluted through a column (100% CH$_2$Cl$_2$ plus 0.5% methanol), to give analog 111 (15 mg) as a solid.

Example 7. Preparation of Medicant-Androsterone 112. Analog 038 (29 mg), androsterone (25.0 mg) and DMAP (5 mg. 0.048 mmol) were dissolved in CH$_2$Cl$_2$ (5.0 mL) at 0° C. To this solution was added CH$_2$Cl$_2$ solution of DCC (150 µL, 1 M), stirred for 30 minutes, allowed to warm to RT then stirred for 2 hours. The filtrate was washed with dilute HCl (1.5%), saturated NaHCO$_3$ and brine in sequence. The organic phase was dried over Na$_2$SO$_4$, and evaporated. The residue was eluted through a column (2:3 ethyl acetate: hexane) to give analog 112 (15 mg) as a solid.

Example 13. Synthesis of Medicant 106. Illudin M (450 mg, 1.845 mmol, 1 equiv.), glutaric anhydride (2.10 g, 18.45 mmol, 10 equiv.) and DMAP (171 mg, 1.4 mmol, 0.76 equiv.) were dissolved in CH$_2$Cl$_2$ (5 mL) at RT. After 3.5 hours the mixture was taken up by CH$_2$Cl$_2$, which was washed with water, and brine in sequence. It was then dried and evaporated. The residue was eluted through a column (Hexane/EtOAc 4:1) to give analog 106 (365 mg, 55%) as a liquid. UV (CHCl$_3$) λ nm (ε): 309 (3387).

Analog 106 was generated from illudin M as outlined in Example 13. The carboxylic acid derivative was activated using DCC/DMAP to synthesize steroid AFC's 107 and 109. In addition, Irofulven carboxylic acid derivative, analog 038 was activated using DCC/DMAP to produce analogs 108, 110, 111, and 112. In general, carboxylate group containing compounds can be activated using a carbodiimide in the presence of an amino acid to form an azlactone. The azlactone formed will react spontaneously with primary amine groups on an amino acid, a peptide, an antibody, a protein, or another drug, and undergo ring opening with the formation of an amide bond. For proteins, antibodies and peptides the amino acids capable of reacting with the azlactone derivative includes arginine and lysine.

To form an Illudin derived azlactone active drug-linker moiety, either analog 106 or analog 038 can be activated by DCC/DMAP in the presence of a small amino acid such as glycine to form the azlactone. DCC cannot be added without the presence of an amine containing target (such as the glycine) or the activated carboxylate reacts with another carboxylate to form a symmetrical anhydride. The azlactone formed will react spontaneously with primary amine groups on a peptide, an antibody, a protein, or a medicant.

Example 14. Activation of analog 038 by DCC to form medicant-azlactone. Part A: Production of Azlactone from carboxylate Acylfulvene analog: Analog 038 (58.5 mg, 0.2035 mmol), and DMAP (5 mg. 0.048 mmol) were dissolved in CH$_2$Cl$_2$ (5.6 mL) at 0° C. The desired amino acid (such as glycine) was added in an equimolar amount. Note that amino acids having substitutions on the C4 carbon (such as alpha-methyl glycine or 2-dimethylglycine) are preferred over conventional amino acids as substitution cannot occur at the C4 position after ring-opening and all nucleophilic coupling reactions must occur at the C5 position, resulting only in the desired amide-bond formation with the amine-containing molecule. To this solution was added CH$_2$Cl$_2$ solution of DCC (250 µL, 1 M, 0.244 mmol), stirred for 30 minutes, allowed to warm to RT then stirred for 1.5 hours. The filtrate was washed with dilute HCl (1.5%), saturated NaHCO$_3$ and brine in sequence. The organic phase was dried over Na$_2$SO$_4$, and evaporated. The residue was eluted through a column (100% CH$_2$Cl$_2$ plus 0.5% methanol), to give the desired azlactone analog as a solid. Part B: Coupling of Azlactone to the protein component (reacting with primary amines on amino acids such as the one on lysine): The typical protein coupling reaction consists of the Azlactone suspended in buffer [25 mM sodium phosphate, 150 mM NaCl (pH 7.5)] and the desired amount of protein (20 µg to 5.0 mg) was added. The mixture was gently rocked for 60 minutes, then the reaction terminated by the addition of the blocking reagent, 1.0 ml of 1.0 M ethanolamine in 25 mM sodium pyrophosphate (titrated to pH 9.0 with HCl) Sample rocked gently for 5 minutes then the residual ethanolamine removed by dialysis or chromatography using pH 7.5 phosphate-NaCl buffer.

Example 15. Reaction of the medicant-azlactone product with an antibody. The azlactone derivative generated in Example 14 (note that other amino acids can be used in place of glycine) was then reacted with the desired peptide or protein or other compound containing a primary amino group at a 1:1 ratio in buffer (25 mM sodium phosphate, 150 mM sodium chloride, pH 7.5) with gentle rocking at RT for 60 minutes. The reaction was terminated by the addition of 1.0 mL of 25 mM ethanolamine (titrated to pH 9.00) with rocking for 5 minutes at RT). The drug-azlactone-ligand product can be purified by column chromatography or dialysis to remove the ethanolamine by-product.

Example 16. Synthesis of Medicant 114. (CH$_3$)$_3$S(O)I (110 mg, 0.4 mmol) and tBuOK (50 mg, 0.4 mmol) were dissolved in anhydrous DMSO (1 mL) and stirred at RT for 40 minutes at RT. Then analog 010 (50 mg, 0.2 mmol) in 1.0 mL of DMSO was added via syringe, and stirred for 3 hours. Reaction quenched with saturated NH$_4$Cl (1 mL), extracted with CH$_2$Cl$_2$, dried over Na$_2$SO$_4$, concentrated then chromatographed (2:3 hexane:ethyl acetate) to yield analog 114 (20 mg, 50% yield).

Example 17. Synthesis of Medicant 115. Analog 010 (40 mg) and NAHCO$_3$ (50 mg) are dissolved in 10 mL of 1:1 Ethanol and water mixture, then hydroxylamine hydrochloride (20 mg) was added, stirred for 30 minutes at RT. Water and ethyl acetate (1:1 mixture) was added, stirred, the organic layer was recovered, washed with saturated NaHCO$_3$ and then brine, dried over Na$_2$SO$_4$, concentrated then chromatographed (2:3 ethyl acetate:hexane) to yield analog 115.

Example 18. Synthesis of Medicant 116. SeO$_2$ (45 mg) and 500 mg SiO2 transferred into a dried RB flask, 5 mL of CH$_2$Cl$_2$ added, and stirred for 1 hour under nitrogen. Then 250 µL of tBuO$_2$H added and stirred for 15 minutes. Then 100 mg of Irofulven in 1 mL CH$_2$Cl$_2$ was added, and stirred for 3 hours at RT under a nitrogen atmosphere. Product was filtered, wash twice with water (25 mL), twice with brine (25 mL), dried over $Na_2SO_4$ and concentrated then chromatographed (4:1 hexane:ethyl acetate) to yield analog 116.

Example 19. Synthesis of Medicant 116. Analog 117: Illudin S (100 mg, 0.378 mmol) and glutaric anhydride (215.46 mg, 1.89 mmol) are dissolved in 5 mL of $CH_2Cl_2$, and DMAP added (92.23 mg, 0.756 mmol), and stirred for 2 hours at RT. The $CH_2Cl_2$ was evaporated, 5 mL of water was added, and stirred for 1 hour. The solution was extracted with 10 mL of $CH_2Cl_2$, washed with water, dried over $Na_2SO_4$ and concentrated to yield analog 117 (120 mg).

Example 20. Synthesis of Analog 118: Analog 302 (75 mg), glutaric anhydride (20 mg) are dissolved in 5 mL of $CH_2Cl_2$, and DMAP added (42 mg), and stirred for 2 hours at RT. The $CH_2Cl_2$ was evaporated, 5 mL of water added, and stirred for 1 hour. Solution was extracted with 10 mL of $CH_2Cl_2$, washed with water, dried over $Na_2SO_4$ and concentrated to yield analog 118 (120 mg).

Example 21. Synthesis of Analog 119: Analog 114 (10 mg) was dissolved in 1.5 mL of acetone with 1.0 mL of 4N $H_2SO_4$, and contents stirred for 1.5 hours at RT. Then 10 mL of $CH_2Cl_2$ and 10 mL of water are added, extracted, and the organic layer recovered which was then washed with saturated $NaHCO_3$ and saline, dried over $Na_2SO_4$ and concentrated, and analog 119 recovered (analog 128 was a byproduct).

Example 22. Synthesis of Analog 120: Analog 010 (50 mg), $NaHCO_3$ are dissolved in 10 mL of 1:1 mixture of water and ethanol, then $NH_2NH_2$ (0.5 mL added with stirring at RT for one hour. The solution was extracted with $CH_2Cl_2$ twice, the organic layer recovered, washed with water, then $NaHCO_3$ solution, dried over $Na_2SO_4$, and evaporated to yield analog 120 (30 mg).

Example 23. Synthesis of Analog 121: Analog 010 (50 mg) and $NaCO_2CH_3$ (75 mg) are dissolved in 10 mL of 1:1 mixture of water and ethanol 1:1, then semicarbazide hydrochloride salt ($H_2NNHCONH_2 \cdot HCl$, 50 mg) added, and stirred for 2 hours at RT. The solution was extracted with $CH_2Cl_2$ twice, the organic layer recovered, washed with water, then $NaHCO_3$ solution, dried over $Na_2SO_4$, and evaporated then chromatographed (5% methanol in ethyl acetate) to yield analog 121.

Example 24. Synthesis of Analog 122: Analog 010 (50 mg) and $NaCO_2CH_3$ (75 mg) are dissolved in 5 mL of ethanol, then phenylhydrazide (50 mg) was added, stirred for 1 hour at RT. Then 5 mL of water was added, followed by extraction with ethyl acetate, washed with water, dried over $Na_2SO_4$ and concentrated and chromatographed (5% methanol in ethyl acetate) to yield analog 122.

Example 25. Synthesis of Analog 123: Analog 010 (50 mg) and $NaCO_2CH_3$ (75 mg) are dissolved in 10 mL of 1:1 water and ethanol, then $H_2NNHTS(H_2\ NNHS(=O)_2$(phenyl)methyl, 50 mg) was added, stirred for 2 hour at RT. Then 5 mL of water was added, followed by extraction with ethyl acetate, washed with water, dried over $Na_2SO_4$ and concentrated and chromatographed (5% methanol in ethyl acetate) to yield analog 123.

Example 26. Synthesis of Analog 124: Analog 115 (15 mg) and NaOAc (15 mg) are dissolved in acetic anhydride (1 mL) and stirred for 2 hours, then sodium acetate (300 mg) was added with stirring for 1 hour. Then the mixture was chromatographed (10% ethyl acetate in hexane) to give analog 124.

Example 27. Synthesis of Analog 125: Analog 010 (50 mg) and $NaCO_2CH_3$ (75 mg) are dissolved in 5 mL of ethanol, then the dinitrophenylhydrazide (50 mg) was added, stirred for 1 hour at RT. Then 5 mL of water was added, followed by extraction with ethyl acetate, washed with water, dried over $Na_2SO_4$ and concentrated and chromatographed (5% methanol in ethyl acetate) to yield analog 125.

Example 28. Synthesis of Analog 126: Analog 011 (40 mg), hydroxylamine (20 mg), $NaHCO_3$ (50 mg) are dissolved in 10 mL of ethanol and water (1:1) then stirred at RT for 90 minutes. Then the mixture was extracted with water (10 mL) and ethyl acetate (20 mL), the organic layer washed with saturated $NaHCO_3$ then brine, dried over $Na_2SO_4$ and concentrated, then chromatographed (2:3 ethyl acetate: hexane) to give analog 126.

Example 29. Synthesis of Analog 127: Analog 010 (100 mg) and $NH_4Cl$ (1.5 equivalent) are dissolved in 1,4-dioxane (5 mL) and water (0.2 mL), then NaCN added (1.3 equivalents), stirred for 1 hour at RT. Then ethyl ether (20 mL) was added, the organic layer recovered, washed with water, washed with brine, then dried over $Na_2SO_4$, then chromatographed (2:3 ethyl acetate:hexane) to yield analog 127.

Example 30. Synthesis of Analog 128: Analog 114 (10 mg) was dissolved in 1.5 mL of acetone with 1.0 mL of 4N $H_2SO_4$, and contents stirred for 1.5 hours at RT. Then 10 mL of $CH_2Cl_2$ and 10 mL of water are added, extracted, and the organic layer recovered which was then washed with saturated $NaHCO_3$ and saline, dried over $Na_2SO_4$ and concentrated, and analog 128 recovered (analog 119 was a byproduct).

Example 31. Synthesis of Analog 129: Analog 001 (200 mg) was dissolved in anhydrous THF (10 mL) at RT then $NaBH_4$ (100 mg) was added slowly for 30 minutes. Reaction was quenched with 1 mL of water then extracted with ethyl acetate (10 mL), washed with saturated $NaHCO_3$, and dried over $Na_2SO_4$, then concentrated to yield analog 129. If need be the compound can be purified by chromatography (1:1 ethyl acetate:hexane).

Example 32. Analog 141: Analog 129 (200 mg) was dissolved in $CH_2Cl_2$ at RT, then 1,4-dimethyl but-2-ynedioate (1.1 equivalent) was added slowly and mixture allowed to react for one hour, then evaporated to yield analog 141. If need be the compound can be purified by chromatography (1:1 ethyl acetate:hexane).

Example 33. Synthesis of Analog 142: Analog 141 (100 mg) was dissolved in $CH_2Cl_2$ at RT then Dess-Martin Periodinane reagent (200 mg) added with stirring for 1 hour to yield analog 142. If need be the compound can be purified by chromatography (1:1 ethyl acetate:hexane).

Example 34. Synthesis of Analog 146: Analog 127 (35 mg, 0.117 mmol), DMAP (5 mg), and diimidazole (22 mg, 1.2 eq) were dissolved in anhydrous $CH_2Cl_2$ under an argon atmosphere, and stirred for 30 minutes. The solution was cooled to 20° C. then tributyl tin hydride ($Bu_3SnH$, 0.6 mL) and azobis isobutylnitrite (4 mg) were added with stirring for 30 minutes. The mixture was filtered then chromatographed (1:10 ethyl acetate:hexane) to remove impurities and starting materials, then chromatographed (2:3 ethyl acetate:hexane) to yield analog 146.

Example 35. Synthesis of Analog 147: Irofulven (10 mg) was dissolved in 3 mL of acetone and 1 M $H_2SO_4$ solution (1:1) with stirring at RT and 2-Mercaptobenzothiazole (1 equivalent) was added, stirred for 2 hours, then partitioned between ethyl acetate and water. The organic extract was washed with saturated $NaHCO_3$ and saline until neutral, dried over $MgSO_4$, concentrated then chromatographed (1:1 ethyl acetate:hexane) to give analog 147.

Example 36. Synthesis of Analog 148: Irofulven (10 mg) was dissolved in 3 mL of acetone and 1 M $H_2SO_4$ solution (1:1) with stirring at RT and 2-Mercaptobenzoxazole (1 equivalent) was added, stirred for 2 hours, then partitioned between ethyl acetate and water. The organic extract was washed with saturated $NaHCO_3$ and saline until neutral, dried over $MgSO_4$, concentrated then chromatographed (1:1 Ethyl acetate:hexane) to give analog 148.

Example 37. Synthesis of Analog 149: Irofulven (10 mg) was dissolved in 4 mL of acetone and 1 M $H_2SO_4$ solution (1:1) with stirring at RT and thiol-imidazole (1 equivalent) was added, stirred for 24 hours, then partitioned between ethyl acetate and water. The organic extract was washed with saturated $NaHCO_3$ and saline until neutral, dried over $MgSO_4$, concentrated then chromatographed (1:1 ethyl acetate:hexane) to give analog 149.

Example 38. Synthesis of Analog 150: Irofulven (10 mg) was dissolved in 4 mL of acetone and 1 M $H_2SO_4$ solution (1:1) with stirring at RT and 2-mercapto-5-methylbenzimidazole (1 equivalent) was added, stirred for 12 hours, then partitioned between ethyl acetate and water. The organic extract was washed with saturated $NaHCO_3$ and saline until neutral, dried over $MgSO_4$, concentrated then chromatographed (1:1 ethyl acetate:hexane) to give analog 150.

Example 39. Synthesis of Analog 151: Irofulven (10 mg) was dissolved in 3 mL of acetone and 1 M $H_2SO_4$ solution (1:1) with stirring at RT and 1-phenyl-1,2,3,4-tetraazole-5-thiol (1 equivalent) was added, stirred for 2 hours, then partitioned between ethyl acetate and water. The organic extract was washed with saturated $NaHCO_3$ and saline until neutral, dried over $MgSO_4$, concentrated then chromatographed (1:1 ethyl acetate:hexane) to give analog 151.

Example 40. Synthesis of Analog 152: Irofulven (10 mg) was dissolved in 3 mL of acetone and 1 M $H_2SO_4$ solution (1:1) with stirring at RT and 2-mercapto-5-nitro benzimidazole (1 equivalent) was added, stirred for 2 hours, then partitioned between ethyl acetate and water. The organic extract was washed with saturated $NaHCO_3$ and saline until neutral, dried over $MgSO_4$, concentrated then chromatographed (1:1 ethyl acetate:hexane) to give analog 152.

Example 41. Synthesis of Analog 153: Irofulven (10 mg) was dissolved in 3 mL of acetone and 1 M $H_2SO_4$ solution (1:1) with stirring at RT and 1,2,4-Triazole-3-thiol (1 equivalent) was added, stirred for 2 hours, then partitioned between ethyl acetate and water. The organic extract was washed with saturated $NaHCO_3$ and saline until neutral, dried over $MgSO_4$, concentrated then chromatographed (1:1 ethyl acetate:hexane) to give analog 153.

Example 42. Synthesis of Analog 154: Irofulven (10 mg) was dissolved in 3 mL of acetone and 1 M $H_2SO_4$ solution (1:1) with stirring at RT and 2-sulfanylpteridin-4-ol (1 equivalent) was added, stirred for 2 hours, then partitioned between ethyl acetate and water. The organic extract was washed with saturated $NaHCO_3$ and saline until neutral, dried over $MgSO_4$, concentrated then chromatographed (1:1 ethyl acetate:hexane) to give analog 154.

Example 43. Synthesis of Analog 155: Irofulven (10 mg) was dissolved in 3 mL of acetone and 1 M $H_2SO_4$ solution (1:1) with stirring at RT and 4-(5-sulfanyl-1H-1,2,3,4-tetrazol-1-yl)phenol (1 equivalent) was added, stirred for 2 hours, then partitioned between ethyl acetate and water. The organic extract was washed with saturated $NaHCO_3$ and saline until neutral, dried over $MgSO_4$, concentrated then chromatographed (1:1 ethyl acetate:hexane) to give analog 155.

Example 44. Synthesis of Analog 156: Irofulven (10 mg) was dissolved in 3 mL of acetone and 1 M $H_2SO_4$ solution (1:1) with stirring at RT and 4-(5-sulfanyl-1-1,2,3,4-tetrazolyl)benzoic acid (1 equivalent) was added, stirred for 2 hours, then partitioned between ethyl acetate and water. The organic extract was washed with saturated $NaHCO_3$ and saline until neutral, dried over $MgSO_4$, concentrated then chromatographed (1:1 ethyl acetate:hexane) to give analog 156.

Example 45. Synthesis of Analog 159: Illudin S (300 mg) was dissolved acetic anhydride (6 mL) and stirred for 15 minutes, then sodium acetate (300 mg) was added with stirring for 1 hour. Water (6 mL) was added, ethyl acetate extraction performed, washed with sodium bicarbonate solution, dried over $Na_2SO_4$, concentrated then chromatographed (2:3 ethyl acetate:hexane) to give analog 159.

Example 46. Synthesis of Analog 160: Analog 159 (60 mg) was dissolved in dry $CH_2Cl_2$ (6 mL) under nitrogen at RT and glutaric anhydride (100 mg) with DMAP (20 mg) was added with stirring for 30 minutes. The solvent was removed, water added, extracted with $CH_2Cl_2$, washed with water, dried over $Na_2SO_4$, concentrated then chromatographed (2:3 ethyl acetate:hexane) to give analog 160.

Example 47. Synthesis of Analog 161: Dehydroilludin S (300 mg) was dissolved acetic anhydride (6 mL) and stirred for 15 minutes, then sodium acetate (300 mg) was added with stirring for 1 hour. Water (6 mL) was added, ethyl acetate extraction performed, washed with sodium bicarbonate solution, dried over $Na_2SO_4$, concentrated then chromatographed (2:3 ethyl acetate:hexane) to give analog 161.

Example 48. Synthesis of Analog 162: Dehydroilludin S (60 mg) was dissolved in dry $CH_2Cl_2$ (6 mL) under nitrogen at RT and glutaric anhydride (150 mg) with DMAP (50 mg) was added with stirring for 30 minutes. The solvent was removed, water added, extracted with $CH_2Cl_2$, washed with water, dried over $Na_2SO_4$, concentrated then chromatographed (2:3 ethyl acetate:hexane) to give analog 162.

Example 49. Synthesis of Analog 163: Analog 159 (20.25 mg), DMAP (20 mg) are dissolved in dry $CH_2Cl_2$ (6 mL) at 0° C. under nitrogen atmosphere and stirred for 10 minutes. Then chloroacetyl chloride (0.2 mL) was added slowly and the mixture stirred for 30 minutes, warmed to RT with stirring over 15 minutes. Then water (6 mL) was added, mixed, and then extracted with $CH_2Cl_2$. The organic layer was washed with saturated $NaHCO_3$ followed by a saline wash, dried over $Na_2SO_4$ then chromatographed (2:3 ethyl acetate:hexane) to yield analog 163 (60% yield).

Example 50. Synthesis of Analog 164: Irofulven (50 mg), DMAP (40 mg) are dissolved in dry $CH_2Cl_2$ (6 mL) at 0° C. under nitrogen atmosphere and stirred for 10 minutes. Then chloroacetyl chloride (0.2 mL) was added slowly and the mixture stirred for 30 minutes, warmed to RT with stirring over 15 minutes. Then water (6 mL) was added, mixed, and then extracted with $CH_2Cl_2$. The organic layer was washed with saturated $NaHCO_3$ followed by a saline wash, dried over $Na_2SO_4$ then chromatographed (2:3 ethyl acetate: hexane) to yield analog 164 (60% yield).

Example 51. Synthesis of Analog 165: Analog 164 (40 mg) was dissolved in dry $CH_2Cl_2$ (6 mL) at RT under nitrogen atmosphere and stirred for 10 minutes. Then 1 mL of morpholine was added drop wise, with stirring for 30 minutes. The reaction was diluted with water (6 mL), extracted with $CH_2Cl_2$ (12 mL). The organic layer was washed with saturated $NaHCO_3$ then washed with saline, dried over $Na_2SO_4$ and chromatographed (2:3 ethyl acetate: hexane) to yield 165 (35% yield).

Example 52. Synthesis of Analog 166 and analog 167 (prepared together): Analog 160 (30 mg) was dissolved in methanol (4 mL) at 0° C., and 1N $H_2SO_4$ (1 mL) was added with stirring for 1 hour. Water (6 mL) was added, extracted with ethyl acetate, washed with $NaHCO_3$ then a brine solution, dried over MgSO$_4$, concentrated and then chromatographed (1:1 ethyl acetate:hexane) to yield analogs 166 and 167 in equal amounts.

Example 53. Synthesis of Analog 168: Analog 162 (20 mg) was dissolved in methanol (5 mL) at 0° C. and stirred for 10 minutes, then 1 mL of 1N H$_2$SO$_4$ in methanol was slowly added, followed by stirring for 30 minutes. Water was added, followed by an ethyl acetate extraction, washed with NaHCO$_3$ then a brine solution, dried over Na$_2$SO$_4$, concentrated then chromatographed (1:1 ethyl acetate:hexane) to yield analog 168.

Example 54. Synthesis of Analog 169: Dehydroilludin S (20 mg), DMAP (20 mg) are dissolved in dry CH$_2$Cl$_2$ (6 mL) at 0° C. under nitrogen atmosphere and stirred for 10 minutes. Then chloroacetyl chloride (0.2 mL) was added slowly and the mixture stirred for 30 minutes, warmed to RT with stirring over 15 minutes. Then water (6 mL) was added, mixed, then extracted with CH$_2$Cl$_2$. The organic layer was washed with saturated NaHCO$_3$ followed by a saline wash, dried over Na$_2$SO$_4$ then chromatographed (2:3 ethyl acetate:hexane) to yield analog 169 (60% yield).

Example 55. Synthesis of Analog 176: To a solution of analog 009 (266 umol), Boc protected leucine amino acid (300 umol) and DMAP (dimethylaminopyridine, 110 umol) in CH$_2$Cl$_2$ (2.5 mL) at 0° C. was added DCC (dicyclohexylcarbodiimide; 1.0M in CH$_2$Cl$_2$, 300 umol)/. The mixture was stirred for 35 minutes then 5 µL of water added to quench the reaction. The mixture was diluted with hexane and precipitate filtered off, solvent evaporated off and crude product chromatographed (2:1 hexanes-ethyl acetate) to give the desired Boc-protected derivative of 176 at 80% yield. The Boc group was removed by dissolving the Boc-protected derivative in a 1:1 mixture (2.0 mL) of 1,4-dioxane and 2M H$_2$SO$_4$, stirred for 18 hours, then partitioned between ethyl acetate and water. Aqueous layer was extracted with ethyl acetate and extracts discarded. Aqueous layer was neutralized with saturated NaHCO$_3$ and extracted again with ethyl acetate. Organic layer was washed with brine, dried with MgSO$_3$, solvent evaporated to yield the analog 009 amino acid derivative. As the amine derivative was unstable over prolonged periods of time it can be converted to the very stable trifluoroacetate salt by dissolving in CH$_2$Cl$_2$ adding the equal molar amount of trifluoroacetic acid and concentrating to dryness.

Example 56. Synthesis of Analog 178: Analog 009 (15 mg) was dissolved in CH$_2$Cl$_2$ (2.0 mL) under a nitrogen atmosphere at RT, succinic anhydride (1 equivalent) was added, followed by DMAP (10 mg) and stirring for 30 minutes. Solvent was removed and product recrystallized to give analog 178.

Example 57. Synthesis of Analog 179: To a solution of Analog 009 (266 µmol), Boc protected glycine amino acid (300 umol) and DMAP (dimethylaminopyridine, 110 umol) in CH$_2$Cl$_2$ (2.5 mL) at 0° C. was added DCC (dicyclohexylcarbodiimide; 1.0M in CH$_2$Cl$_2$, 300 umol)/. The mixture was stirred for 35 minutes then 5 µL of water added to quench the reaction. The mixture was diluted with hexane and precipitate filtered off, solvent evaporated off and crude product chromatographed (2:1 hexanes-ethyl acetate) to give the desired Boc-protected derivative of 179 at 80% yield. The Boc group was removed by dissolving the Boc-protected derivative in a 1:1 mixture (2.0 mL) of 1,4-dioxane and 2M H$_2$SO$_4$, stirred for 18 hours, then partitioned between ethyl acetate and water. Aqueous layer was extracted with ethyl acetate and extracts discarded. Aqueous layer was neutralized with saturated NaHCO$_3$ and extracted again with ethyl acetate. Organic layer was washed with brine, dried with MgSO$_3$, solvent evaporated to yield the analog 009 amino acid derivative. As the amine derivative was unstable over prolonged periods of time it can be converted to the very stable trifluoroacetate salt by dissolving in CH$_2$Cl$_2$ adding the equal molar amount of trifluoroacetic acid and concentrating to dryness.

Example 58. Synthesis of Analog 180: Illudin M (50 mg) was dissolved in dry benzene (10 mL) under a nitrogen atmosphere, and vanadyl acetylacetonate (VO(acac)$_2$, 1.2 mg) was added. Then t-butyl hydroperoxide (t-BuO$_2$H, 0.5 mL) in benzene was added drop wise with stirring for 30 minutes. A saturated solution of Na$_2$S$_2$O$_3$ was added (10 mL), then extraction with ethyl acetate, and the organic layer was dried over Na$_2$SO$_4$, concentrated then chromatographed) (1:1 ethyl acetate:hexane) to give analog 180.

Example 59. Synthesis of Analog 181: Analog 159 (40 mg) was dissolved in dry benzene (8 mL) under a nitrogen atmosphere, and vanadyl acetylacetonate (VO(acac)$_2$, 2 mg) was added. Then t-butyl hydroperoxide (t-BuO$_2$H, 0.5 mL) in benzene was added drop wise with stirring for 30 minutes. A saturated solution of Na$_2$S$_2$O$_3$ was added (10 mL), then extraction with ethyl acetate, followed by a brine wash, and the organic layer was then dried over Na$_2$SO$_4$, concentrated then chromatographed) (1:1 ethyl acetate:hexane) to give analog 181.

Example 60. Synthesis of Analog 189: To a solution of Irofulven (1.00 equivalent), maleimide (1.71 equivalent), triphenylphosphine (PPh$_3$, 1.71 equivalent) in 1.5 mL of THF at −40° C., was added DEAD (diethylazodicarboxylate; 1.68 equivalent). The mixture was stirred for 30 minutes then water (20 µL) added to quench the reaction. The mixture was concentrated on a rotary evaporator and crude product was chromatographed on a silica column (10:3 hexanes:ethyl acetate) to yield an orange compound (20% yield).

Example 61. Synthesis of Analog 190: To a solution of analog 009 (6-hydroxy-n-propylacylfulvene-structure below, 1.00 equivalent), maleimide (1.23 equivalent), triphenylphosphine (PPh$_3$, 1.13 equivalent) in 2.5 mL of THF at −40° C., was added DIAD (diisopropylcarbodiimide; 1.44 equivalent). The mixture was stirred for 1 hour then water (10 µL) added to quench the reaction. The mixture was concentrated on a rotary evaporator and crude product was chromatographed on a silica column (5:1→10:3 hexanes:ethyl acetate) to yield an orange compound (15% yield).

Example 62. Synthesis of Analog 196: To a solution of analog 009 (266 umol), Boc protected proline amino acid (300 umol) and DMAP (dimethylaminopyridine, 110 umol) in CH$_2$Cl$_2$ (2.5 mL) at 0° C. was added DCC (dicyclohexylcarbodiimide; 1.0M in CH$_2$Cl$_2$, 300 umol)/. The mixture was stirred for 35 minutes then 5 µL of water added to quench the reaction. The mixture was diluted with hexane and precipitate filtered off, solvent evaporated off and crude product chromatographed (2:1 hexanes-ethyl acetate) to give the desired Boc-protected derivative of 196 at 80% yield. The Boc group was removed by dissolving the Boc-protected derivative in a 1:1 mixture (2.0 mL) of 1,4-dioxane and 2M H$_2$SO$_4$, stirred for 18 hours, then partitioned between ethyl acetate and water. Aqueous layer was extracted with ethyl acetate and extracts discarded. Aqueous layer was neutralized with saturated NaHCO$_3$ and extracted again with ethyl acetate. Organic layer was washed with brine, dried with MgSO$_3$, solvent evaporated to yield the analog 009 amino acid derivative. As the amine derivative was unstable over prolonged periods of time it can be converted to the very stable trifluoroacetate salt by dissolving in CH$_2$Cl$_2$ adding the equal molar amount of trifluoroacetic acid and concentrating to dryness.

Example 63. Synthesis of Analog 198: Irofulven (26.3 mg, 107 umol), p-nitrophenol (16.2 mg, 116 umol) and PPh3 (30.8 mg, 117 umol) were dissolved in anhydrous THF (1.5 mL) at −40° C., the DEAD (25 µL, 160 umol) was added, followed by stirring for 30 minutes, then diluted with hexane. The precipitate was filtered off, solvent evaporated, and crude product chromatographed (6:1→2:1 hexane:ethyl acetate) to give analog 198 as a yellow product (18.5 mg, 47%).

Example 64. Analogs 199 and 200 (prepared together): Irofulven (25.2 mg, 102 umol), phenol (11.5 mg, 122 umol) and PPh$_3$ (29.1 mg, 117 µmol) were dissolved in anhydrous THF (1.0 mL) at −40° C., the DEAD (25 µL, 192 µmol) was added, followed by stirring for 30 minutes, then diluted with hexane. The precipitate was filtered off, solvent evaporated, and crude product chromatographed (6:1→3:1 hexane:ethyl acetate) to give analog 199 (8.2 mg, 25%) and analog 200 (14.6 mg, 44%) as a yellow products.

Example 65. Synthesis of Analog 201 [6-(acetamidopropyl)acylfulvene]: To a solution of analog 195 (49.1 umol) and water (20 µL in THF (0.5 ml) was added a solution of O-acetyl-2-(diphenylphosphino)phenol (39.0 umol) in THF (0.5 mL). The mixture was stirred for 3 days at RT then concentrated. The crude product was chromatographed (100% ethyl acetate) to yield 8.2 mg of analog 201.

Example 66. Synthesis of Analog 202 (i.e., analog 211 linked to proline): Prepared via Staudinger ligation. To a solution of analog 195 (94 umol) in THF (1.2 mL), water (40 µL) was added, the was added N-Boc-proline, 2-(diphenylphosphino)phenyl ester (101 µmol) in THF (0.8 mL). The mixture was stirred for 3 days at RT then concentrated. The crude product was chromatographed (5:1→1:2 hexanes-ethyl acetate) to yield 31.4 mg (66.7 umol) of analog 202—Boc (71%). The analog 202—Boc was dissolved (66.7 umol) in dioxane (2.0 mL) and 2.0 mL of 2M H$_2$SO$_4$ was added, and the mixture was stirred overnight. Water and ethyl acetate was added, orange color appeared in the aqueous. The aqueous was extracted again with ethyl acetate and organic layer discarded. Sodium bicarbonate was added to aqueous until basic, re-extracted with ethyl acetate. The solution was dried with magnesium sulphate, concentrated to dryness, dissolved in CH$_2$Cl$_2$ and 8 mg of TFA added (1 drop). Analog 202 was obtained in an amount of 22.2 mg (69%).

Example 67. Synthesis of Analog 203: Analog 208 (9.2 mg, 16.5 umol) was dissolved in CH$_2$Cl$_2$ (1.5 mL), 1 drop of anisole added, then 0.5 mL of trifluoro acetic acid for 15 minutes. The mixture was concentrated, dissolved in water, then re-extracted with CH$_2$Cl$_2$, and the orange color remains in the aqueous phase, which was concentrated to give analog 203 as the orange colored TFA salt (10.0 mg).

Example 68. Synthesis of Analog 204: Although the Fmoc-Pro-OH would preferentially react with the primary hydroxyl group on Illudin S, the resulting ester linkage was not stable, as illudin S was recovered after storage in CDCl$_3$ for several days at RT. The secondary hydroxy group of illudin S was therefore used for coupling with peptides. The primary hydroxy group of illudin S first protected with a TBS group (TBSCl, Imidazole, and DMF, 92%) to produce analog 204.

Example 69. Synthesis of Analog 205: Analog 309 (20 mg, 0.050 mmol, 1 equiv.), triphenylphosphine (40 mg, 0.1525 mmol, 3 equiv.) was dissolved in THF (1 mL) at RT. After 20 hours a few drops of water was added and the mixture was heated up at 70° C. After 5 hours the solution was cooled down and evaporated. The residue was chromatographed (hexane/EtOAc/Et$_3$N 4:1:0.1) to give analog 205 (5.3 mg, 29%) as an oil.

Example 70. Synthesis of Analog 206: Analog 205 (14 mg, 0.037 mmol, 1 equiv.) was dissolved in CH$_3$CN (0.5 mL) and pyridine (0.1 mL) at 0° C. To this solution was added HF·Pyridine (7 µL, 0.245 mmol, 35 M, 6.6 equiv.). After 10 min K$_2$CO$_3$ (0.5 mL, 0.5 M) was added and this mixture was chromatographed (CH$_2$Cl$_2$/Methanol/Et$_3$N 5:0.5:0.1) to give analog 206 (10 mg, 68%) as an oil.

Example 71. Synthesis of Analog 207 (211-leucine): Prepared via Staudinger ligation. To a solution of analog 195 (101 umol) in THF (1.0 mL), water (40 µL) was added, then was added N-Boc-leucine,2-(diphenylphosphino)phenyl ester (95.9 µmol) in THF (1.2 mL). The mixture was stirred for 6 days at RT then concentrated. The crude product was chromatographed (1:1 hexanes-ethyl acetate) to yield 27.3 mg of analog 207—Boc. The analog 207—Boc was dissolved (16 µmol) in CH$_2$Cl$_2$ with 3 drops of anisole, TFA was added (0.3 mL), and the mixture was stirred for 15 minutes then concentrated. The crude material was dissolved in water then extracted with CH$_2$Cl$_2$. The aqueous layer was recovered and concentrated to yield 17.4 mg of the analog 207TFA salt (87%).

Example 72. Analog 208: The TFA salt of analog 196 (13.7 mg, 28.2 µmol) was dissolved in anhydrous DMF (2.5 mL), Boc-Serine-OH (9.6 mg, 47 umol) was added, ODHBT (13.0 mg, 79.4 umol), cooled to 0° C. under a nitrogen atmosphere. Next EDC (15.1 mg) was added followed by NMM (10 µL) to adjust pH, and the mixture stirred at 0° C. for 3 hours. The reaction was added to ethyl acetate/water mixture, and the orange product appeared in the organic layer. The aqueous layer was re-extracted with ethyl acetate, organic layers combined, washed with dilute NaHSO$_4$, water, saturated NaHCO$_3$, brine, then dried with MgSO$_4$. The organic layer was concentrated then chromatographed (1:3 hexane:ethyl acetate) to yield analog 208 as an orange residue (63% yield).

Example 73. Synthesis of Analog 209: The TFA salt of analog 196 (12.5 mg, 25.7 µmol) was dissolved in anhydrous DMF (2.5 mL), Boc-Serine-Ser OH (88.6 umol) was added, ODHBT (33.9 mg, 205 umol), cooled to 0° C. under a nitrogen atmosphere. Next EDC (142 umol) was added followed by NMM (10 µL) to adjust pH, and the mixture stirred at 0° C. but allowed to gradually warm as the ice melts. The mixture was stirred a total of 16 hour then 1 mL water added followed by stirring for 50 minutes. The reaction was added to ethyl acetate/water mixture, and the orange product appeared in the organic layer. The aqueous layer was re-extracted with ethyl acetate, organic layers combined, washed with dilute NaHSO$_4$, water, saturated NaHCO$_3$, brine, and then dried with MgSO$_4$. The organic layer was concentrated then chromatographed (10:1 ethyl acetate:methanol) to give analog 209 as an orange residue (5.9 mg, 36% yield).

Example 74. Synthesis of Analog 210 (Ac-Hyp-Ser-Ser-Chg-Gln-Ser-Ser-Pro-O—(CH$_2$)$_3$-acylfulvene): To a mixture of Analog 196 TFA salt (21.6 umol), the peptide Ac-Hyp-Ser-Ser-Chg-Gln-Ser-Ser-OH (30.3 umol), ODHBt (3,4,-dihydroxy-4-oxo-1,2,3-benzo-triazine-3-yl ester, 71.7 µmol) and NMM (N-methylmorpholine; 7.5 ul) in DMF (2.0 ml) at RT was added EDC (1-(3-dimethylaminopropyl)-3-ethylcarbodiimide hydrochloride, 68 µmol), the mixture stirred for 2 hours at RT, then diluted with 10 mL of water. Solution was directly chromatographed on a reverse phase C18 column (4:1→2:1, water/acetonitrile gradient) to yield 69% of analog 210.

Example 75. Synthesis of Analog 212 (Illudin M-proline) Illudin M (20 mg, 0.081 mmol, 1 equivalent), DMAP (1 mg, 0.008 mmol, 0.1 equiv.) and Fmoc-Pro-OH (33 mg, 0.097 mmol, 1.2 equiv.) were dissolved in $CH_2Cl_2$ (1 mL) at 0° C., to which was added a $CH_2Cl_2$ solution of DCC (100 µL, 0.1 mmol, 1 M, 1.2 equiv.). The temperature of the mixture gradually rose to 5° C. in 1.5 hours and then the mixture was filtered through a pad of Celite. The filtrate was concentrated and the residue was chromatographed ($CH_2Cl_2$/EtOAc 5:0.1-5:0.4) to give Illudin-M-proline-Fmoc protected analog (36 mg, 79%) as oil. The proton spectra of this oil showed that it was a mixture of two isomers (rotamers). And then this oil was dissolved in $CH_2Cl_2$ (4 mL) and treated with piperidine (1 mL) at 0° C. After 0.5 hours the solution was concentrated and the concentrate was chromatographed ($CH_2Cl_2$/Methanol 5:0.4) to give analog 212 (15 mg, 54%) as oil.

Example 76. Synthesis of Analog 213: Analog 204 was coupled with Fmoc-Pro-H (DMAP, $CH_2Cl_2$, DCC, 0° C., 85%), followed by deprotection of Fmoc group with 20% piperidine in $CH_2Cl_2$ to produce analog 213 in 78% yield.

Example 77. Synthesis of Analog 214 (Illudin S-Pro-Ser-Ser-HHOAc): The Fmoc protected peptide of H-Ser-Ser-OH was prepared by taking H-Ser-Ser-OH (50 mg, 0.26 mmol, 1 equiv.) and $K_2CO_3$ (89.7 mg, 0.65 mmol, 2.5 equiv.), dissolving in a mixture of water (4 mL) and dioxane (3 mL) at 0° C. To this solution Fmoc (67.3 mg, 0.26 mmol, 1 equiv.) was added in several portions. After 18 hours the mixture was acidified by $KHSO_4$ and the pH raised to 2.5. Then this mixture was taken up by ethyl acetate, which was washed with brine, dried, filtered and evaporated. The residue was chromatographed ($CH_2Cl_2$/Methanol/HOAc 5:1:0.1) to give 3.27 (75 mg, 70%) as a white solid. The analog 212 (Illudin S tosylate-Pro) (42.8 mg 0.09 mmol, 0.9 equiv.), and the Fmoc protected H-Ser-Ser-OH peptide (41.2 mg, 0.1 mmol, 1 equiv.) were dissolved in DMF (1.5 mL) at 0° C. To this solution was added NMM (22 µL, 0.2 mmol, 2 equiv.), ODHBt (29.4 mg, 0.18 mmol, 1.8 equiv.), and EDC (31.1 mg, 0.16 mmol, 1.6 equiv.). The solution temperature was then raised to RT and kept for 3 hours before it was taken up by ethyl acetate. The mixture was then washed with saturated sodium bicarbonate and brine. It was then dried, filtered and evaporated. The residue was chromatographed ($CH_2Cl_2$/Methanol 5:0.3) to give analog 214 (50.5 mg, 67%) as an oil.

Example 78. Synthesis of Analog 215: (Illudin S-Pro-Ser-Ser-Gln-Chg-Ser-Ser-Hyp-Ac) Analog 204 was coupled with Fmoc-Pro-H (DMAP, $CH_2Cl_2$, DCC, 0° C., 85%), followed by deprotection of Fmoc group with 20% piperidine in $CH_2Cl_2$ to produce analog 213 in 78% yield. Peptide conjugate, analog 215 was obtained from further coupling with hepta-peptide Ac-Hyp-Ser-Ser-Chg-Gln-Ser-Ser-OH (ODHBt, NMM, DMF, 0° C., 47%).

Example 79. Synthesis of Analog 216: (Illudin M-Pro-Ser-Ser-Gln-Chg-Ser-Ser-Hyp-Ac). Analog 212 was further coupled with the commercially available hepta-peptide Ac-Hyp-Ser-Ser-Chg-Gln-Ser-Ser-OH (ODHBt, NMM, DMF, EDC, 0° C.) to yield analog 216 at 33%. The low yield resulted from repeated chromatographic purification as the purity of the final raw product was estimated by HPLC to be only 70%.

Example 80. Synthesis of Analog 217: To a solution of Irofulven (1.00 equivalent), epsilon-maleimidocaproic acid (1.27 equivalent), DMAP (0.15 equivalent) in 1.0 mL of methylene chloride ($CH_2Cl_2$) at 0° C., was added DCC (dicyclohexylcarbodiimide; 1.27 equivalent) in methylene chloride ($CH_2Cl_2$). The mixture was stirred for 1.25 hours, diluted with hexane and precipitated was filtered. Residual solvent was evaporated off, and oil residue was chromatographed on a silica column (2:1 hexanes:ethyl acetate) to yield analog 217, an orange compound (77% yield).

Example 81. Synthesis of Analog 218: To a solution of Illudin M (1.00 equivalent), epsilon-maleimidocaproic acid (1.33 equivalent), DMAP (0.18 equivalent) in 1.0 mL of methylene chloride ($CH_2Cl_2$) at 0° C., was added DCC (dicyclohexylcarbodiimide; 1.33 equivalent) in methylene chloride ($CH_2Cl_2$). The mixture was stirred for 2.25 hours, diluted with hexane and precipitated was filtered. Residual solvent was evaporated off, and oil residue was chromatographed on a silica column (2:1 hexane:ethyl acetate) to yield analog 218, an orange compound (83% yield).

Example 82. Synthesis of Analog 219: Analog 204 (33.4 mg) was dissolved in 1.0 mL of anhydrous pyridine under a nitrogen atmosphere, then DMAP (5.1 mg) was added, followed by 4-fluorosulfonyl-benzoyl chloride (86.1 mg). The mixture was stirred for 90 minutes at RT The mixture was diluted with ethyl acetate, washed once with saturated copper sulfate solution, washed twice with water, then dried over $MgSO_4$, concentrated then chromatographed (20% ethyl acetate:hexane) to give analog 219.

Example 83. Synthesis of Analog 221: Prepared from Analog 207 by coupling with Mu-His-Ser-Ser-Lys(Fmoc)-Leu-Gln-OH in DIC/HOBt for 5 minutes, then 5% piperidine/DMF for 1 minute. Followed by TFA quenching to yield analog 221 at 21% yield.

Example 84. Synthesis of Analog 222: Illudin M (63 mg) was dissolved in 1.0 mL of anhydrous pyridine under a nitrogen atmosphere, then DMAP (6.4 mg) was added, followed by 4-fluorosulfonyl-benzoyl chloride (86 mg). The mixture was stirred for 35 minutes at RT then chromatographed (20% ethyl acetate:hexane) to give analog 222 (70.9 mg).

Example 85. Synthesis of Analog 223: The disulfhydryl peptide CNGRC was first converted to a cyclic disulfide peptide by dissolving 355 mg in 3.0 mL DMSO, adding 9 mL of water, allowing to sit overnight at RT, followed by water removal on a rotoevaporator then DMSO removal under high vacuum. The TFA salt of analog 179 (14.5 mg) was dissolved in DMF (2.0 mL) and the CNGRC disulfide peptide added (19.0 mg), 60 µL of DIPEA was added, followed by gradual addition of a solution of Py-BOP (19.6 mg) and HOBt (8.9 mg) in DMF (2.0 mL) over 150 minutes at RT. The reaction was stopped by adding two drops of TFA and water. The mixture was applied to a reverse phase column and analog 223 was eluted with acetonitrile:water (1:4).

Example 86. Synthesis of Analog 224: Analog 001 (116 mg) was dissolved in ethanol (4.0 mL) with stirring, hydroxylamine hydrochloride (84.2 mg) added, Sodium acetate (233 mg) added, then refluxed for 70 minutes at 85° C. The ethanol was removed, then ethyl acetate (10 mL) added to dissolve crude product, then water (10 mL) added, the organic layer was washed with brine, dried over $Na_2SO_4$, concentrated then chromatographed (20% ethyl acetate: hexane) to give analog 224 (63.7 mg, 54% yield).

Example 87. Synthesis of Analog 225: Illudin S (439 mg) was dissolved in ethanol (15 mL) with stirring, hydroxylamine hydrochloride (233 mg) added, sodium acetate (933 mg) added, then refluxed for 130 minutes at 85° C. The solution was cooled to RT, filtered, ethanol was removed, then ethyl acetate (30 mL) added to dissolve crude product, then water (30 mL) added, the organic layer was washed with brine, dried over Na$_2$SO$_4$, concentrated then chromatographed (30%→50%, acetone:hexane) to give analog 225 (372 mg, 80% yield).

Example 88. Synthesis of Analog 226: Irofulven (37.6 mg) was dissolved with stirring in CH$_2$Cl$_2$, elaidic acid (180 mg. 1.3 equivalents) added, DMAP (15 mg) added, cooled to 0° C., then DCC (180 µL) in CH$_2$Cl$_2$ (640 µL) added. Reaction mixture stirred at 0° C. for 1 hour, then additional DCC (120 µL) added, and stirred for 2 more hours. Mixture chromatographed (20% ethyl acetate:hexane) to give analog 226 as a yellow oil (50.5 mg, 48% yield).

Example 89. Synthesis of Analog 227: Analog 009 (87 mg) was dissolved with stirring in CH$_2$Cl$_2$, elaidic acid (108 mg) added, DMAP (15.4 mg) added, cooled to 0° C., then DCC (0.5 mL) in CH$_2$Cl$_2$ (1.5 mL) added. Reaction mixture stirred at 0° C. for 3 hours, then the mixture directly chromatographed (20% ethyl acetate:hexane) to give analog 227 as a yellow oil (105 mg, 61% yield).

Example 90. Synthesis of Analog 228: Illudin S (86 mg) was dissolved with stirring in CH$_2$Cl$_2$, elaidic acid (202 mg) added, DMAP (15.4 mg) added, cooled to 0° C., then DCC (1.0 mL) in CH$_2$Cl$_2$ (3.0 mL) added. Reaction mixture stirred at 0° C. for 3 hours, then the mixture directly chromatographed (20% ethyl acetate:hexane) to give analog 228 as a yellow oil (198 mg, 77% yield).

Example 91. Synthesis of Analog 229: The elaidic ester of 0-diphenylphosphine phenol was first prepared by dissolving with stirring in 3.0 mL of CH$_2$Cl$_2$ the 0-diphenylphosphine phenol (91.3 mg), elaidic acid (94.5 mg, 1 equivalent), DMAP (9.4 mg). The solution was cooled to 0° C. then DDC (0.44 mL, 1.0 M in CH$_2$Cl$_2$) was added with stirring for 3.5 hours. The precipitate was filtered off and discarded. The elaidic ester was chromatographed and concentrated to dryness then dissolved in THF (1.0 mL). Analog 195 (26.1 mg) was dissolved in THF (1.0 mL) and water (80 µL) added. The elaidic ester solution was slowly added to the analog 195 solution with stirring, and reacted for 22 hours at RT. The mixture was directly chromatographed (30% acetone:hexane) to give analog 229 (22.2 mg, 47% yield).

Example 92. Synthesis of Analog 230: Analog 308 (22 mg) was dissolved in anhydrous CH$_2$Cl$_2$ (1.5 mL), diisopropylethylamine (20 µL) added, and the mixture cooled to 0° C., then methylsulfonyl chloride added (15 µL), mixture stirred at 0° C. for 1 hour, and allowed to warm to RT while being stirred for an additional hour. The mixture was chromatographed (30% ethyl acetate in hexane) to yield analog 230 (35% yield).

Example 93. Synthesis of Analog 231: Analog 308 (16 mg) was dissolved in anhydrous CH$_2$Cl$_2$ (1.5 mL), diisopropylethylamine (20 µL) added, and the mixture cooled to 0° C., then tosyl chloride added (18.4 mg), mixture stirred at 0° C. for 1 hour, and allowed to warm to RT while being stirred for an additional 3 hours. The mixture was chromatographed (30% ethyl acetate in hexane) to yield analog 231 (8.6 mg).

Example 94. Synthesis of Analog 240: Analog 232 (25.1 mg) was dissolved in anhydrous CH$_2$Cl$_2$ (2.0 mL), 15 µL of acetic anhydride added, and the mixture cooled to RT, then DMAP added (5 mg), and stirred for 25 minutes. The mixture was partially concentrated then chromatographed (30% ethyl acetate in hexane) to yield analog 240 (26.6 mg, 93% yield).

Example 95. Synthesis of Analog 254: Analog 009 (51.4 mg), 4-carboxybenzene sulfonamide (59.4 mg), and DCC (39.6 mg) were dissolved in anhydrous DMF (1.0 mL) at RT, stirred, then DMAP (15 mg) added. The mixture was stirred for 2 hours at RT then solid material was filtered off. The mixture was then chromatographed (1:1 ethyl acetate:hexane) to give analog 254 (38.6 mg, 45% yield).

Example 96. Synthesis of Analog 255: Analog 009 (244.3 mg) and sulfamoyl chloride (157 mg) were dissolved in anhydrous DMAP (2.0 mL) at RT, and stirred for 3.5 hours. The mixture was concentrated under high vacuum then chromatographed (30% ethyl acetate in hexane) to give analog 255.

Example 97. Synthesis of Analog 259: Analog 255 (64.7 mg), (diacetoxyiodo)benzene (64.7 mg), dirhodiumtetraacetate or Rh$_2$(OAc)$_4$ and magnesium (16.8) dissolved in 5.0 mL of CH$_2$Cl$_2$ are heated to 70° C. and stirred for 7 hours. The mixture was filtered, concentrated, then chromatographed (1:1 ethyl acetate:hexane) to give analog 259.

Example 98. Synthesis of Analog 262 and 263 (prepared together): Analog 025 (44.7 mg) was dissolved in methanol (1.0 mL), Oxone® reagent (246 mg, 3 equivalents) was dissolved in water (1.0 mL). The oxone solution was slowly added to the methanol solution with stirring at RT for 3.5 hours, then an additional amount of Oxone reagent added followed by stirring for 1.5 hours. Then 2 mL of saturated sodium sulfite solution was added, followed by ethyl acetate extraction, dried over Na$_2$SO$_4$, concentrated then chromatographed (1:1 Ethyl acetate:hexane) to yield first analog 263 (21.4 mg) and then analog 262 (14.3 mg).

Example 99. Synthesis of Analog 284 and 289 (prepared together): Analog 034 (174 mg) and uracil (227 mg) are dissolved in CH$_2$Cl$_2$ with stirring and the mixture cooled to 0° C. Then SnCL$_4$ (148.8 µL) was slowly added. The mixture was stirred at 0° C. for 80 minutes, then concentrated, chromatographed (2→5% methanol:CH$_2$Cl$_2$) to give analog 284 (68.9 mg, 33% yield) and analog 289 (21.6 mg, 10% yield).

Example 100. Synthesis of Analog 285: Analog 034 (25 mg) was dissolved in ethanol, and O-(tert-Butyldimethylsilyl) hydroxylamine (25 mg) was added followed by stirring for 2 hours at RT. The secondary amine intermediate (9 mg) was recovered by chromatography (30% ethyl acetate:hexane), dissolved in CH$_2$Cl$_2$, and reacted with sulfamoyl chloride (ClSO$_2$NH$_2$, 5 mg) and DABCO (2 mg) with stirring for one hour, then additional sulfamoyl chloride (6 mg) was added with stirring for another 1.5 hours. The TPS blocked product was recovered by chromatography (30% ethyl acetate:hexane), and the TPS group was removed in THF by adding TBAF (Tetra-n-butylammonium fluoride). The TPS group can also be removed by dissolving the TPS product in pyridine and THF at 0° C., then adding HF-pyridine overnight. After TPS deblocking the mixture was chromatographed (50% ethyl acetate:hexane) to give analog 285.

Example 101. Synthesis of Analog 286 and analog 287 (prepared together): The ketone groups on 5-fluorouracil are first blocked with TMS groups by dissolving 5-fluorouracil (610 mg) and (NH$_4$)$_2$SO$_4$ in HMDS (10 mL) under a nitrogen atmosphere. The solution was refluxed at 142° C. for 2.5 hours, cooled to 60° C. and excess HMDS distilled off, then concentrated to dryness under high vacuum. Analog 034 (180 mg) and the di-TMS 5-fluorouracil are dissolved in CH$_2$Cl$_2$ (5.0 mL) with stirring and the mixture cooled to 0° C. Then SnCL$_4$ (120 µL) was slowly added drop wise. The mixture was stirred at 0° C. for 3.5 hours, then concentrated, chromatographed (80% ethyl acetate:hexane) to give analog 286 (18.9 mg, 9% yield) and analog 287 (84 mg, 38% yield).

Example 102. Synthesis of Analog 289: See the preparation of analog 284 for the preparation of analog 289 (284 and 289 prepared simultaneously then separated by chromatography).

Example 103. Analogs 299 and 300 (prepared together): Analogs 299 and 300 are prepared in equal amounts from Illudin S using the Mitsunobu reaction. Illudin S was directly reacted with $HN_3$(PPh3, DEAD, benzene) at 0° C. under nitrogen for 45 minutes. Mitsunobu, O. *Synthesis* 1:1-28, 1981.

Example 104. Synthesis of Analog 301: Irofulven (31.6 mg, 0.128 mmol), 5-benzoylvaleric acid (35.8 mg, 0.174 mmol) and DMAP (4.7 mg) was dissolved in $CH_2Cl_2$ (2 mL) under a nitrogen atmosphere, cooled to 0° C., the DCC added (170 µL of 1.0M solution in $CH_2Cl_2$). The mixture was stirred for 60 minutes then diluted with hexane (10 mL) and filtered. The organic layer was further diluted with $CH_2Cl_2$, washed with water, then saturated $NaHCO_3$ then brine, dried with $MgSO_4$, concentrated, then dissolved in $CH_2Cl_2$, filtered and chromatographed (10:3 hexane:ethyl acetate), appropriate fractions collected, pooled, concentrated then chromatographed (3:1 hexane:ethyl acetate) to give analog 301 (23.2 mg, 42% yield).

Example 105. Analogs 302 and analog 303 (prepared together): Illudin S (100 mg, 0.378 mmol) was benzoylated by dissolving in pyridine (1.0 mL) then adding 3,5-dintirobenzoyl chloride (110 mg, 0.5 mmol) at RT and stirring for 24 hours. The mixture was poured onto crushed ice then extracted with $CH_2Cl_2$ (10 mL), which was washed twice with water (20 mL). The organic layer was dried over $Na_2SO_4$ and concentrated to yield analogs 302 and 303. The two analogs can be separated by column chromatography (1:1 hexane:ethyl acetate).

Example 106. Synthesis of Analog 304: Analog 009 (84.6 mg) was dissolved in anhydrous $CH_2Cl_2$ (3.0 mL), DCC added (81.2 mg), mixture cooled to 0° C., propiolic acid (35 µL) added, then the reaction started with DMAP (15 mg), stirred and allowed to warm to RT over 1 hour. The mixture was filtered to remove solids then chromatographed (30% ethyl acetate in hexane) to give analog 304 (60% yield).

Example 107. Synthesis of Analog 305: Analog 009 (99.1 mg) was dissolved in anhydrous $CH_2Cl_2$ (3.0 mL), pyridine (150 µL) added, then p-nitrophenylchloroformate and stirred for 3.5 hours at RT. The mixture was concentrated, hexane (20 mL) added, and precipitate filtered before chromatographing (50% ethyl acetate in hexane) to give analog 305 (50% yield).

Example 108. Synthesis of Analog 306: Analog 009 (244 mg) was dissolved in anhydrous $CH_2Cl_2$ (4.0 mL), tosyl chloride (181 mg) added, the mixture cooled to 0° C., to which an aliquot of pyridine (80 µL) was added. The mixture stirred at 0° C. for 1 hour, and allowed to warm to RT while being stirred for an additional 20 hours. The mixture was concentrated then chromatographed (50% ethyl acetate in hexane) to yield analog 306.

Example 109. Synthesis of Analog 307: A solution of 1.0 M $N_3H$ in benzene was first prepared by mixing 654 mg $N_3H$, 0.65 mL water, in 10 mL of benzene. The mixture was cooled to 0° C., 0.5 mL of concentrated $H_2SO_4$ added, and allowed to warm slowly to RT and then stirred for 80 minutes. Next $PPh_3$ (590 mg) was dissolved in anhydrous THF (1.5 mL) and cooled to 0° C. Then 2.1 mL of $N_3H$ 1.0 M solution was added, followed by DEAD (0.475 mL) then Illudin S (282 mg in 1.0 mL anhydrous THF). The mixture was stirred for 3 hours at 0° C., warmed, concentrated, followed by chromatography (30% ethyl acetate in hexane) to give analog 307.

Example 110. Synthesis of Analog 308: Analog 307 (100 mg) was dissolved in anhydrous THF (3.0 mL) at RT and PPH3 added (306 mg, 3 equivalents). The mixture was stirred for 5 hours at RT, then the reaction stooped by adding water (0.15 mL). The mixture was heated to 85° C. for 30 minutes, then concentrated and chromatographed (20% methanol in ethyl acetate) to give analog 308.

Example 111. Synthesis of Analog 309: Analog 204 was reacted with $HN_3$ (DEAD, THF) to yield the azide analog 309 at 68% yield.

Example 112. Synthesis of Analog 310: Irofulven (42.9 mg), 4-carboxybenzene sulfonamide (41.4 mg), and DCC (38.4 mg) were dissolved in anhydrous DMF (1.0 mL) at RT, stirred and then DMAP (10 mg) added. The mixture was stirred for 75 minutes at RT then solid material was filtered off. The mixture was then chromatographed (1:1 ethyl acetate:hexane) to give analog 310 (40% yield).

Example 113. Synthesis of Analog 311: Illudin M (32.4 mg), 4-carboxybenzene sulfonamide (39.7 mg), and DCC (24.4 mg) were dissolved in anhydrous DMF (1.0 mL) at RT, stirred, then DMAP (15 mg) added. The mixture was stirred for 75 minutes at RT, allowed to warm to RT, then stirred for 22 hours. The solid material was filtered off and the mixture was then chromatographed (1:1 ethyl acetate:hexane) to give analog 311 (35% yield).

Example 114. Synthesis of Analog 312: Irofulven (1.18 grams) was dissolved in anhydrous $CH_2Cl_2$ (4.0 mL), tosyl chloride (1.1 equivalent) added, the mixture cooled to 0° C., then pyridine (0.4 mL) added. The mixture stirred at 0° C. for 1 hour, and allowed to warm to RT while being stirred for an additional 3 hours. The mixture was concentrated then chromatographed (50% ethyl acetate in hexane) to yield analog 312.

Example 115. Synthesis of Analog 313: Analog 308 (31 mg) was dissolved in anhydrous $CH_2Cl_2$, cooled to 0° C., with stirring then diisopropylethylamine added (45 µL), then fluorophenylsulfonyl chloride added (36 µL) for 3 hours at 0° C. Mixture was directly chromatographed (20% ethyl acetate:hexane) to give analog 313 (23.3 mg).

Example 116. Synthesis of Analog 314: Analog 009 was dissolved in anhydrous $CH_2Cl_2$ (4.0 mL), tosyl chloride (1.1 equivalent) added, the mixture cooled to 0° C., then pyridine (0.4 mL) added. The mixture stirred at 0° C. for 1 hour, and allowed to warm to RT while being stirred for an additional 3 hours. The mixture was concentrated then chromatographed (50% ethyl acetate in hexane) to yield analog 314.

Example 117. Synthesis of Analog 315: Irofulven was dissolved in a solution of 2,5 dimethylpyrrole (4 fold excess molar solution) in 5 mL of dry $CH_2Cl_2$ at −78° C. Boron trifluoride (equivalent molar amount to the irofulven) was slowly added with stirring. The reaction was allowed to stir for 2 more hours at −78° C., then water slowly added. The mixture was extracted twice with 2 fold equivalent volumes of ethyl acetate, the organic extracts combined, washed with saturated $NaHCO_3$, water, brine, then dried over $MgSO_4$. The solution was concentrated under vacuum until a red residue remained, which was chromatographed on silica gel (50% ethyl acetate in hexane) to yield analog 315 (30% yield).

Example 118. Synthesis of Analog 316: Analog 316 was prepared by dissolving Illudin S (20 mg) in pyridine (0.5 mL) and then 4-fluorosulfonylbenzoyl chloride (equivalent molar amount) was added to the mixture in an ice bath. The solution was allowed to warm slowly and then react overnight. The liquid was then removed under reduced pressure until a crude residue remained. Rather than recrystallize from chloroform, the residue was instead chromatographed on a standard silica gel column using hexane-ethyl acetate (1:1). The mono-adduct (analog 316), a di-adduct and a small amount of unreacted Illudin S were recovered in separate eluates.

Example 119. N₃H 1.0 M Solution: A solution of 1.0 M N3H in benzene was first prepared by mixing 654 mg N₃H, 0.65 mL water, in 10 mL of benzene. The mixture was cooled to 0° C., 0.5 mL of concentrated $H_2SO_4$ added, and allowed to warm slowly to RT and then stirred for 80 minutes.

Example 120. Synthesis of Analog 193: Irofulven (221 mg, 0.897 umol) was dissolved in anhydrous THF (1.5 mL), then PPh₃ (261 mg, 0.995 umol) was added, then 1.0 M N₃H solution (1.0 mL, 1.0 mmol) under nitrogen atmosphere. The solution was cooled to −40° C., and then DIAD (0.21 mL, 1.013 umol) added and stirred for 30 minutes at 0° C. then diluted with hexane, and filtered to remove precipitate. The mixture was concentrated then chromatographed (30% ethyl acetate:hexane) to give analog 193 (171 mg, 71%).

Example 121. Synthesis of Analog 195: Analog 009 (31.9 mg, 116 umol) was dissolved in anhydrous THF (3.0 mL), then PPh₃ (33 mg, 126 umol) was added, then 1.0 M N₃H solution (0.3061 mL) under nitrogen atmosphere. The solution was cooled to 0° C., DIAD (30 μL, 145 umol) added and stirred for 30 minutes at 0° C. then water (5 μL) was added to destroy the PPh₃. The mixture was concentrated then chromatographed (30% ethyl acetate:hexane) to give analog 195 (24.9 mg, 72%).

Example 122. Synthesis of Analog 317: Analog 219 (33 mg) was dissolved in anhydrous acetonitrile (0.5 mL) and pyridine (0.1 mL) at 0° C. under nitrogen. Then add HF-pyridine solution (7 uL, 0.245 mmol, 35M, 6.6 equiv). After 10 minutes $K_2CO_3$ was added (0.5 mL, 0.5M) and the mixture concentrated then chromatographed using $CH_2Cl_2$, methanol, triethylamine (5:0.5:0.1) to yield analog 317.

Example 123. Synthesis of Analog 318: Illudin S (30 mg) was dissolved in 1.0 mL of anhydrous pyridine under a nitrogen atmosphere, then DMAP (5.0 mg) was added, followed by excess 4-fluorosulfonyl-benzoyl chloride (190 mg). The mixture was stirred for 90 minutes at RT then diluted with 5.0 mL of ethyl acetate, washed once with saturated copper sulfate solution, washed twice with water, then dried over $MgSO_4$, concentrated then chromatographed (20% ethyl acetate:hexane) to give analog 318.

Example 124. Synthesis of Analog 332: Analog 034 (200 mg) was dissolved in ethanol (95%) at RT, then 300 mg of O-methylhydroxylamine hydrochloride ($NH_2OMe$ HCl; Note O-methyl not the N-methyl compound) was added with sodium acetate (300 mg), stirred for 6 hours, concentrated, then chromatographed (15% ethyl acetate/hexanes) to yield the analog 332.

Example 125. Synthesis of Analog 333: Prepared by dissolving analog 159 and p-nitrophenylchloroformate in anhydrous $CH_2Cl_2$ under nitrogen for 5 hours at 0° C. with 1.5 equivalents of DIPEA and 1.0 equivalents of DMAP. The $CH_2Cl_2$ was removed and analog 333 was purified using a 7% ethyl acetate/hexane column. Yield was 70%.

Example 126. Synthesis of Analog 334: Prepared by dissolving analog 159 and p-nitrophenylchloroformate in anhydrous $CH_2Cl_2$ under nitrogen at 0° C. with 1.5 equivalents of DIPEA and 1.0 equivalents of DMAP. After 5 hours the Boc-N,N'-dimethylaminoethane was added and the mixture kept at 0° C. under nitrogen for 2 hours then allowed to warm up to RT and react overnight. The $CH_2Cl_2$ was removed and analog 334 purified using a 15% ethyl acetate/hexane column.

Example 127. Synthesis of Analog 335: Analog 334 (19 μmole) was dissolved in 1 mL of methanol and then sodium methoxide in methanol (0.5 M, 100 μmole) was added at RT with stirring for 30 minutes. The reaction was quenched by addition of excess acetic acid (40 μmole). The methanol was removed and analog 335 purified using a 25% ethyl acetate/hexane column.

Example 128. Synthesis of Analog 336: Analog 002 (200 mg) was placed in a dry round bottom, add 10 mL anhydrous $CH_2Cl_2$, stir at 0° C. under nitrogen, add aluminum trichloride (AlCl3). The mixture will turn dark orange, stir additional 10 min at 0° C., add 20 mL of ethylene oxide/$CH_2Cl_2$ solution at 0° C., stir for 30 minutes at 0° C. Wash twice with 10% HCl/ice cold water (2×50 mL), then twice with water (2×25 mL), dry over $Na_2SO_4$, concentrate under reduced pressure and chromatograph using ethyl acetate/hexane mixture.

Example 129. Synthesis of Analog 337: Analog 270 (244 mg) was dissolved in 5.0 mL of $CH_2Cl_2$ and DABCO added (153 mg), and solution cooled to 0° C. Then p-nitrophenylchloroformate (162 mg) was added with stirring for 3 hours at 0° C. Mixture was concentrated and chromatographed (50% ethyl acetate 50% hexanes) to yield 201 mg of analog 337 as a yellow liquid.

Example 130. Synthesis of Analog 338: Analog 211 (82 mg) was dissolved in 5.0 mL of $CH_2Cl_2$ and DABCO added (42 mg), and solution cooled to 0° C. Then p-nitrophenylchloroformate (51 mg) was added with stirring for 5 hours at 0° C. Mixture was concentrated and chromatographed (50% ethyl acetate 50% hexanes) to yield 63 mg of analog 338 as a yellow liquid.

Example 131. Synthesis of Analog 339: Illudin S is dissolved in anhydrous $CH_2Cl_2$ (4.0 mL), tosyl chloride (1.1 equivalent) added, the mixture cooled to OC, then pyridine (400 uL) added. The mixture stirred at OC for 1 hour, and allowed to warm to RT while being stirred for an additional 3 hours. The mixture is concentrated then chromatographed (50% ethyl acetate in hexane) to yield analog 339.

Example 132. Synthesis of Analog 340: Analog 270 (146 mg), DABCO (90 mg) was dissolved in DMF/$CH_2Cl_2$ (1:3; 5.0 mL), cooled to 0° C., then methane sulfonyl chloride (55 uL; Cl—$SO_2$—$CH_3$) added with stirring for 2 hours at 0° C., concentrated then chromatographed using ethyl acetate/hexane=(1:1) to yield analog 340 as a yellow liquid.

Example 133. Synthesis of Analog 347: Illudin S (35 mg) was dissolved in 1.0 mL of anhydrous pyridine under a nitrogen atmosphere, then DMAP (5.0 mg) was added, followed by 4-sulfamidobenzoyl chloride (90 mg). The mixture was stirred for 90 minutes at RT then diluted with ethyl acetate, washed once with saturated copper sulfate solution, washed twice with water, then dried over MgSO4, concentrated, then chromatographed (20% ethyl acetate: hexane) to give analog 347.

Example 134. Synthesis of Analog 348: Illudin M (15 mg) was dissolved in 1.0 mL of anhydrous pyridine under a nitrogen atmosphere, then DMAP (3.0 mg) was added, followed by 4-sulfamidobenzoyl chloride (33 mg). The mixture was stirred for 90 minutes at RT then diluted with ethyl acetate, washed once with saturated copper sulfate solution, washed twice with water, then dried over $MgSO_4$, concentrated then chromatographed (20% ethyl acetate: hexane) to give analog 348.

Example 135. Synthesis of Analog 353: Analog 334 was dissolved in anhydrous $CH_2Cl_2$ at 0° C. and TFA added to a final concentration of 40% for 40 minutes to remove the Boc protecting group. The reaction was stopped by adding additional anhydrous $CH_2Cl_2$ to dilute the final TFA concentration to 10%, then solvent and TFA removed using a roto-evaporator without heat. Next the residue was dissolved in peptide synthesis grade DMF (so no solvent amines are present) and commercially available analog 388 was added at 0° C., followed by triethylamine (8.0 equivalents) with stirring overnight. After concentration the material was purified by preparative HPLC. Solvent A (aqueous) was 0.1% TFA in water. Solvent B (organic) was 60% acetonitrile, 39.9% water, and 0.1% TFA. HPLC gradient was initially 60% B increasing to 100% B over 45 minutes, with analog 353 eluting at approximately 40 minutes.

Example 136. Synthesis of Analog 356: Dissolve analog 334 in $CH_2Cl_2$ at 0° C., then add ice cold TFA to a final concentration of 25%, for 30 minutes to remove Boc group. Excess TFA removed by evaporating to dryness under vacuum, then add 0.5 ml $CH_2Cl_2$, evaporating to dryness under vacuum, repeat $CH_2Cl_2$ addition and evaporation a total of 3 times and keep on ice/cold the entire time. Add 1 ml dry DMF, add triethylamine (5 equiv), and keep on ice. Part B: Take Fmoc-triglycine-OH peptide (1.1 equiv) and dissolve in 3 mls dry DMF at RT, then add EDC (1.1 equiv) and NHS (N-hydroxysuccinimide, 1.1 equiv) to form the active ester, and cool on ice. Add solution B to A on ice, then allow to warm in chiller to RT overnight to produce 356 (yield ~60%).

Example 137. Synthesis of Analog 357: Prepared by dissolving analog 359 in $CH_2Cl_2$ at 0° C., then adding ice cold TFA to a final concentration of 25%, for 30 minutes. Excess TFA removed by evaporating to dryness under vacuum, adding 0.5 ml $CH_2Cl_2$, evaporating to dryness under vacuum total of 3 times.

Example 138. Synthesis of Analog 359: Part A: Dissolve analog 334 in $CH_2Cl_2$ at 0° C., then adding ice cold TFA to a final concentration of 25%, for 30 minutes to remove Boc group. Excess TFA removed by evaporating to dryness under vacuum, adding 0.5 ml $CH_2Cl_2$, evaporating to dryness under vacuum, repeat $CH_2Cl_2$ addition and evaporation a total of 3 times, and keep on ice/cold the entire time. Add 1 ml dry DMF, add triethylamine (5 equiv), and keep on ice. Part B: Take Boc-triglycine-OH peptide (1.1 equiv) and dissolve in 3 ml thy DMF at RT, then add EDC (1.1 equiv) and NHS (N-hydroxysuccinimide, 1.1 equiv) to form the active ester, and cool on ice. Add solution from Part B to solution from Part A on ice, then allow to warm in chiller to RT overnight to produce analog 359.

Example 139. Synthesis of Analog 361: Add analog 159 and N,N'-Disuccinimidyl carbonate (1.1 equiv) in anhydrous dichloromethane, DIPEA (1.1 equiv) and DMAP (1.1 equiv), reflux for four hours.

Example 140. Synthesis of Analog 362: Illudin S and 1.2 equivalents of mesylate anhydride, and 1.2 equivalents of 2,4,6-collidine into dry $CH_2Cl_2$, use molecular sieves. Start the reaction at 0° C. (on ice) then let sit overnight, gradually warming up to RT. The reaction mixture remained colorless, and analog 362 was isolated as a white crystalline material using ethyl acetate/hexane chromatography.

Example 141. Synthesis of Analog 363: Parik-Doering reaction was used with analog 383 in which pyridine sulfur trioxide was used in combination with DIPEA and DMSO under strict anhydrous conditions. At 0° C. the reaction mix contained a minor amount of product compatible with analog 383 when analyzed by LC/MS. When the reaction was precooled to −20° C., allowed to react with illudin S, and then slowly warmed to 0° C., analog 383 was produced at ~60% yield. Analog 383 was reacted with $NH_2$-Boc in the presence of TFA and triethylsilane under the same conditions that analog 002 was reacted with $NH_2$-Boc to produce analog 366. However, the yields were very low at <15%. Analog 383 and 1.1 equivalent of $NH_2$-Boc were dissolved in anhydrous DCM with molecular sieves, 0.2 equivalents of acetic acid added (to produce the —C=N—HR intermediate), and allowed to sit overnight. In the morning sodium triacetoxyborohydride was added (4 equivalents) and the reaction allowed to proceed for 6 hours to produce analog 389. Analog 389 was converted to the primary amine analog 363 using standard Boc deprotection method.

Example 142. Synthesis of Analog 365. Illudin S (150 mg) was reacted with Dess Martin Periodinane reagent (1.1 equiv) for 60 minutes at RT in 15 mls $CH_2Cl_2$ (no molecular sieves are used as traces of water accelerate the reaction). Solvent removed and analog 365 (110 mg) recovered using ethyl acetate/hexane chromatography.

Example 143. Synthesis of Analog 366. Add 5 mg of analog 002 into a small vial with 50 uL of acetone, added $BocNH_2$ 6.5 mg (2.5 equiv), started reaction with 20 ul of 1 N $H_2SO_4$, allowed to go overnight at RT. The yield was >80%.

Example 144. Synthesis of Analog 367: Analog 010 (80 mg) was dissolved in 3 ml of anhydrous acetonitrile with molecular sieves. Add 102 mg $NH_2Boc$ (3 equiv), 140 ul $Et_3SiH$ (3 equiv) stirred at RT for 30 minutes with sieves under nitrogen, added 63 uL of TFA (2.9 equiv). Within 30 minutes solution turning from yellow to red. Eventually turns dark brown (amine product). The solvent was removed, and compound isolated using ethyl acetate/hexane chromatography.

Example 145. Synthesis of Analog 368: Illudin S (185 mg, 0.522 mmol), DIPEA 329 mg/444 ul (5 equiv), was dissolved in 5 ml THF, add acetic anhydride 260 ul (5 equiv) and DMAP 62 mg (1 equiv) and monitor reaction at RT. To recover and purify use an acetone/hexane column (0% acetone, then 2, 4, 6% etc.).

Example 146. Synthesis of Analog 369. Illudin S (1.025 grams) and 385.1 mg of imidazole (1.46 equiv) into 8 mls dry DMF with molecular sieves and stirred for 25 minutes at RT under nitrogen, then 686 mg of TBDMSCl added (1.17 equiv) in two equal portions. The reaction was over in 20 minutes per TLC. Add saturated sodium bicarbonate to quench reaction, extracted ethyl acetate three times, organic phase recovered and washed with brine, and dried with anhydrous magnesium sulfate, then solvent removed under high vacuum and temperature of 45° C.

Example 147. Synthesis of Analog 370: Analog 369 was dissolved in DMF then added to 10 mls of $CH_2Cl_2$, then 316 mg of sodium acetate added (1 equiv), stirred for RT for 15 minutes, then acetic anhydride added (1.02 equiv), and allowed to react overnight. The reaction may not progress unless DMAP was added (0.2 equiv). The next day additional sodium acetate (150 mg, 0.3 equiv) and acetic anhydride (185 ul; 0.5 equiv) and DMAP (0.2 equiv) added. The next day solvent removed under high vacuum and temperature of 45° C.

Example 148. Synthesis of Analog 371: Analog 368 was dissolved in excess 7N $NH_3$/methanol and allow to react slowly for 48 to 72 hours at 40° C. then the primary acetate was selectively removed and analog 371 was primarily produced with a yield of ~65% (illudin S was the other product at ~35%).

Example 149. Synthesis of Analog 372: Dissolve 320 mg of #371 and 620 mg of Dess Martin (1.2 equiv) into 4 mls $CH_2Cl_2$ (no molecular sieves are used as traces of water accelerate the reaction), allowed to react for 45 minutes. Then added 3 mls of saturated bicarbonate, 3 mls of saturated $Na_2S_2O_3$ (to quench Dess Martin reagent), then 15 mls of diethyl ether. Wash the reaction mixture twice more with diethyl ether, dry with anhydrous sodium sulfate and then remove the ether. Store overnight then purified with column (elutes at 15% ethyl acetate/hexane).

Example 150. Synthesis of Analog 373: Place 4.5 mg of analog 372 in 200 ul anhydrous $CH_2Cl_2$ with several molecular sieves. Add triethylsilane (3.0 equiv), TFA (2.9 equiv) and $FmocNH_2$ (3.0 equiv) in dry THF at RT for 6 hours under nitrogen. Purify by ethyl acetate/hexane gradient column. Yield ~40%.

Example 151. Synthesis of Analog 374: The Fmoc moiety of analog 373 was removed using 4-methylpyridine (20% final) in DMF at RT for 30 minutes.

Example 152. Synthesis of Analog 377: Dissolve analog 159 into dry $CH_2Cl_2$ with molecular sieves, add imidazole (1.1 equiv) and stir for 30 minutes at RT. Then 1.2 equiv of TBSCl (chlorotributyl silane) added. After 15 minutes add 0.3 equiv of additional TBSCl.

Example 153. Synthesis of Analog 378: 4.5 mg of analog 372 in 200 ul DMF with molecular sieves under nitrogen. Add triethylsilane (3.0 equiv), TFA (2.9 equiv) and $BocNH_2$ (3.0 equiv) at RT for 6 hours under nitrogen. Purify by ethyl acetate/hexane gradient column. Yield ~40%.

Example 154. Synthesis of Analog 379: Analog 359: Part A: Dissolving analog 334 in $CH_2Cl_2$ at 0° C., then adding ice cold TFA to a final concentration of 25%, for 30 minutes to remove Boc group. Excess TFA removed by evaporating to dryness under vacuum, adding 0.5 ml $CH_2Cl_2$, evaporating to dryness under vacuum total of 3 times and keep on ice/cold the entire time. Add 1 ml thy DMF, triethylamine (5 equiv), and keep on ice. Part B: Take Fmoc-triglycine-Val-cit-PNP peptide (1.1 equiv) and dissolve in 3 mls of dry DMF at 0° C. Add solution B to A on ice, then allow to warm in chiller to RT overnight to produce 379.

Example 155. Synthesis of Analog 380: Prepare from analog 379 by removing Fmoc using 4-methylpyridine (20% final) in DMF at RT for 30 minutes.

Example 156. Synthesis of Analog 381: Prepare from analog 377 using lithium hydroxide (LiOH) (1.0 equiv) in 10% methanol/THF at 4° C. One must have methanol otherwise LiOH acts as a nucleophile and removes the TBS, not the acetate protective group. After 1 hour then add additional 0.2 equiv LiOH, then after 30 minutes remove THF/methanol. Purify immediately using ethyl acetate/hexane column to prevent degradation.

Example 157. Synthesis of Analog 382. Add 0.5 equiv of Dess Martin periodinane reagent to analog 381 at RT in $CH_2Cl_2$. Add another 0.5 equiv after 30 minutes, then another 0.2 equiv after 30 minutes. Added 3 ml saturated bicarbonate, 3 ml of saturated $Na_2S_2O_3$ (to quench Dess Martin reagent), then 15 mls of diethyl ether. Wash reaction mix 2 more times with diethyl ether, dry with anhydrous sodium sulfate and remove ether. The product can be stored overnight then purified with column.

Example 158. Synthesis of Analog 383: Prepared from Analog 382 by treating with 1.5% HCl/methanol at RT for 60 minutes. If one sees a smear by TLC, then leave at 4° C. overnight, and in the morning one will see a main product by TLC that was analog 383. Yield was poor as normally less than 25%.

Example 159. Synthesis of Analog 384: Analog 382 was dissolved in 1.5 ml anhydrous acetonitrile, then add $BocNH_2$ (3.0 equiv), then triethylsilane (3.0 equiv), followed by TFA (2.9 equiv) for 5 hours at RT. Best to add TFA in aliquots so as to not remove the protecting silyl group. Recover product using 10% acetone/hexane column (not ethyl acetate column), but still the yield was low at ~15%.

Example 160. Synthesis of Analog 385: Illudin S (10 mg) was dissolved in anhydrous methanol with molecular sieves; add 0.5 equiv of Indium (II) chloride, 2.0 equiv of triethylsilane). Let sit at RT overnight, remove methanol, and purify using an ethyl acetate/hexane column.

Example 161. Synthesis of Analog 387: Dissolve the boc-triglycine (20 mg/ml) in DMF, then add EDC (0.98 equiv) and pentafluorophenol (1.15 equiv) at RT for 2 hours. Evaporate with high vacuum at 40° C. then add ethyl acetate. If solids present remove by filtration. Wash with saturated sodium bicarbonate solution to remove unreacted triglycine acid and unreacted pentafluorophenol, then wash with brine, dry and evaporate to a flaky white solid. (when an oil was obtained simply add diethyl ether to precipitate a flaky white solid).

Example 162. Synthesis of Analog 389: Analog 383 and 1.1 equivalent of $BocNH_2$ are dissolved in anhydrous $CH_2Cl_2$ with molecular sieves, 0.2 equivalents of acetic acid added (to produce the —C=N—HR intermediate), and allowed to sit overnight. In the morning sodium triacetoxyborohydride was added (4 equivalents) and the reaction allowed to proceed for 6 hours to produce analog 389. Product was purified using an ethyl acetate/hexane column. The yield was ~25%.

Example 163: Synthesis of Analog 392: Part A: Dissolve analog 334 in $CH_2Cl_2$ at 0° C., then adding ice cold TFA to a final concentration of 25%, for 30 minutes to remove Boc group. Excess TFA removed by evaporating to dryness under vacuum, adding 0.5 ml $CH_2Cl_2$, evaporating to dryness under vacuum, repeat $CH_2Cl_2$ addition and evaporation a total of 3 times, and keep on ice/cold the entire time. Add 1 ml dry DMF, add triethylamine (5 equiv), and keep on ice. Part B: Take the Azide $N_3$-triglycine-OH peptide (1.1 equiv) and dissolve in 3 ml dry DMF at RT, then add EDC (1.1 equiv) and NHS (N-hydroxysuccinimide, 1.1 equiv) to form the active ester, and cool on ice. Add solution from Part B to solution from Part A on ice, then allow to warm in chiller to RT overnight to produce analog 392.

Example 164: Synthesis of Analog 394: Dissolve analog 235 into $CH_2CL_2$, chill on ice then add TFA to a final concentration of 10%, and allow to incubate on ice for 60 minutes. Solvent is removed using high vacuum, then the product is purified using an ethyl acetate/hexane column. The yield is ~90%.

Example 165: Synthesis of Analog 397: Into a 50 ml round bottom flask is placed 400 mg of Illudin S and then 20 ml of anhydrous DCM added along with molecular sieves. The reaction is allowed to stir at RT for 30 minutes to extract any water contained in the Illudin S. Then 1.06 ml of DIPEA is added with stirring for 15 minutes. Next the mixture is cooled to −70° C., then 1.0 g of sulfur trioxide pyridine complex (Sigma Aldrich catalog #S7556) is dissolved into 1 ml of anhydrous DMSO containing molecular sieves at RT. The sulfur trioxide pyridine/DMSO oxidizing complex is slowly added to the Illudin S solution at −70° C. with stirring. The reaction is allowed to slowly warm to −20° C., and maintained at that temperature for 15 minutes. The reaction is quenched with 10 ml of water followed immediately by 10 ml of ethyl acetate. Next 300 µl of 20% aqueous ammonia hydroxide is added whereupon a bright red color appears in the aqueous portion. The organic portion is removed, and the aqueous portion is extracted 3 more times with the ammonia hydroxide/ethyl acetate procedure. The organic phases are combined, washed with saturated bicarbonate, and then washed with saturated brine. Finally the organic phase is dried then the solvent removed. The product is purified using by silica gel chromatography using an ethyl acetate/hexane gradient to yield the intermediate primary aldehyde. Yield is approximately 30%. This primary aldehyde of Illudin S is then dissolved in anhydrous THF, then 2 equivalents of anhydrous sodium sulfate added, and the mixture cooled to 4° C. under nitrogen. Then 3.0 equivalents of N-Boc Hydroxylamine are added. After 15 minutes, 3.5 µl of glacial acetic acid are added, followed by 6.0 equivalents of sodium triacetoxy borohydride. The reaction is allowed to proceed for 18 hours at 4° C. under nitrogen. The mixture is filtered and the organic solvent removed by vacuum. The product is purified using silica gel chromatography with an ethyl acetate/hexane gradient to yield the hydroxylamine Boc derivative analog 397.

Example 166: Synthesis of Analog 398: Analog 397 is dissolved in anhydrous THF, without molecular sieves, under nitrogen and cooled to 0° C. Then TFA is added to a final concentration of 35% for 25 minutes. The THF and TFA are removed by high vacuum without external heat to yield the hydroxylamine analog 398 (final yield approximately 20%).

Example 167: Synthesis of Analog 399: Illudin S (700 mg) is dissolved in 70 ml of anhydrous DCM and 5.0 ml of peptide synthesis grade DMF at RT. Then molecular sieves are added and the mixture is stirred at RT for 30 minutes under nitrogen, and 2,4,6-trimethylpyridine (5.7 equivalents) is slowly added until the Illudin S is dissolved. The mixture is then cooled to –4° C. and sulfamoyl chloride (1.2 equivalents) is slowly added over a 15 minute period. The reaction is allowed to proceed for 4 hours at –4° C., then allowed to slowly warm and react overnight at RT for 16 hours. The DCM/DMF reaction mixture is washed with saturated sodium bicarbonate to remove residual sulfonic and hydrochloric acids. The remaining organic phase is dried then removed with high vacuum. The product is purified using silica gel chromatography with an ethyl acetate/hexane gradient to yield analog 399. Yield is approximately 25%. The product should be stored at –20° C.

Example 168: Synthesis of Analog 401: Illudin S (500 mg) is dissolved in a mixture of 300 mg of sodium acetate and 6.0 ml of acetic anhydride. The reaction is allowed to proceed at RT with stirring and monitored. After 3 to 4 hours the reaction is quenched by adding 100 ml of saturated sodium bicarbonate solution. The aqueous solution is extracted four times with ethyl acetate and the organic fractions are combined, dried and removed by vacuum. The desired mono-acetate product is separated from the undesired residual Illudin S, di-acetate and secondary mono-acetate contaminating compounds by silica gel chromatography using an ethyl acetate/hexane gradient. The recovered mono-acetate product is dissolved in anhydrous $CH_2Cl_2$ under nitrogen at 0° C. with 1.15 equivalents of p-nitrophenylchloroformate. Next 1.5 equivalents of DIPEA and 1.0 equivalents of DMAP are slowly added with stirring. Then the Boc-N,N'-dimethylaminoethane reagent (3.0 equivalents) is slowly added and the mixture is kept at 0° C. under nitrogen for 2 hours then allowed to warm up to RT and react overnight. The $CH_2Cl_2$ is removed and the product is purified by silica gel chromatography using an ethyl acetate/hexane gradient to yield the desired product. If not used immediately this intermediate should be stored at –70° C. under an inert gas. The intermediate (41 mg) is dissolved in 1.5 ml of anhydrous $CH_2Cl_2$ under nitrogen at 0° C. into a 25 ml round bottom flask, and 50 µl of anisole is added. Next 1.2 ml of trifluoroacetic acid is slowly added in 6 equal aliquots. The reaction is left stirring on ice, under nitrogen, for 45 minutes. Then 10 ml of pre-cooled (–20° C.) $CHCl_3$ is quickly added. All liquid is quickly removed under high vacuum. The residue is placed back into the ice bath and 1.5 ml of pre-cooled (–20° C.) DMF added. After 15 minutes the Fmoc-Val-Cit-PAB-PNP linker (62 mg, Axis Pharma catalog #AP10017) is added with stirring. After 15 minutes triethylamine (217 µl) is added. The mixture is stirred under nitrogen at 0° C. for 1 hour, then allowed to slowly warm to RT. If desired, the $CH_2Cl_2$ is removed and the product is purified by silica gel chromatography using an ethyl acetate/hexane gradient to yield the desired product analog 401.

Example 169: Synthesis of Analog 404: Analog 401 can be redissolved in 1.5 ml of anhydrous $CH_2Cl_2$ under nitrogen at 0° C., then 200 µl of triethylamine added, the vial sealed and allowed to react at 4° C. for 18 hours. The mixture is purified by silica gel chromatography using an ethanol/chloroform gradient to yield the desired product analog 404 (final yield approximately 20%).

Example 170: Synthesis of Analog 405: 50 mg of VP-PEG4-Acid (1-(6-methyl vinylpyridin-2-yl)-3-oxo-7,110,13,16-tetraoxa-4-azanonadecan-19-oic acid) and N-hydroxysuccinimide (16 mg, 1.20 equivalents) are dissolved in 20 ml of anhydrous $CH_2Cl_2$ under nitrogen. The EDC (1-ethyl-3-(3-dimethylaminopropyl)carbodiimide, 21 mg, 1.20 equivalents) is added and allowed to react at RT for 24 hours to produce the compound VP-PEG4-NHS (2,5-dioxopyrrolidin-1-yl 1-(6-methyl-4-vinylpridin-22-yl)-3-oxo-7,10,13,16-tetraoxa-4-azanondecane-19-oate). The $CH_2Cl_2$ mixture containing the VP-PEG4-NHS is washed with water, then quickly dried and the $CH_2Cl_2$ removed by vacuum. Next analog 404 (74 mg) is dissolved in 3.0 ml of DMF, and then added to the VP-PEG-NHS compound. The mixture is placed under nitrogen, cooled to 0° C., then 210 µl of triethylamine added, and the reaction allowed to continue overnight in the cold. The desired product, analog 405, is recovered using reverse phase HPLC (approximately 50% yield of initial starting material analog 404).

Example 171: Synthesis of Analog 402 and Analog 403: Illudin S (0.95 grams) is dissolved in 100 ml of water, and then 100 ml of hexane is added to form an upper organic layer. With rapid stirring, 2.06 ml of concentrated sulfuric acid is added slowly. After 1 hour the hexane is removed and another 100 ml of hexane is added. This process is repeated one more time. The hexane layers are combined washed with a saturated sodium bicarbonate solution to neutralize residual acid, dried with anhydrous magnesium, then solvent removed to yield a bright yellow oil (AF1). Next paraformaldehyde (0.66 g) is dissolved in 60 ml of water, and concentrated sulfuric acid (5.0 ml) is slowly added. The cloudy solution is slowly heated until the solution is clear. This paraformaldehyde solution is allowed to slowly cool to 30° C. Then the previously prepared bright yellow intermediate (AP1) is dissolved in acetone, and the mixture slowly added with continuous stirring for 24 hours. The reaction mixture is extracted three times with ethyl acetate (100 ml), the extracts are combined, washed with saturated sodium bicarbonate, dried over anhydrous magnesium sulfate, then the organic solvent removed by vacuum. The residue is purified by silica gel chromatography using an ethyl acetate/hexane gradient to yield a bright orange intermediate (IRO1). IRO1 is dissolved in anhydrous dichloromethane, under nitrogen, and 2,4,6-trimethylpyridine (3.0 equivalents) is added, then the mixture is cooled to 0° C. Sulfamoyl chloride (1.15 equivalents) is dissolved in anhydrous peptide-grade DMF (1 ml), and is slowly added to the dichloromethane solution, with mixing. The solution is mixed for one hour at 0° C., then slowly allowed to warm to RT, and continued to react for a total of 4 hours. The reaction mixture is concentrated by vacuum, then purified by silica gel chromatography using an ethyl acetate/hexane gradient to yield analog 402 and analog 403 (final yield of both products is approximately 15%).

Example 172: Synthesis of Analog 407: Illudin S (100 mg) is dissolved in 20 ml of anhydrous DCM and 5.0 ml of DMF at RT. Then molecular sieves are added and the mixture is stirred at RT for 30 minutes under nitrogen, and 2,4,6-trimethylpyridine (5.7 equivalents) is slowly added until the Illudin S is dissolved. The mixture is then cooled to −4° C. and the trifluormethanesulfanyl chloride (Aldrich Catakog #164798, 1.2 equivalents) is slowly added over a 15 minute period. The reaction is allowed to proceed for 4 hours at −4° C., and then allowed to slowly warm and react overnight at RT for 16 hours. The DCM/DMF reaction mixture is washed with saturated sodium bicarbonate to remove residual sulfonic and hydrochloric acids. The remaining organic phase is dried then removed with high vacuum. The product is purified using by silica gel chromatography using an ethyl acetate/hexane gradient to yield analog 407. Yield is approximately 15%. The product is unstable and should be stored at −70° C. under an inert gas.

Example 173: Synthesis of Analog 408: Illudin S (500 mg) is dissolved in a mixture of 300 mg of sodium acetate and 6.0 ml of acetic anhydride. The reaction is allowed to proceed at RT with stirring and monitored. After 3 to 4 hours the reaction is quenched by adding 100 ml of saturated sodium bicarbonate solution. The aqueous solution is extracted four times with ethyl acetate and the organic fractions are combined, dried and removed by vacuum. The desired mono-acetate product is separated from the undesired residual Illudin S, di-acetate and secondary mono-acetate contaminating compounds by silica gel chromatography using an ethyl acetate/hexane gradient. The recovered mono-acetate product is dissolved in anhydrous $CH_2Cl_2$ under nitrogen at 0° C. with 1.15 equivalents of p-nitrophenylchloroformate. Next 1.5 equivalents of DIPEA and 1.0 equivalents of DMAP are slowly added with stirring. After the Boc-N,N'-dimethylaminoethane reagent (3.0 equivalents) is added and the mixture is kept at 0° C. under nitrogen for an 2 hours then allowed to warm up to RT and react overnight. The $CH_2Cl_2$ is removed and the product is purified by silica gel chromatography using an ethyl acetate/hexane gradient to yield the desired intermediate product. If not used immediately this intermediate should be stored at −70° C. under an inert gas. The intermediate (41 mg) is dissolved in 1.5 ml of anhydrous $CH_2Cl_2$ under nitrogen at 0° C. into a 25 ml round bottom flask, and 50 μl of anisole is added. Next 1.2 ml of trifluoroacetic acid is slowly added in 6 equal aliquots. The reaction is left stirring on ice, under nitrogen, for 45 minutes. Then 10 ml of precooled (−20° C.) $CHCl_3$ added. All liquid is removed under high vacuum. The residue is placed back in to the ice bath and 1.5 ml of pre-cooled (−20° C.) DMF added. This solution is added to a solution of 3 ml of DMF containing the Fmoc-Gly3-Val-Cit-PNP peptide (Levena Biopharma Catalog #H1002, 1.1 equivalent) at 0° C. The solution is allowed to slowly warm to RT and react overnight. The desired intermediate is recovered by precipitation with excess diethyl ether. The precipitate is washed twice with ice cold ether, dried to remove the ether, then redissolved in 1.5 ml of DMF, 200 μl of triethylamine added, and the reaction allowed to proceed at 4° C. for 48 hours to produce analog 408 (final yield is approximately 20%).

Example 174: Synthesis of Analog 409: Illudin S (500 mg) is dissolved in a mixture of 300 mg of sodium acetate and 6.0 ml of acetic anhydride. The reaction is allowed to proceed at RT with stirring and monitored. The reaction is quenched after 3-4 hours by adding 100 ml of saturated sodium bicarbonate solution. The aqueous solution is extracted four times with ethyl acetate, the organic fractions are combined, dried and removed by vacuum. The desired mono-acetate product is separated from the undesired residual Illudin S, di-acetate and secondary mono-acetate contaminating compounds by silica gel chromatography using an ethyl acetate/hexane gradient. The recovered mono-acetate product is dissolved in anhydrous $CH_2Cl_2$ under nitrogen at 0° C. with 1.15 equivalents of p-nitrophenylchloroformate. Next is added with stirring 1.5 equivalents of DIPEA and 1.0 equivalents of DMAP. After the Boc-N,N'-dimethylaminoethane reagent (3.0 equivalents) is added and the mixture is kept at 0° C. under nitrogen for an additional 2 hours then allowed to warm up to RT and react overnight. The $CH_2Cl_2$ is removed and the product is purified by silica gel chromatography using an ethyl acetate/hexane gradient to yield the desired product. If not used immediately this intermediate should be stored at −70° C. under an inert gas. This intermediate (41 mg) is dissolved in 1.5 ml of anhydrous $CH_2Cl_2$ under nitrogen at 0° C. into a 2 5 ml round bottom flask, and 50 μl of anisole is added. Next 1.2 ml of trifluoroacetic acid is slowly added in 6 equal aliquots. The reaction is left stirring on ice, under nitrogen, for 45 minutes. Then 10 ml of precooled (−20° C.) $CHCl_3$ is added. All liquid is removed under high vacuum. The residue is placed back in to the ice bath and 1.5 ml of pre-cooled (−20° C.) peptide synthesis grade DMF added. After 15 minutes the Fmoc-Val-Cit-PAB-PNP linker (62 mg. Axis Pharma catalog #AP10017) is added with stirring. After 15 minutes then triethylamine (217 μl) is added. The mixture is stired under nitrogen at 0° C. for 1 hour, then allowed to slowly warm to RT. If desired, the $CH_2Cl_2$ is removed and the product is purified by silica gel chromatography using an ethyl acetate/hexane gradient to yield the desired intermediate product. The intermediate can be redissolved in 1.5 ml of anhydrous $CH_2Cl_2$ under nitrogen at 0° C., then 200 μl of triethylamine added, the vial sealed and allowed to react at 4 C for 18 hours. The desired intermediate is recovered by precipitation with excess ice-cold diethyl ether. The precipitate is washed twice with ice cold ether, dried to remove the ether, then redissolved in 1.5 ml of DMF and 200 μl of triethylamine is added, and the reaction allowed to proceed at 4° C. for 48 hours to produce analog 409 (final yield approximately 30%).

Example 175: Synthesis of Analog 410: Illudin S (500 mg) is dissolved in a mixture of 300 mg of sodium acetate and 6.0 mls of acetic anhydride. The reaction is allowed to proceed at RT with stirring and monitored. The reaction is quenched after 3-4 hours by adding 100 ml of saturated sodium bicarbonate solution. The aqueous solution is extracted four times with ethyl acetate, the organic fractions are combined, dried and removed by vacuum. The desired mono-acetate product is separated from the undesired residual Illudin S, di-acetate and secondary mono-acetate contaminating compounds by silica gel chromatography using an ethyl acetate/hexane gradient. The recovered mono-acetate product is dissolved in anhydrous $CH_2Cl_2$ under nitrogen at 0° C. with 1.15 equivalents of p-nitrophenylchloroformate. Next is added with stirring 1.5 equivalents of DIPEA and 1.0 equivalents of DMAP. After the Boc-N,N'-dimethylaminoethane reagent (3.0 equivalents) is added, the mixture is kept at 0° C. under nitrogen for an additional 2 hours then allowed to warm up to RT and react overnight. The $CH_2Cl_2$ is removed and the product is purified by silica gel chromatography using an ethyl acetate/hexane gradient to yield the desired product. If not used immediately this intermediate should be stored at −70° C. under an inert gas. This intermediate (41 mg) is dissolved in 1.5 mls of anhydrous $CH_2Cl_2$ under nitrogen at 0° C. into a 25 ml round bottom flask, and 50 µl of anisole is added. Next 1.2 ml of trifluoroacetic acid is slowly added in 6 equal aliquots. The reaction is left stirring on ice, under nitrogen, for 45 minutes. Then 10 ml of pre-cooled (−20° C.) CHCl₃ is added. All liquid is removed under high vacuum. The residue is placed back in to the ice bath and 1.5 ml of pre-cooled (−20° C.) DMF added. Next MC-Val-Cit-PAB-PNP (Levena Biopharma Catalog #VC1004, 1.2 equivalents) is directly added with stirring while maintaining the temperature at 0° C. Once all solid material is dissolved then triethylamine (8.0 equivalents) is added and the reaction continued at 4° C. for 48 hours. Analog 410 is recovered by preparative HPLC using an acetonitrile gradient (5% to 95%) with 0.05% trifluoroacetic acid (final yield approximately 15%).

Abbreviations used include: DMAP=4-dimethylaminopyridine; DCC=N,N'-dicycyclohexylcarbodiimide; ODHBt=3,4,-dihydroxy-4-oxo-1,2,3-benzo-triazine-3-yl ester; NMM=N-methylmorpholine; EDC=1-(3-dimethylaminopropyl)-3-ethylcarbodiimide hydrochloride; DIAD=diisopropyl azodicarboxylate; DEAD=diethyl azodicarboxylate; and DIPC=N,N'-diisopropylcarbodiimide. Boc₂O=anhydrous Boc; BocNH₂=t-butyl carbamate; DIPEA=N,N-diisopropylethylamine; ODHBt=3,4,-dihydroxy-4-oxo-1,2,3-benzo-triazine-3-yl ester (refers to ester made from HOOBt); HOOBt=(Hydroxy-3,4-dihydro-4-oxo-1,2,3-benzotriazine); NMM=N-methylmorpholine; RT—room temperature; TBDMSCl=t-butyldimethyl silyl chloride; TEA=triethanolamine.

The foregoing description of embodiments of the methods, systems, and components of the present invention has been provided for the purposes of illustration and description. It is not intended to be exhaustive or to limit the invention to the precise forms disclosed. Many modifications and variations will be apparent to one of ordinary skill in the relevant arts. For example, steps performed in the embodiments of the invention disclosed can be performed in alternate orders, certain steps can be omitted, and additional steps can be added. The embodiments were chosen and described in order to best explain the principles of the invention and its practical application, thereby enabling others skilled in the art to understand the invention for various embodiments and with various modifications that are suited to the particular used contemplated. Other embodiments are possible and are covered by the invention. Such embodiments will be apparent to persons skilled in the relevant art(s) based on the teachings contained herein. The breadth and scope of the present invention should not be limited by any of the above-described exemplary embodiments, but should be defined only in accordance with the following claims and their equivalents.

TABLE I

Cytotoxic data IC$_{50}$ values (micromolar, 2 hour exposure, N = 3, mean ± SD) for Illudin M, analog 108 and analog 110 for cells expressing the estrogen receptor (ER) (MCF7) and cells not expressing the ER (HT29).

| Analog | HT29 (ER Negative) | MCF7 (ER positive) |
|---|---|---|
| Illudin M | 0.52 ± 0.10 | 0.48 ± 0.13 |
| 108 | >55 | 14.1 ± 2.8 |
| 110 | >19 | 2.0 ± 0.1 |

TABLE II

Activity of PSA cleavable illudofulvene analogs (210, 215, 216, 221) compared with Illudin S and illudofulvene precursor analogs (204, 207, 211, 212, 213, 214) against PSA negative and PSA positive cell line (48 hour exposure, N = 3; mean ± SD; IC50 values in nM).

| Analog | Prostate PC3 (negative PSA) | Prostate DuPro (trace PSA) | Prostate LnCAP (positive PSA) |
|---|---|---|---|
| Illudin S | 16 ± 5 | 11 ± 3 | 15 ± 3 |
| 204 | n.t. | n.t. | 3,300 ± 1,000 |
| 207 | 880 ± 330 | 450 ± 40 | 560 ± 60 |
| 211 | 350 ± 80 | 280 ± 20 | 270 ± 50 |
| 212 | 120 ± 20 | 20 ± 2 | 120 ± 30 |
| 213 | 2,200 ± 100 | 360 ± 80 | 900 ± 200 |
| 214 | 300 ± 50 | 90 ± 10 | 190 ± 30 |
| 210 | 4,700 ± 500 | 3,500 ± 400 | 810 ± 130 |
| 215 | n.t. | n.t. | >20,000 |
| 216 | 190 ± 10 | 280 ± 60 | 190 ± 30 |
| 221 | >21,000 | 13,000 ± 1,000 | 800 ± 100 | n.t. denotes not tested

TABLE III

Peptides cleaved by various proteases.

| Protease | Peptide | SEQ. ID's |
|---|---|---|
| PSA | His-Ser-Ser-Lys-Leu-Gln-X | SEQ. ID. 104 |
| | Mu-His-Ser-Ser-Lys-Leu-Gln-X | SEQ. ID. 106 |
| | Mu-His-Ser-Ser-Lys-Leu-Gln-Lys-X | SEQ. ID. 108 |
| | Mu-His-Ser-Ser-Lys-Leu-EDA-Lys-X | |
| | Mc-His-Ser-Ser-Lys-Leu-Gln-X | |
| | Mc-His-Ser-Ser-Lys-Leu-Gln-X | |
| | Hyp-Ala-Ser-Chg-Gln-Ser-X | SEQ. ID. 111 |
| | Hyp-Ala-Ser-Chg-Gln-Ser-Leu-X | SEQ. ID. 116 |
| | Mu-Hyp-Ala-Ser-Chg-Gln-Ser-X | |
| | Mu-Hyp-Ala-Ser-Chg-Gln-Ser-Leu-X | |
| | Mc-Hyp-Ala-Ser-Chg-Gln-Ser-X | |
| | Mc-Hyp-Ala-Ser-Chg-Gln-Ser-Leu-X | |
| | Hyp-Ser-Ser-Chg-GIn-Ser-Ser-Pro-X | SEQ. ID. 127 |
| | Mu-Hyp-Ser-Ser-Chg-Gln-Ser-Ser-Pro-X | SEQ. ID. 131 |
| | Mc-Hyp-Ser-Ser-Chg-Gln-Ser-Ser-Pro-X | |
| | 4-O-Ac-Hyp-Ser-Ser-Chg-Gln-Ser-Ser-Pro-X | |
| | Arg-Arg-Ser-Ser-Tyr-Tyr-Ser-Gly-X | SEQ. ID. 132 |
| | Mu-Arg-Arg-Ser-Ser-Tyr-Tyr-Ser-Gly-X | SEQ. ID. 136 |
| | Mc-Arg-Arg-Ser-Ser-Tyr-Tyr-Ser-Gly-X | |
| | Mc-Ser-Ser-Lys-Tyr-Gln-Leu-X | |
| | Mu-Ser-Ser-Lys-Tyr-Gln-Leu-X | |

TABLE III-continued

Peptides cleaved by various proteases.

| Protease | Peptide | SEQ. ID's |
|---|---|---|
| | N-glutaryl-Hyp-Ala-Ser-chGly-Gln-Ser-Leu<br>Mu-N-glutaryl-Hyp-Ala-Ser-chGly-Gln-Ser-Leu<br>Mc-N-glutaryl-Hyp-Ala-Ser-chGly-Gln-Ser-Leu | SEQ. ID. 137 |
| Caspase-3 | Asp-Glu-Val-Asp-Pro-X<br>Mu-Asp-Glu-Val-Asp-Pro-X<br>Mc-Asp-Glu-Val-Asp-Pro-X | SEQ. ID. 138 |
| | Lys-Gly-Ser-Gly-Asp-Val-Glu-Gly-X<br>Mu-Lys-Gly-Ser-Gly-Asp-Val-Glu-Gly-X<br>Mc-Lys-Gly-Ser-Gly-Asp-Val-Glu-Gly-X | SEQ. ID. 139 |
| Cathepsin B | PLE-X<br>Gly-Phe-Leu-Gly-X<br>Lys-Lys-Phe-D-Ala-X<br>D-Ala-Phe-Lys-Lys-X<br>Mc-Poly-L-glutamic acid-X<br>Mc-Gly-Phe-Leu-Gly-X<br>Mc-Lys-Lys-Phe-D-Ala-X<br>Mc-D-Ala-Phe-Lys-Lys-X<br>Mu-Poly-L-glutamic acid-X<br>Mu-Gly-Phe-Leu-Gly-X<br>Mu-Lys-Lys-Phe-D-Ala-X<br>Mu-D-Ala-Phe-Lys-Lys-X<br>Val-Cit-X | SEQ. ID. 141<br>SEQ. ID. 142<br>SEQ. ID. 144<br>SEQ. ID. 145 |
| FAP | Lys-Gln-Glu-Gln-Asn-Pro-Gly-Ser-Thr-X<br>Mu-Lys-Gln-Glu-Gln-Asn-Pro-Gly-Ser-Thr-X<br>Mc-Lys-Gln-Glu-Gln-Asn-Pro-Gly-Ser-Thr-X | SEQ. ID. 146 |
| Kallikrein 2 | Gly-Lys-Ala-Phe-Arg-Arg-X<br>Mu-Gly-Lys-Ala-Phe-Arg-Arg-X<br>Mc-Gly-Lys-Ala-Phe-Arg-Arg-X | SEQ. ID. 171 |
| MMP-2/-9/ | Glu-Pro-Cit-Gly-Hof-Tyr-Leu-X<br>Mu-Glu-Pro-Cit-Gly-Hof-Tyr-Leu-X<br>Mc-Glu-Pro-Cit-Gly-Hof-Tyr-Leu-X | SEQ. ID. 172 |
| | Gly-Ile-Leu-Gly-Val-Pro-X<br>Mu-Gly-Ile-Leu-Gly-Val-Pro-X<br>Mc-Gly-Ile-Leu-Gly-Val-Pro-X | SEQ. ID. 173 |
| | Gly-Pro-Leu-Gly-Ile-Ala-Gly-Gln-X<br>Mu-Gly-Pro-Leu-Gly-lle-Ala-Gly-Gln-X<br>Mc-Gly-Pro-Leu-Gly-Ile-Ala-Gly-Gln-X | SEQ. ID. 174 |
| MMP-7 | Lys-Arg-Ala-Leu-Gly-Leu-Pro-Gly<br>Mu-Lys-Arg-Ala-Leu-Gly-Leu-Pro-Gly<br>Mc-Lys-Arg-Ala-Leu-Gly-Leu-Pro-Gly | SEQ. ID. 175 |
| | Arg-Pro-Leu-Ala-Leu-Trp-Arg-Ser<br>Mu-Arg-Pro-Leu-Ala-Leu-Trp-Arg-Ser<br>Mc-Arg-Pro-Leu-Ala-Leu-Trp-Arg-Ser | SEQ. ID. 176 |
| TOP | Ala-L-L-Ala-L-Ile<br>Mu-Ala-L-L-Ala-L-lle<br>Mc-Ala-L-L-Ala-L-Ile | |
| uPA | D-Ala-Phe-Lys or<br>D-Ala-Phe-Lys-PABC | SEQ. ID. 177 |
| Cathepsin K | Gly-Gly-Pro-Nle-X<br>Mu-Gly-Gly-Pro-Nle-X<br>Mc-Gly-Gly-Pro-Nle-X | SEQ. ID. 178 |
| Plasmin | D-Ala-Phe-Lys-Lys-X<br>Mu-D-Ala-Phe-Lys-Lys-X<br>Mc-D-Ala-Phe-Lys-Lys-X<br>D-Ala-Phe-Lys-X<br>Mu-D-Ala-Phe-Lys-X<br>Mc-D-Ala-Phe-Lys-X | SEQ. ID. 179 |
| Thrombin | Poly-L-Lys-Gly-D-Phe-Pip-Arg-Ser-Gly-Gly-Gly-Gly-Gly-X | SEQ. ID. 180 |
| Trypsin | Poly-L-Lysine-Gly-Ala-Ser-D-Arg-Phe-Thr-Gly-X | SEQ. ID. 181 |

In Table III, the letter 'X' denotes the end attached to the medicant, Chg denotes cyclohexyl glycine, Cit denotes citrulline, EDA denotes ethanyl-D-Alanine, Hof denotes homophenylalanine, Hyp denotes 4-hydroxyproline, Mc denotes morpholinocarbonyl (carboxy-terminal protecting group), Mu denotes 4-morpholine-carbonyl (amino-terminal protecting group), Nle denotes norleucine, PABC denotes para-aminobenzoylcarboxyl, PLE denotes Poly-L-glutamic acid, and Pip denotes pipecolic acid.

TABLE IV

Mechanisms of Drug Resistance.

| Mechanism of Multi-drug Resistance | Resistance to illudofulvenes |
|---|---|
| Gp170/MDR1 | No |
| Gp180/MRP | No |
| Topoisomerase I | No |
| Topoisomerase II | No |
| MVP/LRP (vault) | No |
| Thiol content/GST pi | No |
| DNA repair | No |
| Myc expression | No |
| Bcl-2 expression | No |
| BRCA status | No |
| P53 status | No |
| P21 status | No |
| MGMT expression | No |
| Microtubulin alteration | No |

TABLE V

IUPAC names of the Illudofulvene analogs.

| Entry # | Illudo-fulvene Analog | IUPAC Name of Illudofulvene Analog |
|---|---|---|
| 1 | 001 | (R)-6'-hydroxy-2',4',6'-trimethylspiro[cyclopropane-1,5'-inden]-7'(6'H)-one |
| 2 | 002 | (6'R)-6'-hydroxy-3'-(hydroxymethyl)-2',4',6'-trimethylspiro[cyclopropane-1,5'-inden]-7'(6'H)-one |
| 3 | 003 | (6'R,6'''R)-3',3'''-methylenebis(6'-hydroxy-2',4',6'-trimethylspiro[cyclopropane-1,5'-inden]-7'(6'H)-one) |
| 4 | 004 | (R)-3'-bromo-6'-hydroxy-2',4',6'-trimethylspiro[cyclopropane-1,5'-inden]-7'(6'H)-one |
| 5 | 005 | (R)-6'-hydroxy-3'-iodo-2',4',6'-trimethylspiro[cyclopropane-1,5'-inden]-7'(6'H)-one |
| 6 | 006 | (R)-6'-hydroxy-3'-(4-hydroxybenzyl)-2',4',6'-trimethylspiro[cyclopropane-1,5'-inden]-7'(6'H)-one |
| 7 | 007 | (R)-6'-hydroxy-3'-(4-methoxybenzyl)-2',4',6'-trimethylspiro[cyclopropane-1,5'-inden]-7'(6'H)-one |
| 8 | 008 | (R)-((6'-hydroxy-2',4',6'-trimethyl-7'-oxo-6',7'-dihydrospiro[cyclopropane-1,5'-inden]-3'-yl)methoxy)methyl acetate |
| 9 | 009 | (R)-6'-hydroxy-3'-(3-hydroxypropyl)-2',4',6'-trimethylspiro[cyclopropane-1,5'-inden]-7'(6'H)-one |
| 10 | 010 | (R)-3-(6'-hydroxy-2',4',6'-trimethyl-7'-oxo-6',7'-dihydrospiro[cyclopropane-1,5'-inden]-3'-yl)propanal |
| 11 | 011 | (R)-6'-hydroxy-2',4',6'-trimethyl-7'-oxo-6',7'-dihydrospiro[cyclopropane-1,5'-indene]-3'-carbaldehyde |
| 12 | 012 | (R)-6'-hydroxy-2',4',6'-trimethyl-3'-nitrospiro[cyclopropane-1,5'-inden]-7'(6'H)-one |
| 13 | 013 | 4-hydroxy-5-(((R)-6'-hydroxy-2',4',6'-trimethyl-7'-oxo-6',7'-dihydrospiro[cyclopropane-1,5'-inden]-3'-yl)methyl)cyclohexane-1,3-dicarbaldehyde |
| 14 | 014 | (4a'S,7'R,9b'S)-7'-hydroxy-4a',7',9'-trimethyl-4a',9b'-dihydro-4'H-spiro[cyclopropane-1,8'-indeno[1,2-d][1,3]dioxin]-6'(7'H)-one |
| 15 | 015 | (R)-3'-(hydroxymethyl)-2',4',6'-trimethyl-7'-oxo-6',7'-dihydrospiro[cyclopropane-1,5'-inden]-6'-yl acetate |
| 16 | 016 | (R)-3'-(ethoxymethyl)-6'-hydroxy-2',4',6'-trimethylspiro[cyclopropane-1,5'-inden]-7'(6'H)-one |
| 17 | 017 | (6'R,6'''R)-3',3'''-(oxybis(methylene))bis(6'-hydroxy-2',4',6'-trimethylspiro[cyclopropane-1,5'-inden]-7'(6'H)-one) |
| 18 | 018 | (R)-6'-hydroxy-2',4',6'-trimethyl-3'-((((2R,3S,4R,5R,6S)-3,4,5-trihydroxy-6-(hydroxymethyl)tetrahydro-2H-pyran-2-yl)oxy)methyl)spiro[cyclopropane-1,5'-inden]-7'(6'H)-one |
| 19 | 019 | (6'R)-3'-((2,3-dihydroxypropoxy)methyl)-6'-hydroxy-2',4',6'-trimethylspiro[cyclopropane-1,5'-inden]-7'(6'H)-one |
| 20 | 020 | (R)-3'-((2-bromoethoxy)methyl)-6'-hydroxy-2',4,6'-trimethylspiro[cyclopropane-1,5'-inden]-7'(6'H)-one |
| 21 | 021 | (R)-6'-hydroxy-3'-(((2-methoxypropan-2-yl)oxy)methyl)-2',4',6'-trimethylspiro[cyclopropane-1,5'-inden]-7'(6'H)-one |
| 22 | 022 | (R)-6'-hydroxy-3'-((2-hydroxyethoxy)methyl)-2',4',6'-trimethylspiro[cyclopropane-1,5'-inden]-7'(6'H)-one |
| 23 | 023 | (R)-6'-hydroxy-3'-(((4-hydroxyphenyl)thio)methyl)-2',4',6'-trimethylspiro[cyclopropane-1,5'-inden]-7'(6'H)-one |
| 24 | 024 | (R)-3'-((benzylthio)methyl)-6'-hydroxy-2',4',6'-trimethylspiro[cyclopropane-1,5'-inden]-7'(6'H)-one |
| 25 | 025 | methyl (R)-2-(((6'-hydroxy-2',4',6'-trimethyl-7'-oxo-6',7'-dihydrospiro[cyclopropane-1,5'-inden]-3'-yl)methyl)thio)acetate |
| 26 | 026 | (R)-6'-hydroxy-2',4',6'-trimethyl-3'-((p-tolylthio)methyl)spiro[cyclopropane-1,5'-inden]-7'(6'H)-one |
| 27 | 027 | (R)-(6'-hydroxy-2',4',6'-trimethyl-7'-oxo-6',7'-dihydrospiro[cyclopropane-1,5'-inden]-3'-yl)methyl phenyl carbonate |
| 28 | 028 | (R)-(6'-hydroxy-2',4',6'-trimethyl-7'-oxo-6',7'-dihydrospiro[cyclopropane-1,5'-inden]-3'-yl)methyl benzoate |
| 29 | 029 | (R)-2-(((6'-hydroxy-2',4',6'-trimethyl-7'-oxo-6',7'-dihydrospiro[cyclopropane-1,5'-inden]-3'-yl)methyl)thio)acetic acid |
| 30 | 030 | methyl (R)-2-(((6'-hydroxy-1'-((2-methoxy-2-oxoethyl)thio)-2',4',6'-trimethyl-7'-oxo-6',7'-dihydrospiro[cyclopropane-1,5'-inden]-3'-yl)methyl)thio)acetate |
| 31 | 031 | methyl 2-((((6'R)-6',7a'-dihydroxy-1'-((2-methoxy-2-oxoethyl)thio)-2',4',6'-trimethyl-7'-oxo-1',6',7',7a'-tetrahydrospiro[cyclopropane-1,5'-inden]-3'-yl)methyl)thio)acetate |
| 32 | 032 | (6'R)-3'-(((2,3-dihydroxypropyl)thio)methyl)-6'-hydroxy-2',4',6'-trimethylspiro[cyclopropane-1,5'-inden]-7'(6'H)-one |
| 33 | 033 | 7'-methyl-4'H-dispiro[cyclopropane-1,6'-indene-5',2''-[1,3]dioxolan]-4'-one |
| 34 | 034 | (R)-(6'-hydroxy-2',4',6'-trimethyl-7'-oxo-6',7'-dihydrospiro[cyclopropane-1,5'-inden]-3'-yl)methyl acetate |
| 35 | 035 | 6'-hydroxy-4'-methylspiro[cyclopropane-1,5'-inden]-7'(6'H)-one |
| 36 | 036 | (R)-3'-((1H-imidazol-1-yl)methyl)-6'-hydroxy-2',4',6'-trimethylspiro[cyclopropane-1,5'-inden]-7'(6'H)-one |
| 37 | 037 | 1-carboxy-2-((((R)-6'-hydroxy-2',4',6'-trimethyl-7'-oxo-6',7'-dihydrospiro[cyclopropane-1,5'-inden]-3'-yl)methyl)thio)ethan-1-aminium |
| 38 | 038 | (R)-3-(6'-hydroxy-2',4',6'-trimethyl-7'-oxo-6',7'-dihydrospiro[cyclopropane-1,5'-inden]-3'-yl)propanoic acid |
| 39 | 039 | (R)-3'-(3,3-dimethoxypropyl)-6'-hydroxy-2',4',6'-trimethylspiro[cyclopropane-1,5'-inden]-7'(6'H)-one |
| 40 | 040 | (R)-3'-(3,3-diethoxypropyl)-6'-hydroxy-2',4',6'-trimethylspiro[cyclopropane-1,5'-inden]-7'(6'H)-one |
| 41 | 041 | (R,Z)-3-(6'-hydroxy-2',4',6'-trimethyl-7'-oxo-6',7'-dihydrospiro[cyclopropane-1,5'-inden]-3'-yl)acrylaldehyde |
| 42 | 042 | (R)-3'-(hydroxymethyl)-4',6'-dimethyl-6'-((triethylsilyl)oxy)spiro[cyclopropane-1,5'-inden]-7'(6'H)-one |

TABLE V-continued

IUPAC names of the Illudofulvene analogs.

| Entry # | Illudo-fulvene Analog | IUPAC Name of Illudofulvene Analog |
|---|---|---|
| 43 | 043 | (R)-6'-hydroxy-2',4',6'-trimethyl-3'-(((triethylsilyl)oxy)methyl)spiro[cyclopropane-1,5'-inden]-7'(6'H)-one |
| 44 | 044 | (R)-2',4',6'-trimethyl-6'-((triethylsilyl)oxy)-3'-(((triethylsilyl)oxy)methyl)spiro[cyclopropane-1,5'-inden]-7'(6'H)-one |
| 45 | 045 | methyl 2-((7-hydroxy-5-(2-hydroxyethyl)-3-(hydroxymethyl)-2,4,6-trimethyl-1H-inden-1-yl)thio)acetate |
| 46 | 046 | (R)-3-(6'-hydroxy-2',4',6'-trimethyl-7'-oxo-6',7'-dihydrospiro[cyclopropane-1,5'-inden]-3'-yl)propyl acetate |
| 47 | 047 | (6'R)-3'-(2-(1,7-dihydroxy-2,4,6-trimethyl-1H-inden-5-yl)ethyl)-6'-hydroxy-2',4',6'-trimethylspiro[cyclopropane-1,5'-inden]-7'(6'H)-one |
| 48 | 048 | (R)-6'-hydroxy-2',4',6'-trimethyl-1'-(p-tolylthio)-3'-((p-tolylthio)methyl)spiro[cyclopropane-1,5'-inden]-7'(6'H)-one |
| 49 | 049 | (R)-6'-hydroxy-2',4',6'-trimethyl-3'-(p-tolylthio)spiro[cyclopropane-1,5'-inden]-7'(6'H)-one |
| 50 | 050 | (R)-6'-hydroxy-2',4',6'-trimethyl-1,3'-bis(p-tolylthio)spiro[cyclopropane-1,5'-inden]-7'(6'H)-one |
| 51 | 051 | (R)-2-(2-(((6'-hydroxy-2',4',6'-trimethyl-7'-oxo-6',7'-dihydrospiro[cyclopropane-1,5'-inden]-3'-yl)methyl)thio)acetoxy)ethyl 2-mercaptoacetate |
| 52 | 052 | ethane-1,2-diyl bis(2-((((R)-6'-hydroxy-2',4',6'-trimethyl-7'-oxo-6',7'-dihydrospiro[cyclopropane-1,5'-inden]-3'-yl)methyl)thio)acetate) |
| 53 | 053 | (R)-3'-((2-(2-bromoethoxy)ethoxy)methyl)-6'-hydroxy-2',4',6'-trimethylspiro[cyclopropane-1,5'-inden]-7'(6'H)-one |
| 54 | 054 | (R)-6'-hydroxy-1'-(((R)-6'-hydroxy-2',4',6'-trimethyl-7'-oxo-6',7'-dihydrospiro[cyclopropane-1,5'-inden]-3'-yl)methyl)-3'-(hydroxymethyl)-2',4',6'-trimethylspiro[cyclopropane-1,5'-inden]-7'(6'H)-one |
| 55 | 055 | 5-(2-hydroxyethyl)-1-((4-hydroxyphenyl)thio)-3-(((4-hydroxyphenyl)thio)methyl)-2,4,6-trimethyl-1H-inden-7-ol |
| 56 | 056 | (R)-6'-hydroxy-3'-((4-hydroxyphenyl)thio)-2',4',6'-trimethylspiro[cyclopropane-1,5'-inden]-7'(6'H)-one |
| 57 | 057 | (R)-6'-hydroxy-1'-((4-hydroxyphenyl)thio)-2',4',6'-trimethylspiro[cyclopropane-1,5'-inden]-7'(6'H)-one |
| 58 | 058 | (R)-6'-hydroxy-1',3'-bis((4-hydroxyphenyl)thio)-2',4',6'-trimethylspiro[cyclopropane-1,5'-inden]-7'(6'H)-one |
| 59 | 059 | (6'S,7'R)-4'-methyl-6'-(((triethylsilyl)oxy)-6',7'-dihydrospiro[cyclopropane-1,5'-inden]-7'-ol |
| 60 | 060 | (R)-7'-methyl-4'H-dispiro[cyclopropane-1,6'-indene-5',2''-[1,3]dioxolan]-4'-ol |
| 61 | 061 | (S)-4'-methyl-6'-((triethylsilyl)oxy)spiro[cyclopropane-1,5'-inden]-7'(6'H)-one |
| 62 | 062 | (R)-6'-hydroxy-2'-(hydroxymethyl)-4',6'-dimethylspiro[cyclopropane-1,5'-inden]-7'(6'H)-one |
| 63 | 063 | (R)-6'-hydroxy-2',3'-bis(hydroxymethyl)-4',6'-dimethylspiro[cyclopropane-1,5'-inden]-7'(6'H)-one |
| 64 | 064 | N-acetyl-S-(((R)-6'-hydroxy-2',4',6'-trimethyl-7'-oxo-6',7'-dihydrospiro[cyclopropane-1,5'-inden]-3'-yl)methyl)-L-cysteine |
| 65 | 065 | (R)-2-acetamido-3-((((R)-6'-hydroxy-4',6'-dimethyl-7'-oxo-6',7'-dihydrospiro[cyclopropane-1,5'-inden]-3'-yl)methyl)thio)-N-((S)-1-phenylethyl)propanamide |
| 66 | 066 | (S)-2-acetamido-3-((((R)-6'-hydroxy-2',4',6'-trimethyl-7'-oxo-6',7'-dihydrospiro[cyclopropane-1,5'-inden]-3'-yl)methyl)thio)-N-((S)-1-phenylethyl)propanamide |
| 67 | 067 | 4-methyl-2,3-dihydro-5H-indeno[5,6-b]furan-5-one |
| 68 | 068 | 5-hydroxy-6-(2-hydroxyethyl)-7-methyl-1H-inden-1-one |
| 69 | 069 | 5-(2-hydroxyethoxy)-6-(2-hydroxyethyl)-7-methyl-1H-inden-1-one |
| 70 | 070 | (3a'R,4'R)-4'-hydroxy-7'-methyl-3a',4'-dihydro-1'H-dispiro[cyclopropane-1,6'-indene-5',2''-[1,3]dioxolan]-1'-one |
| 71 | 071 | (3a'R,4'R)-7'-methyl-4'-((triethylsilyl)oxy)-3a',4'-dihydro-1'H-dispiro[cyclopropane-1,6'-indene-5',2''-[1,3]dioxolan]-1'-one |
| 72 | 072 | (7'R,7a'R)-7'-hydroxy-4'-methyl-7',7a'-dihydrospiro[cyclopropane-1,5'-indene]-3,6'-dione |
| 73 | 073 | (7'R,7a'R)-4'-methyl-7'-((triethylsilyl)oxy)-7',7a'-dihydrospiro[cyclopropane-1,5'-indene]-3',6'-dione |
| 74 | 074 | (6'R)-3'-((((2,2-dimethyl-1,3-dioxolan-4-yl)methyl)thio)methyl)-6'-hydroxy-2',4',6'-trimethylspiro[cyclopropane-1,5'-inden]-7'(6'H)-one |
| 75 | 075 | (R)-(6'-hydroxy-4',6'-dimethyl-7'-oxo-6',7'-dihydrospiro[cyclopropane-1,5'-inden]-2'-yl)methyl acetate |
| 76 | 076 | (R)-(6'-hydroxy-4',6'-dimethyl-7'-oxo-6',7'-dihydrospiro[cyclopropane-1,5'-indene]-2',3'-diyl)bis(methylene) diacetate |
| 77 | 077 | (R)-(6'-hydroxy-3'-(hydroxymethyl)-4',6'-dimethyl-7'-oxo-6',7'-dihydrospiro[cyclopropane-1,5'-inden]-2'-yl)methyl acetate |
| 78 | 078 | (R)-(6'-hydroxy-2'-(hydroxymethyl)-4',6'-dimethyl-7'-oxo-6',7'-dihydrospiro[cyclopropane-1,5'-inden]-3'-yl)methyl acetate |
| 79 | 079 | (R)-6'-hydroxy-2'-(methoxymethyl)-4',6'-dimethylspiro[cyclopropane-1,5'-inden]-7'(6'H)-one |
| 80 | 080 | (R)-6'-hydroxy-3'-(methoxymethyl)-2',4',6'-trimethylspiro[cyclopropane-1,5'-inden]-7'(6'H)-one |
| 81 | 081 | (R)-6'-hydroxy-2'-(hydroxymethyl)-3'-(methoxymethyl)-4',6'-dimethylspiro[cyclopropane-1,5'-inden]-7'(6'H)-one |
| 82 | 082 | (R)-6'-hydroxy-2',3'-bis(methoxymethyl)-4',6'-dimethylspiro[cyclopropane-1,5'-inden]-7'(6'H)-one |
| 83 | 083 | (R)-2-acetamido-3-((((R)-6'-hydroxy-2',4',6'-trimethyl-7'-oxo-6',7'-dihydrospiro[cyclopropane-1,5'-inden]-3'-yl)methyl)thio)-N-((S)-1-((2-(((S)-4-methyl-1-oxopentan-2-yl)amino)-2-oxoethyl)amino)-1-oxo-3-phenylpropan-2-yl)propanamide |
| 84 | 084 | (S)-2-((R)-2-acetamido-3-((((R)-6'-hydroxy-2',4',6'-trimethyl-7'-oxo-6',7'-dihydrospiro[cyclopropane-1,5'-inden]-3'-yl)methyl)thio)propanamido)-4-methyl-N-(2-oxo-2-(((R)-1-oxo-3-phenylpropan-2-yl)amino)ethyl)pentanamide |
| 85 | 085 | (S)-2-((R)-2-acetamido-3-((((R)-6'-hydroxy-2',4',6'-trimethyl-7'-oxo-6',7'-dihydrospiro[cyclopropane-1,5'-inden]-3'-yl)methyl)thio)propanamido)-4-methyl-N-((S)-4-methyl-1-oxo-1-(((R)-1-oxo-3-phenylpropan-2-yl)amino)pentan-2-yl)pentanamide |
| 86 | 086 | (R)-2-acetamido-3-((((R)-6'-hydroxy-2',4',6'-trimethyl-7'-oxo-6',7'-dihydrospiro[cyclopropane-1,5'-inden]-3'-yl)methyl)thio)-N-(2-oxo-2-(((R)-1-oxo-3-phenylpropan-2-yl)amino)ethyl)propanamide |
| 87 | 087 | (S)-2-((R)-2-acetamido-3-((((R)-6'-hydroxy-2',4',6'-trimethyl-7'-oxo-6',7'-dihydrospiro[cyclopropane-1,5'-inden]-3'-yl)methyl)thio)propanamido)-4-methyl-N-((S)-4-methyl-1-(((S)-4-methyl-1-oxopentan-2-yl)amino)-1-oxopentan-2-yl)pentanamide |
| 88 | 088 | (R)-(6'-acetoxy-2',4',6'-trimethyl-7'-oxo-6',7'-dihydrospiro[cyclopropane-1,5'-inden]-3'-yl)methyl acetate |
| 89 | 089 | N5-((R)-1-((carboxymethyl)amino)-3-((((R)-6'-hydroxy-2',4',6'-trimethyl-7'-oxo-6',7'-dihydrospiro[cyclopropane-1,5'-inden]-3'-yl)methyl)thio)-1-oxopropan-2-yl)-D-glutamine |
| 90 | 090 | (R)-2'-(hydroxymethyl)-4',6'-dimethyl-7'-oxo-6',7'-dihydrospiro[cyclopropane-1,5'-inden]-6'-yl acetate |
| 91 | 091 | (R)-3-(6'-hydroxy-2',4',6'-trimethyl-7'-oxo-6',7'-dihydrospiro[cyclopropane-1,5'-inden]-3'-yl)propanoic acid |
| 92 | 092 | (R)-6'-hydroxy-3'-(3-methoxypropyl)-2',4',6'-trimethylspiro[cyclopropane-1,5'-inden]-7'(6'H)-one |

TABLE V-continued

IUPAC names of the Illudofulvene analogs.

| Entry # | Illudofulvene Analog | IUPAC Name of Illudofulvene Analog |
|---|---|---|
| 93 | 093 | (R)-3'-(3,3-diethoxypropyl)-6'-hydroxy-2',4',6-trimethylspiro[cyclopropane-1,5'-inden]-7'(6'H)-one |
| 94 | 094 | (R)-3-(6'-hydroxy-2',4',6'-trimethyl-7'-oxo-6',7'-dihydrospiro[cyclopropane-1,5'-inden]-3'-yl)propyl acetate |
| 95 | 095 | (R)-6'-hydroxy-3'-(3-methoxypropyl)-2',4',6'-trimethylspiro[cyclopropane-1,5'-inden]-7'(6'H)-one |
| 96 | 096 | (R)-6'-hydroxy-2',4',6'-trimethyl-3'-(((1-methyl-1H-imidazol-2-yl)thio)methyl)spiro[cyclopropane-1,5'-inden]-7'(6'H)-one |
| 97 | 097 | S-(((R)-6'-hydroxy-2',4',6'-trimethyl-7'-oxo-6',7'-dihydrospiro[cyclopropane-1,5'-inden]-3'-yl)methyl)homocysteine |
| 98 | 098 | ((S)-3-((((R)-6'-hydroxy-2',4',6'-trimethyl-7'-oxo-6',7'-dihydrospiro[cyclopropane-1,5'-inden]-3'-yl)methyl)thio)-2-methylpropanoyl)proline |
| 99 | 099 | (2'S,6'R)-6'-hydroxy-2'-(hydroxymethyl)-2',4',6'-trimethylspiro[cyclopropane-1,5'-indene]-3',7'(2'H,6'H)-dione |
| 100 | 100 | S-(((R)-6'-hydroxy-2',4',6'-trimethyl-7'-oxo-6',7'-dihydrospiro[cyclopropane-1,5'-inden]-3'-yl)methyl)-N-S-(((R)-6'-hydroxy-2',4',6'-trimethyl-7'-oxo-6',7'-dihydrospiro[cyclopropane-1,5'-inden]-3'-yl)methyl)cysteinyl-L-asparaginylglycyl-L-arginylcysteine |
| 101 | 101 | S-(((R)-6'-hydroxy-2',4',6'-trimethyl-7'-oxo-6',7'-dihydrospiro[cyclopropane-1,5'-inden]-3'-yl)methyl)-N-S-(((R)-6'-hydroxy-2',4',6'-trimethyl-7'-oxo-6',7'-dihydrospiro[cyclopropane-1,5'-inden]-3'-yl)methyl)cysteinyl-L-arginylglycyl-L-asparaginylcysteine |
| 102 | 102 | S-(((R)-6'-hydroxy-2',4',6'-trimethyl-7'-oxo-6',7'-dihydrospiro[cyclopropane-1,5'-inden]-3'-yl)methyl)cysteinyl-L-asparaginylglycyl-L-arginylcysteine |
| 103 | 103 | (R)-(6'-acetoxy-2'-(hydroxymethyl)-4',6'-dimethyl-7'-oxo-6',7'-dihydrospiro[cyclopropane-1,5'-inden]-3'-yl)methyl acetate |
| 104 | 104 | (R)-8'-hydroxy-6',8'-dimethyl-1',5'-dihydrospiro[cyclopropane-1,7'-indeno[1,2-e][1,3]dioxepin]-9'(8'H)-one |
| 105 | 105 | (E)-2-((2R,4S)-4-hydroxy-2-((1R,2S)-2-hydroxy-4,4-dimethylcyclopentyl)-2-methylcyclobutylidene)propanal |
| 106 | 106 | 5-(((3'S,6'R)-6'-hydroxy-2',2',4',6'-tetramethyl-7'-oxo-2',3',6',7'-tetrahydrospiro[cyclopropane-1,5'-inden]-3'-yl)oxy)-5-oxopentanoic acid |
| 107 | 107 | (3'S,6'R)-6'-hydroxy-2',2',4',6'-tetramethyl-7'-oxo-2',3',6',7'-tetrahydrospiro[cyclopropane-1,5'-inden]-3'-yl ((13S)-13-methyl-17-oxo-7,8,9,11,12,13,14,15,16,17-decahydro-6H-cyclopenta[a]phenanthren-3-yl) glutarate |
| 108 | 108 | (13S)-17-hydroxy-13-methyl-7,8,9,11,12,13,14,15,16,17-decahydro-6H-cyclopenta[a]phenanthren-3-yl ((3'S,6'R)-6'-hydroxy-2',2',4',6'-tetramethyl-7'-oxo-2',3',6',7'-tetrahydrospiro[cyclopropane-1,5'-inden]-3'-yl) glutarate |
| 109 | 109 | (13S)-17-hydroxy-13-methyl-7,8,9,11,12,13,14,15,16,17-decahydro-6H-cyclopenta[a]phenanthren-3-yl ((3'S,6'R)-6'-hydroxy-2',2',4',6'-tetramethyl-7'-oxo-2',3',6',7'-tetrahydrospiro[cyclopropane-1,5'-inden]-3'-yl) glutarate |
| 110 | 110 | (13S)-13-methyl-17-oxo-7,8,9,11,12,13,14,15,16,17-decahydro-6H-cyclopenta[a]phenanthren-3-yl 3-((R)-6'-hydroxy-2',4',6'-trimethyl-7'-oxo-6',7'-dihydrospiro[cyclopropane-1,5'-inden]-3'-yl)propanoate |
| 111 | 111 | (10R,13S)-10,13-dimethyl-3-oxo-2,3,6,7,8,9,10,11,12,13,14,15,16,17-tetradecahydro-1H-cyclopenta[a]phenanthren-17-yl 3-(6'-hydroxy-2',4'-dimethyl-7'-oxo-6',7'-dihydrospiro[cyclopropane-1,5'-inden]-3'-yl)propanoate |
| 112 | 112 | (13S)-10,13-dimethyl-17-oxohexadecahydro-1H-cyclopenta[a]phenanthren-3-yl 3-((R)-6'-hydroxy-2',4',6'-trimethyl-7'-oxo-6',7'-dihydrospiro[cyclopropane-1,5'-inden]-3'-yl)propanoate |
| 113 | 113 | (R)-3'-(but-3-en-1-yl)-6'-hydroxy-2',4',6'-trimethylspiro[cyclopropane-1,5'-inden]-7'(6'H)-one |
| 114 | 114 | (6'R)-6'-hydroxy-2',4',6'-trimethyl-3'-(2-(oxiran-2-yl)ethyl)spiro[cyclopropane-1,5'-inden]-7'(6'H)-one |
| 115 | 115 | (R)-3-(6'-hydroxy-2',4',6'-trimethyl-7'-oxo-6',7'-dihydrospiro[cyclopropane-1,5'-inden]-3'-yl)propanal oxime |
| 116 | 116 | (R)-3'-(tert-butoxymethyl)-6'-hydroxy-2',4',6'-trimethylspiro[cyclopropane-1,5'-inden]-7'(6'H)-one |
| 117 | 117 | 5-(((2'S,6'R)-3'-((4-carboxybutanoyl)oxy)-6'-hydroxy-2',4',6'-trimethyl-7'-oxo-2',3',6',7'-tetrahydrospiro[cyclopropane-1,5'-inden]-2'-yl)methoxy)-5-oxopentanoic acid |
| 118 | 118 | 5-(((2'S,6'R)-2'-(((3,5-dinitrobenzoyl)oxy)methyl)-6'-hydroxy-2',4',6'-trimethyl-7'-oxo-2',3',6',7'-tetrahydrospiro[cyclopropane-1,5'-inden]-3'-yl)oxy)-5-oxopentanoic acid |
| 119 | 119 | (6'R)-3'-(3,4-dihydroxybutyl)-6'-hydroxy-2',4',6'-trimethylspiro[cyclopropane-1,5'-inden]-7'(6'H)-one |
| 120 | 120 | (R)-6'-hydroxy-3'-(3-((S)-6'-hydroxy-2',4',6'-trimethyl-7'-oxo-6',7'-dihydrospiro[cyclopropane-1,5'-inden]-3'-yl)propylidene)hydrazineyl)propyl)-2',4',6'-trimethylspiro[cyclopropane-1,5'-inden]-7'(6'H)-one |
| 121 | 121 | (R)-2-(3-(6'-hydroxy-2',4',6'-trimethyl-7'-oxo-6',7'-dihydrospiro[cyclopropane-1,5'-inden]-3'-yl)propylidene)hydrazine-1-carboxamide |
| 122 | 122 | (R)-6'-hydroxy-2',4',6'-trimethyl-3'-(3-(2-phenylhydrazineylidene)propyl)spiro[cyclopropane-1,5'-inden]-7'(6'H)-one |
| 123 | 123 | (R)-N'-(3-(6'-hydroxy-2',4',6'-trimethyl-7'-oxo-6',7'-dihydrospiro[cyclopropane-1,5'-inden]-3'-yl)propylidene)-4-methylbenzenesulfonohydrazide |
| 124 | 124 | (R)-3-(6'-hydroxy-2',4',6'-trimethyl-7'-oxo-6',7'-dihydrospiro[cyclopropane-1,5'-inden]-3'-yl)propanal O-acetyl oxime |
| 125 | 125 | (R)-3'-(3-(2-(2,4-dinitrophenyl)hydrazineylidene)propyl)-6'-hydroxy-2',4',6'-trimethylspiro[cyclopropane-1,5'-inden]-7'(6'H)-one |
| 126 | 126 | (R)-6'-hydroxy-2',4',6'-trimethyl-7'-oxo-6',7'-dihydrospiro[cyclopropane-1,5'-indene]-3'-carbaldehyde oxime |
| 127 | 127 | 2-hydroxy-4-((R)-6'-hydroxy-2',4',6'-trimethyl-7'-oxo-6',7'-dihydrospiro[cyclopropane-1,5'-inden]-3'-yl)butanenitrile |
| 128 | 128 | (6'R)-6'-hydroxy-3'-(3-hydroxybutyl)-2',4',6'-trimethylspiro[cyclopropane-1,5'-inden]-7'(6'H)-one |
| 129 | 129 | (6'R)-2',4',6'-trimethyl-6',7'-dihydrospiro[cyclopropane-1,5'-indene]-6',7'-diol |
| 130 | 130 | (R)-6'-hydroxy-3'-(3-(hydroxyamino)propyl)-2',4',6'-trimethylspiro[cyclopropane-1,5'-inden]-7'(6'H)-one |
| 131 | 131 | (R)-N-benzyl-3-(6'-hydroxy-2',4',6'-trimethyl-7'-oxo-6',7'-dihydrospiro[cyclopropane-1,5'-inden]-3'-yl)propanamide |
| 132 | 133 | (E)-7-(chloromethylene)-5-hydroxy-5,9-dimethylspiro[3.5]non-8-en-6-one |
| 133 | 134 | (E)-6-(chloromethylene)-4-hydroxy-4,8-dimethylspiro[2.5]oct-7-en-5-one |
| 134 | 135 | ((2'S,6'R)-3',6'-dihydroxy-2',4',6'-trimethyl-7'-oxo-2',3',6',7'-tetrahydrospiro[cyclopropane-1,5'-inden]-2'-yl)methyl 4-nitrobenzoate |
| 135 | 136 | ((2'S,6'R)-3',6'-dihydroxy-2',4',6'-trimethyl-7'-oxo-2',3',6',7'-tetrahydrospiro[cyclopropane-1,5'-inden]-2'-yl)methyl 4-(N-acetoxyacetamido)benzoate |
| 136 | 137 | ((2'S,6'R)-6'-hydroxy-2',4',6'-trimethyl-3',7'-dioxo-2',3',6',7'-tetrahydrospiro[cyclopropane-1,5'-inden]-2'-yl)methyl 4-nitrobenzoate |

TABLE V-continued

IUPAC names of the Illudofulvene analogs.

| Entry # | Illudo-fulvene Analog | IUPAC Name of Illudofulvene Analog |
|---|---|---|
| 137 | 138 | ((2'S,6'R)-6'-hydroxy-2',4',6'-trimethyl-3',7'-dioxo-2',3',6',7'-tetrahydrospiro[cyclopropane-1,5'-inden]-2'-yl)methyl 4-(N-acetoxyacetamido)benzoate |
| 138 | 139 | (2'S,6'R)-6'-hydroxy-2',4',6'-trimethyl-2'-(((4-nitrobenzoyl)oxy)methyl)-7'-oxo-2',3',6',7'-tetrahydrospiro[cyclopropane-1,5'-inden]-3'-yl 4-nitrobenzoate |
| 139 | 140 | ((2'S,6'R)-3'-((4-(N-acetoxyacetamido)benzoyl)oxy)-6'-hydroxy-2',4',6'-trimethyl-7'-oxo-2',3',6',7'-tetrahydrospiro[cyclopropane-1,5'-inden]-2'-yl)methyl 4-(N-acetoxyacetamido)benzoate |
| 140 | 141 | dimethyl (5'R)-4',5'-dihydroxy-5',7',9'-trimethyl-4',5'-dihydro-1'H-spiro[cyclopropane-1,6'-[1,3a]ethenoindene]-2',3'-dicarboxylate |
| 141 | 142 | dimethyl (5'R)-5'-hydroxy-5',7',9'-trimethyl-4'-oxo-4',5'-dihydro-1'H-spiro[cyclopropane-1,6'-[1,3a]ethenoindene]-2',3'-dicarboxylate |
| 142 | 143 | (R)-6'-hydroxy-1',2',4',6'-tetramethylspiro[cyclopropane-1,5'-inden]-7'(6'H)-one |
| 143 | 144 | (R)-2-((2'-ethyl-6'-hydroxy-4',6'-dimethyl-7'-oxo-6',7'-dihydrospiro[cyclopropane-1,5'-inden]-3'-yl)methoxy)ethyl acetate |
| 144 | 145 | (R)-5-((6'-hydroxy-2',4',6'-trimethyl-7'-oxo-6',7'-dihydrospiro[cyclopropane-1,5'-inden]-3'-yl)methoxy)-5-oxopentanoic acid |
| 145 | 146 | (R)-4-(6'-hydroxy-2',4',6'-trimethyl-7'-oxo-6',7'-dihydrospiro[cyclopropane-1,5'-inden]-3'-yl)butanenitrile |
| 146 | 147 | (R)-3'-((benzo[d]thiazol-2-ylthio)methyl)-6'-hydroxy-2',4',6'-trimethylspiro[cyclopropane-1,5'-inden]-7'(6'H)-one |
| 147 | 148 | (R)-3'-((benzo[d]oxazol-2-ylthio)methyl)-6'-hydroxy-2',4',6'-trimethylspiro[cyclopropane-1,5'-inden]-7'(6'H)-one |
| 148 | 149 | (R)-6'-hydroxy-2',4',6'-trimethyl-3'-(((1-methyl-1H-tetrazol-5-yl)thio)methyl)spiro[cyclopropane-1,5'-inden]-7'(6'H)-one |
| 149 | 150 | (R)-6'-hydroxy-2',4',6'-trimethyl-3'-(((5-methyl-1H-benzo[d]imidazol-2-yl)methyl)methyl)spiro[cyclopropane-1,5'-inden]-7'(6'H)-one |
| 150 | 151 | (R)-6'-hydroxy-2',4',6'-trimethyl-3'-(((1-phenyl-1H-tetrazol-5-yl)thio)methyl)spiro[cyclopropane-1,5'-inden]-7'(6'H)-one |
| 151 | 152 | (R)-6'-hydroxy-2',4',6'-trimethyl-3'-(((5-nitro-1H-benzo[d]imidazol-2-yl)thio)methyl)spiro[cyclopropane-1,5'-inden]-7'(6'H)-one |
| 152 | 153 | (R)-3'-(((1H-1,2,4-triazol-3-yl)thio)methyl)-6'-hydroxy-2',4',6'-trimethylspiro[cyclopropane-1,5'-inden]-7'(6'H)-one |
| 153 | 154 | (R)-6'-hydroxy-3'-(((4-hydroxypteridin-2-yl)thio)methyl)-2',4',6'-trimethylspiro[cyclopropane-1,5'-inden]-7'(6'H)-one |
| 154 | 155 | (R)-6'-hydroxy-3'-(((1-(4-hydroxyphenyl)-1H-tetrazol-5-yl)thio)methyl)-2',4',6'-trimethylspiro[cyclopropane-1,5'-inden]-7'(6'H)-one |
| 155 | 156 | (R)-4-(5-(((6'-hydroxy-2',4',6'-trimethyl-7'-oxo-6',7'-dihydrospiro [cyclopropane-1,5'-inden]-3'-yl)methyl)thio)-1H-tetrazol-1-yl)phenyl acetate |
| 156 | 157 | 7'-methyl-4'H-dispiro[cyclobutane-1,6'-indene-5',2''-[1,3]dioxolan]-4'-one |
| 157 | 158 | 5-hydroxy-2,2,6,8a-tetramethyl-2,3,3a,8,8a,8b-hexahydro-1H-cyclobuta[d]cyclopenta[b]oxepin-7(5H)-one |
| 158 | 159 | ((6'R)-3',6'-dihydroxy-2',4',6'-trimethyl-7'-oxo-2',3',6',7'-tetrahydrospiro[cyclopropane-1,5'-inden]-2'-yl)methyl acetate |
| 159 | 160 | 5-(((6'R)-2'-(acetoxymethyl)-6'-hydroxy-2',4',6'-trimethyl-7'-oxo-2',3',6',7'-tetrahydrospiro[cyclopropane-1,5'-inden]-3'-yl)oxy)-5-oxopentanoic acid |
| 160 | 161 | ((6'R)-6'-hydroxy-2',4',6'-trimethyl-3',7'-dioxo-2',3',6',7'-tetrahydrospiro[cyclopropane-1,5'-inden]-2'-yl)methyl acetate |
| 161 | 162 | 5-(((6'R)-6'-hydroxy-2',4',6'-trimethyl-3',7'-dioxo-2',3',6',7'-tetrahydrospiro[cyclopropane-1,5'-inden]-2'-yl)methoxy)-5-oxopentanoic acid |
| 162 | 163 | (6'R)-2'-(acetoxymethyl)-6'-hydroxy-2',4',6'-trimethyl-7'-oxo-2',3',6',7'-tetrahydrospiro[cyclopropane-1,5'-inden]-3'-yl 2-chloroacetate |
| 163 | 164 | (R)-(6'-hydroxy-2',4',6'-trimethyl-7'-oxo-6',7'-dihydrospiro[cyclopropane-1,5'-inden]-3'-yl)methyl 2-chloroacetate |
| 164 | 165 | (R)-(6'-hydroxy-2',4',6'-trimethyl-7'-oxo-6',7'-dihydrospiro[cyclopropane-1,5'-inden]-3'-yl)methyl 2-morpholinoacetate |
| 165 | 166 | (6'R)-2'-(acetoxymethyl)-6'-hydroxy-2',4',6'-trimethyl-7'-oxo-2',3',6',7'-tetrahydrospiro[cyclopropane-1,5'-inden]-3'-yl glutarate |
| 166 | 167 | (6'R)-6'-hydroxy-2'-(hydroxymethyl)-2',4',6'-trimethyl-7'-oxo-2',3',6',7'-tetrahydrospiro[cyclopropane-1,5'-inden]-3'-yl methyl glutarate |
| 167 | 168 | ((6'R)-6'-hydroxy-2',4',6'-trimethyl-3',7'-dioxo-2',3',6',7'-tetrahydrospiro[cyclopropane-1,5'-inden]-2'-yl)methyl methyl glutarate |
| 168 | 169 | ((6'R)-6'-hydroxy-2',4',6'-trimethyl-3',7'-dioxo-2',3',6',7'-tetrahydrospiro[cyclopropane-1,5'-inden]-2'-yl)methyl 2-chloroacetate |
| 169 | 170 | 5-(2-hydroxyethyl)-3-(hydroxymethyl)-2,4,6-trimethyl-1H-inden-7-ol |
| 170 | 171 | 6-(2-hydroxyethyl)-2,5,7-trimethyl-1-methylene-1H-inden-4-ol |
| 171 | 172 | 6-ethyl-2,5,7-trimethyl-1-methylene-1H-inden-4-ol |
| 172 | 173 | 2-(4-hydroxy-2,5,7-trimethyl-1-methylene-1H-inden-6-yl)ethyl acetate |
| 173 | 174 | 5-(2-hydroxyethyl)-3-(hydroxymethyl)-2,4,6-trimethyl-1H-indene-1,7-diol |
| 174 | 175 | (2S,3S,4R,5S,6R)-2-(acetoxymethyl)-6-(((R)-6'-hydroxy-2',4',6'-trimethyl-7'-oxo-6',7'-dihydrospiro[cyclopropane-1,5'-inden]-3'-yl)methoxy)tetrahydro-2H-pyran-3,4,5-triyl triacetate |
| 175 | 176 | 3-((R)-6'-hydroxy-2',4',6'-trimethyl-7'-oxo-6',7'-dihydrospiro[cyclopropane-1,5'-inden]-3'-yl)propyl leucinate |
| 176 | 177 | (R)-5-(3-(6'-hydroxy-2',4',6'-trimethyl-7'-oxo-6',7'-dihydrospiro[cyclopropane-1,5'-inden]-3'-yl) propoxy)-5-oxopentanoic acid |
| 177 | 178 | (R)-4-(3-(6'-hydroxy-2',4',6'-trimethyl-7'-oxo-6',7'-dihydrospiro[cyclopropane-1,5'-inden]-3'-yl)propoxy)-4-oxobutanoic acid |
| 178 | 179 | (R)-3-(6'-hydroxy-2',4',6'-trimethyl-7'-oxo-6',7'-dihydrospiro[cyclopropane-1,5'-inden]-3'-yl)propyl glycinate |
| 179 | 180 | (1a'R,3'R,7'S,7a'R)-3',7'-dihydroxy-1a',3',6',6'-tetramethyl-6',7'-dihydro-1a'H-spiro[cyclopropane-1,2'-indeno[3a,4-b]oxiren]-4'(3'H)-one |
| 180 | 181 | ((1a'R,3'R,6'S,7'S,7a'R)-3',7'-dihydroxy-1a',3',6'-trimethyl-4'-oxo-3',4',6',7'-tetrahydro-1a'H-spiro[cyclopropane-1,2'-indeno[3a,4-b]oxiren]-6'-yl)methyl acetate |
| 181 | 182 | (2'R,7'S,7a'S)-2'-chloro-7'-hydroxy-2',4'-dimethyl-1',2',7',7a'-tetrahydrospiro[cyclopropane-1,5'-indene]-3',6'-dione |
| 182 | 183 | (2'S,7'S,7a'S)-7'-hydroxy-2'-isopropoxy-2',4'-dimethyl-1',2',7',7a'-tetrahydrospiro[cyclopropane-1,5'-indene]-3',6'-dione |
| 183 | 184 | (R)-1-hydroxy-1-((6'-hydroxy-2',4',6'-trimethyl-7'-oxo-6',7'-dihydrospiro[cyclopropane-1,5'-inden]-3'-yl)methyl)urea |
| 184 | 185 | (S)-6'-hydroxy-2',4',6'-trimethylspiro[cyclopropane-1,5'-inden]-7'(6'H)-one |
| 185 | 186 | (6'S,7'R)-6',7'-dihydroxy-2',4',6'-trimethyl-7',7a'-dihydrospiro[cyclopropane-1,5'-inden]-3'(6'H)-one |

TABLE V-continued

IUPAC names of the Illudofulvene analogs.

| Entry # | Illudo-fulvene Analog | IUPAC Name of Illudofulvene Analog |
|---|---|---|
| 186 | 187 | (S)-6'-hydroxy-3'-(hydroxymethyl)-2',4',6'-trimethylspiro[cyclopropane-1,5'-inden]-7'(6'H)-one |
| 187 | 188 | (6'S,6'''S)-3',3'''-methylenebis(6'-hydroxy-2',4',6'-trimethylspiro[cyclopropane-1,5'-inden]-7'(6'H)-one) |
| 188 | 189 | (R)-1-((6'-hydroxy-2',4',6'-trimethyl-7'-oxo-6',7'-dihydrospiro[cyclopropane-1,5'-inden]-3'-yl)methyl)-1H-pyrrole-2,5-dione |
| 189 | 190 | (R)-1-(3-(6'-hydroxy-2',4',6'-trimethyl-7'-oxo-6',7'-dihydrospiro[cyclopropane-1,5'-inden]-3'-yl)propyl)-1H-pyrrole-2,5-dione |
| 190 | 191 | 6'-hydroxy-4',6'-dimethylspiro[cyclobutane-1,5'-inden]-7'(6'H)-one |
| 191 | 192 | (R)-2-((6'-hydroxy-2',4',6'-trimethyl-7'-oxo-6',7'-dihydrospiro[cyclopropane-1,5'-inden]-3'-yl)methyl)isoindoline-1,3-dione |
| 192 | 193 | (R)-3'-(azidomethyl)-6'-hydroxy-2',4',6'-trimethylspiro[cyclopropane-1,5'-inden]-7'(6'H)-one |
| 193 | 194 | (R)-3'-(((R)-3'-(azidomethyl)-6'-hydroxy-2',4',6'-trimethyl-7'-oxo-6',7'-dihydrospiro[cyclopropane-1,5'-inden]-1'-yl)methyl)-6'-hydroxy-2',4',6'-trimethylspiro[cyclopropane-1,5'-inden]-7'(6'H)-one |
| 194 | 195 | (R)-3'-(3-azidopropyl)-6'-hydroxy-4',6'-dimethylspiro[cyclopropane-1,5'-inden]-7'(6'H)-one |
| 195 | 196 | 3-((R)-6'-hydroxy-2',4',6'-trimethyl-7'-oxo-6',7'-dihydrospiro[cyclopropane-1,5'-inden]-3'-yl)propyl L-prolinate |
| 196 | 197 | (R)-2-(3-(6'-hydroxy-2',4',6'-trimethyl-7'-oxo-6',7'-dihydrospiro[cyclopropane-1,5'-inden]-3'-yl)propyl)isoindoline-1,3-dione |
| 197 | 198 | (R)-6'-hydroxy-2',4',6'-trimethyl-3'-((4-nitrophenoxy)methyl)spiro[cyclopropane-1,5'-inden]-7'(6'H)-one |
| 198 | 199 | (R)-6'-hydroxy-2',4',6'-trimethyl-3'-(phenoxymethyl)spiro[cyclopropane-1,5'-inden]-7'(6'H)-one |
| 199 | 200 | (R)-6'-hydroxy-3'-(2-hydroxybenzyl)-2',4',6'-trimethylspiro[cyclopropane-1,5'-inden]-7'(6'H)-one |
| 200 | 201 | (R)-N-(3-(6'-hydroxy-2',4',6'-trimethyl-7'-oxo-6',7'-dihydrospiro[cyclopropane-1,5'-inden]-3'-yl)propyl)acetamide |
| 201 | 202 | (S)-N-(3-((R)-6'-hydroxy-2',4',6'-trimethyl-7'-oxo-6',7'-dihydrospiro[cyclopropane-1,5'-inden]-3'-yl)propyl)pyrrolidine-2-carboxamide |
| 202 | 203 | 3-((R)-6'-hydroxy-2',4',6'-trimethyl-7'-oxo-6',7'-dihydrospiro[cyclopropane-1,5'-inden]-3'-yl)propyl L-seryl-L-prolinate |
| 203 | 204 | 2'-(((tert-butyldimethylsilyl)oxy)methyl)-3',6'-dihydroxy-2',4',6'-trimethyl-2',3'-dihydrospiro[cyclopropane-1,5'-inden]-7'(6'H)-one |
| 204 | 205 | (2'R,3'S,6'R)-3'-amino-2'-(((tert-butyldimethylsilyl) oxy)methyl)-6'-hydroxy-2',4',6'-trimethyl-2',3'-dihydrospiro[cyclopropane-1,5'-inden]-7'(6'H)-one |
| 205 | 206 | (2'R,3'S,6'R)-3'-amino-6'-hydroxy-2'-(hydroxymethyl)-2',4',6'-trimethyl-2',3'-dihydrospiro[cyclopropane-1,5'-inden]-7'(6'H)-one |
| 206 | 207 | (S)-2-amino-N-(3-((R)-6'-hydroxy-2',4',6'-trimethyl-7'-oxo-6',7'-dihydrospiro[cyclopropane-1,5'-inden]-3'-yl)propyl)-4-methylpentanamide |
| 207 | 208 | 3-((R)-6'-hydroxy-2',4',6'-trimethyl-7'-oxo-6',7'-dihydrospiro[cyclopropane-1,5'-inden]-3'-yl)propyl (tert-butoxycarbonyl)-L-seryl-L-prolinate |
| 208 | 209 | 3-((R)-6'-hydroxy-2',4',6'-trimethyl-7'-oxo-6',7'-dihydrospiro[cyclopropane-1,5'-inden]-3'-yl)propyl L-seryl-L-seryl-L-prolinate |
| 209 | 210 | 3-((R)-6'-hydroxy-2',4',6'-trimethyl-7'-oxo-6',7'-dihydrospiro[cyclopropane-1,5'-inden]-3'-yl)propyl ((S)-2-((S)-2-((2S,4R)-1-acetyl-4-hydroxypyrrolidine-2-carboxamido)-3-hydroxypropanamido)-3-hydroxypropanamido)-2-cyclohexylacetyl)-L-glutaminyl-L-seryl-L-seryl-L-prolinate |
| 210 | 211 | (R)-3'-(3-aminopropyl)-6'-hydroxy-2',4',6'-trimethylspiro[cyclopropane-1,5'-inden]-7'(6'H)-one |
| 211 | 212 | (3'S,6'R)-6'-hydroxy-2',2',4',6'-tetramethyl-7'-oxo-2',3',6',7'-tetrahydrospiro[cyclopropane-1,5'-inden]-3'-yl L-prolinate |
| 212 | 213 | (2'S,3'R,6'R)-2'-(((tert-butyldimethylsilyl)oxy)methyl)-6'-hydroxy-2',4',6'-trimethyl-7'-oxo-2',3',6',7'-tetrahydrospiro[cyclopropane-1,5'-inden]-3'-yl L-prolinate |
| 213 | 214 | (2'S,3'R,6'R)-2'-(((tert-butyldimethylsilyl)oxy)methyl)-6'-hydroxy-2',4',6'-trimethyl-7'-oxo-2',3',6',7'-tetrahydrospiro[cyclopropane-1,5'-inden]-3'-yl L-seryl-L-seryl-L-prolinate |
| 214 | 215 | (2'S,3'R,6'R)-2'-(((tert-butyldimethylsilyl)oxy)methyl)-6'-hydroxy-2',4',6'-trimethyl-7'-oxo-2',3',6',7'-tetrahydrospiro[cyclopropane-1,5'-inden]-3'-yl ((S)-2-((S)-2-((2S,4R)-1-acetyl-4-hydroxypyrrolidine-2-carboxamido)-3-hydroxypropanamido)-3-hydroxypropanamido)-2-cyclohexylacetyl)-L-glutaminyl-L-seryl-L-seryl-L-prolinate |
| 215 | 216 | (3'S,6'R)-6'-hydroxy-2',2',4',6'-tetramethyl-7'-oxo-2',3',6',7'-tetrahydrospiro[cyclopropane-1,5'-inden]-3'-yl ((S)-2-((S)-2-((2S,4R)-1-acetyl-4-hydroxypyrrolidine-2-carboxamido)-3-hydroxypropanamido)-3-hydroxypropanamido)-2-cyclohexylacetyl)-L-glutaminyl-L-seryl-L-seryl-L-prolinate |
| 216 | 217 | (R)-(6'-hydroxy-2',4',6'-trimethyl-7'-oxo-6',7'-dihydrospiro[cyclopropane-1,5'-inden]-3'-yl)methyl 6-(2,5-dioxo-2,5-dihydro-1H-pyrrol-1-yl)hexanoate |
| 217 | 218 | (3'S,6'R)-6'-hydroxy-2',2',4',6'-tetramethyl-7'-oxo-2',3',6',7'-tetrahydrospiro[cyclopropane-1,5'-inden]-3'-yl 6-(2,5-dioxo-2,5-dihydro-1H-pyrrol-1-yl)hexanoate |
| 218 | 219 | (2'S,3'R,6'R)-2'-(((tert-butyldimethylsilyl)oxy)methyl)-6'-hydroxy-2',4',6'-trimethyl-7'-oxo-2',3',6',7'-tetrahydrospiro[cyclopropane-1,5'-inden]-3'-yl 4-(fluorosulfonyl)benzoate |
| 219 | 220 | (R)-1-acetoxy-1-((6'-hydroxy-2',4',6'-trimethyl-7'-oxo-6',7'-dihydrospiro[cyclopropane-1,5'-inden]-3'-yl)methyl)urea |
| 220 | 221 | (S)-2-((3S,6S,9S,12S,15S)-3-((1H-imidazol-4-yl)methyl)-12-(4-aminobutyl)-6,9-bis(hydroxymethyl)-15-isobutyl-1-morpholino-1,4,7,10,13-pentaoxo-2,5,8,11,14-pentaazahexadecan-16-amido)-N1-((S)-1-((3-((R)-6'-hydroxy-2',4',6'-trimethyl-7'-oxo-6',7'-dihydrospiro[cyclopropane-1,5'-inden]-3'-yl)propyl)amino)-4-methyl-1-oxopentan-2-yl)pentanediamide |
| 221 | 222 | (3'S,6'R)-6'-hydroxy-2',2',4',6'-tetramethyl-7'-oxo-2',3',6',7'-tetrahydrospiro[cyclopropane-1,5'-inden]-3'-yl 4-(fluorosulfonyl)benzoate |
| 222 | 223 | 3-((R)-6'-hydroxy-2',4',6'-trimethyl-7'-oxo-6',7'-dihydrospiro[cyclopropane-1,5'-inden]-3'-yl)propyl ((4R,7S,13S)-13-(2-amino-2-oxoethyl)-7-(3-guanidinopropyl)-6,9,12,15-tetraoxo-1,2-dithia-5,8,14-triazacycloheptadecane-4-carbonyl)glycinate |
| 223 | 224 | (R,E)-6'-hydroxy-2',4',6'-trimethylspiro[cyclopropane-1,5'-inden]-7'(6'H)-one oxime |
| 224 | 225 | (2'R,3'R,6'R,E)-2',3',6'-trihydroxy-2',4',6'-trimethyl-2',3'-dihydrospiro[cyclopropane-1,5'-inden]-7'(6'H)-one oxime |

TABLE V-continued

IUPAC names of the Illudofulvene analogs.

| Entry # | Illudofulvene Analog | IUPAC Name of Illudofulvene Analog |
|---|---|---|
| 225 | 226 | (R)-(6'-hydroxy-2',4',6'-trimethyl-7'-oxo-6',7'-dihydrospiro[cyclopropane-1,5'-inden]-3'-yl)methyl (E)-octadec-9-enoate |
| 226 | 227 | (R)-3-(6'-hydroxy-2',4',6'-trimethyl-7'-oxo-6',7'-dihydrospiro[cyclopropane-1,5'-inden]-3'-yl)propyl (E)-octadec-9-enoate |
| 227 | 228 | (2'S,6'R)-6'-hydroxy-2',4',6'-trimethyl-2'-((((E)-octadec-9-enoyl)oxy)methyl)-7'-oxo-2',3',6',7'-tetrahydrospiro[cyclopropane-1,5'-inden]-3'-yl (E)-octadec-9-enoate |
| 228 | 229 | (R,E)-N-(3-(6'-hydroxy-2',4',6'-trimethyl-7'-oxo-6',7'-dihydrospiro[cyclopropane-1,5'-inden]-3'-yl)propyl)octadec-9-enamide |
| 229 | 230 | N-((3'R,6'R)-6'-hydroxy-2',2',4',6'-tetramethyl-7'-oxo-2',3',6',7'-tetrahydrospiro[cyclopropane-1,5'-inden]-3'-yl)methanesulfonamide |
| 230 | 231 | N-((3'R,6'R)-6'-hydroxy-2',2',4',6'-tetramethyl-7'-oxo-2',3',6',7'-tetrahydrospiro[cyclopropane-1,5'-inden]-3'-yl)-4-methylbenzenesulfonamide |
| 231 | 232 | (R)-3-(6'-hydroxy-2',4',6'-trimethyl-7'-oxo-6',7'-dihydrospiro[cyclopropane-1,5'-inden]-3'-yl)propyl hydroxycarbamate |
| 232 | 233 | ethyl (R)-hydroxy((6'-hydroxy-2',4',6'-trimethyl-7'-oxo-6',7'-dihydrospiro[cyclopropane-1,5'-inden]-3'-yl)methyl)carbamate |
| 233 | 234 | benzyl (R)-hydroxy((6'-hydroxy-2',4',6'-trimethyl-7'-oxo-6',7'-dihydrospiro[cyclopropane-1,5'-inden]-3'-yl)methyl)carbamate |
| 234 | 235 | tert-butyl (R)-hydroxy((6'-hydroxy-2',4',6'-trimethyl-7'-oxo-6',7'-dihydrospiro[cyclopropane-1,5'-inden]-3'-yl)methyl)carbamate |
| 235 | 236 | (R)-6'-hydroxy-3'-(hydroxymethyl)-1',2',4',6'-tetramethylspiro[cyclopropane-1,5'-inden]-7'(6'H)-one |
| 236 | 237 | (R)-3-(6'-hydroxy-2',4',6'-trimethyl-7'-oxo-6',7'-dihydrospiro[cyclopropane-1,5'-inden]-3'-yl)propyl (2-bromoethyl)carbamate |
| 237 | 238 | (R)-3-(6'-hydroxy-2',4',6'-trimethyl-7'-oxo-6',7'-dihydrospiro[cyclopropane-1,5'-inden]-3'-yl)propyl (2-chloroethyl)carbamate |
| 238 | 239 | (R)-3-(6'-hydroxy-2',4',6'-trimethyl-7'-oxo-6',7'-dihydrospiro[cyclopropane-1,5'-inden]-3'-yl)propyl (2-hydroxyethyl)carbamate |
| 239 | 240 | (R)-3-(6'-hydroxy-2',4',6'-trimethyl-7'-oxo-6',7'-dihydrospiro[cyclopropane-1,5'-inden]-3'-yl)propyl acetoxy(acetyl)carbamate |
| 240 | 241 | (R)-N-(3-(6'-hydroxy-2',4',6'-trimethyl-7'-oxo-6',7'-dihydrospiro[cyclopropane-1,5'-inden]-3'-yl)propyl)methanesulfonamide |
| 241 | 242 | (R)-N-(3-(6'-hydroxy-2',4',6'-trimethyl-7'-oxo-6',7'-dihydrospiro[cyclopropane-1,5'-inden]-3'-yl)propyl)-4-methylbenzenesulfonamide |
| 242 | 243 | (R)-3-(6'-hydroxy-2',4',6'-trimethyl-7'-oxo-6',7'-dihydrospiro[cyclopropane-1,5'-inden]-3'-yl)propyl (2-fluoroethyl)carbamate |
| 243 | 244 | (R)-1-hydroxy-1-(3-(6'-hydroxy-2',4',6'-trimethyl-7'-oxo-6',7'-dihydrospiro[cyclopropane-1,5'-inden]-3'-yl)propyl)urea |
| 244 | 245 | (R)-1-hydroxy-1-(3-(6'-hydroxy-2',4',6'-trimethyl-7'-oxo-6',7'-dihydrospiro[cyclopropane-1,5'-inden]-3'-yl)propyl)thiourea |
| 245 | 246 | (R)-3-(6'-hydroxy-2',4',6'-trimethyl-7'-oxo-6',7'-dihydrospiro[cyclopropane-1,5'-inden]-3'-yl)propyl morpholine-4-carboxylate |
| 246 | 247 | (R)-3-(6'-hydroxy-2',4',6'-trimethyl-7'-oxo-6',7'-dihydrospiro[cyclopropane-1,5'-inden]-3'-yl)propyl morpholine-4-carboxylate |
| 247 | 248 | (R)-3-(6'-hydroxy-2',4',6'-trimethyl-7'-oxo-6',7'-dihydrospiro[cyclopropane-1,5'-inden]-3'-yl)propyl [1,4'-bipiperidine]-1'-carboxylate |
| 248 | 249 | (R)-6'-hydroxy-2'-(hydroxymethyl)-3',4',6'-trimethylspiro[cyclopropane-1,5'-inden]-7'(6'H)-one |
| 249 | 250 | ((1a'R,2'S,3'R,6'R,7a'S)-3'-acetoxy-6'-hydroxy-2',4',6'-trimethyl-7'-oxo-1',1a',2',3',6',7'-hexahydrospiro[cyclopropane-1,5'-cyclopropa[c]inden]-2'-yl)methyl acetate |
| 250 | 251 | ((1a'S,2'S,3'R,6'R,7a'R)-3'-acetoxy-6'-hydroxy-2',4',6'-trimethyl-7'-oxo-1',1a',2',3',6',7'-hexahydrospiro[cyclopropane-1,5'-cyclopropa[c]inden]-2'-yl)methyl acetate |
| 251 | 252 | (1a'R,3'S,6'R,7a'S)-3',6'-dihydroxy-2',4',6'-tetramethyl-1',1a',2',3'-tetrahydrospiro[cyclopropane-1,5'-cyclopropa[c]inden]-7'(6'H)-one |
| 252 | 253 | (1a'S,3'S,6'R,7a'R)-3',6'-dihydroxy-2',4',6'-tetramethyl-1',1a',2',3'-tetrahydrospiro[cyclopropane-1,5'-cyclopropa[c]inden]-7'(6'H)-one |
| 253 | 254 | (R)-3-(6'-hydroxy-2',4',6'-trimethyl-7'-oxo-6',7'-dihydrospiro[cyclopropane-1,5'-inden]-3'-yl)propyl 4-sulfamoylbenzoate |
| 254 | 255 | (R)-3-(6'-hydroxy-2',4',6'-trimethyl-7'-oxo-6',7'-dihydrospiro[cyclopropane-1,5'-inden]-3'-yl)propyl sulfamate |
| 255 | 256 | 3-((R)-6'-hydroxy-2',4',6'-trimethyl-7'-oxo-6',7'-dihydrospiro[cyclopropane-1,5'-inden]-3'-yl)propyl 1-(3-((R)-6'-hydroxy-2',4',6'-trimethyl-7'-oxo-6',7'-dihydrospiro[cyclopropane-1,5'-inden]-3'-yl)propyl)-1H-1,2,3-triazole-4-carboxylate |
| 256 | 257 | 3-((R)-6'-hydroxy-2',4',6'-trimethyl-7'-oxo-6',7'-dihydrospiro[cyclopropane-1,5'-inden]-3'-yl)propyl 1-(((R)-6'-hydroxy-2',4',6'-trimethyl-7'-oxo-6',7'-dihydrospiro[cyclopropane-1,5'-inden]-3'-yl)methyl)-1H-1,2,3-triazole-4-carboxylate |
| 257 | 258 | (4-carboxy-4-(4-carboxy-4-((3-((R)-6'-hydroxy-2',4',6'-trimethyl-7'-oxo-6',7'-dihydrospiro[cyclopropane-1,5'-inden]-3'-yl)propyl)amino)butanamido)butanoyl)glutamic acid |
| 258 | 259 | (R)-3'-((S)-2,2-dioxido-1,2,3-oxathiazinan-4-yl)-6'-hydroxy-2',4',6'-trimethylspiro[cyclopropane-1,5'-inden]-7'(6'H)-one |
| 259 | 260 | (R)-N-(3-(6'-hydroxy-2',4',6'-trimethyl-7'-oxo-6',7'-dihydrospiro[cyclopropane-1,5'-inden]-3'-yl)propyl)-[1,4'-bipiperidine]-1'-carboxamide |
| 260 | 261 | (R)-3-(6'-hydroxy-2',4',6'-trimethyl-7'-oxo-6',7'-dihydrospiro[cyclopropane-1,5'-inden]-3'-yl)propyl 1H-imidazole-1-carboxylate |
| 261 | 262 | methyl (R)-2-(((6'-hydroxy-2',4',6'-trimethyl-7'-oxo-6',7'-dihydrospiro[cyclopropane-1,5'-inden]-3'-yl)methyl)sulfonyl)acetate |
| 262 | 263 | methyl 2-((((R)-6'-hydroxy-2',4',6'-trimethyl-7'-oxo-6',7'-dihydrospiro[cyclopropane-1,5'-inden]-3'-yl)methyl)sulfinyl)acetate |
| 263 | 264 | N-[3-(6'-hydroxy-2',6'-dimethyl-7'-oxo-6',7'-dihydrospiro[cyclopropane-1,5'-inden]-3'-yl)propyl]sulfuric diamide |
| 264 | 265 | N-hydroxy-N'-[3-(6'-hydroxy-2',6'-dimethyl-7'-oxo-6,7'-dihydrospiro[cyclopropane-1,5'-inden]-3'-yl)propyl]sulfuric diamide |
| 265 | 266 | N-[3-(6'-hydroxy-2',6'-dimethyl-7'-oxo-6',7'-dihydrospiro[cyclopropane-1,5'-inden]-3'-yl)propyl]-N-methoxysulfuric diamide |
| 266 | 267 | (R)-2-amino-N-((6'-hydroxy-2',4',6'-trimethyl-7'-oxo-6',7'-dihydrospiro[cyclopropane-1,5'-inden]-3'-yl)methyl)-N-methoxyacetamide |
| 267 | 268 | (R)-2,2,2-trifluoro-N-(3-(6'-hydroxy-2',4',6'-trimethyl-7'-oxo-6',7'-dihydrospiro[cyclopropane-1,5'-inden]-3'-yl)propyl)acetamide |
| 268 | 269 | (R)-(6'-hydroxy-2',4',6'-trimethyl-7'-oxo-6',7'-dihydrospiro[cyclopropane-1,5'-inden]-3'-yl)methyl (4-methoxyphenyl)sulfamate |
| 269 | 270 | (R)-3'-(aminomethyl)-6'-hydroxy-2',4',6'-trimethylspiro[cyclopropane-1,5'-inden]-7'(6'H)-one |
| 270 | 271 | (R)-N-((6'-hydroxy-2',4',6'-trimethyl-7'-oxo-6',7'-dihydrospiro[cyclopropane-1,5'-inden]-3'-yl)methyl)methanesulfonamide |
| 271 | 272 | (5S,6S,7S)-3-(((3-((R)-6'-hydroxy-2',4',6'-trimethyl-7'-oxo-6',7'-dihydrospiro[cyclopropane-1,5'-inden]-3'-yl)propanoyl) |

TABLE V-continued

IUPAC names of the Illudofulvene analogs.

| Entry # | Illudo-fulvene Analog | IUPAC Name of Illudofulvene Analog |
|---|---|---|
| 272 | 273 | oxy)methyl)-8-oxo-7-(2-(thiophen-2-yl)acetamido)-5-thia-1-azabicyclo[4.2.0]oct-2-ene-2-carboxylic acid 5-oxide (5S,6S,7S)-3-((((3-((R)-6'-hydroxy-2',4',6'-trimethyl-7'-oxo-6',7'-dihydrospiro[cyclopropane-1,5'-inden]-3'-yl)propyl)carbamoyl)oxy)methyl)-8-oxo-7-(2-(thiophen-2-yl)acetamido)-5-thia-1-azabicyclo[4.2.0]oct-2-ene-2-carboxylic acid 5-oxide |
| 273 | 274 | (6S,7S)-3-((((3-((R)-6'-hydroxy-2',4',6'-trimethyl-7'-oxo-6',7'-dihydrospiro[cyclopropane-1,5'-inden]-3'-yl)propyl)carbamoyl)oxy)methyl)-8-oxo-7-(2-(thiophen-2-yl)acetamido)-5-thia-1-azabicyclo[4.2.0]oct-2-ene-2-carboxylic acid 5,5-dioxide |
| 274 | 275 | N-(((R)-6'-hydroxy-2',4',6'-trimethyl-7'-oxo-6',7'-dihydrospiro[cyclopropane-1,5'-inden]-3'-yl)methyl)pyrrolidine-2-carboxamide |
| 275 | 276 | 2-amino-N-(((R)-6'-hydroxy-2',4',6'-trimethyl-7'-oxo-6',7'-dihydrospiro[cyclopropane-1,5'-inden]-3'-yl)methyl)-4-methylpentanamide |
| 276 | 277 | (R)-1-hydroxy-3-((6'-hydroxy-2',4',6'-trimethyl-7'-oxo-6',7'-dihydrospiro[cyclopropane-1,5'-inden]-3'-yl)methyl)urea |
| 277 | 278 | (R)-1-((6'-hydroxy-2',4',6'-trimethyl-7'-oxo-6',7'-dihydrospiro[cyclopropane-1,5'-inden]-3'-yl)methyl)-3-methoxyurea |
| 278 | 279 | (R)-1-((6'-hydroxy-2',4',6'-trimethyl-7'-oxo-6',7'-dihydrospiro[cyclopropane-1,5'-inden]-3'-yl)methyl)-3-(2-hydroxyethyl)urea |
| 279 | 280 | (R)-1-(3-(6'-hydroxy-2',4',6'-trimethyl-7'-oxo-6',7'-dihydrospiro[cyclopropane-1,5'-inden]-3'-yl)propyl)-3-(2-hydroxyethyl)urea |
| 280 | 281 | (R)-1-(2-chloroethyl)-3-(3-(6'-hydroxy-2',4',6'-trimethyl-7'-oxo-6',7'-dihydrospiro[cyclopropane-1,5'-inden]-3'-yl)propyl)urea |
| 281 | 282 | (R)-1-(2-chloroethyl)-3-((6'-hydroxy-2',4',6'-trimethyl-7'-oxo-6',7'-dihydrospiro[cyclopropane-1,5'-inden]-3'-yl)methyl)urea |
| 282 | 283 | N-[(6'-hydroxy-2',6'-dimethyl-7'-oxo-6',7'-dihydrospiro[cyclopropane-1,5'-inden]-3'-yl)methyl]sulfuric diamide |
| 283 | 284 | (R)-3-((6'-hydroxy-2',4',6'-trimethyl-7'-oxo-6',7'-dihydrospiro[cyclopropane-1,5'-inden]-3'-yl)methyl)pyrimidine-2,4(1H,3H)-dione |
| 284 | 285 | N-hydroxy-N-[(6'-hydroxy-2',6'-dimethyl-7'-oxo-6',7'-dihydrospiro[cyclopropane-1,5'-inden]-3'-yl)methyl]sulfuric diamide |
| 285 | 286 | (R)-5-fluoro-1-((6'-hydroxy-2',4',6'-trimethyl-7'-oxo-6',7'-dihydrospiro[cyclopropane-1,5'-inden]-3'-yl)methyl)pyrimidine-2,4(1H,3H)-dione |
| 286 | 287 | (R)-5-fluoro-3-((6'-hydroxy-2',4',6'-trimethyl-7'-oxo-6',7'-dihydrospiro[cyclopropane-1,5'-inden]-3'-yl)methyl)pyrimidine-2,4(1H,3H)-dione |
| 287 | 288 | (R)-1-hydroxy-3-(3-(6'-hydroxy-2',4',6'-trimethyl-7'-oxo-6',7'-dihydrospiro[cyclopropane-1,5'-inden]-3'-yl)propyl)urea |
| 288 | 289 | (R)-1-((6'-hydroxy-2',4',6'-trimethyl-7'-oxo-6',7'-dihydrospiro[cyclopropane-1,5'-inden]-3'-yl)methyl)pyrimidine-2,4(1H,3H)-dione |
| 289 | 290 | ((S)-6'-hydroxy-2',4',6'-trimethyl-7'-oxo-6',7'-dihydrospiro[cyclopropane-1,5'-inden]-3'-yl)methyl 5-oxo-5-(((S)-1,2,3,10-tetramethoxy-9-oxo-5,6,7,9-tetrahydrobenzo[a]heptalen-7-yl)amino)pentanoate |
| 290 | 291 | 3-((S)-6'-hydroxy-2',4',6'-trimethyl-7'-oxo-6',7'-dihydrospiro[cyclopropane-1,5'-inden]-3'-yl)propyl 5-oxo-5-(((S)-1,2,3,10-tetramethoxy-9-oxo-5,6,7,9-tetrahydrobenzo[a]heptalen-7-yl)amino)pentanoate |
| 291 | 292 | N1-(((S)-6'-hydroxy-2',4',6'-trimethyl-7'-oxo-6',7'-dihydrospiro[cyclopropane-1,5'-inden]-3'-yl)methyl)-N5-((S)-1,2,3,10-tetramethoxy-9-oxo-5,6,7,9-tetrahydrobenzo[a]heptalen-7-yl)glutaramide |
| 292 | 293 | 3-((S)-6'-hydroxy-2',4',6'-trimethyl-7'-oxo-6',7'-dihydrospiro[cyclopropane-1,5'-inden]-3'-yl)-N-((S)-1,2,3,10-tetramethoxy-9-oxo-5,6,7,9-tetrahydrobenzo[a]heptalen-7-yl)propanamide |
| 293 | 294 | 2-amino-N-(((R)-6'-hydroxy-2',4',6'-trimethyl-7'-oxo-6',7'-dihydrospiro[cyclopropane-1,5'-inden]-3'-yl)methyl)-N-methoxypropanamide |
| 294 | 295 | 2-amino-N-(((R)-6'-hydroxy-2',4',6'-trimethyl-7'-oxo-6',7'-dihydrospiro[cyclopropane-1,5'-inden]-3'-yl)methyl)-N-methoxy-4-methylpentanamide |
| 295 | 296 | 2-amino-N-(((R)-6'-hydroxy-2',4',6'-trimethyl-7'-oxo-6',7'-dihydrospiro[cyclopropane-1,5'-inden]-3'-yl)methyl)-N-methoxy-4-(methylthio)butanamide |
| 296 | 297 | 2-amino-N-(((R)-6'-hydroxy-2',4',6'-trimethyl-7'-oxo-6',7'-dihydrospiro[cyclopropane-1,5'-inden]-3'-yl)methyl)-3-(1H-indol-3-yl)-N-methoxypropanamide |
| 297 | 298 | (R)-3-(6'-hydroxy-2',4',6'-trimethyl-7'-oxo-6',7'-dihydrospiro[cyclopropane-1,5'-inden]-3'-yl)propyl (tert-butoxycarbonyl)glycinate |
| 298 | 299 | (2'S,3'R,6'R)-2'-(azidomethyl)-3',6'-dihydroxy-2',4',6'-trimethyl-2',3'-dihydrospiro[cyclopropane-1,5'-inden]-7'(6'H)-one |
| 299 | 300 | (2'R,3'R,6'R)-3'-azido-6'-hydroxy-2'-(hydroxymethyl)-2',4',6'-trimethyl-2',3'-dihydrospiro[cyclopropane-1,5'-inden]-7'(6'H)-one |
| 300 | 301 | (R)-6'-hydroxy-2',4',6'-trimethyl-7'-oxo-6',7'-dihydrospiro[cyclopropane-1,5'-inden]-3'-yl 6-oxo-6-phenylhexanoate |
| 301 | 302 | ((2'S,3'R,6'R)-3',6'-dihydroxy-2',4',6'-trimethyl-7'-oxo-2',3',6',7'-tetrahydrospiro[cyclopropane-1,5'-inden]-2'-yl)methyl 3,5-dinitrobenzoate |
| 302 | 303 | (2'S,3'R,6'R)-2'-(((3,5-dinitrocyclohexa-2,4-diene-1-carbonyl)oxy)methyl)-6'-hydroxy-2',4',6'-trimethyl-7'-oxo-2',3',6',7'-tetrahydrospiro[cyclopropane-1,5'-inden]-3'-yl 3,5-dinitrobenzoate |
| 303 | 304 | (R)-3-(6'-hydroxy-2',4',6'-trimethyl-7'-oxo-6',7'-dihydrospiro[cyclopropane-1,5'-inden]-3'-yl)propyl propiolate |
| 304 | 305 | (R)-3-(6'-hydroxy-2',4',6'-trimethyl-7'-oxo-6',7'-dihydrospiro[cyclopropane-1,5'-inden]-3'-yl)propyl (4-nitrophenyl) carbonate |
| 305 | 306 | (R)-3-(6'-hydroxy-2',4',6'-trimethyl-7'-oxo-6',7'-dihydrospiro[cyclopropane-1,5'-inden]-3'-yl)propyl 4-methylbenzenesulfonate |
| 306 | 307 | (3'R,6'R)-3'-azido-6'-hydroxy-2',2',4',6'-tetramethyl-2',3'-dihydrospiro[cyclopropane-1,5'-inden]-7'(6'H)-one |
| 307 | 308 | (3'R,6'R)-3'-amino-6'-hydroxy-2',2',4',6'-tetramethyl-2',3'-dihydrospiro[cyclopropane-1,5'-inden]-7'(6'H)-one |
| 308 | 309 | (2'R,3'S,6'R)-3'-azido-2'-(((tert-butyldimethylsilyl)oxy)methyl)-6'-hydroxy-2',4',6'-trimethyl-2',3'-dihydrospiro[cyclopropane-1,5'-inden]-7'(6'H)-one |
| 309 | 310 | (R)-(6'-hydroxy-2',4',6'-trimethyl-7'-oxo-6',7'-dihydrospiro[cyclopropane-1,5'-inden]-3'-yl) methyl 4-sulfamoylbenzoate |
| 310 | 311 | (3'S,6'R)-6'-hydroxy-2',2',4',6'-tetramethyl-7'-oxo-2',3',6',7'-tetrahydrospiro[cyclopropane-1,5'-inden]-3'-yl 4-sulfamoylbenzoate |
| 311 | 312 | (R)-(6'-hydroxy-2',4',6'-trimethyl-7'-oxo-6',7'-dihydrospiro[cyclopropane-1,5'-inden]-3'-yl) methyl 4-methylbenzenesulfonate |
| 312 | 313 | 2,3,4,5,6-pentafluoro-N-((3'R,6'R)-6'-hydroxy-2',2',4',6'-tetramethyl-7'-oxo-2',3',6',7'-tetrahydrospiro[cyclopropane-1,5'-inden]-3'-yl)benzenesulfonamide |
| 313 | 314 | (R)-3-(6'-hydroxy-2',4',6'-trimethyl-7'-oxo-6',7'-dihydrospiro[cyclopropane-1,5'-inden]-3'-yl)propyl 4-methylbenzenesulfonate |

TABLE V-continued

IUPAC names of the Illudofulvene analogs.

| Entry # | Illudofulvene Analog | IUPAC Name of Illudofulvene Analog |
|---|---|---|
| 314 | 315 | (R)-3'-((2,5-dimethyl-1H-pyrrol-3-yl)methyl)-6'-hydroxy-2',4',6'-trimethylspiro[cyclopropane-1,5'-inden]-7'(6'H)-one |
| 315 | 316 | ((2'S,3'R,6'R)-3',6'-dihydroxy-2',4',6'-trimethyl-7'-oxo-2',3',6',7'-tetrahydrospiro[cyclopropane-1,5'-inden]-2'-yl)methyl 4-(fluorosulfonyl)benzoate |
| 316 | 317 | (2'S,3'R,6'R)-6'-hydroxy-2'-(hydroxymethyl)-2',4',6'-trimethyl-7'-oxo-2',3',6',7'-tetrahydrospiro[cyclopropane-1,5'-inden]-3'-yl 4-(fluorosulfonyl)benzoate |
| 317 | 318 | ((2'S,3'R,6'R)-3'-((4-(fluorosulfonyl)benzoyl)oxy)-6'-hydroxy-2',4',6'-trimethyl-7'-oxo-2',3',6',7'-tetrahydrospiro[cyclopropane-1,5'-inden]-2'-yl)methyl 4-(fluorosulfonyl)benzoate |
| 318 | 332 | (R)-6'-hydroxy-3'-((methoxyamino)methyl)-2',4',6'-trimethylspiro[cyclopropane-1,5'-inden]-7'(6'H)-one |
| 319 | 333 | ((2'S,3'R,6'R)-6'-hydroxy-2',4',6'-trimethyl-3'-(((4-nitrophenoxy)carbonyl)oxy)-7'-oxo-2',3',6',7'-tetrahydrospiro[cyclopropane-1,5'-inden]-2'-yl)methyl acetate |
| 320 | 334 | ((2'S,3'R,6'R)-3'-(((2-((tert-butoxycarbonyl)(methyl)amino)ethyl)(methyl)carbamoyl)oxy)-6'-hydroxy-2',4',6'-trimethyl-7'-oxo-2',3',6',7'-tetrahydrospiro[cyclopropane-1,5'-inden]-2'-yl)methyl acetate |
| 321 | 335 | tert-butyl ((2'S,3'R,6'R)-6'-hydroxy-2'-(hydroxymethyl)-2',4',6'-trimethyl-7'-oxo-2',3',6',7'-tetrahydrospiro[cyclopropane-1,5'-inden]-3'-yl) ethane-1,2-diylbis(methylcarbamate) |
| 322 | 337 | 4-nitrophenyl (R)-((6'-hydroxy-2',4',6'-trimethyl-7'-oxo-6',7'-dihydrospiro[cyclopropane-1,5'-inden]-3'-yl)methyl)carbamate |
| 323 | 338 | 4-nitrophenyl (R)-(3-(6'-hydroxy-2',4',6'-trimethyl-7'-oxo-6',7'-dihydrospiro[cyclopropane-1,5'-inden]-3'-yl)propyl)carbamate |
| 324 | 339 | ((2'S,3'R,6'R)-3',6'-dihydroxy-2',4',6'-trimethyl-7'-oxo-2',3',6',7'-tetrahydrospiro[cyclopropane-1,5'-inden]-2'-yl)methyl 4-methylbenzenesulfonate |
| 325 | 340 | (R)-N-((6'-hydroxy-2',4',6'-trimethyl-7'-oxo-6',7'-dihydrospiro[cyclopropane-1,5'-inden]-3'-yl)methyl)methanesulfonamide |
| 326 | 345 | (2'S,3'R,6'R)-2'-(acetoxymethyl)-6'-hydroxy-2',4',6'-trimethyl-7'-oxo-2',3',6',7'-tetrahydrospiro[cyclopropane-1,5'-inden]-3'-yl 4-(N-(2-(2-(2-(2-aminoacetamido)acetamido)acetamido)ethyl)-N-methylsulfamoyl)benzoate |
| 327 | 346 | ((2'S,3'R,6'R)-3',6'-dihydroxy-2',4',6'-trimethyl-7'-oxo-2',3',6',7'-tetrahydrospiro[cyclopropane-1,5'-inden]-2'-yl)methyl 4-(N-(2-(2-(2-(2-aminoacetamido)acetamido)acetamido)ethyl)-N-methylsulfamoyl)benzoate |
| 328 | 347 | ((2'S,3'R,6'R)-3',6'-dihydroxy-2',4',6'-trimethyl-7'-oxo-2',3',6',7'-tetrahydrospiro[cyclopropane-1,5'-inden]-2'-yl)methyl 4-sulfamoylbenzoate |
| 330 | 348 | (3'S,6'R)-6'-hydroxy-2',2',4',6'-tetramethyl-7'-oxo-2',3',6',7'-tetrahydrospiro[cyclopropane-1,5'-inden]-3'-yl 4-sulfamoylbenzoate |
| 331 | 351 | (3'S,6'R)-6'-hydroxy-2',2',4',6'-tetramethyl-7'-oxo-2',3',6',7'-tetrahydrospiro[cyclopropane-1,5'-inden]-3'-yl 4-(N-(2-(2-(2-(2-aminoacetamido)acetamido)acetamido)ethyl)-N-methylsulfamoyl)benzoate |
| 332 | 353 | ((6'R)-3'-(((2-(((((4-((S)-2-((S)-2-(6-(2,5-dioxo-2,5-dihydro-1H-pyrrol-1-yl)hexanamido)-3-methylbutanamido)-5-ureidopentanamido)benzyl)oxy)carbonyl)(methyl)amino)ethyl)(methyl)carbamoyl)oxy)-6'-hydroxy-2',4',6'-trimethyl-7'-oxo-2',3',6',7'-tetrahydrospiro[cyclopropane-1,5'-inden]-2'-yl)methyl acetate |
| 333 | 354 | 4-((S)-2-((S)-2-(6-(2,5-dioxo-2,5-dihydro-1H-pyrrol-1-yl)hexanamido)-3-methylbutanamido)-5-ureidopentanamido)benzyl(2-(3-((S)-6'-hydroxy-2',4',6'-trimethyl-7'-oxo-6',7'-dihydrospiro[cyclopropane-1,5'-inden]-3-yl)propylidene)hydrazine-1-carbonyl)carbamate |
| 334 | 356 | ((2'S,3'R,6'R)-3'-(((1-(9H-fluoren-9-yl)-13-methyl-3,6,9,12-tetraoxo-2-oxa-4,7,10,13-tetraazapentadecan-15-yl)(methyl)carbamoyl)oxy)-6'-hydroxy-2',4',6'-trimethyl-7'-oxo-2',3',6',7'-tetrahydrospiro[cyclopropane-1,5'-inden]-2'-yl)methyl acetate |
| 335 | 357 | ((2'S,3'R,6'R)-3'-(((2-(2-(2-(2-aminoacetamido)acetamido)-N-methylacetamido)ethyl)(methyl)carbamoyl)oxy)-6'-hydroxy-2',4',6'-trimethyl-7'-oxo-2',3',6',7'-tetrahydrospiro[cyclopropane-1,5'-inden]-2'-yl)methyl acetate |
| 336 | 359 | ((2'S,3'S,6'R)-6'-hydroxy-2',4',6'-trimethyl-3'-((methyl(2,2,14-trimethyl-4,7,10,13-tetraoxo-3-oxa-5,8,11,14-tetraazahexadecan-16-yl)carbamoyl)oxy)-7'-oxo-2',3',6',7'-tetrahydrospiro[cyclopropane-1,5'-inden]-2'-yl)methyl acetate |
| 337 | 361 | ((2'S,3'R,6'R)-3'-((((2,5-dioxopyrrolidin-1-yl)oxy)carbonyl)oxy)-6'-hydroxy-2',4',6'-trimethyl-7'-oxo-2',3',6',7'-tetrahydrospiro[cyclopropane-1,5'-inden]-2'-yl)methyl acetate |
| 338 | 362 | ((2'S,3'R,6'R)-3',6'-dihydroxy-2',4',6'-trimethyl-7'-oxo-2',3',6',7'-tetrahydrospiro[cyclopropane-1,5'-inden]-2'-yl)methyl methanesulfonate |
| 339 | 363 | (2'S,3'R,6'R)-2'-(aminomethyl)-3',6'-dihydroxy-2',4',6'-trimethyl-2',3'-dihydrospiro[cyclopropane-1,5'-inden]-7'(6'H)-one |
| 340 | 364 | (2'R,3'R,6'R)-3'-amino-6'-hydroxy-2'-(hydroxymethyl)-2',4',6'-trimethyl-2',3'-dihydrospiro[cyclopropane-1,5'-inden]-7'(6'H)-one |
| 341 | 366 | tert-butyl (R)-((6'-hydroxy-2',4',6'-trimethyl-7'-oxo-6',7'-dihydrospiro[cyclopropane-1,5'-inden]-3'-yl)methyl)carbamate |
| 342 | 367 | tert-butyl (R)-(3-(6'-hydroxy-2',4',6'-trimethyl-7'-oxo-6',7'-dihydrospiro[cyclopropane-1,5'-inden]-3'-yl)propyl)carbamate |
| 343 | 368 | ((2'S,3'R,6'R)-3'-acetoxy-6'-hydroxy-2',4',6'-trimethyl-7'-oxo-2',3',6',7'-tetrahydrospiro[cyclopropane-1,5'-inden]-2'-yl)methyl acetate |
| 344 | 369 | (2'S,3'R,6'R)-2'-(((tert-butyldimethylsilyl)oxy)methyl)-3',6'-dihydroxy-2',4',6'-trimethyl-2',3'-dihydrospiro[cyclopropane-1,5'-inden]-7'(6'H)-one |
| 345 | 370 | (2'S,3'R,6'R)-2'-(((tert-butyldimethylsilyl)oxy)methyl)-6'-hydroxy-2',4',6'-trimethyl-7'-oxo-2',3',6',7'-tetrahydrospiro[cyclopropane-1,5'-inden]-3'-yl acetate |
| 346 | 371 | (2'S,3'R,6'R)-6'-hydroxy-2'-(hydroxymethyl)-2',4',6'-trimethyl-7'-oxo-2',3',6',7'-tetrahydrospiro[cyclopropane-1,5'-inden]-3'-yl acetate |
| 347 | 372 | (2'R,3'R,6'R)-2'-formyl-6'-hydroxy-2',4',6'-trimethyl-7'-oxo-2',3',6',7'-tetrahydrospiro[cyclopropane-1,5'-inden]-3'-yl acetate |
| 348 | 373 | (2'S,3'R,6'R)-2'-(((((9H-fluoren-9-yl)methoxy)carbonyl)amino)methyl)-6'-hydroxy-2',4',6'-trimethyl-7'-oxo-2',3',6',7'-tetrahydrospiro[cyclopropane-1,5'-inden]-3'-yl acetate |
| 349 | 374 | (2'S,3'R,6'R)-2'-(aminomethyl)-6'-hydroxy-2',4',6'-trimethyl-7'-oxo-2',3',6',7'-tetrahydrospiro[cyclopropane-1,5'-inden]-3'-yl acetate |
| 350 | 377 | ((2'S,3'R,6'R)-6'-hydroxy-2',4',6'-trimethyl-7'-oxo-3'-((tributylsilyl)oxy)-2',3',6',7'-tetrahydrospiro[cyclopropane-1,5'-inden]-2'-yl)methyl acetate |
| 351 | 378 | (2'S,3'R,6'R)-2'-((tert-butoxycarbonyl)amino)methyl)-6'-hydroxy-2',4',6'-trimethyl-7'-oxo-2',3',6',7'-tetrahydrospiro[cyclopropane-1,5'-inden]-3'-yl acetate |
| 352 | 379 | ((2'S,3'R,6'R)-3'-(((2-(((4-((14S,17S)-1-(9H-fluoren-9-yl)-14-isopropyl-3,6,9,12,15-pentaoxo-17-(3-ureidopropyl)-2-oxa- |

TABLE V-continued

IUPAC names of the Illudofulvene analogs.

| Entry # | Illudo-fulvene Analog | IUPAC Name of Illudofulvene Analog |
|---|---|---|
| 353 | 380 | ((2'S,3'R,6'R)-3'-(((2-((((4-((2S,5S)-14-amino-5-isopropyl-4,7,10,13-tetraoxo-2-(3-ureidopropyl)-3,6,9,12-tetraazatetradecanamido)benzyl)oxy)carbonyl)(methyl)amino)ethyl)(methyl)carbamoyl)oxy)-6'-hydroxy-2',4',6'-trimethyl-7'-oxo-2',3',6',7'-tetrahydrospiro[cyclopropane-1,5'-inden]-2'-yl)methyl acetate |
| 354 | 381 | (2'S,3'R,6'R)-6'-hydroxy-2'-(hydroxymethyl)-2',4',6'-trimethyl-3'-((tributylsilyl)oxy)-2',3'-dihydrospiro[cyclopropane-1,5'-inden]-7'(6'H)-one |
| 355 | 382 | (2'R,3'R,6'R)-6'-hydroxy-2',4',6'-trimethyl-7'-oxo-3'-((tributylsilyl)oxy)-2',3',6',7'-tetrahydrospiro[cyclopropane-1,5'-indene]-2'-carbaldehyde |
| 356 | 383 | (2'R,3'R,6'R)-3',6'-dihydroxy-2',4',6'-trimethyl-7'-oxo-2',3',6',7'-tetrahydrospiro[cyclopropane-1,5'-indene]-2'-carbaldehyde |
| 357 | 384 | tert-butyl (((2'S,3'R,6'R)-6'-hydroxy-2',4',6'-trimethyl-7'-oxo-3'-((tributylsilyl)oxy)-2',3',6',7'-tetrahydrospiro[cyclopropane-1,5'-inden]-2'-yl)methyl)carbamate |
| 358 | 389 | tert-butyl (((2'S,3'R,6'R)-3',6'-dihydroxy-2',4',6'-trimethyl-7'-oxo-2',3',6',7'-tetrahydrospiro[cyclopropane-1,5'-inden]-2'-yl)methyl) carbamate |
| 359 | 392 | ((2'S,3'S,6'R)-3'-(((2-(2-(2-(2-azidoacetamido)acetamido)-N-methylacetamido)ethyl)(methyl)carbamoyl)oxy)-6'-hydroxy-2',4',6'-trimethyl-7'-oxo-2',3',6',7'-tetrahydrospiro[cyclopropane-1,5'-inden]-2'-yl)methyl acetate |
| 360 | 393 | ((2'S,3'R,6'R)-3'-(((2-(2,5-dioxo-2,5-dihydro-1H-pyrrol-1-yl)ethyl)carbamoyl)oxy)-6'-hydroxy-2',4',6'-trimethyl-7'-oxo-2',3',6',7'-tetrahydrospiro[cyclopropane-1,5'-inden]-2'-yl)methyl acetate |
| 361 | 394 | (R)-6'-hydroxy-3'-((hydroxyamino)methyl)-2',4',6'-trimethylspiro[cyclopropane-1,5'-inden]-7'(6'H)-one |
| 362 | 397 | tert-butyl (((2'S,3'R,6'R)-3',6'-dihydroxy-2',4',6'-trimethyl-7'-oxo-2',3',6',7'-tetrahydrospiro[cyclopropane-1,5'-inden]-2'-yl)methyl)(hydroxy)carbamate |
| 363 | 398 | (2'S,3'R,6'R)-3',6'-dihydroxy-2'-((hydroxyamino)methyl)-2',4',6'-trimethyl-2',3'-dihydrospiro[cyclopropane-1,5'-inden]-7'(6'H)-one |
| 364 | 399 | ((2'S,3'R,6'R)-3',6'-dihydroxy-2',4',6'-trimethyl-7'-oxo-2',3',6',7'-tetrahydrospiro[cyclopropane-1,5'-inden]-2'-yl)methyl sulfamate |
| 365 | 401 | ((6'R)-3'-(((2-((((4-((S)-2-((S)-2-(((9H-fluoren-9-yl)methoxy)carbonyl)amino)-3-methylbutanamido)-5-ureidopentanamido)benzyl)oxy)carbonyl)(methyl)amino)ethyl)(methyl)carbamoyl)oxy)-6'-hydroxy-2',4',6'-trimethyl-7'-oxo-2',3',6',7'-tetrahydrospiro[cyclopropane-1,5'-inden]-2'-yl)methyl acetate |
| 366 | 402 | (R)-(6'-hydroxy-2',4',6'-trimethyl-7'-oxo-6',7'-dihydrospiro[cyclopropane-1,5'-inden]-3'-yl)methyl sulfamate |
| 367 | 403 | ((2'S,6'R)-6'-hydroxy-2',6'-dimethyl-4'-methylene-7'-oxo-2',4',6',7'-tetrahydrospiro[cyclopropane-1,5'-inden]-2'-yl)methyl methanesulfonate |
| 368 | 404 | ((6'R)-3'-(((2-((((4-((S)-2-((S)-2-amino-3-methylbutanamido)-5-ureidopentanamido)benzyl)oxy)carbonyl)(methyl)amino)ethyl)(methyl)carbamoyl)oxy)-6'-hydroxy-2',4',6'-trimethyl-7'-oxo-2',3',6',7'-tetrahydrospiro[cyclopropane-1,5'-inden]-2'-yl)methyl acetate |
| 369 | 405 | ((2'S,3'S,6'R)-6'-hydroxy-3'-(((2-((((4-((2S,5S)-5-isopropyl-25-(6-methyl-4-vinylpyridin-2-yl)-4,7,23-trioxo-2-(3-ureidopropyl)-10,13,16,19-tetraoxa-3,6,22-triazapentacosanamido)benzyl)oxy)carbonyl)(methyl)amino)ethyl)(methyl)carbamoyl)oxy)-2',4',6'-trimethyl-7'-oxo-2',3',6',7'-tetrahydrospiro[cyclopropane-1,5'-inden]-2'-yl)methyl acetate |
| 370 | 407 | ((2'S,3'R,6'R)-3',6'-dihydroxy-2',4',6'-trimethyl-7'-oxo-2',3',6',7'-tetrahydrospiro[cyclopropane-1,5'-inden]-2'-yl)methyl trifluoromethanesulfonate |
| 371 | 408 | 4-((2S,5S)-14-amino-5-isopropyl-4,7,10,13-tetraoxo-2-(3-ureidopropyl)-3,6,9,12-tetraazatetradecanamido)benzyl ((2'S,3'R,6'R)-6'-hydroxy-2'-(hydroxymethyl)-2',4',6'-trimethyl-7'-oxo-2',3',6',7'-tetrahydrospiro[cyclopropane-1,5'-inden]-3'-yl) ethane-1,2-diylbis(methylcarbamate) |
| 372 | 409 | 4-((S)-2-((S)-2-amino-3-methylbutanamido)-5-ureidopentanamido)benzyl ((6'R)-6'-hydroxy-2'-(hydroxymethyl)-2',4',6'-trimethyl-7'-oxo-2',3',6',7'-tetrahydrospiro[cyclopropane-1,5'-inden]-3'-yl) ethane-1,2-diylbis(methylcarbamate) |
| 373 | 410 | 4-((S)-2-((S)-2-(6-(2,5-dioxo-2,5-dihydro-1H-pyrrol-1-yl)hexanamido)-3-methylbutanamido)-5-ureidopentanamido)benzyl ((6'R)-6'-hydroxy-2'-(hydroxymethyl)-2',4',6'-trimethyl-7'-oxo-2',3',6',7'-tetrahydrospiro[cyclopropane-1,5'-inden]-3'-yl) ethane-1,2-diylbis(methylcarbamate) |

TABLE VI

Summary NCI DTP 60 Cell Line Data.

| NAME/NSC | Mean GI50 inhibition | Mean TGI cytostatic | Mean LD50 cytotoxic |
|---|---|---|---|
| Pyrrolo-benzodiazepines 694501 | 7 nM | 302 nM | >23,000 nM* |
| Maytansine** 153858 | 19 nM | 318 nM | 49,200 nM |
| Fumagillol 642492 | 6,130 nM | 9,850 nM | >50,000 nM |
| Dolstatin-10 376128 | 17 nM | 2,680 nM | >50,000 nM |
| Auristatins 654663 | 1.4 nM | 902** nM | >5,000 nM** |
| Enadiyne 157365 | 2,900 nM | >100,000 nM | >100,000 nM |
| Halichondrin B 609395 | 1.2 nM | 199 nM | >1,000 nM |
| Tubulysin A | 12 nM | 1,318 nM | >10,000 nM |
| Illudin S | 10 nM | 64 nM | 511 nM |
| Illudin M | 3 nM | 20 nM | 291 nM |

TABLE VII

Ability of Illudofulvene analogs to inhibit tumor cell growth.

Mean IC50 value (nM) ± SD,
N = 3 unless otherwise indicated

| Analog Number | MV522 Target Cell Line | | 8392B Nontarget Cell Line | |
|---|---|---|---|---|
| | 2 hr exposure | 48 hr exposure | 2 hr exposure | 48 hr exposure |
| 001 | 2200 ± 100 | 350 ± 20 | | 830 ± 100 |
| 002 | 110 ± 40 | 70 ± 10 | 26000 ± 4500 | 800 ± 100 |
| 004 | 4200 | 600 | | |
| 008 | 870 ± 90 | 630 ± 80 | 12200 ± 700 | 15100 ± 2200 |
| 009 | 500 ± 30 | 850 ± 180 | 47100 ± 11000 | 43200 ± 2300 |
| 010 | 8900 ± 1500 | 170 ± 60 | 29400 ± 1600 | 14500 ± 1700 |
| 011 | 4900 ± 900 | 1200 (N = 2) | >100000 | 40400 ± 6700 |
| 012 | 5150 ± 1350 | 320 ± 90 | 42200 ± 5000 | 18800 ± 2800 |
| 013 | 5100 ± 700 | 270 ± 130 | 11900 ± 1300 | 4200 ± 400 |
| 014 | 115 ± 30 | 460 ± 120 | 9650 ± 200 | 1100 ± 300 |
| 015 | 1800 ± 200 | 480 ± 110 | 810 ± 260 | 1300 ± 150 |
| 016 | 490 ± 130 | 440 ± 90 | >100000 | 870 ± 60 |
| 017 | 2400 ± 360 | 320 ± 60 | 14700 ± 900 | |
| 018 | 8800 ± 2900 | | 4200 ± 1300 | |
| 019 | 470 ± 60 | 660 ± 80 | >75000 | |
| 020 | 530 ± 140 | 230 ± 10 | 25000 ± 3100 | |
| 021 | 2400 ± 1000 | 930 ± 250 | 34400 ± 9400 | |
| 022 | 700 ± 200 | 680 ± 180 | 31700 ± 1400 | |
| 023 | 2900 ± 1140 | 2750 ± 500 | >138000 | |
| 024 | 1800 ± 200 | 1200 ± 300 | 12800 ± 2100 | |
| 025 | 1300 ± 310 | 1200 ± 100 | >25000 | |
| 030 | | >3000 | | |
| 031 | | >3000 | | |
| 032 | 600 ± 190 | 210 ± 30 | >30000 | |
| 033 | 10000 ± 1100 | 4600 ± 200 | 29900 ± 3300 | |
| 034 | 1400 ± 170 | 490 ± 40 | >100000 | 4400 ± 200 |
| 035 | 5600 ± 600 | | >150000 | |
| 037 | 26000 ± 5000 | 29200 ± 2300 | >85000 | |
| 038 = 091 | 750 ± 60 | | 24900 ± 8000 | |
| 039 = 092 | 1500 ± 240 | 600 ± 40 | 24600 ± 2400 | 820 ± 250 |
| 040 = 093 | 3400 ± 360 | 700 ± 90 | 24000 ± 3300 | 5200 ± 470 |
| 060 | 19400 ± 1800 | | 27600 ± 3000 | |
| 062 | 2600 ± 300 | 660 ± 200 | 37100 ± 2300 | |
| 063 | 43000 ± 5700 | 580 ± 250 | | |
| 064 | 28000 ± 4600 | 1200 ± 300 | | |
| 065 | 6200 ± 1100 | 2500 ± 1200 | | |
| 075 | 19600 ± 9700 | | 62000 ± 3600 | |
| 076 | 24000 ± 6100 | | 39500 ± 7200 | |
| 077 | 9200 ± 1200 | | | |
| 078 | 20400 ± 6300 | | >100000 | |
| 079 | 7700 ± 3500 | | >100000 | |
| 080 | 8800 ± 2400 | | >100000 | |
| 081 | >80000 | | >80000 | |
| 082 | 50600 ± 7100 | | >100000 | |
| 083 | | 37200 ± 2900 | | >42000 |
| 084 | | 28200 ± 1400 | | >42000 |
| 085 | >40000 | >40000 | | |
| 087 | >40000 | 24700 ± 3900 | >40000 | |
| 089 | 19300 ± 5700 | 15500 ± 2800 | >60000 | |
| 090 | 2500 ± 400 | 2900 ± 400 | 1600 ± 200 | 3800 ± 300 |
| 094 | 800 ± 100 | 210 ± 20 | 9000 ± 1700 | 110 ± 10 |
| 096 | 2700 ± 400 | 6200 ± 600 | >88000 | >3000 |
| 097 | 2900 ± 100 | | >82000 | |
| 098 | 18800 ± 2500 | 4600 ± 250 | >65000 | 11700 ± 1800 |
| 099 | 8400 ± 1100 | 1800 ± 200 | 4000 ± 400 | 300 ± 20 |
| 100 | >10000 | 1700 ± 500 | | |
| 101 | >8000 | >7500 | | |
| 102 | >13000 | 1300 ± 100 | | |
| 103 | 31800 ± 4900 | 5900 ± 400 | 12100 ± 2000 | 2300 ± 200 |
| 104 | 6300 ± 400 | 6000 ± 500 | 36400 ± 6500 | 2700 ± 600 |
| 105 | 7300 ± 1200 | 2100 ± 400 | >100000 | |
| 106 | 5200 ± 1000 | | 83000 | |
| 107 | >50000 | 1600 ± 100 | >50000 | |
| 108 | 12300 ± 2300 | 520 ± 50 | >55000 | 6000 ± 1600 |
| 109 | >50000 | | >50000 | |
| 110 | >55000 | 1400 ± 100 | >55000 | 25300 ± 2100 |
| 111 | 16700 ± 2100 | 11900 ± 2800 | 34600 ± 2100 | 10200 ± 1000 |

TABLE VII-continued

Ability of Illudofulvene analogs to inhibit tumor cell growth.

Mean IC50 value (nM) ± SD,
N = 3 unless otherwise indicated

| Analog Number | MV522 Target Cell Line | | 8392B Nontarget Cell Line | |
|---|---|---|---|---|
| | 2 hr exposure | 48 hr exposure | 2 hr exposure | 48 hr exposure |
| 112 | 10000 ± 2000 | 6700 ± 1200 | 14900 ± 100 | 5200 ± 300 |
| 113 | 85000 ± 700 | 14100 ± 3000 | >93000 | 7800 ± 1000 |
| 114 | 1500 ± 100 | 260 ± 70 | 25100 ± 1000 | 700 ± 100 |
| 115 | 1500 ± 100 | 70 ± 5 | 1600 ± 700 | 630 ± 60 |
| 116 | 400 ± 100 | 1000 ± 50 | 7000 ± 400 | 170 ± 30 |
| 117 | 1100 ± 100 | 100 ± 30 | 7900 ± 1600 | 10 ± 2 |
| 118 | 14000 ± 2000 | 740 ± 120 | 24500 ± 4500 | 2000 ± 400 |
| 119 | 1100 ± 70 | 270 ± 40 | >33000 | >10000 |
| 120 | 2800 ± 900 | 600 ± 100 | 19100 ± 4600 | 510 ± 110 |
| 121 | 300 ± 10 | 90 ± 10 | 15200 ± 6000 | 1300 ± 500 |
| 122 | 6400 ± 300 | 2400 ± 300 | 14500 ± 1200 | 1100 ± 300 |
| 123 | 1900 ± 400 | 600 ± 60 | 450 ± 30 | 2400 ± 500 |
| 124 | 2800 ± 700 | 870 ± 350 | >30000 | 2400 ± 550 |
| 125 | 3700 ± 600 | 1200 ± 200 | 15500 ± 1400 | 600 ± 100 |
| 126 | 2100 ± 500 | 900 ± 100 | >30000 | 330 ± 80 |
| 127 | 870 ± 30 | 340 ± 90 | >30000 | 100 ± 40 |
| 128 | 840 ± 230 | 370 ± 50 | >35000 | 800 ± 70 |
| 129 | >136000 | 19700 ± 1900 | >136000 | 39400 ± 9200 |
| 130 | 700 ± 100 | 130 ± 40 | 27,000 ± 7000 | 4400 ± 500 |
| 133 | 58800 ± 6600 | 15800 ± 2600 | 12200 ± 2300 | 2700 ± 400 |
| 134 | 50000 ± 6000 | 28000 ± 4000 | 43900 ± 5100 | 8500 ± 2000 |
| 135 | 1600 ± 300 | 22 ± 4 | 70 ± 20 | 22 ± 2 |
| 136 | 430 ± 10 | 130 ± 10 | >6200 | 25 ± 2 |
| 137 | 850 ± 110 | 1200 ± 100 | 8500 ± 1200 | 710 ± 60 |
| 138 | 2100 ± 200 | 1000 ± 200 | 5400 ± 200 | 820 ± 230 |
| 139 | 6400 ± 900 | 3400 ± 500 | 11600 ± 900 | 2600 ± 1000 |
| 140 | 17100 ± 5100 | >14000 | 12700 ± 300 | >14000 |
| 141 | 11400 ± 1000 | 3700 ± 800 | 13700 ± 1900 | 1100 ± 140 |
| 142 | 90 ± 10 | 24 ± 7 | 6400 ± 1100 | 80 ± 6 |
| 143 | 43500 ± 11300 | 11400 ± 1800 | 56500 ± 20000 | 3600 ± 700 |
| 146 | 2500 ± 400 | 740 ± 280 | 13,000 ± 1200 | |
| 147 | >76000 | 26100 ± 12900 | >76000 | 43800 ± 3000 |
| 148 | 17100 ± 1100 | 6800 ± 1100 | 61000 ± 11600 | 6700 ± 1600 |
| 149 | 2900 ± 1000 | 1500 500 | 44600 ± 1400 | 4100 ± 900 |
| 150 | 9500 ± 1600 | 1400 ± 400 | 59000 ± 5500 | 10600 ± 800 |
| 151 | 7900 ± 400 | 4200 ± 1600 | 25500 ± 1200 | 6600 ± 2300 |
| 152 | | 6400 ± 1200 | 49000 ± 7700 | 9100 ± 100 |
| 153 | 8700 ± 2700 | 10900 ± 3400 | >90000 | 15800 ± 9600 |
| 154 | >70000 | 61300 ± 10000 | >70000 | 46,700 ± 13100 |
| 155 | 8200 ± 1200 | 3600 ± 400 | 17,000 ± 4000 | 9100 ± 1100 |
| 156 | 7200 ± 500 | 3100 ± 100 | 32,300 ± 9,400 | 5500 ± 1200 |
| 157 | >400,000 | >123,000 | >350,000 | 13100 ± 1600 |
| 158 | >175,000 | >175,000 | >200,000 | 61,000 ± 9,000 |
| 159 | 2700 ± 400 | 120 ± 10 | 13,700 ± 4,200 | <10 nM |
| 160 | 1900 ± 200 | 500 ± 200 | 52,400 ± 17,800 | 3200 ± 1100 |
| 161 | 2800 ± 500 | 3300 ± 700 | 13,800 ± 3,400 | >10,000 |
| 163 | 3500 ± 800 | 820 ± 40 | 18600 ± 800 | 910 ± 100 |
| 164 | | 70 ± 10 | 3500 ± 1600 | 130 ± 40 |
| 165 | 7700 ± 1100 | 290 ± 40 | 11000 ± 3300 | 11000 ± 1000 |
| 166 | 6500 ± 600 | 7200 ± 1900 | 6500 ± 2100 | 6000 ± 1500 |
| 167 | 14800 ± 2200 | | 18500 ± 2300 | |
| 169 | 7100 ± 600 | | 2300 ± 600 | |
| 177 | 7500 ± 800 | 1900 ± 800 | 73000 ± 5000 | 4100 ± 1300 |
| 178 | 21000 ± 4000 | 1000 ± 100 | 32000 ± 9000 | >8000 |
| 180 | 19900 ± 300 | >4000 | 5200 ± 1800 | 660 ± 50 |
| 182 | 99000 ± 12000 | 38000 ± 8200 | 39000 ± 7000 | 18700 ± 2700 |
| 183 | >120,000 | >275,000 | >120,000 | >235,000 |
| 184 | 800 ± 300 | 210 ± 20 | >100,000 | >10000 |
| 185 | 1700 ± 600 | 1900 ± 100 | | |
| 186 | 144000 ± 32000 | 70000 ± 16000 | 79000 ± 24000 | 48000 ± 2000 |
| 187 | 1300 ± 400 | 900 ± 200 | 3200 ± 800 | 3200 ± 700 |
| 189 | 8900 ± 2500 | 6100 ± 2600 | 41,000 ± 3700 | |
| 190 | 19,000 ± 4000 | >9,000 | 56,000 ± 2000 | >9,000 |
| 191 | >140,000 | 49,000 ± 13000 | >140,000 | 15000 ± 4000 |
| 192 | 1,600 ± 200 | 700 ± 100 | 8700 ± 1700 | 200 ± 30 |
| 193 | 1400 ± 400 | 2500 ± 600 | 48,000 ± 7000 | >11,000 |
| 195 | 1400 ± 200 | 390 ± 120 | 21,000 ± 6000 | 4300 ± 1200 |
| 196 | 840 ± 100 | 450 ± 120 | 80,000 ± 5000 | >9,200 |
| 197 | 950 ± 70 | 500 ± 100 | 9500 ± 400 | 11,300 ± 100 |
| 198 | 700 ± 100 | 2800 ± 600 | >8,200 | >82,000 |

TABLE VII-continued

Ability of Illudofulvene analogs to inhibit tumor cell growth.

Mean IC50 value (nM) ± SD,
N = 3 unless otherwise indicated

| | MV522 Target Cell Line | | 8392B Nontarget Cell Line | |
|---|---|---|---|---|
| Analog Number | 2 hr exposure | 48 hr exposure | 2 hr exposure | 48 hr exposure |
| 199 | 4700 ± 600 | 2500 ± 1100 | >93,000 | >9,300 |
| 201 | 360 ± 110 | 260 ± 70 | 13,000 ± 1700 | 26,000 ± 7000 |
| 202 | 1200 ± 100 | 650 ± 100 | >62,000 | >6200 |
| 203 | 760 ± 170 | 940 ± 330 | 48,000 ± 6000 | >5500 |
| 204 | 220 ± 40 | 1600 ± 300 | 4100 ± 800 | 8600 ± 800 |
| 205 | 8400 ± 2200 | 1200 ± 4400 | >185,000 | >2,600 |
| 206 | 610 ± 40 | 230 ± 20 | 20,000 ± 1000 | 8200 ± 200 |
| 207 | 570 ± 60 | 410 ± 60 | | |
| 208 | 1200 ± 100 | 930 ± 160 | 25,000 ± 3000 | |
| 209 | 3900 ± 1100 | 610 ± 100 | >90,000 | |
| 210 | 40,000 ± 4000 | 5500 ± 600 | | |
| 211 | 470 ± 120 | 430 ± 100 | 59,000 ± 9000 | |
| 212 | 80 ± 10 | 55 ± 5 | | |
| 213 | 2300 ± 700 | 1700 ± 700 | | |
| 214 | 2900 ± 800 | 360 ± 30 | | |
| 215 | 26,000 ± 3000 | 490 ± 120 | | |
| 216 | 460 ± 60 | 150 ± 40 | | |
| 217 | 2,200 ± 100 | 2,200 ± 100 | 43,000 ± 4,000 | >7,000 |
| 218 | 10,000 ± 3,000 | 600 ± 200 | 15,000 ± 6,000 | 600 ± 100 |
| 219 | >52,000 | >52,00 | >52,000 | >52,000 |
| 220 | 90 ± 10 | 130 ± 10 | 101,000 ± 18,000 | 40,000 ± 3,000 |
| 221 | >21,000 | 2,500 ± 200 | >21,000 | >21,000 |
| 222 | 5,000 ± 100 | 1,100 ± 100 | 9,300 ± 200 | 330 ± 60 |
| 223 | 20,000 ± 3,700 | 2,700 ± 300 | >185,000 | >55,000 |
| 224 | >200,000 | >130,000 | >200,000 | >130,000 |
| 225 | 47,000 ± 4,000 | 55,000 ± 11,000 | >350,000 | 33,000 ± 13,000 |
| 226 | >59,000 | >59,000 | >59,000 | >59,000 |
| 227 | >57,000 | 4,400 ± 700 | >57,000 | 16,000 ± 4,000 |
| 228 | >38,000 | >38,000 | 24,000 ± 3,000 | >38,000 |
| 229 | >56,000 | >2,000 | >56,000 | >2,000 |
| 230 | 620 ± 80 | 100 ± 10 | 38,000 ± 5,000 | 1,000 ± 200 |
| 231 | 1,500 ± 100 | 280 ± 10 | 14,000 ± 4,000 | |
| 232 | 700 ± 100 | 460 ± 60 | 42,000 ± 6,000 | 3,300 ± 600 |
| 233 | 3,200 ± 300 | 350 ± 80 | >150,000 | 2,400 ± 700 |
| 234 | 3,000 ± 300 | 1,100 ± 400 | 24,000 ± 6,000 | 9,000 ± 1,000 |
| 235 | 3,500 ± 400 | 2,200 ± 400 | 49,000 ± 6,000 | 6,500 ± 1,600 |
| 236 | 49,000 ± 11,000 | 29,000 ± 5,000 | 48,000 ± 10,000 | |
| 237 | 1,200 ± 300 | 730 ± 140 | 22,000 ± 1,000 | 6,600 ± 900 |
| 238 | 780 ± 190 | 57 ± 8 | 23,000 ± 2,000 | 4,700 ± 1,200 |
| 239 | 420 ± 60 | 70 ± 20 | 39,000 ± 3,000 | 28,000 ± 4,000 |
| 240 | 2,900 ± 100 | 1,300 ± 200 | >24,000 | 1,300 ± 100 |
| 241 | 560 ± 90 | 110 ± 20 | >28,000 | 18,000 ± 4,000 |
| 242 | 2,400 ± 400 | 580 ± 150 | 18,000 ± 2,000 | 2,900 ± 600 |
| 243 | 2,200 ± 500 | 670 ± 240 | 64,000 ± 10,000 | 26,000 ± 6,000 |
| 244 | 1,600 ± 400 | 150 ± 10 | 87,000 ± 11,000 | 35,000 ± 7,000 |
| 245 | 3,400 ± 1000 | 440 ± 90 | 79,000 ± 7,000 | 14,000 ± 1,700 |
| 246 | 2,800 ± 260 | 1,900 ± 450 | 14,000 ± 2,000 | 6,200 ± 1,300 |
| 247 | 6,100 ± 2,000 | 1,200 ± 250 | 10,000 ± 1,400 | 7,100 ± 1,700 |
| 248 | 830 ± 100 | 200 ± 25 | 23,000 ± 1,000 | 610 ± 120 |
| 249 | 4,100 ± 820 | 420 ± 100 | 18,000 ± 3,500 | 19,000 ± 3,800 |
| 250 | 99,000 ± 21,000 | 137,000 ± 14,000 | >275,000 | 137,000 ± 10,000 |
| 251 | 128,000 ± 4,000 | 51,000 ± 1,000 | >275,000 | 82,000 ± 8,000 |
| 252 | >380,000 | 33,000 ± 3,000 | >380,000 | >380,000 |
| 253 | >380,000 | >38,000 | >380,000 | >380,000 |
| 254 | 2,700 ± 800 | 1,100 ± 100 | 43,000 ± 6,000 | >65,000 |
| 255 | 2,900 ± 500 | 55 ± 2 | 119,000 ± 15,000 | 99,000 ± 4,000 |
| 256 | 1,500 ± 200 | 880 ± 200 | 7,500 ± 800 | 7,100 ± 300 |
| 257 | 2,800 ± 600 | 320 ± 30 | 25,000 ± 2,000 | 26,000 ± 3,000 |
| 258 | >45,000 | >45,000 | >45,000 | >45,000 |
| 259 | 16000 ± 3000 | 2400 ± 200 | >85,000 | 4700 ± 400 |
| 260 | 1600 ± 500 | 150 ± 20 | >64,000 | 19000 ± 4500 |
| 261 | 6300 ± 1100 | 1000 ± 150 | 64000 ± 2000 | 38000 ± 2100 |
| 262 | 8700 ± 1300 | 3900 ± 570 | 287000 ± 14000 | 73000 ± 17000 |
| 263 | 2000 ± 300 | 1400 ± 200 | 124000 ± 18000 | 39000 ± 7000 |
| 264 | 1400 ± 100 | 76 ± 17 | >85,000 | 54000 ± 20000 |
| 265 | 810 ± 20 | 8 ± 1 | 1100 ± 200 | 250 ± 80 |
| 266 | 140 ± 20 | 70 ± 18 | 56000 ± 15000 | 32000 ± 7000 |
| 267 | 900 ± 160 | 160 ± 20 | >90,000 | 28000 ± 8000 |
| 268 | 2100 ± 200 | 330 ± 90 | 54,000 ± 16,000 | >8,000 |
| 269 | 11000 ± 3000 | 850 ± 320 | 52000 ± 4000 | >7,000 |

TABLE VII-continued

Ability of Illudofulvene analogs to inhibit tumor cell growth.

| | Mean IC50 value (nM) ± SD, N = 3 unless otherwise indicated | | | |
|---|---|---|---|---|
| | MV522 Target Cell Line | | 8392B Nontarget Cell Line | |
| Analog Number | 2 hr exposure | 48 hr exposure | 2 hr exposure | 48 hr exposure |
| 270 | 8000 ± 1500 | 1300 ± 100 | >84,000 | 7100 ± 700 |
| 271 | 1700 ± 200 | 200 ± 90 | >93,000 | >9,300 |
| 272 | >46,000 | >4,700 | >47,000 | >4,700 |
| 273 | 30000 ± 5000 | >1,500 | >45,000 | >4,500 |
| 274 | 39000 ± 3000 | 1200 ± 300 | >46,000 | >4,500 |
| 275 | 1500 ± 300 | 370 ± 40 | >62,000 | >6,200 |
| 276 | 1500 ± 200 | 760 ± 100 | >61,000 | >6,100 |
| 277 | 760 ± 70 | 190 ± 20 | 31,000 ± 6000 | 9,800 ± 1000 |
| 278 | 1000 ± 100 | 270 ± 10 | >94000 | >9,400 |
| 279 | 1700 ± 400 | 190 ± 20 | >90000 | >9,000 |
| 280 | 2400 ± 800 | <80 | >83000 | >2,800 |
| 281 | 1800 ± 700 | 170 ± 10 | 27000 ± 2000 | 5000 ± 700 |
| 282 | 680 ± 60 | 110 ± 10 | >85000 | >8,500 |
| 283 | 2900 ± 1200 | 300 ± 20 | 40000 ± 4000 | >9,300 |
| 284 | 13,600(N = 2) | 340 ± 20 | | >8,800 |
| 285 | 3800 ± 1100 | 310 ± 20 | 84000 ± 9000 | 2000 ± 100 |
| 286 | 48000 ± 10000 | 6300 ± 200 | 51000 ± 1700 | >8,800 |
| 287 | 455000 ± 22000 | 1100 ± 100 | 567000 ± 17000 | 4700 ± 400 |
| 288 | 1800 ± 600 | 150 ± 20 | 11000 ± 3200 | ~9,000 |
| 289 | 51 ± 4 | 530 ± 150 | >290000 | >8,800 |
| 294 | 960 ± 170 | | | |
| 295 | 200 ± 44 | | | |
| 296 | 250 (N = 2) | | | |
| 297 | 2200 (N = 1) | | | |
| 298 | >7000 | | | |

TABLE VIII

Screening of Analogs from the National Cancer Institute (NCI) Developmental Therapeutics Program (DTP) NCI 60 cell line screen assay.

| Analog | Activity Value* | Cytotoxicity | MDR Activity |
|---|---|---|---|
| Epothilone A | +31 | No | No |
| MMAE | +21 | No | No |
| DM1 | +8 | No | No |
| 002 | −15 | Yes | Yes |
| 142 | −5 | Yes | Yes |
| 159 | −25 | Yes | Yes |
| 176 | −11 | Yes | Yes |
| 334 | −11 | Yes | Yes |
| 362 | −9 | Yes | Yes |
| 371 | −18 | Yes | Yes |
| 383 | −1 | Yes | Yes |
| 394 | −2 | Yes | Yes |

*Activity Value = the lower or more negative the activity value is an indication of the more active the compound was against tumor cells in the 60 cell line panel. A positive value indicates tumor cells could grow but at a slower rate. A value of Zero (0) indicates that while no cell growth was detected there was no evidence of cell death occurring (i.e., when the drug is removed the cells could grow again). A negative value indicates that the compounds actually lyse tumor cells.

SEQUENCE LISTING

```
Sequence total quantity: 181
SEQ ID NO: 1             moltype = AA  length = 351
FEATURE                  Location/Qualifiers
source                   1..351
                         mol_type = protein
                         organism = Homo sapiens
SEQUENCE: 1
MSFPCKFVAS FLLIFNVSSK GAVSKEITNA LETWGALGQD INLDIPSFQM SDDIDDIKWE  60
KTSDKKKIAQ FRKEKETFKE KDTYKLFKNG TLKIKHLKTD DQDIYKVSIY DTKGKNVLEK  120
IFDLKIQERV SKPKISWTCI NTTLTCEVMN GTDPELNLYQ DGKHLKLSQR VITHKWTTSL  180
SAKFKCTAGN KVSKESSVEP VSCPEKGLDI YLIIGICGGG SLLMVFVALL VFYITKRKKQ  240
RSRRNDEELE TRAHRVATEE RGRKPHQIPA STPQNPATSQ HPPPPPGHRS QAPSHRPPPP  300
GHRVQHQPQK RPPAPSGTQV HQQKGPPLPR PRVQPKPPHG AAENSLSPSS N          351

SEQ ID NO: 2             moltype = AA  length = 209
FEATURE                  Location/Qualifiers
source                   1..209
                         mol_type = protein
```

```
                         organism = Homo sapiens
SEQUENCE: 2
CDMQSGTHWR VLGLCLLSVG VWGQDGNEEM GGITQTPYKV SISGTTVILT CPQYPGSEIL      60
WQHNDKNIGG DEDDKNIGSD EDHLSLKEFS ELEQSGYYVC YPRGSKPEDA NFYLYLRARV     120
CENCMEMDVM SVATIVIVDI CITGGLLLLV YYWSKNRKAK AKPVTRGAGA GGRQRGQNKE     180
RPPPVPNPDY EPIRKGQRDL YSGLNQRRI                                      209

SEQ ID NO: 3             moltype = AA  length = 495
FEATURE                  Location/Qualifiers
source                   1..495
                         mol_type = protein
                         organism = Homo sapiens
SEQUENCE: 3
MPMGSLQPLA TLYLLGMLVA SCLGRLSWYD PDFQARLTRS NSKCQGQLEV YLKDGWHMVC      60
SQSWGRSSKQ WEDPSQASKV CQRLNCGVPL SLGPFLVTYT PQSSIICYGQ LGSFSNCSHS     120
RNDMCHSLGL TCLEPQKTTP PTTRPPPTTT PEPTAPPRLQ LVAQSGGQHC AGVVEFYSGS     180
LGGTISYEAQ DKTQDLENFL CNNLQCGSFL KHLPETEAGR AQDPGEPREH QPLPIQWKIQ     240
NSSCTSLEHC FRKIKPQKSG RVLALLCSGF QPKVQSRLVG GSSICEGTVE VRQGAQWAAL     300
CDSSSARSSL RWEEVCREQQ CGSVNSYRVL DAGDPTSRGL FCPHQKLSQC HELWERNSYC     360
KKVFVTCQDP NPAGLAAGTV ASIILALVLL VVLLVVCGPL AYKKLVKKFR QKKQRQWIGP     420
TGMNQNMSFH RNHTATVRSH AENPTASHVD NEYSQPPRNS HLSAYPALEG ALHRSSMQPD     480
NSSDSDYDLH GAQRL                                                     495

SEQ ID NO: 4             moltype = AA  length = 240
FEATURE                  Location/Qualifiers
source                   1..240
                         mol_type = protein
                         organism = Homo sapiens
SEQUENCE: 4
MAGPPRLLLL PLLLALARGL PGALAAQEVQ QSPHCTTVPV GASVNITCST SGGLRGIYLR      60
QLGPQPQDII YYEDGVVPTT DRRFRGRIDF SGSQDNLTIT MHRLQLSDTG TYTCQAITEV     120
NVYGSGTLVL VTEEQSQGWH RCSDAPPRAS ALPAPPTGSA LPDPQTASAL PDPPAASALP     180
AALAVISFLL GLGLGVACVL ARTQIKKLCS WRDKNSAACV VYEDMSHSRC NTLSSPNQYQ     240

SEQ ID NO: 5             moltype = AA  length = 556
FEATURE                  Location/Qualifiers
source                   1..556
                         mol_type = protein
                         organism = Homo sapiens
SEQUENCE: 5
MPPPRLLFFL LFLTPMEVRP EEPLVVKVEE GDNAVLQCLK GTSDGPTQQL TWSRESPLKP      60
FLKLSLGLPG LGIHMRPLAS WLFIFNVSQQ MGGFYLCQPG PPSEKAWQPG WTVNVEGSGE     120
LFRWNVSDLG GLGCGLKNRS SEGPSSPSGK LMSPKLYVWA KDRPEIWEGE PPCVPPRDSL     180
NQSLSQDLTM APGSTLWLSC GVPPDSVSRG PLSWTHVHPK GPKSLLSLEL KDDRPARDMW     240
VMETGLLLPR ATAQDAGKYY CHRGNLTMSF HLEITARPVL WHWLLRTGGW KVSAVTLAYL     300
IFCLCSLVGI LHLQRALVLR RKRKRMTDPT RRFFKVTPPP GSGPQNQYGN VLSLPTPTSG     360
LGRAQRWAAG LGGTAPSYGN PSSDVQADGA LGSRSPPGVG PEEEEGEGYE EPDSEEDSEF     420
YENDSNLGQD QLSQDGSGYE NPEDEPLGPE DEDSFSNAES YENEDEELTQ PVARTMDFLS     480
PHGSAWDPSR EATSLGSQSY EDMRGILYAA PQLRSIRGQP GPNHEEDADS YENMDNPDGP     540
DPAWGGGGRM GTWSTR                                                    556

SEQ ID NO: 6             moltype = AA  length = 297
FEATURE                  Location/Qualifiers
source                   1..297
                         mol_type = protein
                         organism = Homo sapiens
SEQUENCE: 6
MTTPRNSVNG TFPAEPMKGP IAMQSGPKPL FRRMSSLVGP TQSFFMRESK TLGAVQIMNG      60
LFHIALGGLL MIPAGIYAPI CVTVWYPLWG GIMYIISGSL LAATEKNSRK CLVKGKMIMN     120
SLSLFAAISG MILSMDILN IKISHFLKME SLNFIRAHTP YINIYNCEPA NPSEKNSPST      180
QYCYSIQSLF LGILSVMLIF AFFQELVIAG IVENEWKRTC SRPKSNIVLL SAEEKKEQTI     240
EIKEEVVGLT ETSSQPKNEE DIEIIPIQEE EEEETNFP EPPQDQESSP IENDSSP          297

SEQ ID NO: 7             moltype = AA  length = 847
FEATURE                  Location/Qualifiers
source                   1..847
                         mol_type = protein
                         organism = Homo sapiens
SEQUENCE: 7
MHLLGPWLLL LVLEYLAFSD SSKWVFEHPE TLYAWEGACV WIPCTYRALD GDLESFILFH      60
NPEYNKNTSK FDGTRLYEST KDGKVPSEQK RVQFLGDKNK NCTLSIHPVH LNDSGQLGLR     120
MESKTEKWME RIHLNVSERP FPPHIQLPPE IQESQEVTLT CLLNFSCYGY PIQLQWLLEG     180
VPMRQAAVTS TSLTIKSVFT RSELKFSPQW SHHGKIVTCQ LQDADGKFLS NDTVQLNVKH     240
TPKLEIKVTP SDAIVREGDS VTMTCEVSSS NPEYTTVSWL KDGTSLKKQN TFTLNLREVT     300
KDQSGKYCCQ VSNDVGPGRS EEVFLQVQYA PEPSTVQILH SPAVEGSQVE FLCMSLANPL     360
PTNYTWYHNG KEMQGRTEEK VHIPKILPWH AGTYSCVAEN ILGTGQRPGP AELDVQYPPK     420
KVTTVIQNPM PIREGDTVTL SCNYNSSNPS VTRYEWKPHG AWEEPSLGVL KIQNVGWDNT     480
TIACAACNSW CSWASPVALN VQYAPRDVRV RKIKPLSEIH SGNSVSLQCD FSSSHPKEVQ     540
FFWEKNGRLL GKESQLNFDS ISPEDAGSYS CWVNNSIGQT ASKAWTLEVL YAPRRLRVSM     600
```

```
SPGDQVMEGK SATLTCESDA NPPVSHYTWF DWNNQSLPYH SQKLRLEPVK VQHSGAYWCQ    660
GTNSVGKGRS PLSTLTVYYS PETIGRRVAV GLGSCLAILI LAICGLKLQR RWKRTQSQQG    720
LQENSSGQSF FVRNKKVRRA PLSEGPHSLG CYNPMMEDGI SYTTLRFPEM NIPRTGDAES    780
SEMQRPPPDC DDTVTYSALH KRQVGDYENV IPDFPEDEGI HYSELIQFGV GERPQAQENV    840
DYVILKH                                                              847

SEQ ID NO: 8             moltype = AA  length = 272
FEATURE                  Location/Qualifiers
source                   1..272
                         mol_type = protein
                         organism = Homo sapiens
SEQUENCE: 8
MDSYLLMWGL LTFIMVPGCQ AELCDDDPPE IPHATFKAMA YKEGTMLNCE CKRGFRRIKS     60
GSLYMLCTGN SSHSSWDNQC QCTSSATRNT TKQVTPQPEE QKERKTTEMQ SPMQPVDQAS    120
LPGHCREPPP WENEATERIY HFVVGQMVYY QCVQGYRALH RGPAESVCKM THGKTRWTQP    180
QLICTGEMET SQFPGEEKPQ ASPEGRPESE TSCLVTTTDF QIQTEMAATM ETSIFTTEYQ    240
VAVAGCVFLL ISVLLLSGLT WQRRQRKSRR TI                                  272

SEQ ID NO: 9             moltype = AA  length = 594
FEATURE                  Location/Qualifiers
source                   1..594
                         mol_type = protein
                         organism = Homo sapiens
SEQUENCE: 9
RVLLAALGLL FLGALRAFPQ DRPFEDTCHG NPSHYYDKAV RRCCYRCPMG LFPTQQCPQR     60
PTDCRKQCEP DYYLDEADRC TACVTCSRDD LVEKTPCAWN SSRVCECRPG MFCSTSAVNS    120
CARCFFHSVC PAGMIVKFPG TAQKNTVCEP ASPGVSPACA SPENCKEPSS GTIPQAKPTP    180
VSPATSSAST MPVRGGTRLA QEAASKLTRA PDSPSSVGRP SSDPGLSPTQ PCPEGSGDCR    240
KQCEPDYYLD EAGRCTACVS CSRDDLVEKT PCAWNSSRTC ECRPGMICAT SATNSCARCV    300
PYPICAAETV TKPQDMAEKD TTFEAPPLGT QPDCNPTPEN GEAPASTSPT QSLLVDSQAS    360
KTLPIPTSAP VALSSTGKPV LDAGPVLFWV ILVLVVVVGS SAFLLCHRRA CRKRIRQKLH    420
LCYPVQTSQP KLELVDSRPR RSSTQLRSGA SVTEPVAEER GLMSQPLMET CHSVGAAYLE    480
SLPLPLQDASPA GGPSSPRDLP EPRVSTEHTN NKIEKIYIMK ADTVIVGTVK AELPEGRGLA   540
GPAEPELEEE LEADHTPHYP EQETEPPLGS CSDVMLSVEE EGKEDPLPTA ASGK          594

SEQ ID NO: 10            moltype = AA  length = 364
FEATURE                  Location/Qualifiers
source                   1..364
                         mol_type = protein
                         organism = Homo sapiens
SEQUENCE: 10
MPLLLLLPLL WAGALAMDPN FWLQVQESVT VQEGLCVLVP CTFFHPIPYY DKNSPVHGYW     60
FREGAIISRD SPVATNKLDQ EVQEETQGRF RLLGDPSRNN CSLSIVDARR RDNGSYFFRM    120
ERGSTKYSYK SPQLSVHVTD LTHRPKILIP GTLEPGHSKN LTCSVSWACE QGTPPIFSWL    180
SAAPTSLGPR TTHSSVLIIT PRPQDHGTNL TCQVKFAGAG VTTERTIQLN VTYVPQNPTT    240
GIFPGDGSGK QETRAGVVHG AIGGAGVTAL LALCLCLIFF IVKTHRRKAA RTAVGRNDTH    300
PTTGSASPKH QKKSKLHGPT ETSSCSGAAP TVEMDEELHY ASLNFHGMNP SKDTSTEYSE    360
VRTQ                                                                 364

SEQ ID NO: 11            moltype = AA  length = 281
FEATURE                  Location/Qualifiers
source                   1..281
                         mol_type = protein
                         organism = Homo sapiens
SEQUENCE: 11
MSAQESCLSL IKYFLFVFNL FFFVLGSLIF CFGIWILIDK TSFVSFVGLA FVPLQIWSKV     60
LAISGIFTMG IALLGCVGAL KELRCLLGLY FGMLLLLFAT QITLGILIST QRAQLERSLR    120
DVVEKTIQKY GTNPEETAAE ESWDYVQFQL RCCGWHYPQD WFQVLILRGN GSEAHRVPCS    180
CYNLSATNDS TILDKVILPQ LSRLGHLARS RHSADICAVP AESHIYREGC AQGLQKWLHN    240
NLISIVGICL GVGLLELGFM TLSIFLCRNL DHVYNRLARY R                        281

SEQ ID NO: 12            moltype = AA  length = 742
FEATURE                  Location/Qualifiers
source                   1..742
                         mol_type = protein
                         organism = Homo sapiens
SEQUENCE: 12
MDKFWWHAAW GLCLVPLSLA QIDLNITCRF AGVFHVEKNG RYSISRTEAA DLCKAFNSTL     60
PTMAQMEKAL SIGFETCRYG FIEGHVVIPR IHPNSICAAN NTGVYILTSN TSQYDTYCFN    120
ASAPPEEDCT SVTDLPNAFD GPITITIVNR DGTRYVQKGE YRTNPEDIYP SNPTDDDVSS    180
GSSSERSSTS GGYIFYTFST VHPIPDEDSP WITDSTDRIP ATTLMSTSAT ATETATKRQE    240
TWDWFSWLFL PSESKNHLHT TTQMAGTSSN TISAGWEPNE ENEDERDRHL SFSGSGIDDD    300
EDFISSTIST TPRAFDHTKQ NQDWTQWNPS HSNPEVLLQT TRMTDVDRN GTTAYEGNWN     360
PEAHPPLIHH EHHEEEETPH STSTIQATPS STTEETATQK EQWFGNRWHE GYRQTPKEDS    420
HSTTGTAAAS AHTSHPMQGR TTPSPEDSSW TDFFNPISHP MGRGHQAGRR MDMDSSHSIT    480
LQPTANPNTG LVEDLDRTGP LSMTTQQSNS QSFSTSHEGL EEDKHPTTS TLTSSNRNDV     540
TGGRRDPNHS EGSTTLLEGY TSHYPHTKES RTFIPVTSAK TGSFGVTAVT VGDSNSNVNR    600
SLSGDQDTFH PSGGSHTTHG SESDGHSHGS QEGGANTTSG PIRTPQIPEW LIILASLLAL    660
ALILAVCIAV NSRRRCGQKK KLVINSGNGA VEDRKPSGLN GEASKSQEMV HLVNKESSET    720
```

```
PDQFMTADET RNLQNVDMKI GV                                              742

SEQ ID NO: 13           moltype = AA  length = 429
FEATURE                 Location/Qualifiers
source                  1..429
                        mol_type = protein
                        organism = Homo sapiens
SEQUENCE: 13
MDKFWWHAAW GLCLVPLSLA QIDLNITCRF AGVFHVEKNG RYSISRTEAA DLCKAFNSTL       60
PTMAQMEKAL SIGFETCRYG FIEGHVVIPR IHPNSICAAN NTGVYILTSN TSQYDTYCFN      120
ASAPPEEDCT SVTDLPNAFD GPITITIVNR DGTRYVQKGE YRTNPEDIYP SNPTDDDVSS      180
GSSSERSSTS GGYIFYTFST VHPIPDEDSP WITDSTDRIP ATNRNDVTGG RRDPNHSEGS      240
TTLLEGYTSH YPHTKESRTF IPVTSAKTGS FGVTAVTVGD SNSNVNRSLS GDQDTFHPSG      300
GSHTTHGSES DGHSHGSQEG GANTTSGPIR TPQIPEWLII LASLLALALI LAVCIAVNSR      360
RRCGQKKKLV INSGNGAVED RKPSGLNGEA SKSQEMVHLV NKESSETPDQ FMTADETRNL      420
QNVDMKIGV                                                              429

SEQ ID NO: 14           moltype = AA  length = 848
FEATURE                 Location/Qualifiers
source                  1..848
                        mol_type = protein
                        organism = Homo sapiens
SEQUENCE: 14
MLQTKDLIWT LFFLGTAVSL QVDIVPSQGE ISVGESKFFL CQVAGDAKDK DISWFSPNGE       60
KLTPNQQRIS VVWNDDSSST LTIYNANIDD AGIYKCVVTG EDGSESEATV NVKIFQKLMF      120
KNAPTPQEFR EGEDAVIVCD VVSSLPPTII WKHKGRDVIL KKDVRFIVLS NNYLQIRGIK      180
KTDEGTYRCE GRILARGEIN FKDIQVIVNV PPTIRARQNI VNATANLGQS VTLVCDAERF      240
PEPTMSWTKD GEQIEQEEDD EKYIFSDDSS QLTIKKVDKN DEAEYICIAE NKAGEQDATI      300
HLKVFAKPKI TYVENQTAME LEEQVTLTCE ASGDPIPSIT WRTSTRNISS EEKTLDGHMV      360
VRSHARVSSL TLKSIQYTDA GEYICTASNT IGQDSQSMYL EVQYAPKLQG PVAVYTWEGN      420
QVNITCEVFA YPSATISWFR DGQLLPSSNY SNIKIYNTPS ASYLEVTPDS ENDFGNYNCT      480
AVNRIGQESF EFILVQADTP SSPSIDQVEP YSSTAQVQFD EPEATGGVPI LKYKAEWRAV      540
GEEVWHSKWY DAKEASMEGI VTIVGLKPET TYAVRLAALN GKGLGEISAA SEFKTQPVQG      600
EPSAPKLEGQ MGEDGNSIKV NLIKQDDGGS PIRHYLVRYR ALSSEWKPEI RLPSGSDHVM      660
LKSLDWNAEY EVYVVAENQQ GKSKAAHFVF RTSAQPTAIP ANGSPTSGLS TGAIVGILIV      720
IFVLLLVVVD ITCYFLNKCG LFMCIAVNLC GKAGPGAKGK DMEEGKAAFS KDESKEPIVE      780
VRTEEERTPN HDGGKHTEPN ETTPLTEPEK GPVEAKPECQ ETETKPAPAE VKTVPNDATQ      840
TKENESKA                                                              848

SEQ ID NO: 15           moltype = AA  length = 193
FEATURE                 Location/Qualifiers
source                  1..193
                        mol_type = protein
                        organism = Homo sapiens
SEQUENCE: 15
MPEEGSGCSV RRRPYGCVLR AALVPLVAGL VICLVVCIQR FAQAQQQLPL ESLGWDVAEL       60
QLNHTGPQQD PRLYWQGGPA LGRSFLHGPE LDKGQLRIHR DGIYMVHIQV TLAICSSTTA      120
SRHHPTTLAV GICSPASRSI SLLRLSFHQG CTIASQRLTP LARGDTLCTN LTGTLLPSRN      180
TDETFFGVQW VRP                                                        193

SEQ ID NO: 16           moltype = AA  length = 296
FEATURE                 Location/Qualifiers
source                  1..296
                        mol_type = protein
                        organism = Homo sapiens
SEQUENCE: 16
MHRRRSRSCR EDQKPVMDDQ RDLISNNEQL PMLGRRPGAP ESKCSRGALY TGFSILVTLL       60
LAGQATTAYF LYQQQGRLDK LTVTSQNLQL ENLRMKLPKP PKPVSKMRMA TPLLMQALPM      120
GALPQGPMQN ATKYGNMTED HVMHLLQNAD PLKVYPPLKG SPPENLRHLK NTMETIDWKV      180
FESWMHHWLL FEMSRHSLEQ KPTDAPPKVL TKCQEEVSHI PAVHPGSFRP KCDENGNYLP      240
LQCYGSIGYC WCVFPNGTEV PNTRSRGHHN CSESLELEDP SSGLGVTKQD LGPVPM         296

SEQ ID NO: 17           moltype = AA  length = 226
FEATURE                 Location/Qualifiers
source                  1..226
                        mol_type = protein
                        organism = Homo sapiens
SEQUENCE: 17
MPGGPGVLQA LPATIFLLFL LSAVYLGPGC QALWMHKVPA SLMVSLGEDA HFQCPHNSSN       60
NANVTWWRVL HGNYTWPPEF LGPGEDPNGT LIIQNVNKSH GGIYVCRVQE GNESYQQSCG      120
TYLRVRQPPP RPFLDMGEGT KNRIITAEGI ILLFCAVVPG TLLLFRKRWQ NEKLGLDAGD      180
EYEDENLYEG LNLDDCSMYE DISRGLQGTY QDVGSLNIGD VQLEKP                    226

SEQ ID NO: 18           moltype = AA  length = 229
FEATURE                 Location/Qualifiers
source                  1..229
                        mol_type = protein
                        organism = Homo sapiens
SEQUENCE: 18
```

```
MARLALSPVP SHWMVALLLL LSAEPVAAR SEDRYRNPKG SACSRIWQSP RFIARKRGFT    60
VKMHCYMNSA SGNVSWLWKQ EMDENPQQLK LEKGRMEESQ NESLATLTIQ GIRFEDNGIY   120
FCQQKCNNTS EVYQGCGTEL RVMGFSTLAQ LKQRNTLKDG IIMIQTLLII LFIIVPIFLL   180
LDKDDSKAGM EEDHTYEGLD IDQTATYEDI VTLRTGEVKW SVGEHPGQE               229

SEQ ID NO: 19           moltype = AA   length = 288
FEATURE                 Location/Qualifiers
source                  1..288
                        mol_type = protein
                        organism = Homo sapiens
SEQUENCE: 19
MGHTRRQGTS PSKCPYLNFF QLLVLAGLSH FCSGVIHVTK EVKEVATLSC GHNVSVEELA    60
QTRIYWQKEK KMVLTMMSGD MNIWPEYKNR TIFDITNNLS IVILALRPSD EGTYECVVLK   120
YEKDAFKREH LAEVTLSVKA DFPTPSISDF EIPTSNIRRI ICSTSGGFPE PHLSWLENGE   180
ELNAINTTVS QDPETELYAV SSKLDFNMTT NHSFMCLIKY GHLRVNQTFN WNTTKQEHFP   240
DNLLPSWAIT LISVNGIFVI CCLTYCFAPR CRERRRNERL RRESVRPV               288

SEQ ID NO: 20           moltype = AA   length = 329
FEATURE                 Location/Qualifiers
source                  1..329
                        mol_type = protein
                        organism = Homo sapiens
SEQUENCE: 20
MDPQCTMGLS NILFVMAFLL SGAAPLKIQA YFNETADLPC QFANSQNQSL SELVVFWQDQ    60
ENLVLNEVYL GKEKFDSVHS KYMGRTSFDS DSWTLRLHNL QIKDKGLYQC IIHHKKPTGM   120
IRIHQMNSEL SVLANFSQPE IVPISNITEN VYINLTCSSI HGYPEPKKMS VLLRTKNSTI   180
EYDGVMQKSQ DNVTELYDVS ISLSVSFPDV TSNMTIFCIL ETDKTRLLSS PFSIELEDPQ   240
PPPDHIPWIT AVLPTVIICV MVFCLILWKW KKKKRPRNSY KCGTNTMERE ESEQTKKREK   300
IHIPERSDEA QRVFKSSKTS SCDKSDTCF                                     329

SEQ ID NO: 21           moltype = AA   length = 310
FEATURE                 Location/Qualifiers
source                  1..310
                        mol_type = protein
                        organism = Homo sapiens
SEQUENCE: 21
MRRAALWLWL CALALSLQPA LPQIVATNLP PEDQDGSGDD SDNFSGSGAG ALQDITLSQQ    60
TPSTWKDTQL LTAIPTSPEP TGLEATAAST STLPAGEGPK EGEAVVLPEV EPGLTAREQE   120
ATPRPRETTQ LPTTHQASTT TATTAQEPAT SHPHRDMQPG HHETSTPAGP SQADLHTPHT   180
EDGGPSATER AAEDGASSQL PAAEGSGEQD FTFETSGENT AVVAVEPDRR NQSPVDQGAT   240
GASQGLLDRK EVLGGVIAVG LVGLIFAVCL VGFMLYRMKK KDEGSYSLEE PKQANGGAYQ   300
KPTKQEEFYA                                                          310

SEQ ID NO: 22           moltype = AA   length = 459
FEATURE                 Location/Qualifiers
source                  1..459
                        mol_type = protein
                        organism = Homo sapiens
SEQUENCE: 22
MAPLCPSPWL PLLIPAPAPG LTVQLLLSLL LLVPVHPQRL PRMQEDSPLG GGSSGEDDPL    60
GEEDLPSEED SPREEDPPGE EDLPGEEDLP GEEDLPEVKP KSEEEGSLKL EDLPTVEAPG   120
DPQEPQNNAH RDKEGDDQSH WRYGGDPPWP RVSPACAGRF QSPVDIRPQL AAFCPALRPL   180
ELLGFQLPPL PELRLRNNGH SVQLTLPPGL EMALGPGREY RALQLHLHWG AAGRPGSEHT   240
VEGHRFPAEI HVVHLSTAFA RVDEALGRPG GLAVLAAFLE EGPEENSAYE QLLSRLEEIA   300
EEGSETQVPG LDISALLPSD FSRYFQYEGS LTTPPCAQGV IWTVFNQTVM LSAKQLHTLS   360
DTLWGPGDSR LQLNFRATQP LNGRVIEASF PAGVDSSPRA AEPVQLNSCL AAGDILALVF   420
GLLFAVTSVA FLVQMRRQHR RGTKGGVSYR PAEVAETGA                          459

SEQ ID NO: 23           moltype = AA   length = 1048
FEATURE                 Location/Qualifiers
source                  1..1048
                        mol_type = protein
                        organism = Homo sapiens
SEQUENCE: 23
MAFPPRRRLR LGPRGLPLLL SGLLLPLCRA FNLDVDSPAE YSGPEGSYFG FAVDFFVPSA    60
SSRMFLLVGA PKANTTQPGI VEGGQVLKCD WSSTRRCQPI EFDATGNRDY AKDDPLEFKS   120
HQWFGASVRS KQDKILACAP LYHWRTEMKQ EREPVGTCFL QDGTKTVEYA PCRSQDIDAD   180
GQGFCQGGFS IDFTKADRVL LGGPGSFYWQ GQLISDQVAE IVSKYDPNVY SIKYNNQLAT   240
RTAQAIFDDS YLGYSVAVGD FNGDIDDFV SGVPRAARTL GMVYIYDGKN MSSLYNFTGE    300
QMAAYFGFSV AATDINGDDY ADVFIGAPLF MDRGSDGKLQ EVGQVSVSLQ RASGDFQTTK   360
LNGFEVFARF GSAIAPLGDL DQDGFNDIAI AAPYGGEDKK GIVYIFNGRS TGLNAVPSQI   420
LEGQWAARSM PPSFGYSMKG ATDIDKNGYP DLIVGAFGVD RAILYRARPV ITVNAGLEVY   480
PSILNQDNKT CSLPGTALKV SCFNVRFCLK ADGKGVLPRK LNFQVELLLD KLKQKGAIRR   540
ALFLYSRSPS HSKNMTISRG GLMQCEELIA YLRDESEFRD KLTPITIFME YRLDYRTAAD   600
TTGLQPILNQ FTPANISRQA HILLDCGEDV VCKPKLEVSV DSDQKIIYIG DDNPLTLIVK   660
AQNQGEGAYE AELIVSIPLQ ADFIGVVRNN EALARLSCAF KTENQTRQVV CDLGNPMKAG   720
TQLLAGLRFS VHQQSEMDTS VKFDLQIQSS NLFDKVSPVV SHKVDLAVLA AVEIRGVSSP   780
DHIFLPIPNW EHKENPETEE DVGPVVQHIY ELRNNGPSSF SKAMLHLQWP YKYNNNTLLY   840
ILHYDIDGPM NCTSDMEINP LRIKISSLQT TEKNDTVAGQ GERDHLITKR DLALSEGDIH   900
```

```
TLGCGVAQCL KIVCQVGRLD RGKSAILYVK SLLWTETFMN KENQNHSYSL KSSASFNVIE    960
FPYKNLPIED ITNSTLVTTN VTWGIQPAPM PVPVWVIILA VLAGLLLLAV LVFVMYRMGF   1020
FKRVRPPQEE QEREQLQPHE NGEGNSET                                     1048

SEQ ID NO: 24             moltype = AA   length = 976
FEATURE                   Location/Qualifiers
source                    1..976
                          mol_type = protein
                          organism = Homo sapiens
SEQUENCE: 24
MELQAARACF ALLWGCALAA AAAAQGKEVV LLDFAAAGGE LGWLTHPYGK GWDLMQNIMN    60
DMPIYMYSVC NVMSGDQDNW LRTNWVYRGE AERIFIELKF TVRDCNSFPG GASSCKETFN   120
LYYAESDLDY GTNFQKRLFT KIDTIAPDEI TVSSDFEARH VKLNVEERSV GPLTRKGFYL   180
AFQDIGACVA LLSVRVYYKK CPELLQGLAH FPETIAGSDA PSLATVAGTC VDHAVVPPGG   240
EEPRMHCAVD GEWLVPIGQC LCQAGYEKVE DACQACSPGF FKFEASESPC LECPEHTLPS   300
PEGATSCECE EGFFRAPQDP ASMPCTRPPS APHYLTAVGM GAKVELRWTP PQDSGGREDI   360
VYSVTCEQCW PESGECGPCE ASVRYSEPPH GLTRTSVTVS DLEPHMNYTF TVEARNGVSG   420
LVTSRSFRTA SVSINQTEPP KVRLEGRSTT SLSVSWSIPP PQQSRVWKYE VTYRKKGDSN   480
SYNVRRTEGF SVTLDDLAPD TTYLVQVQAL TQEGQGAGSK VHEFQTLSPE GSGNLAVIGG   540
VAVGVVLLLV LAGVGFFIHR RRKNQRARQS PEDVYFSKSE QLKPLKTYVD PHTYEDPNQA   600
VLKFTTEIHP SCVTRQKVIG AGEFGEVYKG MLKTSSGKKE VPVAIKTLKA GYTEKQRVDF   660
LGEAGIMGQF SHHNIIRLEG VISKYKPMMI ITEYMENGAL DKFLREKDGE FSVLQLVGML   720
RGIAAGMKYL ANMNYVHRDL AARNILVNSN LVCKVSDFGL SRVLEDDPEA TYTTSGGKIP   780
IRWTAPEAIS YRKFTSASDV WSFGIVMWEV MTYGERPYWE LSNHEVMKAI NDGFRLPTPM   840
DCPSAIYQLM MQCWQQERAR RPKFADIVSI LDKLIRAPDS LKTLADFDPR VSIRLPSTSG   900
SEGVPFRTVS EWLESIKMQQ YTEHFMAAGY TAIEKVVQMT NDDIKRIGVR LPGHQKRIAY   960
SLLGLKDQVN TVGIPI                                                  976

SEQ ID NO: 25             moltype = AA   length = 188
FEATURE                   Location/Qualifiers
source                    1..188
                          mol_type = protein
                          organism = Homo sapiens
SEQUENCE: 25
MDCRKMARFS YSVIWIMAIS KVFELGLVAG LGHQEFARPS RGYLAFRDDS IWPQEEPAIR    60
PRSSQRVPPM GIQHSKELNR TCCLNGGTCM LGSFCACPPS FYGRNCEHDV RKENCGSVPH   120
DTWLPKKCSL CKCWHGQLRC FPQAFLPGCD GLVMDEHLVA SRTPELPPSA RTTTFMLVGI   180
CLSIQSYY                                                           188

SEQ ID NO: 26             moltype = AA   length = 264
FEATURE                   Location/Qualifiers
source                    1..264
                          mol_type = protein
                          organism = Homo sapiens
SEQUENCE: 26
MTPGTQSPFF LLLLLTVLTA TTAPKPATVV TGSGHASSTP GGEKETSATQ RSSVPSSTEK    60
NAFNSSLEDP STDYYQELQR DISEMFLQIY KQGGFLGLSN IKFRPGSVVV QLTLAFREGT   120
INVHDVETQF NQYKTEAASR YNLTISDVSV SDVPFPFSAQ SGAGVPGWGI ALLVLVCVLV   180
ALAIVYLIAL AVCQCRRKNY GQLDIFPARD TYHPMSEYPT YHTHGRYVPP SSTDRSPYEK   240
VSAGNGGSSL SYTNPAVAAT SANL                                         264

SEQ ID NO: 27             moltype = AA   length = 875
FEATURE                   Location/Qualifiers
source                    1..875
                          mol_type = protein
                          organism = Homo sapiens
SEQUENCE: 27
MESTLTLATE QPVKKNTLKK YKIACIVLLA LLVIMSLGLG LGLGLRKLEK QGSCRKKCFD    60
ASFRGLENCR CDVACKDRGD CCWDFEDTCV ESTRIWMCNK FRCGETRLEA SLCSCSDDCL   120
QRKDCCADYK SVCQGETSWL EENCDTAQQS QCPEGFDLPP VILFSMDGFR AEYLYTWDTL   180
MPNINKLKTC GIHSKYMRAM YPTKTFPNHY TIVTGLYPES HGIIDNNMYD VNLNKNFSLS   240
SKEQNNPAWW HGQPMWLTAM YQGLKAATYF WPGSEVAING SFPSIYMPYN GSVPFEERIS   300
TLLKWLDLPK AERPRFYTMY FEEPDSSGHA GGPVSARVIK ALQVVDHAFG MLMEGLKQRN   360
LHNCVNIILL ADHGMDQTYC NKMEYMTDYF PRINFFYMYE GPAPRIRAHN IPHDFFSFNS   420
EEIVRNLSCR KPDQHFKPYL TPDLPKRLHY AKNVRIDKVH LFVDQQWLAV RSKSNTNCGG   480
GNHGYNNEFR SMEAIFLAHG PSFKEKTEVE PFENIEVYNL MCDLLRIQPA PNNGTHGSLN   540
HLLKVPFYEP SHAEEVSKFS VCGFANPLPT ESLDCFCPHL QNSTQLEQVN QMLNLTQEEI   600
TATVKVNLPF GRPRVLQKNV DHCLLYHREY VSGFGKAMRM PMWSSYTVPQ LGDTSPLPPT   660
VPDCLRADVR VPPSESQKCS FYLADKNITH GFLYPPASNR TSDSQYDALI TSNLVPMYEE   720
FRKMWDYFHS VLLIKHATER NGVNVVSGPI FDYNYDGHFD APDEITKHLA NTDVPIPTHY   780
FVVLTSCKNK SHTPENCPGW LDVLPFIIPH RPTNVESCPE GKPEALWVEE RFTAHIARVR   840
DVELLTGLDF YQDKVQPVSE ILQLKTYLPT FETTI                              875

SEQ ID NO: 28             moltype = AA   length = 510
FEATURE                   Location/Qualifiers
source                    1..510
                          mol_type = protein
                          organism = Homo sapiens
SEQUENCE: 28
```

```
MPLSLGAEMW GPEAWLLLLL LLASFTGRCP AGELETSDVV TVVLGQDAKL PCFYRGDSGE    60
QVGQVAWARV DAGEGAQELA LLHSKYGLHV SPAYEGRVEQ PPPPRNPLDG SVLLRNAVQA   120
DEGEYECRVS TFPAGSFQAR LRLRVLVPPL PSLNPGPALE EGQGLTLAAS CTAEGSPAPS   180
VTWDTEVKGT TSSRSFKHSR SAAVTSEFHL VPSRSMNGQP LTCVVSHPGL LQDQRITHIL   240
HVSFLAEASV RGLEDQNLWH IGREGAMLKC LSEGQPPPSY NWTRLDGPLP SGVRVDGDTL   300
GFPPLTTEHS GIYVCHVSNE FSSRDSQVTV DVLDPQEDSG KQVDLVSASV VVVGVIAALL   360
FCLLVVVVVL MSRYHRRKAQ QMTQKYEEEL TLTRENSIRR LHSHHTDPRS QPEESVGLRA   420
EGHPDSLKDN SSCSVMSEEP EGRSYSTLTT VREIETQTEL LSPGSGRAEE EEDQDEGIKQ   480
AMNHFVQENG TLRAKPTGNG IYINGRGHLV                                   510

SEQ ID NO: 29          moltype = AA  length = 622
FEATURE                Location/Qualifiers
source                 1..622
                       mol_type = protein
                       organism = Homo sapiens
SEQUENCE: 29
MALPTARPLL GSCGTPALGS LLFLLFSLGW VQPSRTLAGE TGQEAAPLDG VLANPPNISS    60
LSPRQLLGFP CAEVSGLSTE RVRELAVALA QKNVKLSTEQ LRCLAHRLSE PPEDLDALPL   120
DLLLFLNPDA FSGPQACTHF FSRITKANVD LLPRGAPERQ RLLPAALACW GVRGSLLSEA   180
DVRALGGLAC DLPGRFVAES AEVLLPRLVS CPGPLDQDQQ EAARAALQGG GPPYGPPSTW   240
SVSTMDALRG LLPVLGQPII RSIPQGIVAA WRQSSRDPS WRQPERTILR PRFRREVEKT    300
ACPSGKKARE IDESLIFYKK WELEACVDAL LLATQMDRVN AIPFTYEQLD VLKHKLDELY   360
PQGYPESVIQ HLGYLFLKMS PEDIRKWNVT SLETLKALLE VNKGHEMSPQ VATLIDRFVK   420
GRGQLDKDTL DTLTAFYPGY LCSLSPEELS SVPPSSIWAV RPQDLDTCDP RQLDVLYPKA   480
RLAFQNMNGS EYFVKIQSFL GGAPTEDLKA LSQQNVSMDL ATFMKLRTDA VLPLTVAEVQ   540
KLLGPHVEGL KAEERHRPVR DWILRQRQDD LDTLGLGLQG GIPNGYLVLD LSVQEALSGT   600
PCLLGPGPVL TVLALLLAST LA                                           622

SEQ ID NO: 30          moltype = AA  length = 360
FEATURE                Location/Qualifiers
source                 1..360
                       mol_type = protein
                       organism = Homo sapiens
SEQUENCE: 30
DPLGAAKPQW PWRRCLAALL FQLLVAVCFF SYLRVSRDDA TGSPRAPSGS SRQDTTPTRP    60
TLLILLWTWP FHIPVALSRC SEMVPGTADC HITADRKVYP QADTVIVHHW DIMSNPKSRL   120
PPSPRPQGQR WIWFNLEPPP NCQHLEALDR YFNLTMSYRS DSDIFTPYGW LEPWSGQPAH   180
PPLNLSAKTE LVAWAVSNWK PDSARVRYYQ SLQAHLKVDU YGRSHKPLPK GTMMETLSRY   240
KFYLAFENSL HPDYITEKLW RNALEAWAVP VVLGPSRSNY ERFLPPDAFI HVDDFQSPKD   300
LARYLQELDK DHARYLSYFR WRETLRPRSF SWALDFCKAC WKLQQESRYQ TVRSIAAWFT   360

SEQ ID NO: 31          moltype = AA  length = 1210
FEATURE                Location/Qualifiers
source                 1..1210
                       mol_type = protein
                       organism = Homo sapiens
SEQUENCE: 31
MRPSGTAGAA LLALLAALCP ASRALEEKKV CQGTSNKLTQ LGTFEDHFLS LQRMFNNCEV    60
VLGNLEITYV QRNYDLSFLK TIQEVAGYVL IALNTVERIP LENLQIIRGN MYYENSYALA   120
VLSNYDANKT GLKELPMRNL QEILHGAVRF SNNPALCNVE SIQWRDIVSS DFLSNMSMDF   180
QNHLGSCQKC DPSCPNGSCW GAGEENCQKL TKIICAQQCS GRCRGKSPSD CCHNQCAAGC   240
TGPRESDCLV CRKFRDEATC KDTCPPLMLY NPTTYQMDVN PEGKYSFGAT CVKKCPRNYV   300
VTDHGSCVRA CGADSYEMEE DGVRKCKKCE GPCRKVCNGI GIGEFKDSLS INATNIKHFK   360
NCTSISGDLH ILPVAFRGDS FTHTPPLDPQ ELDILKTVKE ITGFLLIQAW PENRTDLHAF   420
ENLEIIRGRT KQHGQFSLAV VSLNITSLGL RSLKEISDGD VIISGNKNLC YANTINWKKL   480
FGTSGQKTKI ISNRGENSCK ATGQVCHALC SPEGCWGPEP RDCVSCRNVS RGRECVDKCK   540
LLEGEPREFV ENSECIQCHP ECLPQAMNIT CTGRGPDNCI QCAHYIDGPH CVKTCPAGVM   600
GENNTLVWKY ADAGHVCHLC HPNCTYGCTG PGLEGCPTNG PKIPSIATGM VGALLLLLVV   660
ALGIGLFMRR RHIVRKRTLR RLLQERELVE PLTPSGEAPN QALLRILKET EFKKIKVLGS   720
GAFGTVYKGL WIPEGEKVKI PVAIKELREA TSPKANKEIL DEAYVMASVD NPHVCRLLGI   780
CLTSTVQLIT QLMPFGCLLD YVREHKDNIG SQYLLNWCVQ IAKGMNYLED RRLVHRDLAA   840
RNVLVKTPQH VKITDFGLAK LLGAEEKEYH AEGGKVPIKW MALESILHRI YTHQSDVWSY   900
GVTVWELMTF GSKPYDGIPA SEISSILEKG ERLPQPPICT VDYMIMVKC WMIDADSRPK    960
FRELIIEFSK MARDPQRYLV IQGDERMHLP SPTDSNFYRA LMDEEDMDDV VDADEYLIPQ  1020
QGFFSSPSTS RTPLLSSLSA TSNNSTVACI DRNGLQSCPI KEDSFLQRYS SDPTGALTED  1080
SIDDTFLPVP EYINQSVPKR PAGSVQNPVY HNQPLNPAPS RDPHYQDPHS TAVGNPEYLN  1140
TVQPTCVNST FDSPAHWAQK GSHQISLDNP DYQQDFFPKE AKPNGIFKGS TAENAEYLRV  1200
APQSSEFIGA                                                        1210

SEQ ID NO: 32          moltype = AA  length = 710
FEATURE                Location/Qualifiers
source                 1..710
                       mol_type = protein
                       organism = Homo sapiens
SEQUENCE: 32
MGGKQRDEDD EAYGKPVKYD PSFRGPIKNR SCTDVICCVL FLLFILGYIV VGIVAWLYGD    60
PRQVLYPRNS TGAYCGMGEN KDKPYLLYFN IFSCILSSNI ISVAENGLQC PTPQVCVSSC   120
PEDPWTVGKN EFSQTVGEVF YTKNRNFCLP GVPWNMTVIT SLQQELCPSF LLPSAPALGR   180
CFPWTNVTPP ALPGITNDTT IQQGISGLID SLNARDISVK IFEDFAQSWY WILVALGVAL   240
```

```
VLSLLFILLL  RLVAGPLVLV  LILGVLGVLA  YGIYYCWEEY  RVLRDKGASI  SQLGFTTNLS   300
AYQSVQETWL  AALIVLAVLE  AILLLMLIFL  RQRIRIAIAL  LKEASKAVGQ  MMSTMFYPLV   360
TFVLLLICIA  YWAMTALYLA  TSGQPQYVLW  ASNISSPGCE  KVPINTSCNP  TAHLVNSSCP   420
GLMCVFQGYS  SKGLIQRSVF  NLQIYGVLGL  FWTLNWVLAL  GQCVLAGAFA  SFYWAFHKPQ   480
DIPTFPLISA  FIRTLRYHTG  SLAFGALILT  LVQIARVILE  YIDHKLRGVQ  NPVARCIMCC   540
FKCCLWCLEK  FIKFLNRNAY  IMIAIYGKNF  CVSAKNAFML  LMRNIVRVVV  LDKVTDLLLF   600
FGKLLVVGGV  GVLSFFFFSG  RIPGLGKDFK  SPHLNYYWLP  IMTSILGAYV  IASGFFSVFG   660
MCVDTLFLCF  LEDLERNNGS  LDRPYYMSKS  LLKILGKKNE  APPDNKKRKK               710

SEQ ID NO: 33           moltype = AA  length = 442
FEATURE                 Location/Qualifiers
source                  1..442
                        mol_type = protein
                        organism = Homo sapiens
SEQUENCE: 33
MQPPPSLCGR  ALVALVLACG  LSRIWGEERG  FPPDRATPLL  QTAEIMTPPT  KTLWPKGSNA   60
SLARSLAPAE  VPKGDRTAGS  PPRTISPPPC  QGPIEIKETF  KYINTVVSCL  VFVLGIIGNS   120
TLLRIIYKNK  CMRNGPNILI  ASLALGDLLH  IVIDIPINVY  KLLAEDWPFG  AEMCKLVPFI   180
QKASVGITVL  SLCALSIDRY  RAVASWSRIK  GIGVPKWTAV  EIVLIWVVSV  VLAVPEAIGF   240
DIITMDYKGS  YLRICLLHPV  QKTAFMQFYK  TAKDWWLFSF  YFCLPLAITA  FFYTLMTCEM   300
LRKKSGMQIA  LNDHLKQRRE  VAKTVFCLVL  VFALCWLPLH  LSRILKLTLY  NQNDPNRCEL   360
LSFLLVLDYI  GINMASLNSC  INPIALYLVS  KRFKNCFKSC  LCCWCQSFEE  KQSLEEKQSC   420
LKFKANDHGY  DNFRSSNKYS  SS                                              442

SEQ ID NO: 34           moltype = AA  length = 1255
FEATURE                 Location/Qualifiers
source                  1..1255
                        mol_type = protein
                        organism = Homo sapiens
SEQUENCE: 34
MELAALCRWG  LLLALLPPGA  ASTQVCTGTD  MKLRLPASPE  THLDMLRHLY  QGCQVVQGNL   60
ELTYLPTNAS  LSFLQDIQEV  QGYVLIAHNQ  VRQVPLQRLR  IVRGTQLFED  NYALAVLDNG   120
DPLNNTTPVT  GASPGGLREL  QLRSLTEILK  GGVLIQRNPQ  LCYQDTILWK  DIFHKNNQLA   180
LTLIDTNRSR  ACHPCSPMCK  GSRCWGESSE  DCQSLTRTVC  AGGCARCKGP  LPTDCCHEQC   240
AAGCTGPKHS  DCLACLHFNH  SGICELHCPA  LVTYNTDTFE  SMPNPEGRYT  FGASCVTACP   300
YNYLSTDVGS  CTLVCPLHNQ  EVTAEDGTQR  CEKCSKPCAR  VCYGLGMEHL  REVRAVTSAN   360
IQEFAGCKKI  FGSLAFLPES  FDGDPASNTA  PLQPEQLQVF  ETLEEITGYL  YISAWPDSLP   420
DLSVFQNLQV  IRGRILHNGA  YSLTLQGLGI  SWLGLRSLRE  LGSGLALIHH  NTHLCFVHTV   480
PWDQLFRNPH  QALLHTANRP  EDECVGEGLA  CHQLCARGHC  WGPGPTQCVN  CSQFLRGQEC   540
VEECRVLQGL  PREYVNARHC  LPCHPECQPQ  NGSVTCFGPE  ADQCVACAHY  KDPPFCVARC   600
PSGVKPDLSY  MPIWKFPDEE  GACQPCPINC  THSCVDLDDK  GCPAEQRASP  LTSIISAVVG   660
ILLVVVLGVV  FGILIKRRQQ  KIRKYTMRRL  LQETELVEPL  TPSGAMPNQA  QMRILKETEL   720
RKVKVLGSGA  FGTVYKGIWI  PDGENVKIPV  AIKVLRENTS  PKANKEILDE  AYVMAGVGSP   780
YVSRLLGICL  TSTVQLVTQL  MPYGCLLDHV  RENRGRLGSQ  DLLNWCMQIA  KGMSYLEDVR   840
LVHRDLAARN  VLVKSPNHVK  ITDFGLARLL  DIDETEYHAD  GGKVPIKWMA  LESILRRRFT   900
HQSDVWSYGV  TVWELMTFGA  KPYDGIPARE  IPDLEKGER   LPQPPICTID  VYMIMVKCWM   960
IDSECRPRFR  ELVSEFSRMA  RDPQRFVVIQ  NEDLGPASPL  DSTFYRSLLE  DDDMGDLVDA   1020
EEYLVPQQGF  FCPDPAPGAG  GMVHHRHRSS  STRSGGGDLT  LGLEPSEEEA  PRSPLAPSEG   1080
AGSDVFDGDL  GMGAAKGLQS  LPTHDPSPLQ  RYSEDPTVPL  PSETDGYVAP  LTCSPQPEYV   1140
NQPDVRPQPP  SPREGPLPAA  RPAGATLERP  KTLSPGKNGV  VKDVFAFGGA  VENPEYLTPQ   1200
GGAAPQPHPP  PAFSPAFDNL  YYWDQDPPER  GAPPSTFKGT  PTAENPEYLG  LDVPV        1255

SEQ ID NO: 35           moltype = AA  length = 760
FEATURE                 Location/Qualifiers
source                  1..760
                        mol_type = protein
                        organism = Homo sapiens
SEQUENCE: 35
MMDQARSAFS  NLFGGEPLSY  TRFSLARQVD  GDNSHVEMKL  AVDEEENADN  NTKANVTKPK   60
RCSGSICYGT  IAVIVFFLIG  FMIGYLGYCK  GVEPKTECER  LAGTESPVRE  EPGEDFPAAR   120
RLYWDDLKRK  LSEKLDSTDF  TGTIKLLNEN  SYVPREAGSQ  KDENLALYVE  NQFREFKLSK   180
VWRDQHFVKI  QVKDSAQNSV  IIVDKNGRLV  YLVENPGGYV  AYSKAATVTG  KLVHANFGTK   240
KDFEDLYTPV  NGSIVIVRAG  KITFAEKVAN  AESLNAIGVL  IYMDQTKFPI  VNAELSFFGH   300
AHLGTGDPYT  PGFPSFNHTQ  FPPSRSSGLP  NIPVQTISRA  AAEKLFGNME  GDCPSDWKTD   360
STCRMVTSES  KNVKLTVSNV  LKEIKILNIF  GVIKGFVEPD  HYVVVGAQRD  AWGPGAAKSG   420
VGTALLLKLA  QMFSDMVLKD  GFQPSRSIIF  ASWSAGDFGS  VGATEWLEGY  LSSLHLKAFT   480
YINLDKAVLG  TSNFKVSASP  LLYTLIEKTM  QNVKHPVTGQ  FLYQDSNWAS  KVEKLTLDNA   540
APPFLAYSGI  PAVSPCFCED  TDYPYLGTTM  DTYKELIERI  PELNKVARAA  AEVAGQPVIK   600
LTHDVELNLD  YERYNSQLLS  FVRDLNQYRA  DIKEMGLSLQ  WLYSARGDFF  RATSRLTTDF   660
GNAEKTDRFV  MKKLNDRVMR  VEYHFLSPYV  SPKESPFRHV  FWGSGSHTLP  ALLENLKLRK   720
QNNGAFNETL  FRNQLALATW  TIQGAANALS  GDVWDIDNEF                           760

SEQ ID NO: 36           moltype = AA  length = 334
FEATURE                 Location/Qualifiers
source                  1..334
                        mol_type = protein
                        organism = Homo sapiens
SEQUENCE: 36
MPLLPVLLVG  TISKHLDWHR  KEEKEHLKGV  QDPQHERIIT  VSTNGSIHSP  RFPHTYPRNT   60
```

```
VLVWRLVAVE ENVWIQLTFD ERFGLEDPED DICKYDFVEV EEPSDGTILG RWCGSGTVPG    120
KQISKGNQIR IRFVSDEYFP SEPGFCIHYN IVMPQFTEAV SPSVLPPSAL PLDDLLNNAIT   180
AFSTLEDLIR YLEPERWQLD LEDLYRPTWQ LLGKAFVFGR KSRVVDLNLL TEEVRLYSCT    240
PRNFSVSIRE ELKRTDTIFW PGCLLVKRCG GNCACCLHNC NECQCVPSKV TKKYHEVLQL    300
RPKTGVRGLH KSLTDVALEH HEECDCVCRG STGG                               334

SEQ ID NO: 37           moltype = AA   length = 370
FEATURE                 Location/Qualifiers
source                  1..370
                        mol_type = protein
                        organism = Homo sapiens
SEQUENCE: 37
MHRLIFVYTL ICANFCSCRD TSATPQSASI KALRNANLRR DESNHLTDLY RRDETIQVKG     60
NGYVQSPRFP NSYPRNLLLT WRLHSQENTR IQLVFDNQFG LEEAENDICR YDFVEVEDIS    120
ETSTIIRGRW CGHKEVPPRI KSRTNQIKIT FKSDDYFVAK PGFKIYYSLL EDFQPAAASE    180
TNWESVTSSI SGVSYNSPSV TDPTLIADAL DKKIAEFDTV EDLLKYFNPE SWQEDLENMY    240
LDTPRYRGRS YHDRKSKVDL DRLNDDAKRY SCTPRNYSVN IREELKLANV VFFPRCLLVQ    300
RCGGNCGCGT VNWRSCTCNS GKTVKKYHEV LQFEPGHIKR RGRAKTMALV DIQLDHHERC    360
DCICSSRPPR                                                          370

SEQ ID NO: 38           moltype = AA   length = 572
FEATURE                 Location/Qualifiers
source                  1..572
                        mol_type = protein
                        organism = Homo sapiens
SEQUENCE: 38
MECLYYFLGF LLLAARLPLD AAKRFHDVLG NERPSAYMRE HNQLNGWSSD ENDWNEKLYP     60
VWKRGDMRWK NSWKGGRVQA VLTSDSPALV GSNITFAVNL IPPRCQKEDA NGNIVYEKNC    120
RNEAGLSADP YVYNWTAWSE DSDGENGTGQ SHHNVFPDGK PFPHHPGWRR WNFIYVFHTL    180
GQYFQKLGRC SVRVSVNTAN VTLGPQLMEV TVYRRHGRAY VPIAQVKDVY VVTDQIPVFV    240
TMFQKNDRNS SDETFLKDLP IMFDVLIHDP SHFLNYSTIN YKWSFGDNTG LFVSTNHTVN    300
HTYVLNGTFS LNLTVKAAAP GPCPPPPPPP RPSKPTPSLA TTLKSYDSNT PGPAGDNPLE    360
LSRIPDENCQ INRYGHFQAT ITIVEGILEV NIIQMTDVLM PVPWPESSLI DFVVTCQGSI    420
PTEVCTIISD PTCEITQNTV CSPVDVDEMC LLTVRRTFNG SGTYCVNLTL GDDTSLALTS    480
TLISVPDRDP ASPLRMANSA LISVGCLAIF VTVISLLVYK KHKEYNPIEN SPGNVVRSKG    540
LSVFLNRAKA VFFPGNQEKD PLLKNQEFKG VS                                 572

SEQ ID NO: 39           moltype = AA   length = 701
FEATURE                 Location/Qualifiers
source                  1..701
                        mol_type = protein
                        organism = Homo sapiens
SEQUENCE: 39
MESPSAPPHR WCIPWQRLLL TASLLTFWNP PTTAKLTIES TPFNVAEGKE VLLLVHNLPQ     60
HLFGYSWYKG ERVDGNRQII GYVIGTQQAT PGPAYSGREI IYPNASLLIQ NIIQNDTGFY    120
TLHVIKSDLV NEEATGQFRV YPELPKPSIS SNNSKPVEDK DAVAFTCEPE TQDATYLWWV    180
NNQSLPVSPR LQLSNGNRTL TLFNVTRNDT ASYKCETQNP VSARRSDSVI LNVLYGPDAP    240
TISPLNTSYR SGENLNLSCH AASNPPAQYS WFVNGTFQQS TQELFIPNIT VNNSGSYTCQ    300
AHNSDTGLNR TTVTTITVYA EPPKPFITSN NSNPVEDEDA VALTCEPEIQ NTTYLWWVNN    360
QSLPVSPRLQ LSNDNRTLTL LSVTRNDVGP YECGIQNELS VDHSDPVILN VLYGPDDPTI    420
SPSYTYYRPG VNLSLSCHAA SNPPAQYSWL IDGNIQQHTQ ELFISNITEK NSGLYTCQAN    480
NSASGHSRTT VKTITVSAEL PKPSISSNNS KPVEDKDAVA FTCEPEAQNT TYLWWVNGQS    540
LPVSPRLQLS NGNRTLTLFN VTRNDARAYV CGIQNSVSAN RSDPVTLDVL YGPDTPIISP    600
PDSSYLSGAN LNLSCHSASN PSPQYSWRIN GIPQQHTQVL FIAKITPNNN GTYACFVSNL    660
ATGRNNSIVK SITVSASGTS PGLSAGATVG IMIGVLVGVA L                       701

SEQ ID NO: 40           moltype = AA   length = 702
FEATURE                 Location/Qualifiers
source                  1..702
                        mol_type = protein
                        organism = Homo sapiens
SEQUENCE: 40
MESPSAPPHR WCIPWQRLLL TASLLTFWNP PTTAKLTIES TPFNVAEGKE VLLLVHNLPQ     60
HLFGYSWYKG ERVDGNRQII GYVIGTQQAT PGPAYSGREI IYPNASLLIQ NIIQNDTGFY    120
TLHVIKSDLV NEEATGQFRV YPELPKPSIS SNNSKPVEDK DAVAFTCEPE TQDATYLWWV    180
NNQSLPVSPR LQLSNGNRTL TLFNVTRNDT ASYKCETQNP VSARRSDSVI LNVLYGPDAP    240
TISPLNTSYR SGENLNLSCH AASNPPAQYS WFVNGTFQQS TQELFIPNIT VNNSGSYTCQ    300
AHNSDTGLNR TTVTTITVYA EPPKPFITSN NSNPVEDEDA VALTCEPEIQ NTTYLWWVNN    360
QSLPVSPRLQ LSNDNRTLTL LSVTRNDVGP YECGIQNELS VDHSDPVILN VLYGPDDPTI    420
SPSYTYYRPG VNLSLSCHAA SNPPAQYSWL IDGNIQQHTQ ELFISNITEK NSGLYTCQAN    480
NSASGHSRTT VKTITVSAEL PKPSISSNNS KPVEDKDAVA FTCEPEAQNT TYLWWVNGQS    540
LPVSPRLQLS NGNRTLTLFN VTRNDARAYV CGIQNSVSAN RSDPVTLDVL YGPDTPIISP    600
PDSSYLSGAN LNLSCHSASN PSPQYSWRIN GIPQQHTQVL FIAKITPNNN GTYACFVSNL    660
ATGRNNSIVK SITVSASGTS PGLSAGATVG IMIGVLVGVA LI                      702

SEQ ID NO: 41           moltype = AA   length = 701
FEATURE                 Location/Qualifiers
source                  1..701
                        mol_type = protein
```

```
                        organism = Homo sapiens
SEQUENCE: 41
MESPSAPPHR WCIPWQRLLL TASLLTFWNP PTTAKLTIES TPFNVAEGKE VLLLVHNLPQ    60
HLFGYSWYKG ERVDGNRQII GYVIGTQQAT PGPAYSGREI IYPNASLLIQ NIIQNDTGFY   120
TLHVIKSDLV NEEATGQFRV YPELPKPSIS SNNSKPVEDK DAVAFTCEPE TQDATYLWVV   180
NNQSLPVSPR LQLSNGNRTL TLFNVTRNDT ASYKCETQNP VSARRSDSVI LNVLYGPDAP   240
TISPLNTSYR SGENLNLSCH AASNPPAQYS WFVNGTFQQS TQELFIPNIT VNNSGSYTCQ   300
AHNSDTGLNR TTVTTITVYA EPPKPFITSN NSNPVEDEDA VALTCEPEIQ NTTYLWWVNN   360
QSLPVSPRLQ LSNDNRTLTL LSVTRNDVGP YECGIQNELS VDHSDPVILN VLYGPDDPTI   420
SPSYTYYRPG VNLSLSCHAA SNPPAQYSWL IDGNIQQHTQ ELFISNITEK NSGLYTCQAN   480
NSASGHSRTT VKTITVSAEL PKPSISSNNS KPVEDKDAVA FTCEPEAQNT TYLWWVNGQS   540
LPVSPRLQLS NGNRTLTLFN VTRNDARAYV CGIQNSVSAN RSDPVTLDVL YGPDTPIISP   600
PDSSYLSGAN LNLSCHSASN PSPQYSWRIN GIPQQHTQVL FIAKITPNNN GTYACFVSNL   660
ATGRNNSIVK SITVSASGTS PGLSAGATVG IMIGVLVGVA L                      701

SEQ ID NO: 42           moltype = AA  length = 750
FEATURE                 Location/Qualifiers
source                  1..750
                        mol_type = protein
                        organism = Homo sapiens
SEQUENCE: 42
MWNLLHETDS AVATARRPRW LCAGALVLAG GFFLLGFLFG WFIKSSNEAT NITPKHNMKA    60
FLDELKAENI KKFLYNFTQI PHLAGTEQNF QLAKQIQSQW KEFGLDSVEL AHYDVLLSYP   120
NKTHPNYISI INEDGNEIFN TSLFEPPPPG YENVSDIVPP FSAFSPQGMP EGDLVYVNYA   180
RTEDFFKLER DMKINCSGKI VIARYGKVFR GNKVKNAQLA GAKGVILYSD PADYFAPGVK   240
SYPDGWNLPG GGVQRGNILN LNGAGDPLTP GYPANEYAYR RGIAEAVGLP SIPVHPIGYY   300
DAQKLLEKMG GSAPPDSSWR GSLKVPYNVG PGFTGNFSTQ KVKMHIHSTN EVTRIYNVIG   360
TLRGAVEPDR YVILGGHRDS WVFGGIDPQS GAAVVHEIVR SFGTLKKEGW RPRRTILFAS   420
WDAEEFGLLG STEWAEENSR LLQERGVAYI NADSSIEGNY TLRVDCTPLM YSLVHNLTKE   480
LKSPDEGFEG KSLYESWTKK SPSPEFSGMP RISKLGSGND FEVFFQRLGI ASGRARYTKN   540
WETNKFSGYP LYHSVYETYE LVEKFYDPMF KYHLTVAQVR GGMVFELANS IVLPFDCRDY   600
AVVLRKYADK IYSISMKHPQ EMKTYSVSFD SLFSAVKNFT EIASKFSERL QDFDKSNPIV   660
LRMMNDQLMF LERAFIDPLG LPDRPFYRHV IYAPSSHNKY AGESFPGIYD ALFDIESKVD   720
PSKAWGEVKR QIYVAAFTVQ AAAETLSEVA                                   750

SEQ ID NO: 43           moltype = AA  length = 22152
FEATURE                 Location/Qualifiers
REGION                  13877..13878
                        note = misc_feature - Xaa can be any naturally occurring
                         amino acid
SITE                    13880
                        note = misc_feature - Xaa can be any naturally occurring
                         amino acid
SITE                    13887
                        note = misc_feature - Xaa can be any naturally occurring
                         amino acid
REGION                  13890..13891
                        note = misc_feature - Xaa can be any naturally occurring
                         amino acid
SITE                    13893
                        note = misc_feature - Xaa can be any naturally occurring
                         amino acid
SITE                    13903
                        note = misc_feature - Xaa can be any naturally occurring
                         amino acid
REGION                  13913..13914
                        note = misc_feature - Xaa can be any naturally occurring
                         amino acid
SITE                    13916
                        note = misc_feature - Xaa can be any naturally occurring
                         amino acid
REGION                  13928..13929
                        note = misc_feature - Xaa can be any naturally occurring
                         amino acid
SITE                    13938
                        note = misc_feature - Xaa can be any naturally occurring
                         amino acid
REGION                  13940..13941
                        note = misc_feature - Xaa can be any naturally occurring
                         amino acid
REGION                  14569..14571
                        note = misc_feature - Xaa can be any naturally occurring
                         amino acid
SITE                    14575
                        note = misc_feature - Xaa can be any naturally occurring
                         amino acid
SITE                    14579
                        note = misc_feature - Xaa can be any naturally occurring
                         amino acid
```

-continued

| | | |
|---|---|---|
| SITE | 14581 | |
| | note = misc_feature - Xaa can be any naturally occurring amino acid | |
| REGION | 14587..14591 | |
| | note = misc_feature - Xaa can be any naturally occurring amino acid | |
| REGION | 14593..14594 | |
| | note = misc_feature - Xaa can be any naturally occurring amino acid | |
| REGION | 14725..14727 | |
| | note = misc_feature - Xaa can be any naturally occurring amino acid | |
| SITE | 14731 | |
| | note = misc_feature - Xaa can be any naturally occurring amino acid | |
| SITE | 14735 | |
| | note = misc_feature - Xaa can be any naturally occurring amino acid | |
| SITE | 14737 | |
| | note = misc_feature - Xaa can be any naturally occurring amino acid | |
| REGION | 14743..14747 | |
| | note = misc_feature - Xaa can be any naturally occurring amino acid | |
| REGION | 14749..14750 | |
| | note = misc_feature - Xaa can be any naturally occurring amino acid | |
| REGION | 15661..15663 | |
| | note = misc_feature - Xaa can be any naturally occurring amino acid | |
| SITE | 15667 | |
| | note = misc_feature - Xaa can be any naturally occurring amino acid | |
| SITE | 15671 | |
| | note = misc_feature - Xaa can be any naturally occurring amino acid | |
| SITE | 15673 | |
| | note = misc_feature - Xaa can be any naturally occurring amino acid | |
| REGION | 15679..15683 | |
| | note = misc_feature - Xaa can be any naturally occurring amino acid | |
| REGION | 15685..15686 | |
| | note = misc_feature - Xaa can be any naturally occurring amino acid | |
| REGION | 15972..15974 | |
| | note = misc_feature - Xaa can be any naturally occurring amino acid | |
| SITE | 15978 | |
| | note = misc_feature - Xaa can be any naturally occurring amino acid | |
| SITE | 15982 | |
| | note = misc_feature - Xaa can be any naturally occurring amino acid | |
| SITE | 15984 | |
| | note = misc_feature - Xaa can be any naturally occurring amino acid | |
| REGION | 15990..15994 | |
| | note = misc_feature - Xaa can be any naturally occurring amino acid | |
| REGION | 15996..15997 | |
| | note = misc_feature - Xaa can be any naturally occurring amino acid | |
| SITE | 16008 | |
| | note = misc_feature - Xaa can be any naturally occurring amino acid | |
| SITE | 16015 | |
| | note = misc_feature - Xaa can be any naturally occurring amino acid | |
| SITE | 16017 | |
| | note = misc_feature - Xaa can be any naturally occurring amino acid | |
| SITE | 16021 | |
| | note = misc_feature - Xaa can be any naturally occurring amino acid | |
| SITE | 16025 | |
| | note = misc_feature - Xaa can be any naturally occurring amino acid | |
| SITE | 16034 | |

-continued

```
                    note = misc_feature - Xaa can be any naturally occurring
                       amino acid
SITE            16037
                    note = misc_feature - Xaa can be any naturally occurring
                       amino acid
SITE            16040
                    note = misc_feature - Xaa can be any naturally occurring
                       amino acid
SITE            16046
                    note = misc_feature - Xaa can be any naturally occurring
                       amino acid
SITE            16051
                    note = misc_feature - Xaa can be any naturally occurring
                       amino acid
REGION          16053..16055
                    note = misc_feature - Xaa can be any naturally occurring
                       amino acid
SITE            16058
                    note = misc_feature - Xaa can be any naturally occurring
                       amino acid
REGION          16062..16063
                    note = misc_feature - Xaa can be any naturally occurring
                       amino acid
SITE            16065
                    note = misc_feature - Xaa can be any naturally occurring
                       amino acid
SITE            16072
                    note = misc_feature - Xaa can be any naturally occurring
                       amino acid
REGION          16075..16076
                    note = misc_feature - Xaa can be any naturally occurring
                       amino acid
SITE            16078
                    note = misc_feature - Xaa can be any naturally occurring
                       amino acid
SITE            16088
                    note = misc_feature - Xaa can be any naturally occurring
                       amino acid
REGION          16268..16269
                    note = misc_feature - Xaa can be any naturally occurring
                       amino acid
SITE            16278
                    note = misc_feature - Xaa can be any naturally occurring
                       amino acid
REGION          16280..16281
                    note = misc_feature - Xaa can be any naturally occurring
                       amino acid
REGION          16373..16374
                    note = misc_feature - Xaa can be any naturally occurring
                       amino acid
SITE            16376
                    note = misc_feature - Xaa can be any naturally occurring
                       amino acid
SITE            16383
                    note = misc_feature - Xaa can be any naturally occurring
                       amino acid
REGION          16386..16387
                    note = misc_feature - Xaa can be any naturally occurring
                       amino acid
SITE            16389
                    note = misc_feature - Xaa can be any naturally occurring
                       amino acid
SITE            16399
                    note = misc_feature - Xaa can be any naturally occurring
                       amino acid
REGION          16409..16410
                    note = misc_feature - Xaa can be any naturally occurring
                       amino acid
SITE            16412
                    note = misc_feature - Xaa can be any naturally occurring
                       amino acid
REGION          16424..16425
                    note = misc_feature - Xaa can be any naturally occurring
                       amino acid
SITE            16434
                    note = misc_feature - Xaa can be any naturally occurring
                       amino acid
REGION          16436..16437
                    note = misc_feature - Xaa can be any naturally occurring
```

-continued

```
                            amino acid
REGION                      16439..16441
                            note = misc_feature - Xaa can be any naturally occurring
                            amino acid
SITE                        16445
                            note = misc_feature - Xaa can be any naturally occurring
                            amino acid
SITE                        16449
                            note = misc_feature - Xaa can be any naturally occurring
                            amino acid
SITE                        16451
                            note = misc_feature - Xaa can be any naturally occurring
                            amino acid
REGION                      16457..16461
                            note = misc_feature - Xaa can be any naturally occurring
                            amino acid
REGION                      16463..16464
                            note = misc_feature - Xaa can be any naturally occurring
                            amino acid
REGION                      16841..16842
                            note = misc_feature - Xaa can be any naturally occurring
                            amino acid
SITE                        16844
                            note = misc_feature - Xaa can be any naturally occurring
                            amino acid
SITE                        16851
                            note = misc_feature - Xaa can be any naturally occurring
                            amino acid
REGION                      16854..16855
                            note = misc_feature - Xaa can be any naturally occurring
                            amino acid
SITE                        16857
                            note = misc_feature - Xaa can be any naturally occurring
                            amino acid
SITE                        16867
                            note = misc_feature - Xaa can be any naturally occurring
                            amino acid
REGION                      16877..16878
                            note = misc_feature - Xaa can be any naturally occurring
                            amino acid
SITE                        16880
                            note = misc_feature - Xaa can be any naturally occurring
                            amino acid
REGION                      16892..16893
                            note = misc_feature - Xaa can be any naturally occurring
                            amino acid
SITE                        16902
                            note = misc_feature - Xaa can be any naturally occurring
                            amino acid
REGION                      16904..16905
                            note = misc_feature - Xaa can be any naturally occurring
                            amino acid
REGION                      16907..16909
                            note = misc_feature - Xaa can be any naturally occurring
                            amino acid
SITE                        16913
                            note = misc_feature - Xaa can be any naturally occurring
                            amino acid
SITE                        16917
                            note = misc_feature - Xaa can be any naturally occurring
                            amino acid
SITE                        16919
                            note = misc_feature - Xaa can be any naturally occurring
                            amino acid
REGION                      16925..16929
                            note = misc_feature - Xaa can be any naturally occurring
                            amino acid
REGION                      16931..16932
                            note = misc_feature - Xaa can be any naturally occurring
                            amino acid
REGION                      17465..17466
                            note = misc_feature - Xaa can be any naturally occurring
                            amino acid
SITE                        17468
                            note = misc_feature - Xaa can be any naturally occurring
                            amino acid
SITE                        17475
                            note = misc_feature - Xaa can be any naturally occurring
                            amino acid
```

-continued

| | | |
|---|---|---|
| REGION | 17478..17479 | |
| | note = misc_feature - Xaa can be any naturally occurring amino acid | |
| SITE | 17481 | |
| | note = misc_feature - Xaa can be any naturally occurring amino acid | |
| SITE | 17491 | |
| | note = misc_feature - Xaa can be any naturally occurring amino acid | |
| REGION | 17501..17502 | |
| | note = misc_feature - Xaa can be any naturally occurring amino acid | |
| SITE | 17504 | |
| | note = misc_feature - Xaa can be any naturally occurring amino acid | |
| REGION | 17516..17517 | |
| | note = misc_feature - Xaa can be any naturally occurring amino acid | |
| SITE | 17526 | |
| | note = misc_feature - Xaa can be any naturally occurring amino acid | |
| REGION | 17528..17529 | |
| | note = misc_feature - Xaa can be any naturally occurring amino acid | |
| REGION | 17531..17533 | |
| | note = misc_feature - Xaa can be any naturally occurring amino acid | |
| SITE | 17537 | |
| | note = misc_feature - Xaa can be any naturally occurring amino acid | |
| SITE | 17541 | |
| | note = misc_feature - Xaa can be any naturally occurring amino acid | |
| SITE | 17543 | |
| | note = misc_feature - Xaa can be any naturally occurring amino acid | |
| REGION | 17549..17553 | |
| | note = misc_feature - Xaa can be any naturally occurring amino acid | |
| REGION | 17555..17556 | |
| | note = misc_feature - Xaa can be any naturally occurring amino acid | |
| SITE | 17567 | |
| | note = misc_feature - Xaa can be any naturally occurring amino acid | |
| SITE | 17574 | |
| | note = misc_feature - Xaa can be any naturally occurring amino acid | |
| SITE | 17576 | |
| | note = misc_feature - Xaa can be any naturally occurring amino acid | |
| SITE | 17580 | |
| | note = misc_feature - Xaa can be any naturally occurring amino acid | |
| SITE | 17584 | |
| | note = misc_feature - Xaa can be any naturally occurring amino acid | |
| SITE | 17593 | |
| | note = misc_feature - Xaa can be any naturally occurring amino acid | |
| SITE | 17596 | |
| | note = misc_feature - Xaa can be any naturally occurring amino acid | |
| SITE | 17599 | |
| | note = misc_feature - Xaa can be any naturally occurring amino acid | |
| SITE | 17605 | |
| | note = misc_feature - Xaa can be any naturally occurring amino acid | |
| SITE | 17610 | |
| | note = misc_feature - Xaa can be any naturally occurring amino acid | |
| REGION | 17612..17614 | |
| | note = misc_feature - Xaa can be any naturally occurring amino acid | |
| SITE | 17617 | |
| | note = misc_feature - Xaa can be any naturally occurring amino acid | |
| REGION | 17621..17622 | |

-continued

| | |
|---|---|
| | note = misc_feature - Xaa can be any naturally occurring amino acid |
| SITE | 17624 |
| | note = misc_feature - Xaa can be any naturally occurring amino acid |
| SITE | 17631 |
| | note = misc_feature - Xaa can be any naturally occurring amino acid |
| REGION | 17777..17778 |
| | note = misc_feature - Xaa can be any naturally occurring amino acid |
| SITE | 17780 |
| | note = misc_feature - Xaa can be any naturally occurring amino acid |
| SITE | 17787 |
| | note = misc_feature - Xaa can be any naturally occurring amino acid |
| REGION | 17790..17791 |
| | note = misc_feature - Xaa can be any naturally occurring amino acid |
| SITE | 17793 |
| | note = misc_feature - Xaa can be any naturally occurring amino acid |
| SITE | 17803 |
| | note = misc_feature - Xaa can be any naturally occurring amino acid |
| REGION | 17813..17814 |
| | note = misc_feature - Xaa can be any naturally occurring amino acid |
| SITE | 17816 |
| | note = misc_feature - Xaa can be any naturally occurring amino acid |
| REGION | 17828..17829 |
| | note = misc_feature - Xaa can be any naturally occurring amino acid |
| SITE | 17838 |
| | note = misc_feature - Xaa can be any naturally occurring amino acid |
| REGION | 17840..17841 |
| | note = misc_feature - Xaa can be any naturally occurring amino acid |
| REGION | 17843..17845 |
| | note = misc_feature - Xaa can be any naturally occurring amino acid |
| SITE | 17849 |
| | note = misc_feature - Xaa can be any naturally occurring amino acid |
| SITE | 17853 |
| | note = misc_feature - Xaa can be any naturally occurring amino acid |
| SITE | 17855 |
| | note = misc_feature - Xaa can be any naturally occurring amino acid |
| REGION | 17861..17865 |
| | note = misc_feature - Xaa can be any naturally occurring amino acid |
| REGION | 17867..17868 |
| | note = misc_feature - Xaa can be any naturally occurring amino acid |
| SITE | 17879 |
| | note = misc_feature - Xaa can be any naturally occurring amino acid |
| SITE | 17886 |
| | note = misc_feature - Xaa can be any naturally occurring amino acid |
| SITE | 17888 |
| | note = misc_feature - Xaa can be any naturally occurring amino acid |
| SITE | 17892 |
| | note = misc_feature - Xaa can be any naturally occurring amino acid |
| SITE | 17896 |
| | note = misc_feature - Xaa can be any naturally occurring amino acid |
| SITE | 17905 |
| | note = misc_feature - Xaa can be any naturally occurring amino acid |
| SITE | 17908 |
| | note = misc_feature - Xaa can be any naturally occurring |

-continued

| | | |
|---|---|---|
| SITE | 17911 | |
| | note = misc_feature - Xaa can be any naturally occurring amino acid | |
| SITE | 17917 | |
| | note = misc_feature - Xaa can be any naturally occurring amino acid | |
| SITE | 17922 | |
| | note = misc_feature - Xaa can be any naturally occurring amino acid | |
| REGION | 17924..17926 | |
| | note = misc_feature - Xaa can be any naturally occurring amino acid | |
| SITE | 17929 | |
| | note = misc_feature - Xaa can be any naturally occurring amino acid | |
| REGION | 17933..17934 | |
| | note = misc_feature - Xaa can be any naturally occurring amino acid | |
| SITE | 17936 | |
| | note = misc_feature - Xaa can be any naturally occurring amino acid | |
| SITE | 17943 | |
| | note = misc_feature - Xaa can be any naturally occurring amino acid | |
| REGION | 17946..17947 | |
| | note = misc_feature - Xaa can be any naturally occurring amino acid | |
| SITE | 17949 | |
| | note = misc_feature - Xaa can be any naturally occurring amino acid | |
| SITE | 17959 | |
| | note = misc_feature - Xaa can be any naturally occurring amino acid | |
| REGION | 18089..18090 | |
| | note = misc_feature - Xaa can be any naturally occurring amino acid | |
| SITE | 18092 | |
| | note = misc_feature - Xaa can be any naturally occurring amino acid | |
| SITE | 18099 | |
| | note = misc_feature - Xaa can be any naturally occurring amino acid | |
| REGION | 18102..18103 | |
| | note = misc_feature - Xaa can be any naturally occurring amino acid | |
| SITE | 18105 | |
| | note = misc_feature - Xaa can be any naturally occurring amino acid | |
| SITE | 18115 | |
| | note = misc_feature - Xaa can be any naturally occurring amino acid | |
| REGION | 18125..18126 | |
| | note = misc_feature - Xaa can be any naturally occurring amino acid | |
| SITE | 18128 | |
| | note = misc_feature - Xaa can be any naturally occurring amino acid | |
| REGION | 18140..18141 | |
| | note = misc_feature - Xaa can be any naturally occurring amino acid | |
| SITE | 18150 | |
| | note = misc_feature - Xaa can be any naturally occurring amino acid | |
| REGION | 18152..18153 | |
| | note = misc_feature - Xaa can be any naturally occurring amino acid | |
| REGION | 18155..18157 | |
| | note = misc_feature - Xaa can be any naturally occurring amino acid | |
| SITE | 18161 | |
| | note = misc_feature - Xaa can be any naturally occurring amino acid | |
| SITE | 18165 | |
| | note = misc_feature - Xaa can be any naturally occurring amino acid | |
| SITE | 18167 | |
| | note = misc_feature - Xaa can be any naturally occurring amino acid | |

```
-continued

REGION      18173..18177
            note = misc_feature - Xaa can be any naturally occurring
            amino acid
REGION      18179..18180
            note = misc_feature - Xaa can be any naturally occurring
            amino acid
SITE        18191
            note = misc_feature - Xaa can be any naturally occurring
            amino acid
SITE        18198
            note = misc_feature - Xaa can be any naturally occurring
            amino acid
SITE        18200
            note = misc_feature - Xaa can be any naturally occurring
            amino acid
SITE        18204
            note = misc_feature - Xaa can be any naturally occurring
            amino acid
SITE        18208
            note = misc_feature - Xaa can be any naturally occurring
            amino acid
SITE        18217
            note = misc_feature - Xaa can be any naturally occurring
            amino acid
SITE        18220
            note = misc_feature - Xaa can be any naturally occurring
            amino acid
SITE        18223
            note = misc_feature - Xaa can be any naturally occurring
            amino acid
SITE        18229
            note = misc_feature - Xaa can be any naturally occurring
            amino acid
SITE        18234
            note = misc_feature - Xaa can be any naturally occurring
            amino acid
REGION      18236..18238
            note = misc_feature - Xaa can be any naturally occurring
            amino acid
SITE        18241
            note = misc_feature - Xaa can be any naturally occurring
            amino acid
REGION      18245..18246
            note = misc_feature - Xaa can be any naturally occurring
            amino acid
SITE        18248
            note = misc_feature - Xaa can be any naturally occurring
            amino acid
SITE        18255
            note = misc_feature - Xaa can be any naturally occurring
            amino acid
REGION      18258..18259
            note = misc_feature - Xaa can be any naturally occurring
            amino acid
SITE        18261
            note = misc_feature - Xaa can be any naturally occurring
            amino acid
SITE        18271
            note = misc_feature - Xaa can be any naturally occurring
            amino acid
REGION      18401..18402
            note = misc_feature - Xaa can be any naturally occurring
            amino acid
SITE        18404
            note = misc_feature - Xaa can be any naturally occurring
            amino acid
SITE        18411
            note = misc_feature - Xaa can be any naturally occurring
            amino acid
REGION      18414..18415
            note = misc_feature - Xaa can be any naturally occurring
            amino acid
SITE        18417
            note = misc_feature - Xaa can be any naturally occurring
            amino acid
SITE        18427
            note = misc_feature - Xaa can be any naturally occurring
            amino acid
REGION      18437..18438
```

| | | |
|---|---|---|
| | | note = misc_feature - Xaa can be any naturally occurring amino acid |
| SITE | 18440 | |
| | | note = misc_feature - Xaa can be any naturally occurring amino acid |
| REGION | 18452..18453 | |
| | | note = misc_feature - Xaa can be any naturally occurring amino acid |
| SITE | 18462 | |
| | | note = misc_feature - Xaa can be any naturally occurring amino acid |
| REGION | 18464..18465 | |
| | | note = misc_feature - Xaa can be any naturally occurring amino acid |
| REGION | 18467..18469 | |
| | | note = misc_feature - Xaa can be any naturally occurring amino acid |
| SITE | 18473 | |
| | | note = misc_feature - Xaa can be any naturally occurring amino acid |
| SITE | 18477 | |
| | | note = misc_feature - Xaa can be any naturally occurring amino acid |
| SITE | 18479 | |
| | | note = misc_feature - Xaa can be any naturally occurring amino acid |
| REGION | 18485..18489 | |
| | | note = misc_feature - Xaa can be any naturally occurring amino acid |
| REGION | 18491..18492 | |
| | | note = misc_feature - Xaa can be any naturally occurring amino acid |
| SITE | 18503 | |
| | | note = misc_feature - Xaa can be any naturally occurring amino acid |
| SITE | 18510 | |
| | | note = misc_feature - Xaa can be any naturally occurring amino acid |
| SITE | 18512 | |
| | | note = misc_feature - Xaa can be any naturally occurring amino acid |
| SITE | 18516 | |
| | | note = misc_feature - Xaa can be any naturally occurring amino acid |
| SITE | 18520 | |
| | | note = misc_feature - Xaa can be any naturally occurring amino acid |
| SITE | 18529 | |
| | | note = misc_feature - Xaa can be any naturally occurring amino acid |
| SITE | 18532 | |
| | | note = misc_feature - Xaa can be any naturally occurring amino acid |
| SITE | 18535 | |
| | | note = misc_feature - Xaa can be any naturally occurring amino acid |
| SITE | 18541 | |
| | | note = misc_feature - Xaa can be any naturally occurring amino acid |
| SITE | 18546 | |
| | | note = misc_feature - Xaa can be any naturally occurring amino acid |
| REGION | 18548..18550 | |
| | | note = misc_feature - Xaa can be any naturally occurring amino acid |
| SITE | 18553 | |
| | | note = misc_feature - Xaa can be any naturally occurring amino acid |
| REGION | 18557..18558 | |
| | | note = misc_feature - Xaa can be any naturally occurring amino acid |
| SITE | 18560 | |
| | | note = misc_feature - Xaa can be any naturally occurring amino acid |
| SITE | 18567 | |
| | | note = misc_feature - Xaa can be any naturally occurring amino acid |
| REGION | 18570..18571 | |
| | | note = misc_feature - Xaa can be any naturally occurring |

-continued

| | | |
|---|---|---|
| SITE | 18573 | |
| | note = misc_feature - Xaa can be any naturally occurring amino acid | |
| SITE | 18583 | |
| | note = misc_feature - Xaa can be any naturally occurring amino acid | |
| REGION | 18713..18714 | |
| | note = misc_feature - Xaa can be any naturally occurring amino acid | |
| SITE | 18716 | |
| | note = misc_feature - Xaa can be any naturally occurring amino acid | |
| SITE | 18723 | |
| | note = misc_feature - Xaa can be any naturally occurring amino acid | |
| REGION | 18726..18727 | |
| | note = misc_feature - Xaa can be any naturally occurring amino acid | |
| SITE | 18729 | |
| | note = misc_feature - Xaa can be any naturally occurring amino acid | |
| SITE | 18739 | |
| | note = misc_feature - Xaa can be any naturally occurring amino acid | |
| REGION | 18749..18750 | |
| | note = misc_feature - Xaa can be any naturally occurring amino acid | |
| SITE | 18752 | |
| | note = misc_feature - Xaa can be any naturally occurring amino acid | |
| REGION | 18764..18765 | |
| | note = misc_feature - Xaa can be any naturally occurring amino acid | |
| SITE | 18774 | |
| | note = misc_feature - Xaa can be any naturally occurring amino acid | |
| REGION | 18776..18777 | |
| | note = misc_feature - Xaa can be any naturally occurring amino acid | |
| REGION | 18779..18781 | |
| | note = misc_feature - Xaa can be any naturally occurring amino acid | |
| SITE | 18785 | |
| | note = misc_feature - Xaa can be any naturally occurring amino acid | |
| SITE | 18789 | |
| | note = misc_feature - Xaa can be any naturally occurring amino acid | |
| SITE | 18791 | |
| | note = misc_feature - Xaa can be any naturally occurring amino acid | |
| REGION | 18797..18801 | |
| | note = misc_feature - Xaa can be any naturally occurring amino acid | |
| REGION | 18803..18804 | |
| | note = misc_feature - Xaa can be any naturally occurring amino acid | |
| SITE | 18815 | |
| | note = misc_feature - Xaa can be any naturally occurring amino acid | |
| SITE | 18822 | |
| | note = misc_feature - Xaa can be any naturally occurring amino acid | |
| SITE | 18824 | |
| | note = misc_feature - Xaa can be any naturally occurring amino acid | |
| SITE | 18828 | |
| | note = misc_feature - Xaa can be any naturally occurring amino acid | |
| SITE | 18832 | |
| | note = misc_feature - Xaa can be any naturally occurring amino acid | |
| SITE | 18841 | |
| | note = misc_feature - Xaa can be any naturally occurring amino acid | |
| SITE | 18844 | |
| | note = misc_feature - Xaa can be any naturally occurring amino acid | |

| | |
|---|---|
| SITE | 18847<br>note = misc_feature - Xaa can be any naturally occurring amino acid |
| SITE | 18853<br>note = misc_feature - Xaa can be any naturally occurring amino acid |
| SITE | 18858<br>note = misc_feature - Xaa can be any naturally occurring amino acid |
| REGION | 18860..18862<br>note = misc_feature - Xaa can be any naturally occurring amino acid |
| SITE | 18865<br>note = misc_feature - Xaa can be any naturally occurring amino acid |
| REGION | 18869..18870<br>note = misc_feature - Xaa can be any naturally occurring amino acid |
| SITE | 18872<br>note = misc_feature - Xaa can be any naturally occurring amino acid |
| SITE | 18879<br>note = misc_feature - Xaa can be any naturally occurring amino acid |
| REGION | 18882..18883<br>note = misc_feature - Xaa can be any naturally occurring amino acid |
| SITE | 18885<br>note = misc_feature - Xaa can be any naturally occurring amino acid |
| SITE | 18895<br>note = misc_feature - Xaa can be any naturally occurring amino acid |
| REGION | 19091..19093<br>note = misc_feature - Xaa can be any naturally occurring amino acid |
| SITE | 19097<br>note = misc_feature - Xaa can be any naturally occurring amino acid |
| SITE | 19101<br>note = misc_feature - Xaa can be any naturally occurring amino acid |
| SITE | 19103<br>note = misc_feature - Xaa can be any naturally occurring amino acid |
| REGION | 19109..19113<br>note = misc_feature - Xaa can be any naturally occurring amino acid |
| REGION | 19115..19116<br>note = misc_feature - Xaa can be any naturally occurring amino acid |
| SITE | 19127<br>note = misc_feature - Xaa can be any naturally occurring amino acid |
| SITE | 19134<br>note = misc_feature - Xaa can be any naturally occurring amino acid |
| SITE | 19136<br>note = misc_feature - Xaa can be any naturally occurring amino acid |
| SITE | 19140<br>note = misc_feature - Xaa can be any naturally occurring amino acid |
| SITE | 19144<br>note = misc_feature - Xaa can be any naturally occurring amino acid |
| SITE | 19153<br>note = misc_feature - Xaa can be any naturally occurring amino acid |
| SITE | 19156<br>note = misc_feature - Xaa can be any naturally occurring amino acid |
| SITE | 19159<br>note = misc_feature - Xaa can be any naturally occurring amino acid |
| SITE | 19165<br>note = misc_feature - Xaa can be any naturally occurring amino acid |
| SITE | 19170 |

-continued

| | | |
|---|---|---|
| | | note = misc_feature - Xaa can be any naturally occurring amino acid |
| REGION | 19172..19174 | |
| | | note = misc_feature - Xaa can be any naturally occurring amino acid |
| SITE | 19177 | |
| | | note = misc_feature - Xaa can be any naturally occurring amino acid |
| REGION | 19181..19182 | |
| | | note = misc_feature - Xaa can be any naturally occurring amino acid |
| SITE | 19184 | |
| | | note = misc_feature - Xaa can be any naturally occurring amino acid |
| SITE | 19191 | |
| | | note = misc_feature - Xaa can be any naturally occurring amino acid |
| REGION | 19194..19195 | |
| | | note = misc_feature - Xaa can be any naturally occurring amino acid |
| SITE | 19197 | |
| | | note = misc_feature - Xaa can be any naturally occurring amino acid |
| SITE | 19207 | |
| | | note = misc_feature - Xaa can be any naturally occurring amino acid |
| REGION | 19337..19338 | |
| | | note = misc_feature - Xaa can be any naturally occurring amino acid |
| SITE | 19340 | |
| | | note = misc_feature - Xaa can be any naturally occurring amino acid |
| SITE | 19347 | |
| | | note = misc_feature - Xaa can be any naturally occurring amino acid |
| REGION | 19350..19351 | |
| | | note = misc_feature - Xaa can be any naturally occurring amino acid |
| SITE | 19353 | |
| | | note = misc_feature - Xaa can be any naturally occurring amino acid |
| SITE | 19363 | |
| | | note = misc_feature - Xaa can be any naturally occurring amino acid |
| REGION | 19373..19374 | |
| | | note = misc_feature - Xaa can be any naturally occurring amino acid |
| SITE | 19376 | |
| | | note = misc_feature - Xaa can be any naturally occurring amino acid |
| REGION | 19388..19389 | |
| | | note = misc_feature - Xaa can be any naturally occurring amino acid |
| SITE | 19398 | |
| | | note = misc_feature - Xaa can be any naturally occurring amino acid |
| REGION | 19400..19401 | |
| | | note = misc_feature - Xaa can be any naturally occurring amino acid |
| REGION | 19403..19405 | |
| | | note = misc_feature - Xaa can be any naturally occurring amino acid |
| SITE | 19409 | |
| | | note = misc_feature - Xaa can be any naturally occurring amino acid |
| SITE | 19413 | |
| | | note = misc_feature - Xaa can be any naturally occurring amino acid |
| SITE | 19415 | |
| | | note = misc_feature - Xaa can be any naturally occurring amino acid |
| REGION | 19421..19425 | |
| | | note = misc_feature - Xaa can be any naturally occurring amino acid |
| REGION | 19427..19428 | |
| | | note = misc_feature - Xaa can be any naturally occurring amino acid |
| SITE | 19439 | |
| | | note = misc_feature - Xaa can be any naturally occurring |

-continued

| | |
|---|---|
| SITE | 19446<br>note = misc_feature - Xaa can be any naturally occurring amino acid |
| SITE | 19448<br>note = misc_feature - Xaa can be any naturally occurring amino acid |
| SITE | 19452<br>note = misc_feature - Xaa can be any naturally occurring amino acid |
| SITE | 19456<br>note = misc_feature - Xaa can be any naturally occurring amino acid |
| SITE | 19465<br>note = misc_feature - Xaa can be any naturally occurring amino acid |
| SITE | 19468<br>note = misc_feature - Xaa can be any naturally occurring amino acid |
| SITE | 19471<br>note = misc_feature - Xaa can be any naturally occurring amino acid |
| SITE | 19477<br>note = misc_feature - Xaa can be any naturally occurring amino acid |
| SITE | 19482<br>note = misc_feature - Xaa can be any naturally occurring amino acid |
| REGION | 19484..19486<br>note = misc_feature - Xaa can be any naturally occurring amino acid |
| SITE | 19489<br>note = misc_feature - Xaa can be any naturally occurring amino acid |
| REGION | 19493..19494<br>note = misc_feature - Xaa can be any naturally occurring amino acid |
| SITE | 19496<br>note = misc_feature - Xaa can be any naturally occurring amino acid |
| SITE | 19503<br>note = misc_feature - Xaa can be any naturally occurring amino acid |
| REGION | 19506..19507<br>note = misc_feature - Xaa can be any naturally occurring amino acid |
| SITE | 19509<br>note = misc_feature - Xaa can be any naturally occurring amino acid |
| SITE | 19519<br>note = misc_feature - Xaa can be any naturally occurring amino acid |
| REGION | 19649..19650<br>note = misc_feature - Xaa can be any naturally occurring amino acid |
| SITE | 19652<br>note = misc_feature - Xaa can be any naturally occurring amino acid |
| SITE | 19659<br>note = misc_feature - Xaa can be any naturally occurring amino acid |
| REGION | 19662..19663<br>note = misc_feature - Xaa can be any naturally occurring amino acid |
| SITE | 19665<br>note = misc_feature - Xaa can be any naturally occurring amino acid |
| SITE | 19675<br>note = misc_feature - Xaa can be any naturally occurring amino acid |
| REGION | 19685..19686<br>note = misc_feature - Xaa can be any naturally occurring amino acid |
| SITE | 19688<br>note = misc_feature - Xaa can be any naturally occurring amino acid |
| REGION | 19700..19701<br>note = misc_feature - Xaa can be any naturally occurring amino acid |

| | | |
|---|---|---|
| SITE | 19710 | |
| | note = misc_feature - Xaa can be any naturally occurring amino acid | |
| REGION | 19712..19713 | |
| | note = misc_feature - Xaa can be any naturally occurring amino acid | |
| REGION | 19715..19717 | |
| | note = misc_feature - Xaa can be any naturally occurring amino acid | |
| SITE | 19721 | |
| | note = misc_feature - Xaa can be any naturally occurring amino acid | |
| SITE | 19725 | |
| | note = misc_feature - Xaa can be any naturally occurring amino acid | |
| SITE | 19727 | |
| | note = misc_feature - Xaa can be any naturally occurring amino acid | |
| REGION | 19733..19737 | |
| | note = misc_feature - Xaa can be any naturally occurring amino acid | |
| REGION | 19739..19740 | |
| | note = misc_feature - Xaa can be any naturally occurring amino acid | |
| SITE | 19751 | |
| | note = misc_feature - Xaa can be any naturally occurring amino acid | |
| SITE | 19758 | |
| | note = misc_feature - Xaa can be any naturally occurring amino acid | |
| SITE | 19760 | |
| | note = misc_feature - Xaa can be any naturally occurring amino acid | |
| SITE | 19764 | |
| | note = misc_feature - Xaa can be any naturally occurring amino acid | |
| SITE | 19768 | |
| | note = misc_feature - Xaa can be any naturally occurring amino acid | |
| SITE | 19777 | |
| | note = misc_feature - Xaa can be any naturally occurring amino acid | |
| SITE | 19780 | |
| | note = misc_feature - Xaa can be any naturally occurring amino acid | |
| SITE | 19783 | |
| | note = misc_feature - Xaa can be any naturally occurring amino acid | |
| SITE | 19789 | |
| | note = misc_feature - Xaa can be any naturally occurring amino acid | |
| SITE | 19794 | |
| | note = misc_feature - Xaa can be any naturally occurring amino acid | |
| REGION | 19796..19798 | |
| | note = misc_feature - Xaa can be any naturally occurring amino acid | |
| SITE | 19801 | |
| | note = misc_feature - Xaa can be any naturally occurring amino acid | |
| REGION | 19805..19806 | |
| | note = misc_feature - Xaa can be any naturally occurring amino acid | |
| SITE | 19808 | |
| | note = misc_feature - Xaa can be any naturally occurring amino acid | |
| SITE | 19815 | |
| | note = misc_feature - Xaa can be any naturally occurring amino acid | |
| REGION | 19818..19819 | |
| | note = misc_feature - Xaa can be any naturally occurring amino acid | |
| SITE | 19821 | |
| | note = misc_feature - Xaa can be any naturally occurring amino acid | |
| SITE | 19831 | |
| | note = misc_feature - Xaa can be any naturally occurring amino acid | |
| REGION | 19960..19961 | |

-continued

```
                    note = misc_feature - Xaa can be any naturally occurring
                    amino acid
SITE                19963
                    note = misc_feature - Xaa can be any naturally occurring
                    amino acid
SITE                19970
                    note = misc_feature - Xaa can be any naturally occurring
                    amino acid
REGION              19973..19974
                    note = misc_feature - Xaa can be any naturally occurring
                    amino acid
SITE                19976
                    note = misc_feature - Xaa can be any naturally occurring
                    amino acid
SITE                19986
                    note = misc_feature - Xaa can be any naturally occurring
                    amino acid
REGION              19996..19997
                    note = misc_feature - Xaa can be any naturally occurring
                    amino acid
SITE                19999
                    note = misc_feature - Xaa can be any naturally occurring
                    amino acid
REGION              20011..20012
                    note = misc_feature - Xaa can be any naturally occurring
                    amino acid
SITE                20021
                    note = misc_feature - Xaa can be any naturally occurring
                    amino acid
REGION              20023..20024
                    note = misc_feature - Xaa can be any naturally occurring
                    amino acid
REGION              20026..20028
                    note = misc_feature - Xaa can be any naturally occurring
                    amino acid
SITE                20032
                    note = misc_feature - Xaa can be any naturally occurring
                    amino acid
SITE                20036
                    note = misc_feature - Xaa can be any naturally occurring
                    amino acid
SITE                20038
                    note = misc_feature - Xaa can be any naturally occurring
                    amino acid
REGION              20044..20048
                    note = misc_feature - Xaa can be any naturally occurring
                    amino acid
REGION              20050..20051
                    note = misc_feature - Xaa can be any naturally occurring
                    amino acid
SITE                20062
                    note = misc_feature - Xaa can be any naturally occurring
                    amino acid
SITE                20069
                    note = misc_feature - Xaa can be any naturally occurring
                    amino acid
SITE                20071
                    note = misc_feature - Xaa can be any naturally occurring
                    amino acid
SITE                20075
                    note = misc_feature - Xaa can be any naturally occurring
                    amino acid
SITE                20079
                    note = misc_feature - Xaa can be any naturally occurring
                    amino acid
SITE                20088
                    note = misc_feature - Xaa can be any naturally occurring
                    amino acid
SITE                20091
                    note = misc_feature - Xaa can be any naturally occurring
                    amino acid
SITE                20094
                    note = misc_feature - Xaa can be any naturally occurring
                    amino acid
SITE                20100
                    note = misc_feature - Xaa can be any naturally occurring
                    amino acid
SITE                20105
                    note = misc_feature - Xaa can be any naturally occurring
```

| | | |
|---|---|---|
| REGION | 20107..20109 | |
| | note = misc_feature - Xaa can be any naturally occurring amino acid | |
| SITE | 20112 | |
| | note = misc_feature - Xaa can be any naturally occurring amino acid | |
| REGION | 20116..20117 | |
| | note = misc_feature - Xaa can be any naturally occurring amino acid | |
| SITE | 20119 | |
| | note = misc_feature - Xaa can be any naturally occurring amino acid | |
| SITE | 20126 | |
| | note = misc_feature - Xaa can be any naturally occurring amino acid | |
| REGION | 20129..20130 | |
| | note = misc_feature - Xaa can be any naturally occurring amino acid | |
| SITE | 20132 | |
| | note = misc_feature - Xaa can be any naturally occurring amino acid | |
| SITE | 20142 | |
| | note = misc_feature - Xaa can be any naturally occurring amino acid | |
| REGION | 20272..20273 | |
| | note = misc_feature - Xaa can be any naturally occurring amino acid | |
| SITE | 20275 | |
| | note = misc_feature - Xaa can be any naturally occurring amino acid | |
| SITE | 20282 | |
| | note = misc_feature - Xaa can be any naturally occurring amino acid | |
| REGION | 20285..20286 | |
| | note = misc_feature - Xaa can be any naturally occurring amino acid | |
| SITE | 20288 | |
| | note = misc_feature - Xaa can be any naturally occurring amino acid | |
| SITE | 20298 | |
| | note = misc_feature - Xaa can be any naturally occurring amino acid | |
| REGION | 20308..20309 | |
| | note = misc_feature - Xaa can be any naturally occurring amino acid | |
| SITE | 20311 | |
| | note = misc_feature - Xaa can be any naturally occurring amino acid | |
| REGION | 20323..20324 | |
| | note = misc_feature - Xaa can be any naturally occurring amino acid | |
| SITE | 20333 | |
| | note = misc_feature - Xaa can be any naturally occurring amino acid | |
| REGION | 20335..20336 | |
| | note = misc_feature - Xaa can be any naturally occurring amino acid | |
| REGION | 20806..20808 | |
| | note = misc_feature - Xaa can be any naturally occurring amino acid | |
| SITE | 20812 | |
| | note = misc_feature - Xaa can be any naturally occurring amino acid | |
| SITE | 20816 | |
| | note = misc_feature - Xaa can be any naturally occurring amino acid | |
| SITE | 20818 | |
| | note = misc_feature - Xaa can be any naturally occurring amino acid | |
| REGION | 20824..20828 | |
| | note = misc_feature - Xaa can be any naturally occurring amino acid | |
| REGION | 20830..20831 | |
| | note = misc_feature - Xaa can be any naturally occurring amino acid | |
| source | 1..22152 | |
| | mol_type = protein | |
| | organism = Homo sapiens | |

```
SEQUENCE: 43
MLKPSGLPGS SSPTRSLMTG SRSTKATPEM DSGLTGATLS PKTSTGAIVV TEHTLPFTSP    60
DKTLASPTSS VVGRTTQSLG VMSSALPEST SRGMTHSEQR TSPSLSPQVN GTPSRNYPAT   120
SMVSGLSSPR TRTSSTEGNF TKEASTYTLT VETTSGPVTE KYTVPTETST TEGDSTETPW   180
DTRYIPVKIT SPMKTFADST ASKENAPVSM TPAETTVTDS HTPGRTNPSF GTLYSSFLDL   240
SPKGTPNSRG ETSLELILST TGYPFSSPEP GSAGHSRIST SAPLSSSASV LDNKISETSI   300
FSGQSLTSPL SPGVPEARAS TMPNSAIPFS MTLSNAETSA ERVRSTISSL GTPSISTKQT   360
AETILTFHAF AETMDIPSTH IAKTLASEWL GSPGTLGGTS TSALTTTSPS TTLVSEETNT   420
HHSTSGKETE GTLNTSMTPL ETSAPGEESE MTATLVPTLG FTTLDSKIRS PSQVSSSHPT   480
RELRTTGSTS GRQSSSTAAH GSSDILRATT SSTSKASSWT SESTAQQFSE PQHTQWVETS   540
PSMKTERPPA STSVAAPITT SVPSVVSGFT TLKTSSTKGI WLEETSADTL IGESTAGPTT   600
HQFAVPTGIS MTGGSSTRGS QGTTHLLTRA TASSETSADL TLATNGVPVS VSPAVSKTAA   660
GSSPPGGTKP SYTMVSSVIP ETSSLQSSAF REGTLSGLTP LNTRHPFSSP EPDSAGHTKI   720
STSIPLLSSA SVLEDKVSAT STFSHHKATS SITTGTPEIS TKTKPSSAVL SSMTLSNAAT   780
SPERVRNATS PLTHPSPSGE ETAGSVLTLS TSAETTDSPN IHPTGTLTSE SSESPSTLSL   840
PSVSGVKTTF SSSTPSTHLF TSGEETEETS NPSVSQPETS VSRVRTTLAS TSVPTPVFPT   900
MDTWPTRSAQ FSSSHLVSEL RATSSSTVTN STGSALPKIS HLTGTATMSQ TNRDTFNDSA   960
APQSTTWPET SPRFKTGLPS ATTTVSTSAT SLSATVMVSK FTSPATSSME ATSIREPSTT  1020
ILTTETTNGP GSMAVASTNI PIGKGYITEG RLDTSHLPIG TTASSETSMD FTMAKESVSM  1080
SVSPSQSMDA AGSSTPGRTS QFVDTFSDDV YHLTSREITI PRDGTSSALT PQMTATHPPS  1140
PDPGSARSTW LGILSSSPSS PTPKVTMSST FSTQRVTTSM IMDTVETSRW NMPNLPSTTS  1200
LTPSNIPTSG AIGKSTLVPL DTPSPATSLE ASEGGLPTLS TYPESTNTPS IHLGAHASSE  1260
SPSTIKLTMA SVVKPGSYTP LTFPSIETHI HVSTARMAYS SGSSPEMTAP GETNTGSTWD  1320
PTTYITTTDP KDTSSAQVST PHSVRTLRTT ENHPKTESAT PAAYSGSPKI SSSPNLTSPA  1380
TKAWTITDTT EHSTQLHYTK LAEKSSGFET QSAPGPVSVV IPTSPTIGSS TLELTSDVPG  1440
EPLVLAPSEQ TTITLPMATW LSTSLTEEMA STDLDISSPS SPMSTFAIFP PMSTPSHELS  1500
KSEADTSAIR NTDSTTLDQH LGIRSLGRTG DLTTVPITPL TTTWTSVIEH STQAQDTLSA  1560
TMSPTHVTQS LKDQTSIPAS ASPSHLTEVY PELGTQGRSS SEATTFWKPS TDTLSREIET  1620
GPTNIQSTPP MDNTTTGSSS SGVTLGIAHL PIGTSSPAET STNMALERRS STATVSMAGT  1680
MGLLVTSAPG RSISQSLGRV SSVLSESTTE GVTDSSKGSS PRLNTQGNTA LSSSLEPSYA  1740
EGSQMSTSIP LTSSPTTPDV EFIGGSTFWT KEVTTVMTSD ISKSSARTES SSATLMSTAL  1800
GSTENTGKEK LRTASMDLPS PTPSMEVTPW ISLTLSNAPN TTDSLDLSHG VHTSSAGTLA  1860
TDRSLNTGVT RASRLENGSD TSSKSLSMGN STHTSMTDTE KSEVSSSIHP RPETSAPGAE  1920
TTLTSTPGNR AISLTLPFSS IPVEEVISTG ITSGPDINSA PMTHSPITPP TIVWTSTGTI  1980
EQSTQPLHAV SSEKVSVQTQ STPYVNSVAV SASPTHENSV SSGSSTSSPY SSASLESLDS  2040
TISRRNAITS WLWDLTTSLP TTTWPSTSLS EALSSGHSGV SNPSSTTTEF PLFSAASTSA  2100
AKQRNPETET HGPQNTAAST LNTDASSVTG LSETPVGASI SSEVPLPMAI TSRSDVSGLT  2160
SESTANPSLG TASSAGTKLT RTISLPTSES LVSFRMNKDP WTVSIPLGSH PTTNTETSIP  2220
VNSAGPPGLS TVASDVIDTP SDGAESIPTV SFSPSPDTEV TTISHFPEKT THSFRTISSL  2280
THELTSRVTP IPGDWMSSAM STKPTGASPS ITLGERRTIT SAAPTTSPIV LTASFTETST  2340
VSLDNETTVK TSDILDARKT NELPSDSSSS SDLINTSIAS STMDVTKTAS ISPTSISGMT  2400
ASSSPSLFSS DRPQVPTSTT ETNTATSPSV SSNTYSLDGG SNVGGTPSTL PPFTITHPVE  2460
TSSALLAWSR PVRTFSTMVS TDTASGENPT SSNSVVTSVP APGTWASVGS TTDLPAMGFL  2520
KTSPAGEAHS LLASTIEPAT AFTPHLSAAV VTGSSATSEA SLLTTSESKA IHSSPQTPTT  2580
PTSGANWETS ATPESLLVVT ETSDTTLTSK ILVTDTILFS TVSTPPSKFP STGTLSGASF  2640
PTLLPDTPAI PLTATEPTSS LATSFDSTPL VTIASDSLGT VPETTLTMSE TSNGDALVLK  2700
TVSNPDRSIP GITIQGVTES PLHPSSTSPS KIVAPRNTTY EGSITVALST LPAGTTGSLV  2760
FSQSSENSET TALVDSSAGL ERASVMPLTT GSQGMASSGG IRSGSTHSTG TKTFSSLPLT  2820
MNPGEVTAMS EITTNRLTAT QSTAPKGIPV KPTSAESGLL TPVSASSSPS KAFASLTTAP  2880
PSTWGIPQST LTFEFSEVPS LDTKSASLPT PGQSLNTIPD SDASTASSSL SKSPEKNPRA  2940
RMMTSTKAIS ASSFQSTGFT ETPEGSASPS MAGHEPRVPT SGTGDPRYAS ESMSYPDPSK  3000
ASSAMTSTSL ASKLTTLFST GQAARSGSSS SPISLSTEKE TSFLSPTAST SRKTSLFLGP  3060
SMARQPNILV HLQTSALTLS PTSTLNMSQE EPPELTSSQT IAEEEGTTAE TQTLTFTPSE  3120
TPTSLLPVSS PTEPTARRKS SPETWASSIS VPAKTSLVET TDGTLVTTIK MSSQAAQGNS  3180
TWPAPAEETG TSPAGTSPGS PEVSTTLKIM SSKEPSISPE IRSTVRNSPW KTPETTVPME  3240
TTVEPVTLQS TALGSGSTSI SHLPTGTTSP TKSPTENMLA TERVSLSPSP PEAWTNLYSG  3300
TPGGTRQSLA TMSSVSLESP TARSITGTGQ QSSPELVSKT TGMEFSMWHG STGGTTGDTH  3360
VSLSTSSNIL EDPVTSPNSV SSLTDKSKHK TETWVSTTAI PSTVLNNKIM AAEQQTSRSV  3420
DEAYSSTSSW SDQTSGSDIT LGASPDVTNT LYITSTAQTT SLVSLPSGDQ GITSLTNPSG  3480
GKTSSASSVT SPSIGLETLR ANVSAVKSDI APTAGHLSQT SSPAEVSILD VTTAPTPGIS  3540
TTITTTMGTNS ISTTTPNPEV GMSTMDSTPA TERRTSTEH PSTWSSTAAS DSWTVTDMTS  3600
NLKVARSPGT ISTMHTTSFL ASSTELDSMS TPHGRITVIG TSLVTPSSDA SAVKTETSTS  3660
ERTLSPSDTT ASTPISTFSR VQRMSISVPD ILSTSWTPSS TEAEDVPVSM VSTDHASTKT  3720
DPNTPLSTFL FDSLSTLDWD TGRSLSSATA TTSAPQGATT PQELTLETMI SPATSQLPFS  3780
IGHITSAVTP AAMARSSGVT FSRPDPTSKK AEQTSTQLPT TTSAHPGQVP RSAATTLDVI  3840
PHTAKTPDAT FQRQGQTALT TEARATSDSW NEKEKSTPSA PWITEMMNSV SEDTIKEVTS  3900
SSSVLKDPEY AGHKLGIWDD FIPKFGKAAH MRELPLLSPP QDKEAIHPST NTVETTGWVT  3960
SSEHASHSTI PAHSASSKLT SPVVTTSTRE QAIVSMSTTT WPESTRARTE PNSFLTIELR  4020
DVSPYMDTSS TTQTSIISSP GSTAITKGPR TEITSSKRIS SSFLAQSMRS SDSPSEAITR  4080
LSNFPAMTES GGMILAMQTS PPGATSLSAP TLDTSATASW TGTPLATTQR FTYSEKTTLF  4140
SKGPEDTSQP SPPSVEETSS SSSLVPIHAT TSPSNILLTS QGHSPSSTPP VTSVFLSETS  4200
GLGKTTDMSR ISLEPGTSLP PNLSSTAGEA LSTYEASRDT KAIHHSADTA VTNMEATSSE  4260
YSPIPGHTKP SKATSPLVTS HIMGDITSST SVFGSSETTE IETVSSVNQG LQERSTSQVA  4320
SSATETSTVI THVSSGDATT HVTKTQATFS SGTSSISSPHQ FITSTNTFTD VSTNPSTSLI  4380
MTESSGVTIT TQTGPTGAAT QGPYLLDTST MPYLTETPLA VTPDFMQSEK TTLISKGPKD  4440
VTWTSPPSVA ETSYPSSLTP FLVTTIPPAT STLGQHTSS PVSATSVLTS GLVKTTDMLN  4500
TSMEPVTNSP QNLNNPSNEI LATLAATTDI ETIHPSINKA VTNMGTASSA HVLHSTLPVS  4560
SEPSTATSPM VPASSMGDAL ASISIPGSET TDIEGEPTSS LTAGRKENST LQEMNSTTES  4620
NIILSNVSVG AITEATKMEV PSFDATFIPT PAQSTKFPDI FSVASSRLSN SPPMTISTHM  4680
```

```
TTTQTGSSGA TSKIPLALDT STLETSAGTP SVVTEGFAHS KITTAMNNDV KDVSQTNPPF  4740
QDEASSPSSQ APVLVTTLPS SVAFTPQWHS TSSPVSMSSV LTSSLVKTAG KVDTSLETVT  4800
SSPQSMSNTL DDISVTSAAT TDIETTHPSI NTVVTNVGTT GSAFESHSTV SAYPEPSKVT  4860
SPNVTTSTME DTTISRSIPK SSKTTRTETE TTSSLTPKLR ETSISQEITS STETSTVPYK  4920
ELTGATTEVS RTDVTSSSST SFPGPDQSTV SLDISTETNT RLSTSPIMTE SAEITITTQT  4980
GPHGATSQDT FTMDPSNTTP QAGIHSAMTH GFSQLDVTTL MSRIPQDVSW TSPPSVDKTS  5040
SPSSFLSSPA MTTPSLISST LPEDKLSSPM TSLLTSGLVK ITDILRTRLE PVTSSLPNFS  5100
STSDKILATS KDSKDTKEIF PSINTEETNV KANNSGHESH SPALADSETP KATTQMVITT  5160
TVGDPAPSTS MPVHGSSETT NIKREPTYFL TPRLRETSTS QESSFPTDTS FLLSKVPTGT  5220
ITEVSSTGVN SSSKISTPDH DKSTVPPDTF TGEIPRVFTS SIKTKSAEMT ITTQASPPES  5280
ASHSTLPLDT STTLSQGGTH STVTQGFPYS EVTTLMGMGP GNVSWMTTPP VEETSSVSSL  5340
MSSPAMTSPS PVSSTSPQSI PSSPLPVTAL PTSVLVTTTD VLGTTSPESV TSSPPNLSSI  5400
THERPATYKD TAHTEAAMHH STNTAVTNVG TSGSGHKSQS SVLADSETSK ATPLMSTTST  5460
LGDTSVSTST PNISQTNQIQ TEPTASLSPR LRESSTSEKT SSTTETNTAF SYVPTGAITQ  5520
ASRTEISSSR TSISDLDRPT IAPDISTGMI TRLFTSPIMT KSAEMTVTTQ TTTPGATSQG  5580
ILPWDTSTTL FQGGTHSTVS QGFPHSEITT LRSRTPGDVS WMTTPPVEET SSGFSLMSPS  5640
MTSPSPVSST SPESIPSSPL PVTALLTSVL VTTTNVGTT SPETVTSSPP NLSSPTQERL   5700
TTYKDTAHTE AMHASMHTNT AVANVGTSIS GHESQSSVPA DSHTSKATSP MGITFAMGDT  5760
SVSTSTPAFF ETRIQTESTS SLIPGLRDTR TSEEINTVTE TSTVLSEVPT TTTTEVSRTE  5820
VITSSRTTIS GPDHSKMSPY ISTETITRLS TFPPVTGSTE MAITNQTGPI GTISQATLTL  5880
DTSSTASWEG THSPVTQRFP HSEETTTMSR STKGVSWQSP PSVEETSSPS SPVPLPAITS  5940
HSSLYSAVSG SSPTSALPVT SLLTSGRRKT IDMLDTHSEL VTSSLPSASS FSGEILTSEA  6000
STNTETIHFS ENTAETNMGT TNSMHKLLHS VSIHSQPSGH TPPKVTGSMM EDAIVSTSTP  6060
GSPETKNVDR DSTSPLTPEL KEDSTALVMN STTESNTVFS SVSLDAATEV SRAEVTYYDP  6120
TFMPASAQST KSPDISPEAS SSHSNSPPLT ISTHKTIATQ TGPSGVTSLG QLTLDTSTIA  6180
TSAGTPSART QDFVDSETTS VMNNDLNDVL KTSPFSAEEA NSLSSQAPLL VTTSPSPVTS  6240
TLQEHSTSSL VSVTSVPTPT LAKITDMDTN LEPVTRSPQN LRNTLATSEA TTDTHTMHPS  6300
INTAMANVGT TSSPNEFYFT VSPDSDPYKA TSAVVITSTS GDSIVSTSMP RSSAMKKIES  6360
ETTFSLIFRL RETSTSQKIG SSSDTSTVFD KAFTAATTEV SRTELTSSSR TSIQGTEKPT  6420
MSPDTSTRSV TMLSTFAGLT KSEERTIATQ TGPHRATSQG TLTWDTSITT SQAGTHSAMT  6480
HGFSQLDLST LTSRVPEYIS GTSPPSVEKT SSSSSLLSLP AITSPSPVPT TLPESRPSSP  6540
VHLTSLPTSG LVKTTDMLAS VASLPPNLGS TSHKIPTTSE DIKDTEKMYP STNIAVTNVG  6600
TTTSEKESYS SVPAYSEPPK VTSPMVTSFN IRDTIVSTSM PGSSEITRIE MESTFSVAHG  6660
LKGTSTSQDP IVSTEKSAVL HKLTTGATET SRTEVASSRR TSIPGPDHST ESPDISTEVI  6720
PSLPISLGIT ESSNMTIITR TGPPLGSTSQ GTFTLDTPTT SSRAGTHSMA TQEFPHSEMT  6780
TVMNKDPEIL SWTIPPSIEK TSFSSSLMPS PAMTSPPVSS TLPKTIHTTP SPMTSLLTPS  6840
LVMTTDTLGT SPEPTTSSPP NLSSTSHVIL TTDEDTTAIE AMHPSTSTAA TNVETTCSGH  6900
GSQSSVLTDS EKTKATAPMD TTSTMGHTTV STSMSVSSET TKIKRESTYS LTPGLRETSI  6960
SQNASFSTDT SIVLSEVPTG TTAEVSRTEV TSSGRTSIPG PSQSTVLPEI STRTMTRLFA  7020
SPTMTESAEM TIPTQTGPSG STSQDTLTLD TSTTKSQAKT HSTLTQRFPH SEMTTLMSRG  7080
PGDMSWQSSP SLENPSSLPS LLSLPATTSP PPISSTLPVT ISSSPLPVTS LLTSSPVTTT  7140
DMLHTSPELV TSSPPKLSHT SDERLTTGKD TTNTEAVHPS TNTAASNVEI PSFGHESPSS  7200
ALADSETSKA TSPMFITSTQ EDTTVAISTP HFLETSRIQK ESISSLSPKL RETGSSVETS  7260
SAIETSAVLS EVSIGATTEI SRTEVTSSSR TSISGSAEST MLPEISTTRK IIKFPTSPIL  7320
AESSEMTIKT QTSPPGSTSE STFTLDTSTT PSLVITHSTM TQRLPHSEIT TLVSRGAGDV  7380
PRPSSLPVEE TSPPSSQLSL SAMISPSPVS STLPASSHSS SASVTSPLTP GQVKTTEVLD  7440
ASAEPETSSP PSLSSTSVEI LATSEVTTDT EKIHPFPNTA VTKVGTSSSG HESPSSVLTD  7500
SETTKATSAM GTISIMGDTS VSTLTPALSN TRKIQSEPAS SLTTRLRETS TSEETSLATE  7560
ANTVLSKVST GATTEVSRTE AISFSRTSMS GPEQSTMSQD ISIGTIPRIS ASSVLTESAK  7620
MTITTQTGPS ESTLESTLNL NTATTPSWVE THSIVIQGFP HPEMTTSMGR GPGGVSWPSP  7680
PPFVKETSPPS SPLSLPAVTS PHPVSTTFLA HIPPSPLPVT SLLTSGPATT TDILGTSTEP  7740
GTSSSSSLST TSHERLTTYK DTAHTEAVHP STNTGGTNVA TTSSGYKSQS SVLADSSPMC  7800
TTSTMGDTSV LTSTPAFLET RRIQTELASS LTPGLRESSG SEGTSSGTKM STVLSKVPTG  7860
ATTEISKEDV TSIPGPAQST ISPDISTRTV SWFSTSPVMT ESAEITMNTH TSPLGATTQG  7920
TSTLATSSTT SLTMTHSTIS QGFSHSQMST LMRRGPEDVS WMSPPLLEKT RPSFSLMSSP  7980
ATTSPSPVSS TLPESISSSP LPVTSLLTSG LAKTTDMLHK SSEPVTNSPA NLSSTSVEIL  8040
ATSEVTTDTE KTHPSSNRTV TDVGTSSSGH ESTSFVLADS QTSKVTSPMV ITSTMEDTSV  8100
STSTPGFFET SRIQTEPTSS LTLGLRKTSS SEGTSLATEM STVLSGVPTG ATAEVSRTEV  8160
TSSSRTSISG FAQLTVSPET STETITRLPT SSIMTESAEM MIKTQTDPPG STPESTHTVD  8220
ISTTPNWVET HSTVTQRFSH SEMTTLVSRS PGDMLWPSQS SVEETSSASS LLSLPATTSP  8280
SPVSSTLVED FPSASLPVTS LLTPGLVITT DRMGISREPG TSSSNLSST SHERLTTLED  8340
TVDTEDMQPS THTAVTNVRT SISGHESQSS VLSDSETPKA TSPMGTTYTM GETSVSISTS  8400
DFFETSRIQI EPTSSLTSGL RETSSSERIS SATEGSTVLS EVPSGATTEV SRTEVISSRG  8460
TSMSGPDQFT ISPDISTEAI TRLSTSPIMT ESAESAITIE TGSPGATSEG TLTLDTSTTT  8520
FWSGTHSTAS PGFSHSEMTT LMSRTPGDVP WPSLPSVEEA SSVSSSLSSP AMTSTSFFSA  8580
LPESISSSPH PVTALLTLGP VKTTDMLRTS SEPETSSPPN LSSTSAEILA TSEVTKDREK  8640
IHPSSNTPVV NVGTVIYKHL SPSSVLADLV TTKPTSPMAT TSTLGNTSVS TSTPAFPETM  8700
MTQPTSSLTS GLREISTSQE TSSATERSAS LSGMPTGATT KVSRTEALSL GRTSTPGPAQ  8760
STISPEISTE TITRISTPLT TTGSAEMTIT PKTGHSGASS QGTFTLDTSS RASWPGTHSA  8820
ATHRSPHSGM TTPMSRGPED VSWPSRPSVE KTSPPSSLVS LSAVTSPSPL YSTPSESSHS  8880
SPLRVTSLFT PVMMKTTDML DTSLEPVTTS PPSMNITSDE SLATSKATME TEAIQLSENT  8940
AVTQMGTISA RQEFYSSYPG LPEPSKVTSP VVTSSTIKDI VSTTIPASSE ITRIEMESTS  9000
TLTPTPRETS TSQEIHSATK PSTVPYKALT SATIEDSMTQ VMSSSRGPSP DQSTMSQDIS  9060
SEVITRLSTS PIKAESTEMT ITTQTGPSGA TSRGTLTLDT STTFMSGTHS TASQGFSHSQ  9120
MTALMSRTPG DVPWLSHPSV EEASSASFSL SSPVMTSSSP VSSTLPDSIH SSSLPVTSLL  9180
TSGLVKTTEL LGTSSEPETS SPPNLSSTSA EILATTEVTT DTEKLEMTNV VTSGYTHESP  9240
SSVLADSVTT KATSSMGITY PTGDTNVLTS TPAFSDTSRI QTKSKLSLTP GLMETSISEE  9300
TSSATEKSTV LSSVPTGATT EVSRTEAISS SRTSIPGPAQ STMSSDTSME TITRISTPLT  9360
RKESTDMAIT PKTGPSGATS QGTFTLDSSS TASWPGTHSA TTQRFPQSVV TTPMSRGPED  9420
```

```
VSWPSPLSVE KNSPPSSLVS SSSVTSPSPL YSTPSGSSHS SPVPVTSLFT SIMMKATDML   9480
DASLEPETTS APNMNITSDE SLATSKATTE TEAIHVFENT AASHVETTSA TEELYSSSPG   9540
FSEPTKVISP VVTSSSIRDN MVSTTMPGSS GITRIEIESM SSLTPGLRET RTSQDITSST   9600
ETSTVLYKMS SGATPEVSRT EVMPSSRTSI PGPAQSTMSL DISDEVVTRL STSPIMTESA   9660
EITITTQTGY SLATSQVTLP LGTSMTFLSG THSTMSQGLS HSEMTNLMSR GPESLSWTSP   9720
RFVETTRSSS SLTSLPLTTS LSPVSSTLLD SSPSSPLPVT SLILPGLVKT TEVLDTSSEP   9780
KTSSSPNLSS TSVEIPATSE IMTDTEKIHP SSNTAVAKVR TSSSVHESHS SVLADSETTI   9840
TIPSMGITSA VDDTTVFTSN PAFSETRRIP TEPTFSLTPG FRETSTSEET TSITETSAVL   9900
YGVPTSATTE VSMTEIMSSN RTHIPDSDQS TMSPDIITEV ITRLSSSSMM SESTQMTITT   9960
QKSSPGATAQ STLTLATTTA PLARTHSTVP PRFLHSEMTT LMSRSPENPS WKSSPFVEKT  10020
SSSSSLLLSLP VTTSPSVSST LPQSIPSSSF SVTSLLTPGM VKTTDTSTEP GTSLSPNLSG  10080
TSVEILAASE VTTDTEKIHP SSSMAVTNVG TTSSGHELYS SVSIHSEPSK ATYPVGTPSS  10140
MAETSISTSM PANFETTGFE AEPFSHLTSG FRKTNMSLDT SSVTPTNTPS SPGSTHLLQS  10200
SKTDFTSSAK TSSPDWPPAS QYTEIPVDII TPFNASPSIT ESTGITSFPE SRFTMSVTES  10260
THHLSTDLLP SAETISTGTV MPSLSEAMTS FATTGVPRAI SGSGSPFSRT ESGPGDATLS  10320
TIAESLPSST PVPFSSSTFT TTDSSTIPAL HEITSSSATP YRVDTSLGTE SSTTEGRLVM  10380
VSTLDTSSQP GRTSSTPILD TRMTESVELG TVTSAYQVPS LSTRLTRTDG IMEHITKIPN  10440
EAAHRGTIRP VKGPQTSTSP ASPKGLHTGG TKRMETTTTA LKTTTTALKT TSRATLTTSV  10500
YTPTLGTLTP LNASRQMAST ILTEMMITTP YVFPDVPETT SSLATSLGAE TSTALPRTTP  10560
SVLNRESETT ASLVSRSGAE RSPVIQTLDV SSSEPDTTAS WVIHPAETIP TVSKTTPNFF  10620
HSELDTVSST ATSHGADVSS AIPTNISPSE LDALTPLVTI SGTDTSTTFP TLTKSPHETE  10680
TRTTWLTHPA ETSSTIPRTI PNFSHHESDA TPSIATSPGA ETSSAIPIMT VSPGAEDLVT  10740
SQVTSSGTDR NMTIPTLTLS PGEPKTIASL VTHPEAQTSS AIPTSTISPA VSRLVTSMVT  10800
SLAAKTSTTN RALTNSPGEP ATTVSLVTHP AQTSPTVPWT TSIFFHSKSD TTPSMTTSHG  10860
AESSSAVPTP TVSTEVPGVV TPLVTSSRAV ISTTIPILTL SPGEPETTPS MATSHGEEAS  10920
SAIPTPTVSP GVPGVVTSLV TSSRAVTSTT IPILTFSLGE PETTPSMATS HGTEAGSAVP  10980
TVLPEVPGMV TSLVASSRAV TSTTLPTLTL SPGEPETTPS MATSHGAEAS STVPTVSPEV  11040
PGVVTSLVTS SSGVNSTSIP TLILSPGELE TTPSMATSHG AEASSAVPTP TVSPGVSGVV  11100
TPLVTSSRAV TSTTIPILTL SSSEPETTPS MATSHGVEAS SAVLTVSPEV PGMVTSLVTS  11160
SRAVTSTTIP TLTISSDEPE TTTSLVTHSE AKMISAIPTL AVSPTVQGLV TSLVTSSGSE  11220
TSAFSNLTVA SSQPETIDSW VAHPGTEASS VVPTLTVSTG EPFTNISLVT HPAESSSTLP  11280
RTTSRFSHSE LDTMPSTVTS PEAESSSAIS TTISPGIPGV LTSLVTSSGR DISATFPTVP  11340
ESPHESEATA SWVTHPAVTS TTVPRTTPNY SHSEPDTTPS IATSPGAEAT SDFPTITVSP  11400
DVPDMVTSQV TSSGTDSIT IPTLTLSSGE PETTTSFITY SETHTSSAIP TLPVSPGASK  11460
MLTSLVISSG TDSTTTFPTL TETPYEPETT AIQLIHPAET NTMVPKTTPK FSHSKSDTTL  11520
PVAITSPGPE ASSAVSTTTI SPDMSDLVTS LVPSSGTDTS TTFPTLSETP YEPETTVTWL  11580
THPAETSTTV SGTIPNFSHR GSDTAPSMVT SPGVDTRSGV PTTTIPPSIP GVVTSQVTSS  11640
ATDTSTAIPT LTPSPGEPET TASSATHPGT QTGFTVPIRT VPSSEPDTMA SWVTHPPQTS  11700
TPVSRTTSSF SHSSPDATPV MATSPRTEAS SAVLTTISPG APEMVTSQIT SSGAATSTTV  11760
PTLTHSPGMP ETTALLSTHP RTGTSKTFPA STVFPQVSET TASLTIRPGA ETSTALPTQT  11820
TSSLFTLLVT GTSRVDLSPT ASPGVSAKTA PLSTHPGTET STMIPTSTLS LGLLETTGLL  11880
ATSSSAETST STLTLTVSPA VSGLSSASIT TDKPQTVTSW NTETSPSVTS VGPPEFSRTV  11940
TGTTMTLIPS EMPTPPKTSH GEGVSPTTIL RTTMVEATNL ATTGSSPTVA KTTTTFNTLA  12000
GSLFTPLTTP GMSTLASESV TSRTSYNHRS WISTTSSYNR RYWTPATSTP VTSTFSPGIS  12060
TSSIPSSTAA TVPFMVPFTL NFTITNLQYE EDMRHPGSRK FNATERELQG LLKPLFRNSS  12120
LEYLYSGCRL ASLRPEKDSS AMAVDAICTH RPDPEDLGLD RERLYWELSN LTNGIQELGP  12180
YTLDRNSLYV NGFTHRSSMP TTSTPGTSTV DVGTSGTPSS SPSPTAAGPL LMPFTLNFTI  12240
TNLQYEEDMR RTGSRKFNTM ESVLQGLLKP LFKNTSVGPL YSGCRLTLLR PEKDGAATGV  12300
DAICTHRLDP KSPGLNREQL YWELSKLTND IEELGPYTLD RNSLYVNGFT HQSSVSTTST  12360
PGTSTVDLRT SGTPSSLSSP TIMAAGPLLV PFTLNFTITN LQYGEDMGHP GSRKFNTTER  12420
VLQGLLGPIF KNTSVGPLYS GCRLTSLRSE KDGAATGVDA ICIHHLDPKS PGLNRERLYW  12480
ELSQLTNGIK ELGPYTLDRN SLYVNGFTHR TSVPTTSTPG TSTVDLGTSG TPFSLPSPAT  12540
AGPLLVLFTL NFTITNLKYE EDMHRPGSRK FNTTERVLQT LLGPMFKNTS VGLLYSGCRL  12600
TLLRSEKDGA ATGVDAICTH RLDPKSPGLD REQLYWELSQ LTNGIKELGP YTLDRNSLYV  12660
NGFTHWIPVP TSSTPGTSTV DLGSGTPSSL PSPTAAGPLL VPFTLNFTIT NLQYEEDMHH  12720
PGSRKFNTTE RVLQGLLGPM FKNTSVGLLY SGCRLTLLRS EKDGAATGVD AICTHRLDPK  12780
SPGVDREQLY WELSQLTNGI KELGPYTLDR NSLYVNGFTH QTSAPNTSTP GTSTVDLGTS  12840
GTPSSLPSPT SAGPLLVPFT LNFTITNLQY EEDMRHPGSR KFNTTERVLQ GLLKPLFKST  12900
SVGPLYSGCR LTLLRSEKDG AATGVDAICT HRLDPKSPGV DREQLYWELS QLTNGIKELG  12960
PYTLDRNSLY VNGFTHQTSA PNTSTPGTST VDLGTSGTPS SLPSPTSAGP LLVPFTLNFT  13020
ITNLQYEEDM HHPGSRKFNT TERVLQGLLP MFKNTSVGL LYSGCRLTLL RPEKNGAATG  13080
MDAICSHRLD PKSPGLNREQ LYWELSQLTH GIKELGPYTL DRNSLYVNGF THRSSVAPTS  13140
TPGTSTVDLG TSGTPSSLPS PTTAVPLLVP FTLNFTITNL QYEDMRHPG SRKFNTTERV  13200
LQGLLGPLFK NSSVGPLYSG CRLISLRSEK DGAATGVDAI CTHHLNPQSP GLDREQLYWQ  13260
LSQMTNGIKE LGPYTLDRNS LYVNGFTHRS SGLTTSTPWT STVDLGTSGT PSPVPSPTTA  13320
GPLLVPFTLN FTITNLQYEE DMHRPGSRKF NTTERVLQGL LSPIFKNSSV GPLYSGCRLT  13380
SLRPEKDGAA TGMDAVCLYH PNPKRPGLDR EQLYWELSQL THNITELGPY SLDRDSLYVN  13440
GFTHQNSVPT TSTPGTSTVY WATTGTPSSF PGHTEPGPLL IPTFNFTIT NLHYEENMQH  13500
PGSRKFNTTE RVLQGLLKPL FKNTSVGPLY SGCRLTSLRP EKDGAATGMD AVCLYHPNPK  13560
RPGLDREQLY WELSQLTHNI TELGPYSLDR DSLYVNGFTH QNSVPTTSTP GTSTVYWATT  13620
GTPSSFPGHT EPGPLLIPFT FNFTITNLHY EENMQHPGSR KFNTTERVLQ GLLKPLFKNT  13680
SVGPLYSGCR LTLLRPEKHE AATGVDTICT HRVDPIGPGL DRERLYWELS QLTNSITELG  13740
PYTLDRDSLY VNGFNPRSSV PTTSTPGTST VHLATSGTPS VHLATSGTPS VHPTAVP LLIPFTLNFT  13800
ITNLHYEENM QHPGSRKFNT TERVLQGLLK PLFKNTSVGP LYSGCRLTLL RPEKHEAATG  13860
VDTICTHRVD PIGPGLXXEX LYWELSXLTX XIXELGPYTL DRXSLYVNGF THXXSXPTTS  13920
TPGTSTVXXG TSGTPSSXPX XTSAGPLLVP FTLNFTITNL QYEEDMHPG SRKFNTTERV  13980
LQGLLGPMFK NTSVGLLYSG CRLTLLRPEK NGAATGMDAI CSHRLDPKSP GLDREQLYWE  14040
LSQLTHGIKE LGPYTLDRNS LYVNGFTHRS SVAPTSTPGT STVDLGTSGT PSSLPSPTTA  14100
VPLLVPFTLN FTITNLQYGE DMRHPGSRKF NTTERVLQGL LGPLFKNSSV GPLYSGCRLI  14160
```

```
SLRSEKDGAA TGVDAICTHH LNPQSPGLDR EQLYWQLSQM TNGIKELGPY TLDRNSLYVN   14220
GFTHRSSGLT TSTPWTSTVD LGTSGTPSPV PSPTTAGPLL VPFTLNFTIT NLQYEEDMHR   14280
PGSRKFNATE RVLQGLLSPI FKNSSVGPLY SGCRLTSLRP EKDGAATGMD AVCLYHPNPK   14340
RPGLDREQLY WELSQLTHNI TELGPYSLDR DSLYVNGFTH QSSMTTTRTP DTSTMHLATS   14400
RTPASLSGPT TASPLLVFT  INCTITNLQY EEDMRRTGSR KFNTMESVLQ GLLKPLFKNT   14460
SVGPLYSGCR LTLLRPKKDG AATGVDAICT HRLDPKSPGL NREQLYWELS KLTNDIEELG   14520
PYTLDRNSLY VNGFTHQSSV STTSTPGTST VDLRTSGTPS SLSSPTIMXX XPLLXPFTXN   14580
XTITNLXXXX XMXXPGSRKF NTTERVLQGL LRPLFKNTSV SSLYSGCRLT LLRPEKDGAA   14640
TRVDAACTYR PDPKSPGLDR EQLYWELSQL THSITELGPY TLDRVSLYVN GFNPRSSVPT   14700
TSTPGTSTVH LATSGTPSSL PGHTXXXPLL XPFTXNXTIT NLXXXXXMXX PGSRKFNTTE   14760
RVLQGLLKPL FRNSSLEYLY SGCRLASLRP EKDSSAMAVD AICTHRPDPE DLGLDRERLY   14820
WELSNLTNGI QELGPYTLDR NSLYVNGFTH RSSGLTTSTP WTSTVDLGTS GTPSPVPSPT   14880
TAGPLLVPFT LNFTITNLQY EEDMHRPGSR RFNTTERVLQ GLLTPLFKNT SVGPLYSGCR   14940
LTLLRPEKQE AATGVDTICT HRVDPIGPGL DRERLYWELS QLTNSITELG PYTLDRDSLY   15000
VNGFNPWSSV PTTSTPGTST VHLATSGTPS SLPGHTAPVP LLIPFTLNFT ITDLHYEENM   15060
QHPGSRKFNT TERVLQGLLK PLFKSTSVGP LYSGCRLTLL RPEKHGAATG VDAICTLRLD   15120
PTGPGLDRER LYWELSQLTN SVTELGPYTL DRDSLYVNGF THRSSVPTTS IPGTSAVHLE   15180
TSGTPASLPG HTAPGPLLVP FTLNFTITNL QYEEDMRHPG SRKFSTTERV LQGLLKPLFK   15240
NTSVSSLYSG CRLTLLRPEK DGAATRVDAV CTHRPDPKSP GLDRERLYWK LSQLTHGITE   15300
LGPYTLDRHS LYVNGFTHQS SMTTTRTPDT STMHLATSRT PASLSGPTTA SPLLVLFTIN   15360
FTITNLRYEE NMHHPGSRKF NTTERVLQGL LRPVFKNTSV GPLYSGCRLT TLRPKKDGAA   15420
TKVDAICTYR PDPKSPGLDR EQLYWELSQL THSITELGPY TQDRDSLYVN GFTHRSSVPT   15480
TSIPGTSAVH LETSGTPASL PGHTAPGPLL VPFTLNFTIT NLQYEEDMRH PGSRKFNTTE   15540
RVLQGLLKPL FKSTSVGPLY SGCRLTLLRP EKRGAATGVD TICTHRLDPL NPGLDREQLY   15600
WELSKLTRGI IELGPYLLDR GSLYVNGFTH RTSVPTTSTP GTSTVDLGTS GTPFSLPSPA   15660
XXXPLLXPFT XNXTITNLXX XXXMXXPGSR KFNTTERVLQ TLLGPMFKNT SVGLLYSGCR   15720
LTLLRSEKDG AATGVDAICT HRLDPKSPGL DREQLYWELS QLTNGIKELG PYTLDRNSLY   15780
VNGFTHWIPV PTSSTPGTST VDLGSGTPSS LPSPTTAGPL LVPFTLNFTI TNLKYEEDMH   15840
CPGSRKFNTT ERVLQSLLGP MFKNTSVGPL YSGCRLTLLR SEKDGAATGV DAICTHRLDP   15900
KSPGVDREQL YWELSQLTNG IKELGPYTLD RNSLYVNGFH HQTSAPNTST PGTSTVDLGT   15960
SGTPSSLPSP TXXXPLLXPF TXNXTITNLX XXXXXMXXPGS RKFNTTEXVL QGLLXPXFKN   16020
XSVGXLYSGC RLTXLRXEKX GAATGXDAIC XHXXXPKXPG LXXEXLYWEL SXLTXXIXEL   16080
GPYTLDRXSL YVNGFTHWIP VPTSSTPGTS TVDLGSGTPS SLPSPTTAGP LLVPFTLNFT   16140
ITNLKYEEDM HCPGSRKFNT TERVLQSLLG PMFKNTSVGP LYSGCRLTSL RSEKDGAATG   16200
VDAICTHRVD PKSPGVDREQ LYWELSQLTN GIKELGPYTL DRNSLYVNGF THQTSAPNTS   16260
TPGTSTVXXG TSGTPSSXPX XTSAGPLLVP FTLNFTITNL QYEEDMHHPG SRKFNTTERV   16320
LQGLLGPMFK NTSVGLLYSG CRLTLLRPEK NGATTGMDAI CTHRLDPKSP GLXXEXLYWE   16380
LSXLTXXIXE LGPYTLDRXS LYVNGFTHXX SXPTTSTPGT STVXXGTSGT PSSXPXXTXX   16440
XPLLXPFTXN XTITNLXXXX XMXXPGSRKF NTTERVLQGL LKPLFRNSSL EYLYSGCRLA   16500
SLRPEKDSSA MAVDAICTHR PDPEDLGLDR ERLYWELSNL TNGIQELGPY TLDRNSLYVN   16560
GFTHRSSMPT TSTPGTSTVD VGTSGTPSSS PSPTTAGPLL IPFTLNFTIT NLQYGEDMGH   16620
PGSRKFNTTE RVLQGLLGPI FKNTSVGPLY SGCRLTSLRS EKDGAATGVD AICIHHLDPK   16680
SPGLNRERLY WELSQLTNGI KELGPYTLDR NSLYVNGFTH RTSVPTTSTP GTSTVDLGTS   16740
GTPFSLPSPA TAGPLLVLFT LNFTITNLKY EEDMHRPGSR KFNTTERVLQ TLLGPMFKNT   16800
SVGLLYSGCR LTLLRSEKDG AATGVDAICT HRLDPKSPGL XXEXLYWELS XLTXXIXELG   16860
PYTLDRXSLY VNGFTHXXSX PTTSTPGTST VXXGTSGTPS SXPXXTXXXP LLXPFTXNXT   16920
ITNLXXXXXM XXPGSRKFNT TERVLQGLLR PVFKNTSVGX LTLLRPKKDGAATK         16980
VDAICTYRPD PKSPGLDREQ LYWELSQLTH SITELGPYTQ DRDSLYVNGF THRSSVPTTS   17040
IPGTSAVHLE TTGTPSSFPG HTEPGPLLIP FTFNFTITNL RYEENMQHPG SRKFNTTERV   17100
LQGLLTPLFK NTSVGPLYSG CRLTLLRPEK QEAATGVDTI CTHRVDPIGP GLDRERLYWE   17160
LSQLTNSITE LGPYTLDRDS LYVDGFNPWS SVPTTSTPGT STVHLATSGT PSPLPGHTAP   17220
VPLLIPFTLN FTITDLHYEE NMQHPGSRKF NTTERVLQGL LKPLFKSTSV GPLYSGCRLT   17280
LLRPEKHGAA TGVDAICTLR LDPTGPGLDR ERLYWELSQL TNSITELGPY TLDRDSLYVN   17340
GFNPWSSVPT TSTPGTSTVH LATSGTPSSL PGHTTAGPLL VPFTLNFTIT NLKYEEDMHC   17400
PGSRKFNTTE RVLQSLHGPM FKNTSVGPLY SGCRLTLLRS EKDGAATGVD AICTHRLDPK   17460
SPGLXXEXLY WELSXLTXXI XELGPYTLDR XSLYVNGFTH XXSXPTTSTP GTSTVXXGTS   17520
GTPSSXPXXT XXXPLLXPFT XNXTITNLXX XXXMXXPGSR KFNTTEXVLQ GLLXPXFKNX   17580
SVGXLYSGCR LTXLRXEKXG AATGXDAICX HXXXPKXPGL XXEXLYWELS XLTNSITELG   17640
PYTLDRDSLY VNGFTHRSSM PTTSIPGTSA VHLETSGTPA SLPGHTAGP  LLVPFTLNFT   17700
ITNLQYEEDM RHPGSRKFNT TERVLQGLLK PLFKSTSVGP LYSGCRLTLL RPEKRGAATG   17760
VDTICTHRLD PLNPGLXXEX LYWELSXLTX XIXELGPYTL DRXSLYVNGF THXXSXPTTS   17820
TPGTSTVXXG TSGTPSSXPX XTXXXPLLXP FTXNXTITNL XXXXXMXXPG SRKFNTTEXV   17880
LQGLLXPXFK NXSVGXLYSG CRLTXLRXEK XGAATGXDAI CXHXXXPKXP GLXXEXLYWE   17940
LSXLTXXIXE LGPYTLDRXS LYVNGFHPRS SVPTTSTPGT STVHLATSGT PSSLPGHTAP   18000
VPLLIPFTLN FTITNLHYEE NMQHPGSRKF NTTERVLQGL LGPMFKNTSV GLLYSGCRLT   18060
LLRPEKNGAA TGMDAICSHR LDPKSPGLXX EXLYWELSXL TXXIXELGPY TLDRXSLYVN   18120
GFTHXXSXPT TSTPGTSTVX XGTSGTPSSX PXXTXXXPLL XPFTXNXTIT NLXXXXXMXX   18180
PGSRKFNTTE XVLQGLLXPX FKNXSVGXLY SGCRLTXLRX EKXGAATGXD AICXHXXXPK   18240
XPGLXXEXLY WELSXLTXXI XELGPYTLDR XSLYVNGFTH QNSVPTTSTP GTSTVYWATT   18300
GTPSSFPGHT EPGPLLIPFT FNFTITNLHY EENMQHPGSR KFNTTERVLQ GLLTPLFKNT   18360
SVGPLYSGCR LTLLRPEKQE AATGVDTICT HRVDPIGPGL XXEXLYWELS XLTXXIXELG   18420
PYTLDRXSLY VNGFTHXXSX PTTSTPGTST VXXGTSGTPS SXPXXTXXXP LLXPFTXNXT   18480
ITNLXXXXXM XXPGSRKFNT TEXVLQGLLX PXFKNXSVGX LTXLRXEKXG AATG         18540
XDAICXHXXX PKXPGLXXEX LYWELSXLTX XIXELGPYTL DRXSLYVNGF THRSSVPTTS   18600
SPGTSTVHLA TSGTPSSLPG HTAPVPLLIP FTLNFTITNL HYEENMQHPG SRKFNTTERV   18660
LQGLLKPLFK STSVGPLYSG CRLTLLRPEK HGAATGVDAI CTLRLDPTGP GLXXEXLYWE   18720
LSXLTXXIXE LGPYTLDRXS LYVNGFTHXX SXPTTSTPGT STVXXGTSGT PSSXPXXTXX   18780
XPLLXPFTXN XTITNLXXXX XMXXPGSRKF NTTEXVLQGL LXPXFKNXSV GXLYSGCRLT   18840
XLRXEKXGAA TGXDAICXHX XXPKXPGLXX EXLYWELSXL TXXIXELGPY TLDRXSLYVN   18900
```

```
GFTHRTSVPT TSTPGTSTVH LATSGTPSSL PGHTAPVPLL IPFTLNFTIT NLQYEEDMHR     18960
PGSRKFNTTE RVLQGLLSPI FKNSSVGPLY SGCRLTSLRP EKDGAATGMD AVCLYHPNPK     19020
RPGLDREQLY CELSQLTHNI TELGPYSLDR DSLYVNGFTH QNSVPTTSTP GTSTVYWATT     19080
GTPSSFPGHT XXXPLLXPFT XNXTITNLXX XXXMXXPGSR KFNTTEXVLQ GLLXPXFKNX     19140
SVGXLYSGCR LTXLRXEKXG AATGXDAICX HXXXPKXPGL XXEXLYWELS XLTXXIXELG     19200
PYTLDRXSLY VNGFTHWSSG LTTSTPWTST VDLGTSGTPS PVPSPTTAGP LLVPFTLNFT     19260
ITNLQYEEDM HRPGSRKFNA TERVLQGLLS PIFKNTSVGP LYSGCRLTLL RPEKQEAATG     19320
VDTICTHRVD PIGPGLXXEX LYWELSXLTX XIXELGPYTL DRXSLYVNGF THXXSXPTTS     19380
TPGTSTVXXG TSGTPSSXPX XTXXXPLLXP FTXNXTITNL XXXXMXXPG SRKFNTTEXV     19440
LQGLLXPXFK NXSVGXLYSG CRLTXLRXEK XGAATGXDAI CXHXXXPKXP GLXXEXLYWE     19500
LSXLTXXIXE LGPYTLDRXS LYVNGFTHRS FGLTTSTPWT STVDLGTSGT PSPVPSPTTA     19560
GPLLVPFTLN FTITNLQYEE DMHRPGSRKF NTTERVLQGL LTPLFRNTSV SSLYSGCRLT     19620
LLRPEKDGAA TRVDAVCTHR PDPKSPGLXX EXLYWELSXL XXEXLYWELS XLTXXIXELGP    19680
GFTHXXSXPT TSTPGTSTVX XGTSGTPSSX PXXTXXXPLL XPFTXNXTIT NLXXXXXMXX     19740
PGSRKFNTTE XVLQGLLXPX FKNXSVGXLY SGCRLTXLRX EKXGAATGXD AICXHXXXPK     19800
XPGLXXEXLY WELSXLTXXI XELGPYTLDR XSLYVNGFTH WIPVPTSSTP GTSTVDLGSG     19860
TPSSLPSPTT AGPLLVPFTL NFTITNLQYG EDMGHPGSRK NTTERVLQG LLGPIFKNTS     19920
VGPLYSGCRL TSLRSEKDGA ATGVDAICIH HLDPKSPGLX XEXLYWELSX LTXXIXELGP     19980
YTLDRXSLYV NGFTHXXSXP TTSTPGTSTV XXGTSGTPSS XPXXTXXXPL LXPFTXNXTI     20040
TNLXXXXXMX XPGSRKFNTT EXVLQGLLXP XFKNXSVGXL YSGCRLTXLR XEKXGAATGX     20100
DAICXHXXXP KXPGLXXEXL YWELSXLTXX IXELGPYTLD RXSLYVNGFT HQTFAPNTST     20160
PGTSTVDLGT SGTPSSLPSP TSAGPLLVPF TLNFTITNLQ YEEDMHHPGS RKFNTTERVL     20220
QGLLGPMFKN TSVGLLYSGC RLTTLLRPEKN GAATRVDAVC THRPDPKSPG LXXEXLYWEL     20280
SXLTXXIXEL GPYTLDRXSL YVNGFTHXXS XPTTSTPGTS TVXXGTSGTP SSXPXXTAPV     20340
PLLIPFTLNF TITNLHYEEN MQHPGSRKFN TTERVLQGLL KPLFKSTSVG PLYSGCRLTL     20400
LRPEKHGAAT GVDAICTLRL DPTGPGLDRE RLYWELSQLT NSVTELGPYT LDRDSLYVNG     20460
FTQRSSVPTT SIPGTSAVHL ETSGTPASLP GHTAPGPLLV PFTLNFTITN LQYEVDMRHP     20520
GSRKFNTTER VLQGLLKPLF KSTSVGPLYS GCRLTLLRPE KRGAATGVDT ICTHRLDPLN     20580
PGLDREQLYW ELSKLTRGII ELGPYLLDRG SLYVNGFTHR NFVPITSTPG TSTVHLGTSE     20640
TPSSLPRPIV PGPLLVPFTL NFTITNLQYE EAMRHPGSRK FNTTERVLQG LLRPLFKNTS     20700
IGPLYSSCRL TLLRPEKDKA ATRVDAICTH HPDPQSPGLN REQLYWELSQ LTHGITELGP     20760
YTLDRDSLYV DGFTHWSPIP TTSTPGTSIV NLGTSGIPPS LPETTXXXPL LXPFTXNXTI     20820
TNLXXXXXMX XPGSRKFNTT ERVLQGLLKP LFKSTSVGPL YSGCRLTLLR PEKDGVATRV     20880
DAICTHRPDP KIPGLDRQQL YWELSQLTHS ITELGPYTLD RQRSSVPTTS             20940
PGTFTVQPET SETPSSLPGP TATGPVLLPF TLNFTITNLQ YEEDMHRPGS RKFNTTERVL     21000
QGLLMPLFKN TSVSSLYSGC RLTLLRPEKD GAATRVDAVC THRPDPKSPG LDRERLYWKL     21060
SQLTHGITEL GPYTLDRHSL YVNGFTHQSS MTTTRTPDTS TMHLATSRTP ASLSGPTTAS     21120
PLLVLFTINF TITNLRYEEN MHHPGSRKFN TTERVLQGLL RPVFKNTSVG PLYSGCRLTL     21180
LRPKKDGAAT KVDAICTYRP DPKSPGLDRE QLYWELSQLT HSITELGPYT LDRDSLYVNG     21240
FTQRSSVPTT SIPGTPTVDL GTSGTPVSKP GPSAASPLLV LFTLNFTITN LRYEENMQHP     21300
GSRKFNTTER VLQGLLRSLF KSTSVGPLYS GCRLTLLRPE KDGTATGVDA ICTHHPDPKS     21360
PRLDREQLYW ELSQLTHNIT ELGHYALDND SLFVNGFTHR SSVSTTSTPG TPTVYLGASK     21420
TPASIFGPSA ASHLLILFTL NFTITNLRYE ENMWPGSRKF NTTERVLQGL LRPLFKNTSV     21480
GPLYSGSRLT LLRPEKDGEA TGVDAICTHR PDPTGPGLDR EQLYLELSQL THSITELGPY     21540
TLDRDSLYVN GFTHRSSVPT TSTGVVSEEP FTLNFTINNL RYMADMGQPG SLKFNITDNV     21600
MKHLLSPLFQ RSSLGARYTG CRVIALRSVK NGAETRVDLL CTYLQPLSGP GLPIKQVFHE     21660
LSQQTHGITR LGPYSLDKDS LYLNGYNEPG LDEPPTTPKP ATTFLPPLSE ATTAMGYHLK     21720
TLTLNFTISN LQYSPDMGKG SATFNSTEGV LQHLLRPLFQ KSSMGPFYLG CQLISLRPEK     21780
DGAATGVDTT CTYHPDPVGP GLDIQQLYWE LSQLTHGVTQ LGFYVLDRDS LFINGYAPQN     21840
LSIRGEYQIN FHIVNWNLSN PDPTSSEYIT LLRDIQDKVT TLYKGSQLHD TFRFCLVTNL     21900
TMDSVLVTVK ALFSSNLDPS LVEQVFLDKT LNASFHWLGS TYQLVDIHVT EMESSVYQPT     21960
SSSSTQHFYL NFTITNLPYS QDKAQPGTTN YQRNKRNIED ALNQLFRNSS IKSYFSDCQV     22020
STFRSVPNRH HTGVDSLCNF SPLARRVDRV AIYEEFLRMT RNGTQLQNFT LDRSSVLVDG     22080
YSPNRNEPLT GNSDLPFWAV ILIGLAGLLG LITCLICGVL VTTRRKKEG EYNVQQCPG       22140
YYQSHLDLED LQ                                                         22152

SEQ ID NO: 44         moltype = AA  length = 255
FEATURE               Location/Qualifiers
source                1..255
                      mol_type = protein
                      organism = Homo sapiens
SEQUENCE: 44
MTPGTQSPFF LLLLLTVLTV VTGSGHASST PGGEKETSAT QRSSVPSSTE KNAFNSSLED     60
PSTDYYQELQ RDISEMFLQI YKQGGFLGLS NIKFRPGSVV VQLTLAFREG TINVHDVETQ     120
FNQYKTEAAS RYNLTISDVS VSDVPFPFSA QSGAGVPGWG IALLVLVCVL VALAIVYLIA     180
LAVCQCRRKN YGQLDIFPAR DTYHPMSEYP TYHTHGRYVP PSSTDRSPYE KVSAGNGGSS     240
LSYTNPAVAA TSANL                                                     255

SEQ ID NO: 45         moltype = AA  length = 560
FEATURE               Location/Qualifiers
source                1..560
                      mol_type = protein
                      organism = Homo sapiens
SEQUENCE: 45
MECLYYFLGF LLLAARLPLD AAKRFHDVLG NERPSAYMRE HNQLNGWSSD ENDWNEKLYP     60
VWKRGDMRWK NSWKGGRVQA VLTSDSPALV GSNITFAVNL IPPRCQKEDA NGNIVYEKNC     120
RNEAGLSADP YVVNWTAWSE DSDGENGTGQ SHHNVFPDGK PFPHHPGWRR WNFIYVFHTL     180
GQYFQKLGRC SVRVSNTAN VTLGPQLMEV TVYRRHGRAY VPIAQVKDVY VVTDQIPVFV     240
TMFQKNDRNS SDETFLKDLP IMFDVLIHDP SHFLNYSTIN YKWSFGDNTG LFVSTNHTVN     300
```

```
HTYVLNGTFS LNLTVKAAAP GPCPPPPPPP RPSKPTPSLG PAGDNPLELS RIPDENCQIN    360
RYGHFQATIT IVEGILEVNI IQMTDVLMPV PWPESSLIDF VVTCQGSIPT EVCTIISDPT    420
CEITQNTVCS PVDVDEMCLL TVRRTFNGSG TYCVNLTLGD DTSLALTSTL ISVPDRDPAS    480
PLRMANSALI SVGCLAIFVT VISLLVYKKH KEYNPIENSP GNVVRSKGLS VFLNRAKAVF    540
FPGNQEKDPL LKNQEFKGVS                                                560

SEQ ID NO: 46           moltype = AA  length = 551
FEATURE                 Location/Qualifiers
source                  1..551
                        mol_type = protein
                        organism = Homo sapiens
SEQUENCE: 46
MAAPALSWRL PLLILLLPLA TSWASAAVNG TSQFTCFYNS RANISCVWSQ DGALQDTSCQ     60
VHAWPDRRRW NQTCELLPVS QASWACNLIL GAPDSQKLTT VDIVTLRVLC REGVRWRVMA    120
IQDFKPFENL RLMAPISLQV VHVETHRCNI SWEISQASHY FERHLEFEAR TLSPGHTWEE    180
APLLTLKQKQ EWICLETLTP DTQYEFQVRV KPLQGEFTTW SPWSQPLAFR TKPAALGKDT    240
IPWLGHLLVG LSGAFGFIIL VYLLINCRNT GPWLKKVLKC NTPDPSKFFS QLSSEHGGDV    300
QKWLSSPFPS SSFSPGGLAP EISPLEVLER DKVTQLLLQQ DKVPEPASLS SNHSLTSCFT    360
NQGYFFFHLP DALEIEACQV YFTYDPYSEE DPDEGVAGAP TGSSPQPLQP LSGEDDAYCT    420
FPSRDDLLLF SPSLLGGPSP PSTAPGGSGA GEERMPPSLQ ERVPRDWDPQ PLGPPTPGVP    480
DLVDFQPPPE LVLREAGEEV PDAGPREGVS FPWSRPPGQG EFRALNARLP LNTDAYLSLQ    540
ELQGQDPTHL V                                                         551

SEQ ID NO: 47           moltype = AA  length = 427
FEATURE                 Location/Qualifiers
source                  1..427
                        mol_type = protein
                        organism = Homo sapiens
SEQUENCE: 47
MEWPARLCGL WALLLCAGGG GGGGGAAPTE TQPPVTNLSV SVENLCTVIW TWNPPEGASS     60
NCSLWYFSHF GDKQDKKIAP ETRRSIEVPL NERICLQVGS QCSTNESEKP SILVEKCISP    120
PEGDPESAVT ELQCIWHNLS YMKCSWLPGR NTSPDTNYTL YYWHRSLEKI HQCENIFREG    180
QYFGCSFDLT KVKDSSFEQH SVQIMVKDNA GKIKPSFNIV PLTSRVKPDP PHIKNLSFHN    240
DDLYVQWENP QNFISRCLFY EVEVNNSQTE THNVFYVQEA KCENPEFERN VENTSCFMVP    300
GVLPDTLNTV RIRVKTNKLC YEDDKLWSNW SQEMSIGKKR NSTLYITMLL IVPVIVAGAI    360
IVLLLYLKRL KIIIFPPIPD PGKIFKEMFG DQNDDTLHWK KYDIYEKQTK EETDSVVLIE    420
NLKKASQ                                                              427

SEQ ID NO: 48           moltype = AA  length = 323
FEATURE                 Location/Qualifiers
source                  1..323
                        mol_type = protein
                        organism = Homo sapiens
SEQUENCE: 48
MARGPGLAPP PLRLPLLLLV LAAVTGHTAA QDNCTCPTNK MTVCSPDGPG GRCQCRALGS     60
GMAVDCSTLT SKCLLLKARM SAPKNARTLV RPSEHALVDN DGLYDPDCDP EGRFKARQCN    120
QTSVCWCVNS VGVRRTDKGD LSLRCDELVR THHILIDLRH RPTAGAFNHS DLDAELRRLF    180
RERYRLHPKF VAAVHYEQPT IQIELRQNTS QKAAGDVDIG DAAYYFERDI KGESLFQGRG    240
GLDLRVRGEP LQVERTLIYY LDEIPPKFSM KRLTAGLIAV IVVVVALVA GMAVLVITNR    300
RKSGKYKKVE IKELGELRKE PSL                                            323

SEQ ID NO: 49           moltype = AA  length = 257
FEATURE                 Location/Qualifiers
source                  1..257
                        mol_type = protein
                        organism = Homo sapiens
SEQUENCE: 49
MAQRMTTQLL LLLVWVAVVG EAQTRIAWAR TELLNVCMNA KHHKEKPGPE DKLHEQCRPW     60
RKNACCSTNT SQEAHKDVSY LYRFNWNHCG EMAPACKRHF IQDTCLYECS PNLGPWIQQV    120
DQSWRKERVL NVPLCKEDCE QWWEDCRTSY TCKSNWHKGW NWTSGFNKCA VGAACQPFHF    180
YPPTPTVLCN EIWTHSYKVS NYSRGSGRCI QMWFDPAQGN PNEEVARFYA AAMSGAGPWA    240
AWPFLLSLAL MLLWLLS                                                   257

SEQ ID NO: 50           moltype = AA  length = 4130
FEATURE                 Location/Qualifiers
source                  1..4130
                        mol_type = protein
                        organism = Homo sapiens
SEQUENCE: 50
MLKPSGLPGS SSPTRSLMTG SRSTKATPEM DSGLTGATLS PKTSTGAIVV TEHTLPFTSP     60
DKTLASPTSS VVGRTTQSLG VMSSALPEST SRGMTHSEQR TSPSLSPQVN GTPSRNYPAT    120
SMVSGLSSPR TRTSSTEGNF TKEASTYTLT VETTSGPVTE KYTVPTETST TEGDSTETPW    180
DTRYIPVKIT SPMKTFADST ASKENAPVSM TPAETTVTDS HTPGRTNPSF GTLYSSFLDL    240
SPKGTPNSRG ETSLELILST TGYPFSSPEP GSAGHSRIST SAPLSSSASV LDNKISETSI    300
FSGQSLTSPL SPGVPEARAS TMPNSAIPFS MTLSNAETSA ERVRSTISSL GTPSISTKQT    360
AETILTPHAF AETMDIPSTH IAKTLASEWL GSPGTLGGTS TSALTTTSPS TTLVSEETNT    420
HHSTSGKETE GTLNTSMTPL ETSAPGEESE MTATLVPTLG FTTLDSKIRS PSQVSSSHPT    480
RELRTTGSTS GRQSSSTAAH GSSDILRATT SSTSKASSWT SESTAQQFSE PQHTQWVETS    540
PSMKTERPPA STSVAAPITT SVPSVVSGFT TLKTSSSTKGI WLEETSADTL IGESTAGPTT    600
```

```
HQFAVPTGIS MTGGSSTRGS QGTTHLLTRA TASSETSADL TLATNGVPVS VSPAVSKTAA   660
GSSPPGGTKP SYTMVSSVIP ETSSLQSSAF REGTSLGLTP LNTRHPFSSP EPDSAGHTKI   720
STSIPLLSSA SVLEDKVSAT STFSHHKATS SITTGTPEIS TKTKPSSAVL SSMTLSNAAT   780
SPERVRNATS PLTHPSPSGE ETAGSVLTLS TSAETTDSPN IHPTGTLTSE SSESPSTLSL   840
PSVSGVKTTF SSSTPSTHLF TSGEETEETS NPSVSQSTTS VSRVRTTLAS TSVPTPVFPT   900
MDTWPTRSAQ FSSSHLVSEL RATSSTSVTN STGSALPKIS HLTGTATMSQ TNRDTFNDSA   960
APQSTTWPET SPRFKTGLPS ATTTVSTSAT SLSATVMVSK FTSPATSSME ATSIREPSTT  1020
ILTTETTNGP GSMAVASTNI PIGKGYITEG RLDTSHLPIG TTASSETSMD FTMAKESVSM  1080
SVSPSQSMDA AGSSTPGRTS QFVDTFSDDV YHLTSREITI PRDGTSSALT PQMTATHPPS  1140
PDPGSARSTW LGILSSSPSS PTPKVTMSST FSTQRVTTSM IMDTVETSRW NMPNLPSTTS  1200
LTPSNIPTSG AIGKSTLVPL DTPSPATSLE ASEGGLPTLS TYPESTNTPS IHLGAHASSE  1260
SPSTIKLTMA SVVKPGSYTP LTFPSIETHI HVSTARMAYS SGSSPEMTAP GETNTGSTWD  1320
PTTYITTTDP KDTSSAQVST PHSVRTLRTT ENHPKTESAT PAAYSGSPKI SSSPNLTSPA  1380
TKAWTITDTT EHSTQLHYTK LAEKSSGFET QSAPGPVSVV IPTSPTIGSS TLELTSDVPG  1440
EPLVLAPSEQ TTITLPMATW LSTSLTEEMA STDLDISSPS SPMSTFAIFP PMSTPSHELS  1500
KSEADTSAIR NTDSTTLDQH LGIRSLGRTG DLTTVPITPL TTTWTSVIEH STQAQDTLSA  1560
TMSPTHVTQS LKDQTSIPAS ASPSHLTEVY PELGTQGRSS SEATTFWKPS TDTLSREIET  1620
GPTNIQSTPP MDNTTTGSSS SGVTLGIAHL PIGTSSPAET STNMALERRS STATVSMAGT  1680
MGLLVTSAPG RSISQSLGRV SSVLSESTTE GVTDSSKGSS PRLNTQGNTA LSSSLEPSYA  1740
EGSQMSTSIP LTSSPTTPDV EFIGGSTFWT KEVTTVMTSD ISKSSARTES SSATLMSTAL  1800
GSTENTGKEK LRTASMDLPS PTPSMEVTPW ISLTLSNAPN TTDSLDLSHG VHTSSAGTLA  1860
TDRSLNTGVT RASRLENGSD TSSKSLSMGN STHTSMTYTE KSEVSSSIHP RPETSAPGAE  1920
TTLTSTPGNR AISLTLPFSS IPVEEVISTG ITSGPDINSA PMTHSPITPP TIVWTSTGTI  1980
EQSTQPLHAV SSEKVSVQTQ STPYVNSVAV SASPTHENSV SSGSSTSSPY SSASLESLDS  2040
TISRRNAITS WLWDLTTSLP TTTWPSTSLS EALSSGHSGV SNPSSTTTEF PLFSAASTSA  2100
AKQRNPETET HGPQNTAAST LNTDASSVTG LSETPVGASI SSEVPLPMAI TSRSDVGLT   2160
SESTANPSLG TASSAGTKLT RTISLPTSES LVSFRMNKDP WTVSIPLGSH PTTNTETSIP  2220
VNSAGPPGLS TVASDVIDTP SDGAESIPTV SFSPSPDTEV TTISHFPEKT THSFRTISSL  2280
THELTSRVTP IPGDWMSSAM STKPTGASPS ITLGERRTIT SAAPTTSPIV LTASFTETST  2340
VSLDNETTVK TSDILDARKT NELPSDSSSS SDLINTSIAS STMDVTKTAS ISPTSISGMT  2400
ASSSPSLFSS DRPQVPTSTT ETNTATSPSV SSNTYSLDGG SNVGGTPSTL PPFTITHPVE  2460
TSSALLAWSR PVRTFSTMVS TDTASGENPT SSNSVVTSVP APGTWTSVGS TTDLPAMGFL  2520
KTSPAGEAHS LLASTIEPAT AFTPHLSAAV VTGSSATSEA SLLTTSESKA IHSSPQTPTT  2580
PTSGANWETS ATPESLLVVT ETSDTTLTSK ILVTDTILFS TVSTPPSKFP STGTLSGASF  2640
PTLLPDTPAI PLTATEPTSS LATSFDSTPL VTIASDSLGT VPETTLTMSE TSNGDALVLK  2700
TVSNPDRSIP GITIQGVTES PLHPSSTSPS KIVAPRNTTY EGSITVALST LPAGTTGSLV  2760
FSQSSENSET TALVDSSAGL ERASVMPLTT GSQGMASSGG IRSGSTHSTG TKTFSSLPLT  2820
MNPGEVTAMS EITTNRLTAT QSTAPKGIPV KPTSAESGLL TPVSASSSPS KAFASLTTAP  2880
PTWGIPQSTL TFEFSEVPSL DTKSASLPTP GQSLNTIPDS DASTASSSLS KSPEKNPRAR  2940
MMTSTKAISA SSFQSTGFTE TPEGSASPSM AGHEPRVPTS GTGDPRYASE SMSYPDPSKA  3000
SSAMTSTSLA SKLTTLFSTG QAARSGSSSS PISLSTEKET SFLSPTASTS RKTSLFLGPS  3060
MARQPNILVH LQTSALTLSP TSTLNMSQEE PPELTSSQTI AEEEGTTAET QTLTFTPSET  3120
PTSLLPVSSP TEPTARRKSS PETWASSISV PAKTSLVETT DGTLVTTIKM SSQAAQGNST  3180
WPAPAEETGS SPAGTSPGSP EMSTTLKIMS SKEPSISPEI RSTVRNSPWK TPETTVPMET  3240
TVEPVTLQST ALGSGSTSIS HLPTGTTSPT KSPTENMLAT ERVSLSPSPP EAWTNLYSGT  3300
PGGTRQSLAT MSSVSLESPT ARSITGTGQQ SSPELVSKTT GMEFSMWHGS TGGTTGDTHV  3360
SLSTSSNILE DPVTSPNSVS SLTDKSKHKT ETWVSTTAIP TVLNNKIMA AEQQTSRSVD   3420
EAYSSTSSWS DQTSGSDITL GASPDVTNTL YITTSAQTTS LVSLPSGDQG ITSLTNPSGG  3480
KTSSASSVTS PSIGLETLRA NVSAVKSDIA PTAGHLSQTS SPAEVSILDV TTAPTPGIST  3540
TITTMGTNSI STTTPNPEVG MSTMDSTPAT ERRTTSTEHP STWSSTAASD SWTVTDMTSN  3600
LKVARSPGTI STMHTTSFLA SSTELDSMST PHGRITVGTI SLVTPSSDAS AVKTETSTSE  3660
RTLSPSDTTA STPISTFSRV QRMSISVPDI LSTSWTPSST EAEDVPVSMV STDHASTKTD  3720
PNTPLSTFLF DSLSTLDWDT GRSLSSATAT TSAPQGATTP QELTLETMIS PATSQLPFSI  3780
GHITSAVTPA AMARSSGVTF SRPDPTSKKA EQTSTQLPTT TSAHPGQVPR SAATTLDVIP  3840
HTAKTPDATF QRQGQTALTT EARATSDSWN EKEKSTPSAP WITEMMNSVS EDTIKEVTSS  3900
SSVLRTLNTL DINLESGTTS SPSWKSSPYE RIAPSESTTD KEAIHPSTNT VETTGWVTSS  3960
EHASHSTIPA HSASSKLTSP VVTTSTREQA IVSMSTTTWP ESTRARTEPN SPLTIELRDV  4020
SPYMDTSSTT QTSIISSPGS TAITKGPRTE ITSSKRISSS FLAQSMRSSD SPSEAITRLS  4080
NFPAMTESGG MILAMQTSPP GATSLSAPTL DTSATASWTG TPLATTQRFT              4130

SEQ ID NO: 51           moltype = AA  length = 442
FEATURE                 Location/Qualifiers
source                  1..442
                        mol_type = protein
                        organism = Homo sapiens
SEQUENCE: 51
MQPPPSLCGR ALVALLLACG LLGVWGEERG FPPDKATPLL QTAEIMTPPT KTLWPKGSNA    60
SLARSLAPAE VPKGDRTAGS PPRTISPPPC QGPIEIKTET KYINTVVSCL VFVLGIIGNS   120
TLLRIIYKNK CMRNGPNILV ASLALGDLLH IVIDIPINVY KLLAEDWPFG AEMCKLVPFI   180
QKASVGITVL SLCALSIDRY RAVASWSRIK GIGVPKWTAV EIVLIWVVSV VLAVPEAIGF   240
DIITMDYKGS YLRICLLHPV QKTAFMQFYK TAKDWWLFSF YFCLPLAITA FFYTLMTCEM   300
LRKKSGMQIA LNDHLKQRRE VAKTVFCLVL VFALCWLPLH LSRILKLTLY NQNDPNRCEL   360
LSFLLVLDYI GINMASLNSC INPIALYLVS KRFKNCFKSC LCCWCQSFEE KQSLEEKQSC   420
LKFKANDHGY DNFRSSNKYS SS                                           442

SEQ ID NO: 52           moltype = AA  length = 339
FEATURE                 Location/Qualifiers
source                  1..339
                        mol_type = protein
```

```
                         organism = Homo sapiens
SEQUENCE: 52
MESRKDITNQ EELWKMKPRR NLEEDDYLHK DTGETSMLKR PVLLHLHQTA HADEFDCPSE  60
LQHTQELFPQ WHLPIKIAAI IASLTFLYTL LREVIHPLAT SHQQYFYKIP ILVINKVLPM  120
VSITLLALVY LPGVIAAIVQ LHNGTKYKKF PHWLDKWMLT RKQFGLLSFF FAVLHAIYSL  180
SYPMRRSYRY KLLNWAYQQV QQNKEDAWIE HDVWRMEIYV SLGIVGLAIL ALLAVTSIPS  240
VSDSLTWREF HYIQSKLGIV SLLLGTIHAL IFAWNKWIDI KQFVWYTPPT FMIAVFLPIV  300
VLIFKSILFL PCLRKKILKI RHGWEDVTKI NKTEICSQL                         339

SEQ ID NO: 53            moltype = AA  length = 710
FEATURE                  Location/Qualifiers
source                   1..710
                         mol_type = protein
                         organism = Homo sapiens
SEQUENCE: 53
MGGKQRDEDD EAYGKPVKYD PSFRGPIKNR SCTDVICCVL FLLFILGYIV VGIVAWLYGD  60
PRQVLYPRNS TGAYCGMGEN KDKPYLLYFN IFSCILSSNI ISVAENGLQC PTPQVCVSSC  120
PEDPWTVGKN EFSQTVGEVF YTKNRNFCLP GVPWNMTVIT SLQQELCPSF LLPSAPALGR  180
CFPWTNVTPP ALPGITNDTT IQQGISGLID SLNARDISVK IFEDFAQSWY WILVALGVAL  240
VLSLLFILLL RLVAGPLVLV LILGVLGVLA YGIYYCWEEY RVLRDKGASI SQLGFTTNLS  300
AYQSVQETWL AALIVLAVLE AILLLMLIFL RQRIRIAIAL LKEASKAVGQ MMSTMFYPLV  360
TFVLLLICIA YWAMTALYLA TSGQPQYVLW ASNISSPGCE KVPINTSCNP TAHLVNSSCP  420
GLMCVFQGYS SKGLIQRSVF NLQIYGVLGL FWTLNWVLAL GQCVLAGAFA SFYWAFHKPQ  480
DIPTFPLISA FIRTLRYHTG SLAFGALILT LVQIARVILE YIDHKLRGVQ NPVARCIMCC  540
FKCCLWCLEK FIKFLNRNAY IMIAIYGKNF CVSAKNAFML LMRNIVRVVV LDKVTDLLLF  600
FGKLLVVGGV GVLSFFFFSG RIPGLGKDFK SPHLNYYWLP IMTSILGAYV IASGFFSVFG  660
MCVDTLFLCF LEDLERNNGS LDRPYYMSKS LLKILGKKNE APPDNKKRKK             710

SEQ ID NO: 54            moltype = AA  length = 441
FEATURE                  Location/Qualifiers
source                   1..441
                         mol_type = protein
                         organism = Yersinia pestis
SEQUENCE: 54
MKERSTELVQ GFRHSVPYIN AHRGKTFVVM LGGEAIEHEN FSSIVNDIGL LHSLGIRLVV  60
VYGARPQIDS NLADHNYEPI YHKHTRVTDA RTLEMVKQAA GLLQLDITAR LSMSLNNTPL  120
QGAHINVVSG NFIIAQPLGV DDGVDYCHSG RIRRIDEEAI HRQLDNGAIV LLGPVAVSVT  180
GESFNLTSEE VATQLAIKLK AEKMIGFCSS QGVTDSEGNI ISELFPNDAQ KRIEDLEQDG  240
DYNSGTVRFL RGAVKACRSG VRRSHLLSYQ EDGALIQELF SRDGIGTQIV MESAEQVRRA  300
TINDIGGILE LIRPLEQQGI LVRRSREQLE MEIDKFTIIE RDNLTIACAA LYPFPDEHIG  360
EMACVAVHPD YRSSSRGEML LNRITNQARQ MGLKKLFVLT TRSIHWFQER GFTPAEVDVL  420
PIQKQELYNY QRRSKILLAD L                                            441

SEQ ID NO: 55            moltype = AA  length = 1073
FEATURE                  Location/Qualifiers
source                   1..1073
                         mol_type = protein
                         organism = Homo sapiens
SEQUENCE: 55
MKTLLLDLAL WSLLFQPGWL SFSSQVSQNC HNGSYEISVL MMGNSAFAEP LKNLEDAVNE  60
GLEIVRGRLQ NAGLNVTVNA TFMYSDGLIH NSGDCRSSTC EGLDLLRKIS NAQRMGCVLI  120
GPSCTYSTFQ MYLDTELSYP MISAGSFGLS CDYKETLTRL MSPARKLMYF LVNFWKTNDL  180
PFKTYSWSTS YVYKNGTETE DCFWYLNALE ASVSYFSHEL GFKVVLRQDK EFQDILMDHN  240
RKSNVIIMCG GPEFLYKLKG DRAVAEDIVI ILVDLFNDQY FEDNVTAPDY MKNVLVLTLS  300
PGNSLLNSSF SRNLSPTKRD FALAYLNGIL LFGHMLKIFL ENGENITTPK FAHAFRNLTF  360
EGYDGPVTLD DWGDVDSTMV LLYTSVDTKK YKVLLTYDTH VNKTYPVDMS PTFTWKNSKL  420
PNDITGRGPQ ILMIAVFTLT GAVVLLLLVA LLMLRKYRKD YELRQKKWSH IPPENIFPLE  480
TNETNHVSLK IDDDKRRDTI QRLRQCKYDK KRVILKDLKH NDGNFTEKQK IELNKLLQID  540
YYNLTKFYGT VKLDTMIFGV IEYCERGSLR EVLNDTISYP DGTFMDWEFK ISVLYDIAKG  600
MSYLHSSKTE VHGRLKSTNC VVDSRMVVKI TDFGCNSILP PKKDLWTAPE HLRQANISQK  660
GDVYSYGIIA QEIILRKETF YTLSCRDRNE KIFRVENSNG MKPFRPDLFL ETAEEKELEV  720
YLLVKNCWEE DPEKRPDFKK IETTLAKIFG LFHDQKNESY MDTLIRRLQL YSRNLEHLVE  780
ERTQLYKAER DRADRLNFML LPRLVVKSLK EKGFVEPELY EEVTIYFSDI VGFTTICKYS  840
TPMEVVDMLN DIYKSFDHIV DHHDVYKVET IGDAYMVASG LPKRNGNRHA IDIAKMALEI  900
LSFMGTFELE HLPGLPIWIR IGVHSGPCAA GVVGIKMPRY CLFGDTVNTA SRMESTGLPL  960
RIHVSGSTIA ILKRTECQFL YEVRGETYLK GRGNETTYWL TGMKDQKFNL PTPPTVENQQ  1020
RLQAEFSDMI ANSLQKRQAA GIRSQKPRRV ASYKKGTLEY LQLNTTDKES TYF          1073

SEQ ID NO: 56            moltype = AA  length = 239
FEATURE                  Location/Qualifiers
source                   1..239
                         mol_type = protein
                         organism = Homo sapiens
SEQUENCE: 56
MAHAGRTGYD NREIVMKYIH YKLSQRGYEW DAGDVGAAPP GAAPAPGIFS SQPGHTPHPA  60
ASRDPVARTS PLQTPAAPGA AAGPALSPVP PVVHLTLRQA GDDFSRRYRR DFAEMSSQLH  120
LTPFTARGRF ATVVEELFRD GVNWGRIVAF FEFGGVMCVE SVNREMSPLV DNIALWMTEY  180
LNRHLHTWIQ DNGGWDAFVE LYGPSMRPLF DFSWLSLKTL LSLALVGACI TLGAYLGHK   239
```

| | | |
|---|---|---|
| SEQ ID NO: 57 | moltype = AA length = 393 | |
| FEATURE | Location/Qualifiers | |
| source | 1..393 | |
| | mol_type = protein | |
| | organism = Homo sapiens | |
| SEQUENCE: 57 | | |

```
MEEPQSDPSV EPPLSQETFS DLWKLLPENN VLSPLPSQAM DDLMLSPDDI EQWFTEDPGP   60
DEAPRMPEAA PRVAPAPAAP TPAAPAPAPS WPLSSSVPSQ KTYQGSYGFR LGFLHSGTAK  120
SVTCTYSPAL NKMFCQLAKT CPVQLWVDST PPPGTRVRAM AIYKQSQHMT EVVRRCPHHE  180
RCSDSDGLAP PQHLIRVEGN LRVEYLDDRN TFRHSVVVPY EPPEVGSDCT TIHYNYMCNS  240
SCMGGMNRRP ILTIITLEDS SGNLLGRNSF EVHVCACPGR DRRTEEENLR KKGEPHHELP  300
PGSTKRALSN NTSSSPQPKK KPLDGEYFTL QIRGRERFEM FRELNEALEL KDAQAGKEPG  360
GSRAHSSHLK SKKGQSTSRH KKLMFKTEGP DSD                              393
```

| | | |
|---|---|---|
| SEQ ID NO: 58 | moltype = AA length = 164 | |
| FEATURE | Location/Qualifiers | |
| source | 1..164 | |
| | mol_type = protein | |
| | organism = Homo sapiens | |
| SEQUENCE: 58 | | |

```
MSEPAGDVRQ NPCGSKACRR LFGPVDSEQL SRDCDALMAG CIQEARERWN FDFVTETPLE   60
GDFAWERVRG LGLPKLYLPT GPRRGRDELG GGRRPGTSPA LLQGTAEEDH VDLSLSCTLV  120
PRSGEQAEGS PGGPGDSQGR KRRQTSMTDF YHSKRRLIFS KRKP                   164
```

| | | |
|---|---|---|
| SEQ ID NO: 59 | moltype = AA length = 110 | |
| FEATURE | Location/Qualifiers | |
| source | 1..110 | |
| | mol_type = protein | |
| | organism = Homo sapiens | |
| SEQUENCE: 59 | | |

```
MALWMRLLPL LALLALWGPD PAAAFVNQHL CGSHLVEALY LVCGERGFFY TPKTRREAED   60
LQVGQVELGG GPGAGSLQPL ALEGSLQKRG IVEQCCTSIC SLYQLENYCN            110
```

| | | |
|---|---|---|
| SEQ ID NO: 60 | moltype = AA length = 267 | |
| FEATURE | Location/Qualifiers | |
| source | 1..267 | |
| | mol_type = protein | |
| | organism = Homo sapiens | |
| SEQUENCE: 60 | | |

```
MPRSCCSRSG ALLLALLLQA SMEVRGWCLE SSQCQDLTTE SNLLECIRAC KPDLSAETPM   60
FPGNGDEQPL TENPRKYVMG HFRWDRFGRR NSSSSGSSGA GQKREDVSAG EDCGPLPEGG  120
PEPRSDGAKP GPREGKRSYS MEHFRWGKPV GKKRRPVKVY PNGAEDESAE AFPLEFKREL  180
TGQRLREGDG PDGPADDGAG AQADLEHSLL VAAEKKDEGP YRMEHFRWGS PPKDKRYGGF  240
MTSEKSQTPL VTLFKNAIIK NAYKKGE                                     267
```

| | | |
|---|---|---|
| SEQ ID NO: 61 | moltype = AA length = 462 | |
| FEATURE | Location/Qualifiers | |
| source | 1..462 | |
| | mol_type = protein | |
| | organism = Homo sapiens | |
| SEQUENCE: 61 | | |

```
MASNSSSCPT PGGGHLNGYP VPPYAFFFPP MLGGLSPPGA LTTLQHQLPV SGYSTPSPAT   60
IETQSSSSEE IVPSPPSPPP LPRIYKPCFV CQDKSSGYHY GVSACEGCKG FFRRSIQKNM  120
VYTCHRDKNC IINKVTRNRC QYCRLQKCFE VGMSKESVRN DRNKKKKEVP KPECSESYTL  180
TPEVGELIEK VRKAHQETFP ALCQLGKYTT NNSSEQRVKL DIDLWDKFSE LSTKCIIKTV  240
EFAKQLPGFT TLTIADQITL LKAACLDILI LRICTRYTPE QDTMTFSDGL TLNRTQMHNA  300
GFGPLTDLVF AFANQLLPLE MDDAETGLLS AICLICGDRQ DLEQPDRVDM LQEPLLEALK  360
VYVRKRRPSR PHMFPKMLMK ITDLRSISAK GAERVITLKM EIPGSMPPLI QEMLENSEGL  420
DTLSGQPGGG GRDGGGLAPP PGSCSPSLSP SSNRSSPATH SP                    462
```

| | | |
|---|---|---|
| SEQ ID NO: 62 | moltype = AA length = 455 | |
| FEATURE | Location/Qualifiers | |
| source | 1..455 | |
| | mol_type = protein | |
| | organism = Homo sapiens | |
| SEQUENCE: 62 | | |

```
MTTSGHACPV PAVNGHMTHY PATPYPLLFP PVIGGLSLPP LHGLHGHPPP SGCSTPSPAT   60
IETQSTSSEE LVPSPPSPLP PPRVYKPCFV CQDKSSGYHY GVSACEGCKG FFRRSIQKNM  120
IYTCHRDKNC VINKVTRNRC QYCRLQKCFE VGMSKESVRN DRNKKKKETS KQECTESYEM  180
TAELDDLTEK IRKAHQETFP SLCQLGKYTT NSSADHRVRL DLGLWDKFSE LATKCIIKIV  240
EFAKRLPGFT GLTIADQITL LKAACLDILI LRICTRYTPE QDTMTFSDGL TLNRTQMHNA  300
GFGPLTDLVF TFANQLLPLE MDDTETGLLS AICLICGDRQ DLEEPTKVDK LQEPLLEALK  360
IYIRKRRPSK PHMFPKILMK ITDLRSISAK GAERVITLKM EIPGSMPPLI QEMLENSEGH  420
EPLTPSSSGN TAEHSPSISP SSVENSGVSQ SPLVQ                            455
```

| | | |
|---|---|---|
| SEQ ID NO: 63 | moltype = AA length = 455 | |
| FEATURE | Location/Qualifiers | |
| source | 1..455 | |
| | mol_type = protein | |

```
                        organism = Homo sapiens
SEQUENCE: 63
MTTSGHACPV PAVNGHMTHY PATPYPLLFP PVIGGLSLPP LHGLHGHPPP SGCSTPSPAT    60
IETQSTSSEE LVPSPPSPLP PPRVYKPCFV CQDKSSGYHY GVSACEGCKG FFRRSIQKNM   120
IYTCHRDKNC VINKVTRNRC QYCRLQKCFE VGMSKESVRN DRNKKKKETS KQECTESYEM   180
TAELDDLTEK IRKAHQETFP SLCQLGKYTT NSSADHRVRL DLGLWDKFSE LATKCIIKIV   240
EFAKRLPGFT GLTIADQITL LKAACLDILI LRICTRYTPE QDTMTFSDGL TLNRTQMHNA   300
GFGPLTDLVF TFANQLLPLE MDDTETGLLS AICLICGDRQ DLEEPTKVDK LQEPLLEALK   360
IYIRKRRPSK PHMFPKILMK ITDLRSISAK GAERVITLKM EIPGSMPPLI QEMLENSEGH   420
EPLTPSSSGN TAEHSPSISP SSVENSGVSQ SPLVQ                              455

SEQ ID NO: 64           moltype = AA  length = 462
FEATURE                 Location/Qualifiers
source                  1..462
                        mol_type = protein
                        organism = Homo sapiens
SEQUENCE: 64
MDTKHFLPLD FSTQVNSSLT SPTGRGSMAA PSLHPSLGPG IGSPGQLHSP ISTLSSPING    60
MGPPFSVISS PMGPHSMSVP TTPTLGFSTG SPQLSSPMNP VSSSEDIKPP LGLNGVLKVP   120
AHPSGNMASF TKHICAICGD RSSGKHYGVY SCEGCKGFFK RTVRKDLTYT CRDNKDCLID   180
KRQRNRCQYC RYQKCLAMGM KREAVQEERQ RGKDRNENEV ESTSSANEDM PVERILEAEL   240
AVEPKTETYV EANMGLNPSS PNDPVTNICQ AADKQLFTLV EWAKRIPHFS ELPLDDQVIL   300
LRAGWNELLI ASFSHRSIAV KDGILLATGL HVHRNSAHSA GVGAIFDRVL TELVSKMRDM   360
QMDKTELGCL RAIVLFNPDS KGLSNPAEVE ALREKVYASL EAYCKHKYPE QPGRFAKLLL   420
RLPALRSIGL KCLEHLFFFK LIGDTPIDTF LMEMLEAPHQ MT                       462

SEQ ID NO: 65           moltype = AA  length = 533
FEATURE                 Location/Qualifiers
source                  1..533
                        mol_type = protein
                        organism = Homo sapiens
SEQUENCE: 65
MSWAARPPFL PQRHAAGQCG PVGVRKEMHC GVASRWRRRR PWLDPAAAAA AAVAGGEQQT    60
PEPEPGEAGR DGMGDSGRDS RSPDSSSPNP LPQGVPPPSP PGPPLPPSTA PSLGGSGAPP   120
PPPMPPPPLG SPFPVISSSM GSPGLPPPAP PGFSGPVSSP QINSTVSLPG GGSGPPEDVK   180
PPVLGVRGLH CPPPPGGPGA GKRLCAICGD RSSGKHYGVY SCEGCKGFFK RTIRKDLTYS   240
CRDNKDCTVD KRQRNRCQYC RYQKCLATGM KREAVQEERQ RGKDKDGDGE GAGGAPEEMP   300
VDRILEAELA VEQKSDQGVE GPGGTGGSGS SPNDPVTNIC QAADKQLFTL VEWAKRIPHF   360
SSLPLDDQVI LLRAGWNELL IASFSHRSID VRDGILLATG LHVHRNSAHS AGVGAIFDRV   420
LTELVSKMRD MRMDKTELGC LRAIILFNPD AKGLSNPSEV EVLREKVYAS LETYCKQKYP   480
EQQGRFAKLL LRLPALRSIG LKCLEHLFFF KLIGDTPIDT FLMEMLEAPH QLA           533

SEQ ID NO: 66           moltype = AA  length = 463
FEATURE                 Location/Qualifiers
source                  1..463
                        mol_type = protein
                        organism = Homo sapiens
SEQUENCE: 66
MYGNYSHFMK FPAGYGGSPG HTGSTSMSPS AALSTGKPMD SHPSYTDTPV SAPRTLSAVG    60
TPLNALGSPY RVITSAMGPP SGALAAPPGI NLVAPPSSQL NVVNSVSSSE DIKPLPGLPG   120
IGNMNYPSTS PGSLVKHICA ICGDRSSGKH YGVYSCEGCK GFFKRTIRKD LIYTCRDNKD   180
CLIDKRQRNR CQYCRYQKCL VMGMKREAVQ EERQRSRERA ESEAECATSG HEDMPVERIL   240
EAELAVEPKT ESYGDMNMEN STNDPVTNIC HAADKQLFTL VEWAKRIPHF SDLTLEDQVI   300
LLRAGWNELL IASFSHRSVS VQDGILLATG LHVHRSSAHS AGVGSIFDRV LTELVSKMKD   360
MQMDKSELGC LRAIVLFNPD AKGLSNPSEV ETLREKVYAT LEAYTKQKYP EQPGRFAKLL   420
LRLPALRSIG LKCLEHLFFF KLIGDTPIDT FLMEMLETPL QIT                     463

SEQ ID NO: 67           moltype = AA  length = 493
FEATURE                 Location/Qualifiers
source                  1..493
                        mol_type = protein
                        organism = Homo sapiens
SEQUENCE: 67
MLAATVLTLA LLGNAHACSK GTSHEAGIVC RITKPALLVL NHETAKVIQT AFQRASYPDI    60
TGEKAMMLLG QVKYGLHNIQ ISHLSIASSQ VELVEAKSID VSIQNVSVVF KGTLKYGYTT   120
AWWLGIDQSI DFEIDSAIDL QINTQLTCDS GRVRTDAPDC YLSFHKLLLH LQGEREPGWI   180
KQLFTNFISF TLKLVLKGQI CKEINVISNI MADFVQTRAA SILSDGDIGV DISLTGDPVI   240
TASYLESHHK GHFIYKNVSE DLPLPTFSPT LLGDSRMLYF WFSERVPHSL AKVAFQDGRL   300
MLSLMGDEFK AVLETWGFNT NQEIFQEVVG GFPSQAQVTV HCLKMPKISC QNKGVVVNSS   360
VMVKFLPRP DQQHSVAYTF EEDIVTTVQA SYSKKKLFLS LLDFQITPKT VSNLTESSSE   420
SVQSFLQSMI TAVGIPEVMS RLEVVFTALM NSKGVSLFDI INPEIITRDG FLLLQMDFGF   480
PEHLLVDFLQ SLS                                                      493

SEQ ID NO: 68           moltype = AA  length = 185
FEATURE                 Location/Qualifiers
source                  1..185
                        mol_type = protein
                        organism = Homo sapiens
SEQUENCE: 68
```

```
MKLVSVALMY LGSLAFLGAD TARLDVASEF RKKWNKWALS RGKRELRMSS SYPTGLADVK    60
AGPAQTLIRP QDMKGASRSP EDSSPDAARI RVKRYRQSMN NFQGLRSFGC RFGTCTVQKL   120
AHQIYQFTDK DKDNVAPRSK ISPQGYGRRR RRSLPEAGPG RTLVSSKPQA HGAPAPPSGS   180
APHFL                                                              185

SEQ ID NO: 69           moltype = AA  length = 498
FEATURE                 Location/Qualifiers
source                  1..498
                        mol_type = protein
                        organism = Homo sapiens
SEQUENCE: 69
MTVFLSFAFL AAILTHIGCS NQRRSPENSG RRYNRIQHGQ CAYTFILPEH DGNCRESTTD    60
QYNTNALQRD APHVEPDFSS QKLQHLEHVM ENYTQWLQKL ENYIVENMKS EMAQIQQNAV   120
QNHTATMLEI GTSLLSQTAE QTRKLTDVET QVLNQTSRLE IQLLENSLST YKLEKQLLQQ   180
TNEILKIHEK NSLLEHKILE MEGKHKEELD TLKEEKENLQ GLVTRQTYII QELEKQLNRA   240
TTNNSVLQKQ QLELMDTVHN LVNLCTKEGV LLKGGKREEE KPFRDCADVY QAGFNKSGIY   300
TIYINNMPEP KKVFCNMDVN GGGWTVIQHR EDGSLDFQRG WKEYKMGFGN PSGEYWLGNE   360
FIFAITSQRQ YMLRIELMDW EGNRAYSQYD RFHIGNEKQN YRLYLKGHTG TAGKQSSLIL   420
HGADFSTKDA DNDNCMCKCA LMLTGGWWFD ACGPSNLNGM FYTAGQNHGK LNGIKWHYFK   480
GPSYSLRSTT MMIRPLDF                                                498

SEQ ID NO: 70           moltype = AA  length = 558
FEATURE                 Location/Qualifiers
source                  1..558
                        mol_type = protein
                        organism = Homo sapiens
SEQUENCE: 70
MAALTRDPQF QKLQQWYREH RSELNLRRLF DANKDRFNHF SLTLNTNHGH ILVDYSKNLV    60
TEDVMRMLVD LAKSRGVEAA RERMFNGEKI NYTEGRAVLH VALRNRSNTP ILVDGKDVMP   120
EVNKVLDKMK SFCQRVRSGD WKGYTGKTIT DVINIGIGGS DLGPLMVTEA LKPYSSGGPR   180
VWYVSNIDGT HIAKTLAQLN PESSLFIIAS KTFTTQETIT NAETAKEWFL QAAKDPSAVA   240
KHFVALSTNT TKVKEFGIDP QNMFEFWDWV GGRYSLWSAI GLSIALHVGF DNFEQLLSGA   300
HWMDQHFRTT PLEKNAPVLL ALLGIWYINC FGCETHAMLP YDQYLHRFAA YFQQGDMESN   360
GKYITKSGTR VDHQTGPIVW GEPGTNGQHA FYQLIHQGTK MIPCDFLIPV QTQHPIRKGL   420
HHKILLANFL AQTEALMRGK STEEARKELQ AAGKSPEDLE RLLPHKVFEG NRPTNSIVFT   480
KLTPFMLGAL VAMYEHKIFV QGIIWDINSF DQWGVELGKQ LAKKIEPELD GSAQVTSHDA   540
STNGLINFIK QQREARVQ                                                558

SEQ ID NO: 71           moltype = AA  length = 307
FEATURE                 Location/Qualifiers
source                  1..307
                        mol_type = protein
                        organism = Homo sapiens
SEQUENCE: 71
MPGQELRTVN GSQMLLVLLV LSWLPHGGAL SLAEASRASF PGPSELHSED SRFRELRKRY    60
EDLLTRLRAN QSWEDSNTDL VPAPAVRILT PEVRLGSGGH LHLRISRAAL PEGLPEASRL   120
HRALFRLSPT ASRSWDVTRP LRRQLSLARP QAPALHLRLS PPPSQSDQLL AESSSARPQL   180
ELHLRPQAAR GRRRARARNG DHCPLGPGRC CRLHTVRASL EDLGWADWVL SPREVQVTMC   240
IGACPSQFRA ANMHAQIKTS LHRLKPDTVP APCCVPASYN PMVLIQKTDT GVSLQTYDDL   300
LAKDCHC                                                            307

SEQ ID NO: 72           moltype = AA  length = 247
FEATURE                 Location/Qualifiers
source                  1..247
                        mol_type = protein
                        organism = Homo sapiens
SEQUENCE: 72
MTILFLTMVI SYFGCMKAAP MKEANIRGQG GLAYPGVRTH GTLESVNGPK AGSRGLTSLA    60
DTFEHVIEEL LDEDHKVRPN EENNKDADLY TSRVMLSSQV PLEPPLLFLL EEYKNYLDAA   120
NMSMMVLRHS DPARRGELSV CDSISEWVTA ADKKTAVDMS GGTVTVLEKV PVSKGQLKQY   180
FYETKCNPMG YTKEGCRGID KRHWNSQCRT TQSYVRALTM DSKKRIGWRF IRIDTSCVCT   240
LTIKRGR                                                            247

SEQ ID NO: 73           moltype = AA  length = 1754
FEATURE                 Location/Qualifiers
source                  1..1754
                        mol_type = protein
                        organism = Homo sapiens
SEQUENCE: 73
MAPYPCGCHI LLLLFCCLAA ARANLLNLNW LWFNNEDTSH AATTIPEPQG PLPVQPTADT    60
TTHVTPRNGS TEPATAPGSP EPPSELLEDG QDTPTSAESP DAPEENIAGV GAEILNVAKG   120
IRSFVQLWND TVPTESLARA ETLVLETPVG PLALAGPSST PQENGTTLWP SRGIPSSPGA   180
HTTEAGTLPA PTPSPPSLGR PWAPLTGPSV PPPSSGRASL SSLLGGAPPW GSLQDPDSQG   240
LSPAAAAPSQ QLRPDVRLRL TPLLHPLVMG SLGKHAAPSA FSSGLPGALS QVAVTTLTRD   300
SGAWVSHVAN SVGPGLANNS ALLGADPEAP AGRCLPLPPS LPVCGHLGIS RFWLPNHLHH   360
ESGEQVRAGA RAWGGLLQTH CHPFLAWFFC LLLVPPCGSV PPPAPPPCCQ FCEALQDACW   420
SRLGGGRLPV ACASLPTQED GYCVLIGPAA ERISEEVGLL QLLGDPPPQQ VTQTDDPDVG   480
LAYVFGPDAN SGQVARYHFP SLFFRDFSLL FHIRPATEGP GVLFAITDSA QAMVLLGVKL   540
SGVQDGHQDI SLLYTEPGAG QTHTAASFRL PAFVGQWTHL ALSVAGGFVA LYVDCEEFQR   600
```

```
MPLARSSRGL ELEPGAGLFV AQAGGADPDK FQGVIAELKV RRDPQVSPMH CLDEEGDDSD    660
GASGDSGSGL GDARELLREE TGAALKPRLP APPPVTTPPL AGGSSTEDSR SEEVEEQTTV    720
ASLGAQTLPG SDSVSTWDGS VRTPGGRVKE GGLKGQKGEP GVPGPPGRAG PPGSPCLPGP    780
PGLPCPVSPL GPAGPALQTV PGPQGPPGPP GRDGTPGRDG EPGDPGEDGK PGDTGPQGFP    840
GTPGDVGPKG DKGDPGVGER GPPGPQGPPG PPGPSFRHDK LTFIDMEGSG FGGDLEALRG    900
PRGFPGPPGP PGVPGLPGEP GRFGVNSSDV PGPAGLPGVP GREGPPGFPG LPGPPGPPGR    960
EGPPGRTGQK GSLGEAGAPG HKGSKGAPGP AGARGESGLA GAPGPAGPPG PPGPPGPPGP   1020
GLPAGFDDME GSGGPFWSTA RSADGPQGPP GLPGLKGDPG VPGLPGAKGE VGADGVPGFP   1080
GLPGREGIAG PQGPKGDRGS RGEKGDPGKD GVGQPGLPGP PGPPGPVVYV SEQDGSVLSV   1140
PGPEGRPGFA GFPGPAGPKG NLGSKGERGS PGPKGEKGEP GSIFSPDGGA LGPAQKGAKG   1200
EPGFRGPPGP YGRPGYKGEI GFPGRPGRPG MNGLKGEKGE PGDASLGFGM RGMPGPPGPP   1260
GPPGPPGTPV YDSNVFAESS RPGPPGLPGN QGPPGPKGAK GEVGPPGPPG QFPFDFLQLE   1320
AEMKGEKGDR GDAGQKGERG EPGGGGFFGS SLPGPPGPPG PPGPRGYPGI PGPKGESIRG   1380
QPGPPGPQGP PGIGYEGRQG PPGPPGPPGP PSFPGPHRQT ISVPGPPGPP GPPGPPGTMG   1440
ASSGVRLWAT RQAMLGQVHE VPEGWLIFVA EQEELYVRVQ NGFRKVQLEA RTPLPRGTDN   1500
EVAALQPPVV QLHDSNPYPR REHPHPTARP WRADDILASP PRLPEPQPYP GAPHHSSYVH   1560
LRPARPTSPP AHSHRDFQPV LHLVALNSPL SGGMRGIRGA DFQCFQQARA VGLAGTFRAF   1620
LSSRLQDLYS IVRRADRAAV PIVNLKDELL FPSWEALFSG SEGPLKPGAR IFSFDGKDVL   1680
RHPTWPQKSV WHGSDPNGRR LTESYCETWR TEAPSATGQA SSLLGGRLLG QSAASCHHAY   1740
IVLCIENSFM TASK                                                    1754

SEQ ID NO: 74           moltype = AA  length = 1763
FEATURE                 Location/Qualifiers
source                  1..1763
                        mol_type = protein
                        organism = Homo sapiens
SEQUENCE: 74
MAPYPCGCHI LLLLFCCLAA ARANLLNLNW LWFNNEDTSH AATTIPEPQG PLPVQPTADT     60
TTHVTPRNGS TEPATAPGSP EPPSELLEDG QDTPTSAESP DAPEENIAGV GAEILNVAKG    120
IRSFVQLWND TVPTESLARA ETLVLETPVG PLALAGPSST PQENGTTLWP SRGIPSSPGA    180
HTTEAGTLPA PTPSPPSLGR PWAPLTGPSV PPPSSGRASL SSLLGGAPPW GSLQDPDSQG    240
LSPAAAAPSQ QLQRPDVRLR TPLLHPLVMG SLGKHAAPSA FSSGLPGALS QVAVTTLTRD    300
SGAWVSHVAN SVGPGLANNS ALLGADPEAP AGRCLPLPPS LPVCGHLGIS RFWLPNHLHH    360
ESGEQVRAGA RAWGGLLQTH CHPFLAWFFC LLLVPPCGSV PPPAPPPCCQ FCEALQDACW    420
SRLGGGRLPV ACASLPTQED GYCVLIGPAA ERISEEVGLL QLLGDPPPQQ VTQTDDPDVG    480
LAYVFGPDAN SGQVARYHFP SLFFRDFSLL FHIRPATEGP GVLFAITDSA QAMVLLGVKL    540
SGVQDGHQDI SLLYTEPGAG QTHTAASFRL PAFVGQWTHL ALSVAGGFVA LYVDCEEFQR    600
MPLARSSRGL ELEPGAGLFV AQAGGADPDK FQGVIAELKV RRDPQVSPMH CLDEEGDDSD    660
GASGDSGSGL GDARELLREE TGAALKPRLP APPPVTTPPL AGGSSTEDSR SEEVEEQTTV    720
ASLGAQTLPG SDSVSTWDGS VRTPGGRVKE GGLKGQKGEP GVPGPPGRAG PPGSPCLPGP    780
PGLPCPVSPL GPAGPALQTV PGPQGPPGPP GRDGTPGRDG EPGDPGEDGK PGDTGPQGFP    840
GTPGDVGPKG DKGDPGVGER GPPGPQGPPG PPGPSFRHDK LTFIDMEGSG FGGDLEALRG    900
PRGFPGPPGP PGVPGLPGEP GRFGVNSSDV PGPAGLPGVP GREGPPGFPG LPGPPGPPGR    960
EGPPGRTGQK GSLGEAGAPG HKGSKGAPGP AGARGESGLA GAPGPAGPPG PPGPPGPPGP   1020
GLPAGFDDME GSGGPFWSTA RSADGPQGPP GLPGLKGDPG VPGLPGAKGE VGADGVPGFP   1080
GLPGREGIAG PQGPKGDRGS RGEKGDPGKD GVGQPGLPGP PGPPGPVVYV SEQDGSVLSV   1140
PGPEGRPGFA GFPGPAGPKG NLGSKGERGS PGPKGEKGEP GSIFSPDGGA LGPAQKGAKG   1200
EPGFRGPPGP YGRPGYKGEI GFPGRPGRPG MNGLKGEKGE PGDASLGFGM RGMPGPPGPP   1260
GPPGPPGTPV YDSNVFAESS RPGPPGLPGN QGPPGPKGAK GEVGPPGPPG QFPFDFLQLE   1320
AEMKGEKGDR GDAGQKGERG EPGGGGFFGS SLPGPPGPPG PPGPRGYPGI PGPKGESIRG   1380
QPGPPGPQGP PGIGYEGRQG PPGPPGPPGP PSFPGPHRQT ISVPGPPGPP GPPGPPGTMG   1440
ASSGVRLWAT RQAMLGQVHE VPEGWLIFVA EQEELYVRVQ NGFRKVQLEA RTPLPRGTDN   1500
EVAALQPPVV QLHDSNPYPR REHPHPTARP WRADDILASP PRLPEPQPYP GAPHHSSYVH   1560
LRPARPTSPP AHSHRDFQPV LHLVALNSPL SGGMRGIRGA DFQCFQQARA VGLAGTFRAF   1620
LSSRLQDLYS IVRRADRAAV PIVNLKDELL FPSWEALFSG SEGPLKPGAR IFSFDGKDVL   1680
RHPTWPQKSV WHGSDPNGRR LTESYCETWR TEAPSATGQA SSLLGGRLLG QSAASCHHAY   1740
IVLCIENSFM TASKMGGSHH HHH                                          1763

SEQ ID NO: 75           moltype = AA  length = 1166
FEATURE                 Location/Qualifiers
source                  1..1166
                        mol_type = protein
                        organism = Homo sapiens
SEQUENCE: 75
MLLTLIILLP VVSKFSFVSL SAPQHWSCPE GTLAGNGNST CVGPAPFLIF SHGNSIFRID     60
TEGTNYEQLV VDAGVSVIMD FHYNEKRIYW VDLERQLLQR VFLNGSRQER VCNIEKNVSG    120
MAINWINEEV IWSNQQEGII TVTDMKGNNS HILLSALKYP ANVAVDPVER FIFWSSEVAG    180
SLYRADLDGV GVKALLETSE KITAVSLDVL DKRLFWIQYN REGSNSLICS CDYDGGSVHI    240
SKHPTQHNLF AMSLFGDRIF YSTWKMKTIW IANKHTGKDM VRINLHSSFV PLGELKVVHP    300
LAQPKAEDDT WEPEQKLCKL RKGNCSSTVC GQDLQSHLCM CAEGYALSRD RKYCEDVNEC    360
AFWNHGCTLG CKNTPGSYYC TCPVGFVLLP DGKRCHQLVS CPRNVSECSH DCVLTSEGPL    420
CFCPEGSVLE RDGKTCSGCS SPDNGGCSQL CVPLSPVSWE CDCFPGYDLQ LDEKSCAASG    480
PQPFLLFANS QDIRHMHFDG TDYGTLLSQQ MGMVYALDHD PVENKIYFAH TALKWIERAN    540
MDGSQRERLI EEGVDVPEGL AVDWIGRRFY WTDRGKSLIG RSDLNGKRSK IITKENISQP    600
RGIAVHPMAK RLFWTDTGIN PRIESSSLQG LGRLVIASSD LIWPSGITID FLTDKLYWCD    660
AKQSVIEMAN LDGSKRRRLT QNDVGHPFAV AVFEDYWFS DWAMPSVMRV NKRTGKDRVR    720
LQGSMLKPSS LVVVHPLAKP GADPCLYQNG GCEHICKKRL GTAWCSCREG FMKASDGKTC    780
LALDGHQLLA GGEVDLKNQV TPLDILSKTR VSEDNITESQ HMLVAEIMVS DQDDCAPVGC    840
SMYARCISEG EDATCQCLKG FAGDGKLCSD IDECEMGVPV CPPASSKCIN TEGGYVCRCS    900
```

```
EGYQGDGIHC  LDSTPPPHLR  EDDHHYSVRN  SDSECPLSHD  GYCLHDGVCM  YIEALDKYAC   960
NCVVGYIGER  CQYRDLKWWE  LRHAGHGQQQ  KVIVVAVCVV  VLVMLLLLSL  WGAHYYRTQK  1020
LLSKNPKNPY  EESSRDVRSR  RPADTEDGMS  SCPQPWFVVI  KEHQDLKNGG  QPVAGEDGQA  1080
ADGSMQPTSW  RQEPQLCGMG  TEQGCWIPVS  SDKGSCPQVM  ERSFHMPSYG  TQTLEGGVEK  1140
PHSLLSANPL  WQQRALDPPH  QMELTQ                                          1166

SEQ ID NO: 76           moltype = AA  length = 193
FEATURE                 Location/Qualifiers
source                  1..193
                        mol_type = protein
                        organism = Homo sapiens
SEQUENCE: 76
MGVHECPAWL  WLLLSLLSLP  LGLPVLGAPP  RLICDSRVLQ  RYLLEAKEAE  NITTGCAEHC    60
SLNENITVPD  TKVNFYAWKR  MEVGQQAVEV  WQGLALLSEA  VLRGQALLVN  SSQPWEPLQL   120
HVDKAVSGLR  SLTTLLRALG  AQKEAISPPD  AASAAPLRTI  TADTFRKLFR  VYSNFLRGKL   180
KLYTGEACRT  GDR                                                          193

SEQ ID NO: 77           moltype = AA  length = 288
FEATURE                 Location/Qualifiers
source                  1..288
                        mol_type = protein
                        organism = Homo sapiens
SEQUENCE: 77
MVGVGGGDVE  DVTPRPGGCQ  ISGRGARGCN  GIPGAAAWEA  ALPRRRPRRH  PSVNPRSRAA    60
GSPRTRGRRT  EERPSGSRLG  DRGRGRALPG  GRLGGRGRGR  APERVGGRGR  GRGTAAPRAA   120
PAARGSRPGP  AGTMAAGSIT  TLPALPEDGG  SGAFPPGHFK  DPKRLYCKNG  GFFLRIHPDG   180
RVDGVREKSD  PHIKLQLQAE  ERGVVSIKGV  CANRYLAMKE  DGRLLASKCV  TDECFFFERL   240
ESNNYNTYRS  RKYTSWYVAL  KRTGQYKLGS  KTGPGQKAIL  FLPMSAKS                 288

SEQ ID NO: 78           moltype = AA  length = 211
FEATURE                 Location/Qualifiers
source                  1..211
                        mol_type = protein
                        organism = Homo sapiens
SEQUENCE: 78
MKLWDVVAVC  LVLLHTASAF  PLPAGKRPPE  APAEDRSLGR  RRAPPFALSSD  SNMPEDYPDQ   60
FDDVMDFIQA  TIKRLKRSPD  KQMAVLPRRE  RNRQAAAANP  ENSRGKGRRG  QRGKNRGCVL   120
TAIHLNVTDL  GLGYETKEEL  IFRYCSGSCD  AAETTYDKIL  KNLSRNRRLV  SDKVGQACCR   180
PIAFDDDLSF  LDDNLVYHIL  RKHSAKRCGC  I                                    211

SEQ ID NO: 79           moltype = AA  length = 204
FEATURE                 Location/Qualifiers
source                  1..204
                        mol_type = protein
                        organism = Homo sapiens
SEQUENCE: 79
MAGPATQSPM  KLMALQLLLW  HSALWTVQEA  TPLGPASSLP  QSFLLKCLEQ  VRKIQGDGAA    60
LQEKLCATYK  LCHPEELVLL  GHSLGIPWAP  LSSCPSQALQ  LAGCLSQLHS  GLFLYQGLLQ   120
ALEGISPELG  PTLDTLQLDV  ADFATTIWQQ  MEELGMAPAL  QPTQGAMPAF  ASAFQRRAGG   180
VLVASHLQSF  LEVSYRVLRH  LAQP                                             204

SEQ ID NO: 80           moltype = AA  length = 144
FEATURE                 Location/Qualifiers
source                  1..144
                        mol_type = protein
                        organism = Homo sapiens
SEQUENCE: 80
MWLQSLLLLG  TVACSISAPA  RSPSPSTQPW  EHVNAIQEAR  RLLNLSRDTA  AEMNETVEVI    60
SEMFDLQEPT  CLQTRLELYK  QGLRGSLTKL  KGPLTMMASH  YKQHCPPTPE  TSCATQIITF   120
ESFKENLKDF  LLVIPFDCWE  PVQE                                             144

SEQ ID NO: 81           moltype = AA  length = 454
FEATURE                 Location/Qualifiers
source                  1..454
                        mol_type = protein
                        organism = Homo sapiens
SEQUENCE: 81
MARPNKFLLW  FCCFAWLCFP  ISLGSQASGG  EAQIAASAEL  ESGAMPWSLL  QHIDERDRAG    60
LLPALFKVLS  VGRGGSPRLQ  PDSRALHYMK  KLYKTYATKE  GIPKSNRSHL  YNTVRLFTPC   120
TRHKQAPGDQ  VTGILPSVEL  LFNLDRITTV  EHLLKSVLLY  NINNSVSFSS  AVKCVCNLMI   180
KEPKSSSRTL  GRAPYSFTFN  SQFEFGKKHK  WIQIDVTSLL  QPLVASNKRS  IHMSINFTCM   240
KDQLEHPSAQ  NGLFNMTLVS  PSLILYLNDT  SAQAYHSWYS  LHYKRRPSQG  PDQERSLSAY   300
PVGEEAAEDG  RSSHHRHRRG  QETVSSELKK  PLGPASFNLS  EYFRQFLLPQ  NECELHDFRL   360
SFSQLKWDNW  IVAPHRYNPR  YCKGDCPRAV  GHRYGSPVHT  MVQNIIYEKL  DSSVPRPSCV   420
PAKYSPLSVL  TIEPDGSIAY  KEYEDMIATK  CTCR                                 454

SEQ ID NO: 82           moltype = AA  length = 728
FEATURE                 Location/Qualifiers
source                  1..728
```

```
                          mol_type = protein
                          organism = Homo sapiens
SEQUENCE: 82
MWVTKLLPAL LLQHVLLHLL LLPIAIPYAE GQRKRRNTIH EFKKSAKTTL IKIDPALKIK     60
TKKVNTADQC ANRCTRNKGL PFTCKAFVFD KARKQCLWFP FNSMSSYVKK EFGHEFDLYE    120
NKDYIRNCII GKGRSYKGTV SITKSGIKCQ PWSSMIPHEH SFLPSSYRGK DLQENYCRNP    180
RGEEGGPWCF TSNPEVRYEV CDIPQCSEVE CMTCNGESYR GLMDHTESGK ICQRWDHQTP    240
HRHKFLPERY PDKGFDDNYC RNPDGQPRPW CYTLDPHTRW EYCAIKTCAD NTMNDTDVPL    300
ETTECIQGQG EGYRGTVNTI WNGIPCQRWD SQYPHEHDMT PENFKCKDLR ENYCRNPDGS    360
ESPWCFTTDP NIRVGYCSQI PNCDMSHGQD CYRGNGKNYM GNLSQTRSGL TCSMWDKNME    420
DLHRHIFWEP DASKLNENYC RNPDDDAHGP WCYTGNPLIP WDYCPISRCE GDTTPTIVNL    480
DHPVISCAKT KQLRVVNGIP TRTNIGWMVS LRYRNKHICG GSLIKESWVL TARQCFPSRD    540
LKDYEAWLGI HDVHGRGDEK CKQVLNVSQL VYGPEGSDLV LMKLARPAVL DDFVSTIDLP    600
NYGCTIPEKT SCSVYGWGYT GLINYDGLLR VAHLYIMGNE KCSQHHRGKV TLNESEICAG    660
AEKIGSGPCE GDYGGPLVCE QHKMRMVLGV IVPGRGCAIP NRPGIFVRVA YYAKWIHKII    720
LTYKVPQS                                                             728

SEQ ID NO: 83              moltype = AA   length = 240
FEATURE                    Location/Qualifiers
source                     1..240
                           mol_type = protein
                           organism = Homo sapiens
SEQUENCE: 83
MSRSNRQKEY KCGDLVFAKM KGYPHWPARI DEMPEAAVKS TANKYQVFFF GTHETAFLGP     60
KDLFPYEESK EKFGKPNKRK GFSEGLWEIE NNPTVKASGY QSSQKKSCVE EPEPEPEAAE    120
GDGDKKGNAE GSSDEEGKLV IDEPAKEKNE KGALKRRAGD LLEDSPKRPK EAENPEGEEK    180
EAATLEVERP LPMEVEKNST PSEPGSGRGP PQEEEEEEDE EEEATKEDAE APGIRDHESL    240

SEQ ID NO: 84              moltype = AA   length = 153
FEATURE                    Location/Qualifiers
source                     1..153
                           mol_type = protein
                           organism = Homo sapiens
SEQUENCE: 84
MGKISSLPTQ LFKCCFCDPL KVKMHTMSSS HLFYLALCLL TFTSSATAGP ETLCGAELVD     60
ALQFVCGDRG FYFNKPTGYG SSSRRAPQTG IVDECCFRSC DLRRLEMYCA PLKPAKSARS    120
VRAQRHTDMP KTQKEVHLKN ASRGSAGNKN YRM                                 153

SEQ ID NO: 85              moltype = AA   length = 657
FEATURE                    Location/Qualifiers
source                     1..657
                           mol_type = protein
                           organism = Homo sapiens
SEQUENCE: 85
MLRGPGPGLL LLAVQCLGTA VPSTGASKSK RQAQQMVQPQ SPVAVSQSKP GCYDNGKHYQ     60
INQQWERTYL GNALVCTCYG GSRGFNCESK PEAEETCFDK YTGNTYRVGD TYERPKDSMI    120
WDCTCIGAGR GRISCTIANR CHEGGQSYKI GDTWRRPHET GGYMLECVCL GNGKGEWTCK    180
PIAEKCFDHA AGTSYVVGET WEKPYQGWMM VDCTCLGEGS GRITCTSRNR CNDQDTRTSY    240
RIGDTWRKKD NRGNLLQCIC TGNGRGEWKC ERHTSVQTTS SGSGPFTDVR AAVYQPQPHP    300
QPPPYGHCVT DSGVVYSVGM QWLKTQGNKQ MLCTCLGNGV SCQETAVTQT YGGNSNGEPC    360
VLPFTYNGRT FYSCTTEGRQ DGHLWCSTTS NYEQDQKYSF CTDHTVLVQT RGGNSNGALC    420
HFPFLYNNHN YTDCTSEGRR DNMKWCGTTQ NYDADQKFGF CPMAAHEEIC TTNEGVMYRI    480
GDQWDKQHDM GHMMRCTCVG NGRGEWTCIA YSQLRDQCIV DDITYNVNDT FHKRHEEGHM    540
LNCTCFGQGR GRWKCDPVDQ CQDSETGTFY QIGDSWEKYV HGVRYQCYCY GRGIGEWHCQ    600
PLQTYPSSSG PVEVFITETP SQPNSHPIQW NAPQPSHISK YILRWRPKNS VSI PPRNLGY    657

SEQ ID NO: 86              moltype = AA   length = 375
FEATURE                    Location/Qualifiers
source                     1..375
                           mol_type = protein
                           organism = Homo sapiens
SEQUENCE: 86
MQKLQLCVYI YLFMLIVAGP VDLNENSEQK ENVEKEGLCN ACTWRQNTKS SRIEAIKIQI     60
LSKLRLETAP NISKDVIRQL LPKAPPLREL IDQYDVQRDD SSDGSLEDDD YHATTETIIT    120
MPTESDFLMQ VDGKPKCCFF KFSSKIQYNK VVKAQLWIYL RPVETPTTVF VQILRLIKPM    180
KDGTRYTGIR SLKLDMNPGT GIWQSIDVKT VLQNWLKQPE SNLGIEIKAL DENGHDLAVT    240
FPGPGEDGLN PFLEVKVTDT PKRSRRDFGL DCDEHSTESR CCRYPLTVDF EAFGWDWIIA    300
PKRYKANYCS GECEFVFLQK YPHTHLVHQA NPRGSAGPCC TPTKMSPINM LYFNGKEQII    360
YGKIPAMVVD RCGCS                                                     375

SEQ ID NO: 87              moltype = AA   length = 257
FEATURE                    Location/Qualifiers
source                     1..257
                           mol_type = protein
                           organism = Homo sapiens
SEQUENCE: 87
MSILFYVIFL AYLRGIQGNN MDQRSLPEDS LNSLIIKLIQ ADILKNKLSK QMVDVKENYQ     60
STLPKAEAPR EPERGGPAKS AFQPVIAMDT ELLRQQRRYN SPRVLLSDST PLEPPPLYLM    120
EDYVGSPVVA NRTSRRKRYA EHKSHRGEYS VCDSESLWVT DKSSAIDIRG HQVTVLGEIK    180
```

```
TGNSPVKQYF YETRCKEARP VKNGCRGIDD KHWNSQCKTS QTYVRALTSE NNKLVGWRWI   240
RIDTSCVCAL SRKIGRT                                                  257

SEQ ID NO: 88           moltype = AA  length = 211
FEATURE                 Location/Qualifiers
source                  1..211
                        mol_type = protein
                        organism = Homo sapiens
SEQUENCE: 88
MRTLACLLLL GCGYLAHVLA EEAEIPREVI ERLARSQIHS IRDLQRLLEI DSVGSEDSLD    60
TSLRAHGVHA TKHVPEKRPL PIRRKRSIEE AVPAVCKTRT VIYEIPRSQV DPTSANFLIW   120
PPCVEVKRCT GCCNTSSVKC QPSRVHHRSV KVAKVEYVRK KPKLKEVQVR LEEHLECACA   180
TTSLNPDYRE EDTGRPRESG KKRKRKRLKP T                                  211

SEQ ID NO: 89           moltype = AA  length = 353
FEATURE                 Location/Qualifiers
source                  1..353
                        mol_type = protein
                        organism = Homo sapiens
SEQUENCE: 89
MELTELLLVV MLLPTARLTL SSPAPPACDL RVLSKLLRDS HVLHSKLSQC PEVHPLPTPV    60
LLPAVDFSLG EWKTQMEETK AQDILGAVTL LLEGVMAARG QLGPTCLSSL LGQLSEQVRL   120
LLGALQSLLG TQLPPQGRTT AHKDPNAIFL SFQHLLRGKV RFLMLVGGST LCVRRAPPTT   180
AVPSRTSLVL TLNELPNRTS GLLETNFTAS ARTTGSGLLK WQQGFRAKIP GLLNQTSRSL   240
DQIPGYLNRI HELLNGTRGL FPGPSRRTLG APDISSGTSD TGSLPPNLQP GYSPSPTHPP   300
TGQYTLFPLP PTLPTPVVQL HPLLDPDSAP TPTPTSPLLN TSYTHSQNLS QEG          353

SEQ ID NO: 90           moltype = AA  length = 159
FEATURE                 Location/Qualifiers
source                  1..159
                        mol_type = protein
                        organism = Homo sapiens
SEQUENCE: 90
MVPSAGQLAL FALGIVLAAC QALENSTSPL SDPPVAAAVV SHFNDCPDSH TQFCFHGTCR    60
FLVQEDKPAC VCHSGYVGAR CEHADLLAVV AASQKKQAIT ALVVVSIVAL AVLIITCVLI   120
HCCQVRKHCE WCRALICRHE KPSALLKGRT ACCHSETVV                          159

SEQ ID NO: 91           moltype = AA  length = 390
FEATURE                 Location/Qualifiers
source                  1..390
                        mol_type = protein
                        organism = Homo sapiens
SEQUENCE: 91
MPPSGLRLLL LLLPLLWLLV LTPGRPAAGL STCKTIDMEL VKRKRIEAIR GQILSKLRLA    60
SPPSQGEVPP GPLPEAVLAL YNSTRDRVAG ESAEPEPEPE ADYYAKEVTR VLMVETHNEI   120
YDKFKQSTHS IYMFFNTSEL REAVPEPVLL SRAELRLLRL KLKVEQHVEL YQKYSNNSWR   180
YLSNRLLAPS DSPEWLSFDV TGVVRQWLSR GGEIEGFRLS AHCSCDSRDN TLQVDINGFT   240
TGRRGDLATI HGMNRPFLLL MATPLERAQH LQSSRHRRAL DTNYCFSSTE KNCCVRQLYI   300
DFRKDLGWKW IHEPKGYHAN FCLGPCPYIW SLDTQYSKVL ALYNQHNPGA SAAPCCVPQA   360
LEPLPIVYYV GRKPKVEQLS NMIVRSCKCS                                    390

SEQ ID NO: 92           moltype = AA  length = 233
FEATURE                 Location/Qualifiers
source                  1..233
                        mol_type = protein
                        organism = Homo sapiens
SEQUENCE: 92
MSTESMIRDV ELAEEALPKK TGGPQGSRRC LFLSLFSFLI VAGATTLFCL LHFGVIGPQR    60
EEFPRDLSLI SPLAQAVRSS SRTPSDKPVA HVVANPQAEG QLQWLNRRAN ALLANGVELR   120
DNQLVVPSEG LYLIYSQVLF KGQGCPSTHV LLTHTISRIA VSYQTKVNLL SAIKSPCQRE   180
TPEGAEAKPW YEPIYLGGVF QLEKGDRLSA EINRPDYLDF AESGQVYFGI IAL          233

SEQ ID NO: 93           moltype = AA  length = 191
FEATURE                 Location/Qualifiers
source                  1..191
                        mol_type = protein
                        organism = Homo sapiens
SEQUENCE: 93
MNFLLSWVHW SLALLLYLHH AKWSQAAPMA EGGGQNHHEV VKFMDVYQRS YCHPIETLVD    60
IFQEYPDEIE YIFKPSCVPL MRCGGCCNDE GLECVPTEES NITMQIMRIK PHQGQHIGEM   120
SFLQHNKCEC RPKKDRARQE NPCGPCSERR KHLFVQDPQT CKCSCKNTDS RCKARQLELN   180
ERTCRCDKPR R                                                        191

SEQ ID NO: 94           moltype = AA  length = 170
FEATURE                 Location/Qualifiers
source                  1..170
                        mol_type = protein
                        organism = Homo sapiens
SEQUENCE: 94
```

-continued

```
MPVMRLFPCF LQLLAGLALP AVPPQQWALS AGNGSSEVEV VPFQEVWGRS YCRALERLVD  60
VVSEYPSEVE HMFSPSCVSL LRCTGCCGDE NLHCVPVETA NVTMQLLKIR SGDRPSYVEL  120
TFSQHVRCEC RPLREKMKPE RRRPKGRGKR RREKQRPTDC HLCGDAVPRR             170

SEQ ID NO: 95          moltype = AA  length = 270
FEATURE                Location/Qualifiers
source                 1..270
                       mol_type = protein
                       organism = Ricinus communis
SEQUENCE: 95
DNNIFPKQYP IINFTTAGAT VQSYTNFIRA VRGRLTTGAD VRHEIPVLPN RVGLPINQRF  60
ILVELSNHAE LSVTLALDVT NAYVVGYRAG NSAYFFHPDN QEDAEAITHL FTDVQNRYTF  120
AFGGNYDRLE QLAGNLRENI ELGNGPLEEA ISALYYYSTG GTQLPTLARS FIICIQMISE  180
AARFQYIEGE MRTRIRYNRR SAPDPSVITL ENSWGRLSTA IQESNQGAFA SPIQLQRRNG  240
SKFSVYDVSI LIPIIALMVY RCAPPPSSQF                                   270

SEQ ID NO: 96          moltype = AA  length = 262
FEATURE                Location/Qualifiers
source                 1..262
                       mol_type = protein
                       organism = Ricinus communis
SEQUENCE: 96
ADVCMDPEPI VRIVGRNGLC VDVRDGRFHN GNAIQLWPCK SNTDANQLWT LKRDNTIRSN  60
GKCLTTYGYS PGVYVMIYDC NTAATDATRW QIWDNGTIIN PRSSLVLAAT SGNSGTTLTV  120
QTNIYAVSQG WLPTNNTQPF VTTIVGLYGL CLQANSGQVW IEDCSSEKAE QQWALYADGS  180
IRPQQNRDNC LTSDSNIRET VVKILSCGPA SSGQRWMFKN DGTILNLYSG LVLDVRASDP  240
SLKQIILYPL HGDPNQIWLP LF                                           262

SEQ ID NO: 97          moltype = AA  length = 560
FEATURE                Location/Qualifiers
SITE                   9
                       note = misc_feature - Xaa can be any naturally occurring
                        amino acid
SITE                   139
                       note = misc_feature - Xaa can be any naturally occurring
                        amino acid
SITE                   149
                       note = misc_feature - Xaa can be any naturally occurring
                        amino acid
SITE                   510
                       note = misc_feature - Xaa can be any naturally occurring
                        amino acid
SITE                   525
                       note = misc_feature - Xaa can be any naturally occurring
                        amino acid
SITE                   558
                       note = misc_feature - Xaa can be any naturally occurring
                        amino acid
source                 1..560
                       mol_type = protein
                       organism = Corynebacterium diphtheriae
SEQUENCE: 97
MSRKLFASXL IGALLGIGAP PSAHAGADDV VDSSKSFVME NFSSYHGTKP GYVDSIQKGI  60
QKPKSGTQRN YDDDWKGFYS TDNKYDAAGY SVDNENPLSG KAGDVVKVTY PGLTKVLALK  120
VDNAETIKKE LGLSLTEPXM EQVGTEEFXK RFGDGASRVV LSLPFAEGSS SVEYINNWEQ  180
AKALSVKLEI NFETRGKRGQ DAMYEYMAQA CAGNRVRRSV GRSLSCINLD WDVIRDKTKT  240
KIESLKEHGP IKNKMSESPN KTVSQEKAKQ YLEEFHQTAL EHPQLSELKT VTGTNPLFAG  300
ANYAAWAVNV AQVIDSETAD NLEKTTAALS ILPGIGSVMG IADGAVHHNT EEIVAQSIAL  360
SSLMVAQAIP LVGELVDIGF APYNFVESII NLFQVVHNSY NRSAYSPGHK TQPFLHDGYA  420
VSWNTVEDSI IRTGFQGESG HDIKITAENT PLPIASVLLP TIPGKLDVNK SKTHISVNGR  480
KIRMRCRAID GDVTFCRPKS PVYVGNGVHX NLHVAFHRSS SEKIXSNEIS SDSIGVLGYQ  540
KTVDHTKVNS KLSLFFEXKS                                              560

SEQ ID NO: 98          moltype = AA  length = 638
FEATURE                Location/Qualifiers
source                 1..638
                       mol_type = protein
                       organism = Pseudomonas aeruginosa
SEQUENCE: 98
MHLTPHWIPL VASLGLLAGG SFASAAEEAF DLWNECAKAC VLDLKDGVRS SRMSVDPAIA  60
DTNGQGVLHY SMVLEGGNDA LKLAIDNALS ITSDGLTIRL EGGVEPNKPV RYSYTRQARG  120
SWSLNWLVPI GHEKPSNIKV FIHELNAGNQ LSHMSPIYTI EMGDELLAKL ARDATFFVRA  180
HESNEMQPTL AISHAGVSVV MAQAQPRREK RWSEWASGKV LCLLDPLDGV YNYLAQQRCN  240
LDDTWEGKIY RVLAGNPAKH DLDIKPTVIS HRLHFPEGGS LAALTAHQAC HLPLETFTRH  300
RQPRGWEQLE QCGYPVQRLV ALYLAARLSW NQVDQVIRNA LASPGSGGDL GEAIREQPEQ  360
ARLALTLAAA ESERFVRQGT GNDEAGAASA DVVSLTCPVA AGECAGPADS GDALLERNYP  420
TGAEFLGDGG DISFSTRGTQ NWTVERLLQA HRQLEERGYV FVGYHGTFLE AAQSIVFGGV  480
RARSQDLDAI WRGFYIAGDP ALAYGYAQDQ EPDARGRIRN GALLRVYVPR SSLPGFYRTG  540
LTLAAPEAAG EVERLIGHPL PLRLDAITGP EEEGGRLETI LGWPLAERTV VIPSAIPTDP  600
```

```
RNVGGDLDPS SIPDKEQAIS ALPDYASQPG KPPREDLK                              638

SEQ ID NO: 99            moltype = AA   length = 316
FEATURE                  Location/Qualifiers
source                   1..316
                         mol_type = protein
                         organism = Gelonium multiflorum
SEQUENCE: 99
MKGNMKVYWI KIAVATWFCC TTIVLGSTAR IFSLPTNDEE ETSKTLGLDT VSFSTKGATY       60
ITYVNFLNEL RVKLKPEGNS HGIPLLRKKC DDPGKCFVLV ALSNDNGQLA EIAIDVTSVY      120
VVGYQVRNRS YFFKDAPDAA YEGLFKNTIK TRLHFGGSYP SLEGEKAYRE TTDLGIEPLR      180
IGIKKLDENA IDNYKPTEIA SSLLVVIQMV SEAARFTFIE NQIRNNFQQR IRPANNTISL      240
ENKWGKLSFQ IRTSGANGMF SEAVELERAN GKKYYVTAVD QVKPKIALLK FVDKDPKTSL      300
AAELIIQNYE SLVGFD                                                     316

SEQ ID NO: 100           moltype = AA   length = 292
FEATURE                  Location/Qualifiers
source                   1..292
                         mol_type = protein
                         organism = Saponaria officinalis
SEQUENCE: 100
MKIYVVATIA WILLQFSAWT TTDAVTSITL DLVNPTAGQY SSFVDKIRNN VKDPNLKYGG       60
TDIAVIGPPS KDKFLRINFQ SSRGTVSLGL KRDNLYVVAY LAMDNTNVNR AYYFKSEITS      120
AELTALFPEA TTANQKALEY TEDYQSIEKN AQITQGDKSR KELGLGIDLL LTFMEAVNKK      180
ARVVKNEARF LLIAIQMTAE VARFRYIQNL VTKNFPNKFD SDNKVIQFEV SWRKISTAIY      240
GDAKNGVFNK DYDFGFGKVR QVKDLQMGLL MYLGKPKSSN EANSTAYATT VL             292

SEQ ID NO: 101           moltype = AA   length = 386
FEATURE                  Location/Qualifiers
source                   1..386
                         mol_type = protein
                         organism = Pseudomonas aeruginosa
SEQUENCE: 101
LAGNPAKHDL DIKPTVISHR LHFPEGGSLA ALTAHQACHL PLETFTRHRQ PRGWEQLEQC       60
GYPVQRLVAL YLAARLSWNQ VDQVIRNALA SPGSGGDLGE AIREQPEQAR LALTLAAAES      120
ERFVRQGTGN DEAGAASADV VSLTCPVAAG ECAGPADSGD ALLERNYPTG AEFLGDGGDI      180
SFSTRGTQNW TVERLLQAHR QLEERGYVFV GYHGTFLEAA QSIVFGGVRA RSQDLDAIWR      240
GFYIAGDPAL AYGYAQDQEP DARGRIRNGA LLRVYVPRSS LPGFYRTGLT LAAPEAAGEV      300
ERLIGHPLPL RLDAITGPEE EGGRLETILG WPLAERTVVI PSAIPTDPRN VGGDLDPSSI      360
PDKEQAISAL PDYASQPGKP PREDLK                                          386

SEQ ID NO: 102           moltype = AA   length = 370
FEATURE                  Location/Qualifiers
source                   1..370
                         mol_type = protein
                         organism = Pseudomonas aeruginosa
SEQUENCE: 102
LAGNPAKHDL DIKPTVISHR LHFPEGGSLA ALTAHQACHL PLETFTRHRQ PRGWEQLEQC       60
GYPVQRLVAL YLAARLSWNQ VDQVIRNALA SPGSGGDLGE AIREQPEQAR LAGNDEAGAA      120
SADVVSLTCP VAAGECAGPA DSGDALLERN YPTGAEFLGD GGDISFSTRG TQNWTVERLL      180
QAHRQLEERG YVFVGYHGTF LEAAQSIVFG GVRARSQDLD AIWRGFYIAG DPALAYGYAQ      240
DQEPDARGRI RNGALLRVYV PRSSLPGFYR TGLTLAAPEA AGEVERLIGH PLPLRLDAIT      300
GPEEEGGRLE TILGWPLAER TVVIPSAIPT DPRNVGGDLD PSSIPDKEQA ISALPDYASQ      360
PGKPPREDLK                                                            370

SEQ ID NO: 103           moltype = AA   length = 1620
FEATURE                  Location/Qualifiers
source                   1..1620
                         mol_type = protein
                         organism = Homo sapiens
SEQUENCE: 103
MGAIGLLWLL PLLLSTAAVG SGMGTGQRAG SPAAGPPLQP REPLSYSRLQ RKSLAVDFVV       60
PSLFRVYARD LLLPPSSSEL KAGRPEARGS LALDCAPLLR LLGPAPGVSW TAGSPAPAEA      120
RTLSRVLKGG SVRKLRRAKQ LVLELGEEAI LEGCVGPPGE AAVGLLQFNL SELFSWWIRQ      180
GEGRLRIRLM PEKKASEVGR EGRLSAAIRA SQPRLLFQIF GTGHSSLESP TNMPSPSPDY      240
FTWNLTWIMK DSFPFLSHRS RYGLECSFDF PCELEYSPPL HDLRNQSWSW RRIPSEEASQ      300
MDLLDGPGAE RSKEMPRGSF LLLNTSADSK HTILSPWMRS SSEHCTLAVS VHRHLQPSGR      360
YIAQLLPHNE AAREILMPT PGKHGWTVLQ GRIGRPDNPF RVALEYISSG NRSLSAVDFF      420
ALKNCSEGTS PGSKMALQSS FTCWNGTVLQ LGQACDFHQD CAQGEDESQM CRKLPVGFYC      480
NFEDGFCGWT QGTLSPHTPQ WQVRTLKDAR FQDHQDHALL LSTTDVPASE SATVTSATFP      540
APIKSSPCEL RMSWLIRGVL RGNVSLVLVE NKTGKEQGRM VWHVAAYEGL SLWQWMVLPL      600
LDVSDRFWLQ MVAWWGQGSR AIVAFDNISI SLDCYLTISG EDKILQNTAP KSRNLFERNP      660
NKELKPGENS PRQTPIFDPT VHWLFTTCGA SGPHGPTQAQ CNNAYQNSNL SVEVGSEGPL      720
KGIQIWKVPA TDTYSISGYG AAGGKGGKNT MMRSHGVSVL GIFNLEKDDM LYILVGQQGE      780
DACPSTNQLI QKVCIGENNV IEEEIRVNRS VHEWAGGGGG GGGATYVFKM KDGVPVPLII      840
AAGGGGGRAYG AKTDTFHPER LENNSSVLGL NGNSGAAGGG GWNDNTSLL WAGKSLQEGA      900
TGGHSCPQAM KKWGWETRGG FGGGGGGCSS GGGGGGYIGG NAASNNDPEM DGEDGVSFIS      960
PLGILYTPAL KVMEGHGEVN IKHYLNCSHC EVDECHMDPE SHKVICFCDH GTVLAEDGVS     1020
CIVSPTPEPH LPLSLILSVV TSALVAALVL AFSGIMIVYR RKHQELQAMQ MELQSPEYKL     1080
```

```
SKLRTSTIMT DYNPNYCFAG KTSSISDLKE VPRKNITLIR GLGHGAFGEV YEGQVSGMPN   1140
DPSPLQVAVK TLPEVCSEQD ELDFLMEALI ISKFNHQNIV RCIGVSLQSL PRFILLELMA   1200
GGDLKSFLRE TRPRPSQPSS LAMLDLLHVA RDIACGCQYL EENHFIHRDI AARNCLLTCP   1260
GPGRVAKIGD FGMARDIYRA SYYRKGGCAM LPVKWMPPEA FMEGIFTSKT DTWSFGVLLW   1320
EIFSLGYMPY PSKSNQEVLE FVTSGGRMDP PKNCPGPVYR IMTQCWQHQP EDRPNFAIIL   1380
ERIEYCTQDP DVINTALPIE YGPLVEEEEK VPVRPKDPEG VPPLLVSQQA KREEERSPAA   1440
PPPLPTTSSG KAAKKPTAAE ISVRVPRGPA VEGGHVNMAF SQSNPPSELH KVHGSRNKPT   1500
SLWNPTYGSW FTEKPTKKNN PIAKKEPHDR GNLGLEGSCT VPPNVATGRL PGASLLLEPS   1560
SLTANMKEVP LFRLRHFPCG NVNYGYQQQG LPLEAATAPG AGHYEDTILK SKNSMNQPGP   1620

SEQ ID NO: 104         moltype = AA   length = 6
FEATURE                Location/Qualifiers
REGION                 1..6
                       note = PSA derived synthetic polypeptide
source                 1..6
                       mol_type = protein
                       organism = synthetic construct
SEQUENCE: 104
HSSKLQ                                                                6

SEQ ID NO: 105         moltype = AA   length = 1255
FEATURE                Location/Qualifiers
source                 1..1255
                       mol_type = protein
                       organism = Homo sapiens
SEQUENCE: 105
MTPGTQSPFF LLLLLTVLTV VTGSGHASST PGGEKETSAT QRSSVPSSTE KNAVSMTSSV    60
LSSHSPGSGS STTQGQDVTL APATEPASGS AATWGQDVTS VPVTRPALGS TTPPAHDVTS   120
APDNKPAPGS TAPPAHGVTS APDTRPAPGS TAPPAHGVTS APDTRPAPGS TAPPAHGVTS   180
APDTRPAPGS TAPPAHGVTS APDTRPAPGS TAPPAHGVTS APDTRPAPGS TAPPAHGVTS   240
APDTRPAPGS TAPPAHGVTS APDTRPAPGS TAPPAHGVTS APDTRPAPGS TAPPAHGVTS   300
APDTRPAPGS TAPPAHGVTS APDTRPAPGS TAPPAHGVTS APDTRPAPGS TAPPAHGVTS   360
APDTRPAPGS TAPPAHGVTS APDTRPAPGS TAPPAHGVTS APDTRPAPGS TAPPAHGVTS   420
APDTRPAPGS TAPPAHGVTS APDTRPAPGS TAPPAHGVTS APDTRPAPGS TAPPAHGVTS   480
APDTRPAPGS TAPPAHGVTS APDTRPAPGS TAPPAHGVTS APDTRPAPGS TAPPAHGVTS   540
APDTRPAPGS TAPPAHGVTS APDTRPAPGS TAPPAHGVTS APDTRPAPGS TAPPAHGVTS   600
APDTRPAPGS TAPPAHGVTS APDTRPAPGS TAPPAHGVTS APDTRPAPGS TAPPAHGVTS   660
APDTRPAPGS TAPPAHGVTS APDTRPAPGS TAPPAHGVTS APDTRPAPGS TAPPAHGVTS   720
APDTRPAPGS TAPPAHGVTS APDTRPAPGS TAPPAHGVTS APDTRPAPGS TAPPAHGVTS   780
APDTRPAPGS TAPPAHGVTS APDTRPAPGS TAPPAHGVTS APDTRPAPGS TAPPAHGVTS   840
APDTRPAPGS TAPPAHGVTS APDTRPAPGS TAPPAHGVTS APDTRPAPGS TAPPAHGVTS   900
APDTRPAPGS TAPPAHGVTS APDTRPAPGS TAPPAHGVTS APDNRPALGS TAPPVHNVTS   960
ASGSASGSAS TLVHNGTSAR ATTTPASKST PFSIPSHHSD TPTTLASHST KTDASSTHHS  1020
SVPPLTSSNH STSPQLSTGV SFFFLSFHIS NLQFNSSLED PSTDYYQELQ RDISEMFLQI  1080
YKQGGFLGLS NIKFRPGSVV VQLTLAFREG TINVHDVETQ FNQYKTEAAS RYNLTISDVS  1140
VSDVPFPFSA QSGAGVPGWG IALLLVLCVL VALAIVYLIA LAVCQCRRKN YGQLDIFPAR  1200
DTYHPMSEYP TYHTHGRYVP PSSTDRSPYE KVSAGNGGSS LSYTNPAVAA TSANL       1255

SEQ ID NO: 106         moltype = AA   length = 7
FEATURE                Location/Qualifiers
REGION                 1..7
                       note = PSA SYNTHETIC POLYPEPTIDE FRAGMENT
source                 1..7
                       mol_type = protein
                       organism = synthetic construct
SEQUENCE: 106
HSSKLQK                                                               7

SEQ ID NO: 107         moltype = AA   length = 202
FEATURE                Location/Qualifiers
source                 1..202
                       mol_type = protein
                       organism = Homo sapiens
SEQUENCE: 107
MCYGKCARCI GHSLVGLALL CIAANILLYF PNGETKYASE NHLSRFVWFF SGIVGGGLLM    60
LLPAFVFIGL EQDDCCGCCG HENCGKRCAM LSSVLAALIG IAGSGYCVIV AALGLAEGPL   120
CLDSLGQWNY TFASTEGQYL LDTSTWSECT EPKHIVEWNV SLFSILLALG GIEFILCLIQ   180
VINGVLGGIC GFCCSHQQQY DC                                            202

SEQ ID NO: 108         moltype = AA   length = 7
FEATURE                Location/Qualifiers
REGION                 1..7
                       note = PSA SYNTHETIC POLYPEPTIDE FRAGMENT
SITE                   6
                       note = X - ETHANYL-D-ALANINE
source                 1..7
                       mol_type = protein
                       organism = synthetic construct
SEQUENCE: 108
```

```
HSSKLXK                                                                            7

SEQ ID NO: 109          moltype = AA  length = 530
FEATURE                 Location/Qualifiers
source                  1..530
                        mol_type = protein
                        organism = Homo sapiens
SEQUENCE: 109
MRRLWGAARK PSGAGWEKEW AEAPQEAPGA WSGRLGPGRS GRKGRAVPGW ASWPAHLALA    60
ARPARHLGGA GQGPRPLHSG TAPFHSRASG ERQRRLEPQL QHESRCRSST PADAWRAEAA   120
LPVRAMGAPW GSPTAAAGGR RGWRRGRGLP WTVCVLAAAG LTCTALITYA CWGQLPPLPW   180
ASPTPSRPVG VLLWWEPFGG RDSAPRPPPD CRLRFNISGC RLLTDRASYG EAQAVLFHHR   240
DLVKGPPDWP PPWGIQAHTA EEVDLRVLDY EEAAAAAEAL ATSSPRPPGQ RWVWMNFESP   300
SHSPGLRSLA SNLFNWTLSY RADSDVFVPY GYLYPRSHPG DPPSGLAPPL SRKQGLVAWV   360
VSHWDERQAR VRYYHQLSQH VTVDVFGRGG PGQPVPEIGL LHTVARYKFY LAFENSQHLD   420
YITEKLWRNA LLAGAVPVVL GPDRANYERF VPRGAFIHVD DFPSASSLAS YLLFLDRNPA   480
VYRRYFHWRR SYAVHITSFW DEPWCRVCQA VQRAGDRPKS IRNLASWFER             530

SEQ ID NO: 110          moltype = AA  length = 609
FEATURE                 Location/Qualifiers
source                  1..609
                        mol_type = protein
                        organism = Homo sapiens
SEQUENCE: 110
MKWVESIFLI FLLNFTESRT LHRNEYGIAS ILDSYQCTAE ISLADLATIF FAQFVQEATY    60
KEVSKMVKDA LTAIEKPTGD EQSSGCLENQ LPAFLEELCH EKEILEKYGH SDCCSQSEEG   120
RHNCFLAHKK PTPASIPLFQ VPEPVTSCEA YEEDRETFMN KFIYEIARRH PFLYAPTILL   180
WAARYDKIIP SCCKAENAVE CFQTKAATVT KELRESSLLN QHACAVMKNF GTRTFQAITV   240
TKLSQKFTKV NFTEIQKLVL DVAHVHEHCC RGDVLDCLQD GEKIMSYICS QQDTLSNKIT   300
ECCKLTTLER GQCIIHAEND EKPEGLSPNL NRFLGDRDPN QFSSGEKNIF LASFVHEYSR   360
RHPQLAVSVI LRVAKGYQEL LEKCFQTENP LECQDKGEEE LQKYIQESQA LAKRSCGLFQ   420
KLGEYYLQNA FLVAYTKKAP QLTSSELMAI TRKMAATAAT CCQLSEDKLL ACGEGAADII   480
IGHLCIRHEM TPVNPGVGQC CTSSYANRRP CFSSLVVDET YVPPAFSDDK FIFHKDLCQA   540
QGVALQTMKQ EFLINLVKQK PQITEEQLEA VIADFSGLLE KCCQGQEQEV CFAEEGQKLI   600
SKTRAALGV                                                          609

SEQ ID NO: 111          moltype = AA  length = 6
FEATURE                 Location/Qualifiers
REGION                  1..6
                        note = PSA SYNTHETIC POLYPEPTIDE FRAGMENT
SITE                    1
                        note = B - 4Hyp
SITE                    4
                        note = X - CYCLOHEXYL GLYCINE
source                  1..6
                        mol_type = protein
                        organism = synthetic construct
SEQUENCE: 111
BASXQS                                                                             6

SEQ ID NO: 112          moltype = AA  length = 550
FEATURE                 Location/Qualifiers
source                  1..550
                        mol_type = protein
                        organism = Homo sapiens
SEQUENCE: 112
MPRIPASPLS CCPPDMLGPC MLLLLLLLGL RLQLSLGIIP VEEENPDFWN REAAEALGAA    60
KKLQPAQTAA KNLIIFLGDG MGVSTVTAAR ILKGQKKDKL GPEIPLAMDR FPYVALSKTY   120
NVDKHVPDSG ATATAYLCGV KGNFQTIGLS AAARFNQCNT TRGNEVISVM NRAKKAGKSV   180
GVVTTTRVQH ASPAGTYAHT VNRNWYSDAD VPASARQEGC QDIATQLISN MDIDVILGGG   240
RKYMFRMGTP DPEYPDDYSQ GGTRLDGKNL VQEWLAKRQG ARYVWNRTEL MQASLDPSVT   300
HLMGLFEPGD MKYEIHRDST LDPSLMEMTE AALRLLSRNP RGFFLFVEGG RIDHGHHESR   360
AYRALTETIM FDDAIERAGQ LTSEEDTLSL VTADHSHVFS FGGYPLRGSS IPGLAPGKAR   420
DRKAYTVLLY GNGPGYVLKD GARPDVTESE SGSPEYRQQS AVPLDEETHA GEDVAVFARG   480
PQAHLVHGVQ EQTFIAHVMA FAACLEPYTA CDLAPPAGTT DAAHPGRSVV PALLPLLAGT   540
LLLLETATAP                                                         550

SEQ ID NO: 113          moltype = AA  length = 261
FEATURE                 Location/Qualifiers
source                  1..261
                        mol_type = protein
                        organism = Homo sapiens
SEQUENCE: 113
MWVPVVFLTL SVTWIGAAPL ILSRIVGGWE CEKHSQPWQV LVASRGRAVC GGVLVHPQWV    60
LTAAHCIRNK SVILLGRHSL FHPEDTGQVF QVSHSFPHPL YDMSLLKNRF LRPGDDSSHD   120
LMLLRLSEPA ELTDAVKVMD LPTQEPALGT TCYASGWGSI EPEEFLTPKK LQCVDLHVIS   180
NDVCAQVHPQ KVTKFMLCAG RWTGGKSTCS GDSGGPLVCN GVLQGITSWG SEPCALPERP   240
SLYTKVVHYR KWIKDTIVAN P                                            261
```

```
SEQ ID NO: 114            moltype = AA  length = 750
FEATURE                   Location/Qualifiers
source                    1..750
                          mol_type = protein
                          organism = Homo sapiens
SEQUENCE: 114
MWNLLHETDS AVATARRPRW LCAGALVLAG GFFLLGFLFG WFIKSSNEAT NITPKHNMKA   60
FLDELKAENI KKFLYNFTQI PHLAGTEQNF QLAKQIQSQW KEFGLDSVEL AHYDVLLSYP  120
NKTHPNYISI INEDGNEIFN TSLFEPPPPG YENVSDIVPP FSAFSPQGMP EGDLVYVNYA  180
RTEDFFKLER DMKINCSGKI VIARYGKVFR GNKVKNAQLA GAKGVILYSD PADYFAPGVK  240
SYPDGWNLPG GGVQRGNILN LNGAGDPLTP GYPANEYAYR RGIAEAVGLP SIPVHPIGYY  300
DAQKLLEKMG GSAPPDSSWR GSLKVPYNVG PGFTGNFSTQ KVKMHIHSTN EVTRIYNVIG  360
TLRGAVEPDR YVILGGHRDS WVFGGIDPQS GAAVVHEIVR SFGTLKKEGW RPRRTILFAS  420
WDAEEFGLLG STEWAEENSR LLQERGVAYI NADSSIEGNY TLRVDCTPLM YSLVHNLTKE  480
LKSPDEGFEG KSLYESWTKK SPSPEFSGMP RISKLGSGND FEVFFQRLGI ASGRARYTKN  540
WETNKFSGYP LYHSVYETYE LVEKFYDPMF KYHLTVAQVR GGMVFELANS IVLPFDCRDY  600
AVVLRKYADK IYSISMKHPQ EMKTYSVSFD SLFSAVKNFT EIASKFSERL QDFDKSNPIV  660
LRMMNDQLMF LERAFIDPLG LPDRPFYRHV IYAPSSHNKY AGESFPGIYD ALFDIESKVD  720
PSKAWGEVKR QIYVAAFTVQ AAAETLSEVA                                   750

SEQ ID NO: 115            moltype = AA  length = 386
FEATURE                   Location/Qualifiers
source                    1..386
                          mol_type = protein
                          organism = Homo sapiens
SEQUENCE: 115
MRAAPLLLAR AASLNLGFLF LLFFWLDRSV LAKELKFVTL VFRHGDRSPI DTFPTDPIKE   60
SSWPQGFGQL TQLGMEQHYE LGEYIRKRYR KFLNESYKHE QVYIRSTDVD RTLMSAMTNL  120
AALVPPEGVS IWNPILLWQP IPVHTVPLSE DQLLYLPFRN CPRFQELESE TLKSEEFQKR  180
LHPYKDFIAT LGKLSGLHGQ DLFGIWSKVY DPLYCESVHN FTLPSRATED TMTKLRELSE  240
LSLLSLYGIH KQKEKSRLQG GVLVNEILNH MKRATQIPSY KKLIMYSAHD TTVSGLQMAL  300
DVYNGLLPPY ASCHLTELYF EKGEYFVEMY YRNETQHEPY PLMLPGCSPS CPLERFAELV  360
GPVIPQDWST ECMTTNSHQG TEDSTD                                       386

SEQ ID NO: 116            moltype = AA  length = 7
FEATURE                   Location/Qualifiers
REGION                    1..7
                          note = PSA SYNTHETIC POLYPEPTIDE FRAGMENT
SITE                      1
                          note = B - 4Hyp
SITE                      4
                          note = X - CYCLOHEXYL GLYCINE
source                    1..7
                          mol_type = protein
                          organism = synthetic construct
SEQUENCE: 116
BASXQSL                                                              7

SEQ ID NO: 117            moltype = AA  length = 309
FEATURE                   Location/Qualifiers
source                    1..309
                          mol_type = protein
                          organism = Homo sapiens
SEQUENCE: 117
MSLEQRSLHC KPEEALEAQQ EALGLVCVQA ATSSSSPLVL GTLEEVPTAG STDPPQSPQG   60
ASAFPTTINF TRQRQPSEGS SSREEEGPST SCILESLFRA VITKKVADLV GFLLLKYRAR  120
EPVTKAEMLE SVIKNYKHCF PEIFGKASES LQLVFGIDVK EADPTGHSYV LVTCLGLSYD  180
GLLGDNQIMP KTGFLIIVLV MIAMEGGHAP EEEIWEELSV MEVYDGREHS AYGEPRKLLT  240
QDLVQEKYLE YRQVPDSDPA RYEFLWGPRA LAETSYVKVL EYVIKVSARV RFFFPSLREA  300
ALREEEEGV                                                          309

SEQ ID NO: 118            moltype = AA  length = 314
FEATURE                   Location/Qualifiers
source                    1..314
                          mol_type = protein
                          organism = Homo sapiens
SEQUENCE: 118
MPLEQRSQHC KPEEGLEARG EALGLVGAQA PATEEQQTAS SSSTLVEVTL GEVPAADSPS   60
PPHSPQGASS FSTTINYTLW RQSDEGSSNQ EEEGPRMFPD LESEFQAAIS RKMVELVHFL  120
LLKYRAREPV TKAEMLESVL RNCQDFFPVI FSKASEYLQL VFGIEVVEVV PISHLYILVT  180
CLGLSYDGLL GDNQVMPKTG LLIIVLAIIA IEGDCAPEEK IWEELSMLEV FEGREDSVFA  240
HPRKLLMQDL VQENYLEYRQ VPGSDPACYE FLWGPRALIE TSYVKVLHHT LKIGGEPHIS  300
YPPLHERALR EGEE                                                    314

SEQ ID NO: 119            moltype = AA  length = 314
FEATURE                   Location/Qualifiers
source                    1..314
                          mol_type = protein
                          organism = Homo sapiens
```

-continued

```
SEQUENCE: 119
MPLEQRSQHC KPEEGLEARG EALGLVGAQA PATEEQEAAS SSSTLVEVTL GEVPAAESPD    60
PPQSPQGASS LPTTMNYPLW SQSYEDSSNQ EEEGPSTFPD LESEFQAALS RKVAELVHFL   120
LLKYRAREPV TKAEMLGSVV GNWQYFFPVI FSKASSSLQL VFGIELMEVD PIGHLYIFAT   180
CLGLSYDGLL GDNQIMPKAG LLIIVLAIIA REGDCAPEEK IWEELSVLEV FEGREDSILG   240
DPKKLLTQHF VQENYLEYRQ VPGSDPACYE FLWGPRALVE TSYVKVLHHM VKISGGPHIS   300
YPPLHEWVLR EGEE                                                    314

SEQ ID NO: 120          moltype = AA  length = 317
FEATURE                 Location/Qualifiers
source                  1..317
                        mol_type = protein
                        organism = Homo sapiens
SEQUENCE: 120
MSLEQKSQHC KPEEGVEAQE EALGLVGAQA PTTEEQEAAV SSSSPLVLGT LEKVPAAESA    60
DPPQSPQGAS ALPTTISFTC WRQPNEGSSS QEEEEASTSP DAESLFREAL SNKVDELAHF   120
LLRKYRAKEL VTKAEMLERV IKNYKRCFPV IFGKASESLK MIFGIDVKEV DPASNTYTLV   180
TCLGLSYDGL LGNNQIFPKT GLLIIVLGTI AMEGDSASEE EIWEELGVMG VYDGREHTVY   240
GEPRKLLTQD WVQENYLEYR QVPGSNPARY EFLWGPRALA ETSYVKVLEH VVRVNARVRI   300
AYPSLREAAL LEEEEGV                                                 317

SEQ ID NO: 121          moltype = AA  length = 760
FEATURE                 Location/Qualifiers
source                  1..760
                        mol_type = protein
                        organism = Homo sapiens
SEQUENCE: 121
MMDQARSAFS NLFGGEPLSY TRFSLARQVD GDNSHVEMKL AVDEEENADN NTKANVTKPK    60
RCSGSICYGT IAVIVFFLIG FMIGYLGYCK GVEPKTECER LAGTESPVRE EPGEDFPAAR   120
RLYWDDLKRK LSEKLDSTDF TGTIKLLNEN SYVPREAGSQ KDENLALYVE NQFREFKLSK   180
VWRDQHFVKI QVKDSAQNSV IIVDKNGRLV YLVENPGGYV AYSKAATVTG KLVHANFGTK   240
KDFEDLYTPV NGSIVIVRAG KITFAEKVAN AESLNAIGVL IYMDQTKFPI VNAELSFFGH   300
AHLGTGDPYT PGFPSFNHTQ FPPSRSSGLP NIPVQTISRA AAEKLFGNME GDCPSDWKTD   360
STCRMVTSES KNVKLTVSNV LKEIKILNIF GVIKGFVEPD HYVVVGAQRD AWGPGAAKSG   420
VGTALLLKLA QMFSDMVLKD GFQPSRSIIF ASWSAGDFGS VGATEWLEGY LSSLHLKAFT   480
YINLDKAVLG TSNFKVSASP LLYTLIEKTM QNVKHPVTGQ FLYQDSNWAS KVEKLTLDNA   540
AFPFLAYSGI PAVSFCFCED TDYPLGTTM DTYKELIERI PELNKVARAA AEVAGQFVIK   600
LTHDVELNLD YERYNSQLLS FVRDLNQYRA DIKEMGLSLQ WLYSARGDFF RATSRLTTDF   660
GNAEKTDRFV MKKLNDRVMR VEYHFLSPYV SPKESPFRHV FWGSGSHTLP ALLENLKLRK   720
QNNGAFNETL FRNQLALATW TIQGAANALS GDVWDIDNEF                        760

SEQ ID NO: 122          moltype = AA  length = 1058
FEATURE                 Location/Qualifiers
source                  1..1058
                        mol_type = protein
                        organism = Homo sapiens
SEQUENCE: 122
MDLGPLNICE EMTILHGGFL LAEQLFHPKA LAELTKSDWE RVGRPIVEAL REISSAAAHS    60
QPFAWKKKAL IIIWAKVLQP HPVTPSDTET RWQEDLFFSV GNMIPTINHT ILFELLKSLE   120
ASGLFIQLLM ALPTTICHAE LERFLEHVTI DTSAEDVAFF LDVWWEVMKH KGHPQDPLLS   180
QFSAMAHKYL PALDEFPHPP KRLRSDPDAC PTMPLLAMLL RGLTQIQSRI LGPGRKCCAL   240
ANLADMLTVF ALTEDDPQEV SATVYLDKLA TVISVWNSDT QNPYHQQALA EKVKEAERDV   300
SLTSLAKLPS ETIFVGCEFL HHLLREWGEE LQAVLRSSQG TSYDSYRLCD SLTSFSQNAT   360
LYLNRTSLSK EDRQVVSELA ECVRDFLRKT STVLKNRALE DITASIAMAV IQQKMDRHME   420
VCYIFASEKK WAFSDEWVAC LGSNRALFRQ PDLVLRLLET VIDVSTADRA IPESQIRQVI   480
HLILECYADL SLPGKNKVLA GILRSWGRKG LSEKLLAYVE GFQEDLNTTF NQLTQSASEQ   540
GLAKAVASVA RLVIVHPEVT VKKMCSLAVV NLGTHKFLAQ ILTAFPALRF VEEQGPNSSA   600
TFMVSCLKET VWMKFSTPKE EKQFLELLNC LMSPVKPQGI PVAALLEPDE VLKEFVLPFL   660
RLDVEEVDLS LRIFIQTLEA NACREEYWLQ TCSPFPLLFS LCQLLDRFSK YWQLPKEKRC   720
LSLDRKDLAI HILELLCEIV SANAETFSPD VWIKSLSWLH RKLEQLDWTV GLRLKSFFEG   780
HFKCEVPATL FEICKLSEDE WTSQAHPGYG AGTGLLAWME CCCVSSGISE RMLSLLVVDV   840
GNPEEVRLFS KGFLVALVQV MPWCSPQEWQ RLHQLTRRLL EKQLLHVPYS LEYIQFVPLL   900
NLKPFAQELQ LSVLFLRTFQ FLCSHSCRDW LPLEGWNHVV KLLCGSLTRL LDSVRAIQAA   960
GPWVQGPEQD LTQEALFVYT QVFCHALHIM AMLHPEVCEP LYVLALETLT CYETLSKTNP  1020
SVSSLLQRAH EQRFLKSIAE GIGPEERRQT LLQKMSSF                         1058

SEQ ID NO: 123          moltype = AA  length = 255
FEATURE                 Location/Qualifiers
source                  1..255
                        mol_type = protein
                        organism = Homo sapiens
SEQUENCE: 123
MTPGTQSPFF LLLLLTVLTV VTGSGHASST PGGEKETSAT QRSSVPSSTE KNAFNSSLED    60
PSTDYYQELQ RDISEMFLQI YKQGGFLGLS NIKFRPGSVV VQLTLAFREG TINVHDVETQ   120
FNQYKTEAAS RYNLTISDVS VSDVPFPFSA QSGAGVPGWG IALLVLVCVL VALAIVYLIA   180
LAVCQCRRKN YGQLDIFPAR DTYHPMSEYP TYHTHGRYVP PSSTDRSPYE KVSAGNGGSS   240
LSYTNPAVAA TSANL                                                   255

SEQ ID NO: 124          moltype = AA  length = 702
```

```
FEATURE                 Location/Qualifiers
source                  1..702
                        mol_type = protein
                        organism = Homo sapiens
SEQUENCE: 124
MESPSAPPHR WCIPWQRLLL TASLLTFWNP PTTAKLTIES TPFNVAEGKE VLLLVHNLPQ     60
HLFGYSWYKG ERVDGNRQII GYVIGTQQAT PGPAYSGREI IYPNASLLIQ NIIQNDTGFY    120
TLHVIKSDLV NEEATGQFRV YPELPKPSIS SNNSKPVEDK DAVAFTCEPE TQDATYLWWV    180
NNQSLPVSPR LQLSNGNRTL TLFNVTRNDT ASYKCETQNP VSARRSDSVI LNVLYGPDAP    240
TISPLNTSYR SGENLNLSCH AASNPPAQYS WFVNGTFQQS TQELFIPNIT VNNSGSYTCQ    300
AHNSDTGLNR TTVTTITVYA EPPKPFITSN NSNPVEDEDA VALTCEPEIQ NTTYLWWVNN    360
QSLPVSPRLQ LSNDNRTLTL LSVTRNDVGP YECGIQNELS VDHSDPVILN VLYGPDDPTI    420
SPSYTYYRPG VNLSLSCHAA SNPPAQYSWL IDGNIQQHTQ ELFISNITEK NSGLYTCQAN    480
NSASGHSRTT VKTITVSAEL PKPSISSNNS KPVEDKDAVA FTCEPEAQNT TYLWWVNGQS    540
LPVSPRLQLS NGNRTLTLFN VTRNDARAYV CGIQNSVSAN RSDPVTLDVL YGPDTPIISP    600
PDSSYLSGAN LNLSCHSASN PSPQYSWRIN GIPQQHTQVL FIAKITPNNN GTYACFVSNL    660
ATGRNNSIVK SITVSASGTS PGLSAGATVG IMIGVLVGVA LI                       702

SEQ ID NO: 125          moltype = AA  length = 661
FEATURE                 Location/Qualifiers
source                  1..661
                        mol_type = protein
                        organism = Homo sapiens
SEQUENCE: 125
MDLVLKRCLL HLAVIGALLA VGATKVPRNQ DWLGVSRQLR TKAWNRQLYP EWTEAQRLDC     60
WRGGQVSLKV SNDGPTLIGA NASFSIALNF PGSQKVLPDG QVIWVNNTII NGSQVWGGQP    120
VYPQETDDAC IFPDGGPCPS GSWSQKRSFV YVWKTWGQYW QVLGGPVSGL SIGTGRAMLG    180
THTMEVTVYH RRGSRSYVPL AHSSSAFTIT DQVPFSVSVS QLRALDGGNK HPLRNQPLTF    240
ALQLHDPSGY LAEADLSYTW DFGDSSGTLI SRALVVTHTY LEPGPVTAQV VLQAAIPLTS    300
CGSSPVPGTT DGHRPTAEAP NTTAGQVPTT EVVGTTPGQA PTAEPSGTTS VQVPTTEVIS    360
TAPVQMPTAE STGMTPEKVP VSEVMGTTLA EMSTPEATGM TPAEVSIVVL SGTTAAQVTT    420
TEWVETTARE LPIPEPEGPD ASSIMSTESI TGSLGPLLDG TATLRLVKRQ VPLDCVLYRY    480
GSFSVTLDIV QGIESAEILQ AVPSGEGDAF ELTVSCQGGL PKEACMEISS PGCQPPAQRL    540
CQPVLPSPAC QLVLHQILKG GSGTYCLNVS LADTNSLAVV STQLIMPGQE AGLGQVPLIV    600
GILLVLMAVV LASLIYRRRL MKQDFSVPQL PHSSSHWLRL PRIFCSCPIG ENSPLLSGQQ    660
V                                                                   661

SEQ ID NO: 126          moltype = AA  length = 118
FEATURE                 Location/Qualifiers
source                  1..118
                        mol_type = protein
                        organism = Homo sapiens
SEQUENCE: 126
MPREDAHFIY GYPKKGHGHS YTTAEEAAGI GILTVILGVL LLIGCWYCRR RNGYRALMDK     60
SLHVGTQCAL TRRCPQEGFD HRDSKVSLQE KNCEPVVPNA PPAYEKLSAE QSPPPYSP     118

SEQ ID NO: 127          moltype = AA  length = 8
FEATURE                 Location/Qualifiers
REGION                  1..8
                        note = PSA SYNTHETIC POLYPEPTIDE FRAGMENT
SITE                    1
                        note = B - 4Hyp
SITE                    4
                        note = X - CYCLOHEXYL GLYCINE
source                  1..8
                        mol_type = protein
                        organism = synthetic construct
SEQUENCE: 127
BSSXQSSP                                                               8

SEQ ID NO: 128          moltype = AA  length = 351
FEATURE                 Location/Qualifiers
source                  1..351
                        mol_type = protein
                        organism = Homo sapiens
SEQUENCE: 128
MSFPCKFVAS FLLIFNVSSK GAVSKEITNA LETWGALGQD INLDIPSFQM SDDIDDIKWE     60
KTSDKKKIAQ FRKEKETFKE KDTYKLFKNG TLKIKHLKTD DQDIYKVSIY DTKGKNVLEK    120
IFDLKIQERV SKPKISWTCI NTTLTCEVMN GTDPELNLYQ DGKHLKLSQR VITHKWTTSL    180
SAKFKCTAGN KVSKESSVEP VSCPEKGLDI YLIIGICGGG SLLMVFVALL VFYITKRKKQ    240
RSRRNDEELE TRAHRVATEE RGRKPHQIPA STPQNPATSQ HPPPPPGHRS QAPSHRPPPP    300
GHRVQHQPQK RPPAPSGTQV HQQKGPPLPR PRVQPKPPHG AAENSLSPSS N             351

SEQ ID NO: 129          moltype = AA  length = 297
FEATURE                 Location/Qualifiers
source                  1..297
                        mol_type = protein
                        organism = Homo sapiens
SEQUENCE: 129
```

```
MTTPRNSVNG TFPAEPMKGP IAMQSGPKPL FRRMSSLVGP TQSFFMRESK TLGAVQIMNG    60
LFHIALGGLL MIPAGIYAPI CVTVWYPLWG GIMYIISGSL LAATEKNSRK CLVKGKMIMN   120
SLSLFAAISG MILSIMDILN IKISHFLKME SLNFIRAHTP YINIYNCEPA NPSEKNSPST   180
QYCYSIQSLF LGILSVMLIF AFFQELVIAG IVENEWKRTC SRPKSNIVLL SAEEKKEQTI   240
EIKEEVVGLT ETSSQPKNEE DIEIIPIQEE EEEETETNFP EPPQDQESSP IENDSSP     297

SEQ ID NO: 130           moltype = AA   length = 61
FEATURE                  Location/Qualifiers
source                   1..61
                         mol_type = protein
                         organism = Homo sapiens
SEQUENCE: 130
MKRFLFLLLT ISLLVMVQIQ TGLSGQNDTS QTSSPSASSS MSGGIFLFFV ANAIIHLFCF    60
S                                                                   61

SEQ ID NO: 131           moltype = AA   length = 8
FEATURE                  Location/Qualifiers
REGION                   1..8
                         note = PSA SYNTHETIC POLYPEPTIDE FRAGMENT
SITE                     1
                         note = Z - 4-O-acetyl-hydroxyproline
SITE                     4
                         note = X - CYCLOHEXYL GLYCINE
source                   1..8
                         mol_type = protein
                         organism = synthetic construct
SEQUENCE: 131
ZSSXQSSP                                                             8

SEQ ID NO: 132           moltype = AA   length = 8
FEATURE                  Location/Qualifiers
REGION                   1..8
                         note = PSA SYNTHETIC POLYPEPTIDE FRAGMENT
source                   1..8
                         mol_type = protein
                         organism = synthetic construct
SEQUENCE: 132
RRSSYYSG                                                             8

SEQ ID NO: 133           moltype = AA   length = 164
FEATURE                  Location/Qualifiers
source                   1..164
                         mol_type = protein
                         organism = Homo sapiens
SEQUENCE: 133
EMLQGLLLLL LLSMGGTWAS KEPLRPRCRP INATLAVEKE GCPVCITVNT TICAGYCPTM    60
TRVLQGVLPA LPQVVCNYRD VRFESIRLPG CPRGVNPVVS YAVALSCQCA LCRRSTTDCG   120
GPKDHPLTCD DPRFQDSSSS KAPPPSLPSP SRLPGPSDTP ILPQ                    164

SEQ ID NO: 134           moltype = AA   length = 300
FEATURE                  Location/Qualifiers
source                   1..300
                         mol_type = protein
                         organism = Homo sapiens
SEQUENCE: 134
MANCEFSPVS GDKPCCRLSR RAQLCLGVSI LVLILVVVLA VVVPRWRQQW SGPGTTKRFP    60
ETVLARCVKY TEIHPEMRHV DCQSVWDAFK GAFISKHPCN ITEEDYQPLM KLGTQTVPCN   120
KILLWSRIKD LAHQFTQVQR DMFTLEDTLL GYLADDLTWC GEFNTSKINY QSCPDWRKDC   180
SNNPVSVFWK TVSRRFAEAA CDVVHVMLNG SRSKIFDKNS TFGSVEVHNL QPEKVQTLEA   240
WVIHGGREDS RDLCQDPTIK ELESIISKRN IQFSCKNIYR PDKFLQCVKN PEDSSCTSEI   300

SEQ ID NO: 135           moltype = AA   length = 277
FEATURE                  Location/Qualifiers
source                   1..277
                         mol_type = protein
                         organism = Homo sapiens
SEQUENCE: 135
MVRLPLQCVL WGCLLTAVHP EPPTACREKQ YLINSQCCSL CQPGQKLVSD CTEFTETECL    60
PCGESEFLDT WNRETHCHQH KYCDPNLGLR VQQKGTSETD TICTCEEGWH CTSEACESCV   120
LHRSCSPGFG VKQIATGVSD TICEPCPVGF FSNVSSAFEK CHPWTSCETK DLVVQQAGTN   180
KTDVVCGPQD RLRALVVIPI IFGILFAILL VLVFIKKVAK KPTNKAPHPK QEPQEINFPD   240
DLPGSNTAAP VQETLHGCQP VTQEDGKESR ISVQERQ                            277

SEQ ID NO: 136           moltype = AA   length = 6
FEATURE                  Location/Qualifiers
REGION                   1..6
                         note = PSA SYNTHETIC POLYPEPTIDE FRAGMRNT
source                   1..6
                         mol_type = protein
```

```
                        organism = synthetic construct
SEQUENCE: 136
SSKYQL                                                                      6

SEQ ID NO: 137          moltype = AA  length = 7
FEATURE                 Location/Qualifiers
REGION                  1..7
                        note = PSA SYNTHGETIC POLYPEPTIDE FRAGMENT
SITE                    1
                        note = B - N-glutaryl-4-hydroxyproline
SITE                    4
                        note = X - CYCLOHEXYL GLYCINE
source                  1..7
                        mol_type = protein
                        organism = synthetic construct
SEQUENCE: 137
BASXQSL                                                                     7

SEQ ID NO: 138          moltype = AA  length = 5
FEATURE                 Location/Qualifiers
REGION                  1..5
                        note = CASPASE-3 SYNTHETIC POLYPEPTIDE FRAGMENT
source                  1..5
                        mol_type = protein
                        organism = synthetic construct
SEQUENCE: 138
DEVDP                                                                       5

SEQ ID NO: 139          moltype = AA  length = 8
FEATURE                 Location/Qualifiers
REGION                  1..8
                        note = CASPASE-3 SYNTHETIC POLYPEPTIDE FRAGMENT
source                  1..8
                        mol_type = protein
                        organism = synthetic construct
SEQUENCE: 139
KGSGDVEG                                                                    8

SEQ ID NO: 140          moltype = AA  length = 646
FEATURE                 Location/Qualifiers
source                  1..646
                        mol_type = protein
                        organism = Homo sapiens
SEQUENCE: 140
MGLPRLVCAF LLAACCCCPR VAGVPGEAEQ PAPELVEVEV GSTALLKCGL SQSQGNLSHV    60
DWFSVHKEKR TLIFRVRQGQ GQSEPGEYEQ RLSLQDRGAT LALTQVTPQD ERIFLCQGKR   120
PRSQEYRIQL RVYKAPEEPN IQVNPLGIPV NSKEPEEVAT CVGRNGYPIP QVIWYKNGRP   180
LKEEKNRVHI QSSQTVESSG LYTLQSILKA QLVKEDKDAQ FYCELNYRLP SGNHMKESRE   240
VTVPVFYPTE KVWLEVEPVG MLKEGDRVEI RCLADGNPPP HFSISKQNPS TREAEEETTN   300
DNGVLVLEPA RKEHSGRYEC QAWNLDTMIS LLSEPQELLV NYVSDVRVSP AAPERQEGSS   360
LTLTCEAESS QDLEFQWLRE ETDQVLERGP VLQLHDLKRE AGGGYRCVAS VPSIPGLNRT   420
QLVKLAIFGP PWMAFKERKV WVKENMVLNL SCEASGHPRP TISWNVNGTA SEQDQDPQRV   480
LSTLNVLVTP ELLETGVECT ASNDLGKNTS ILFLELVNLT TLTPDSNTTT GLSTSTASPH   540
TRANSTSTER KLPEPESRGV VIVAVIVCIL VLAVLGAVLY FLYKKGKLPC RRSGKQEITL   600
PPSRKTELVV EVKSDKLPEE MGLLQGSSGD KRAPGDQGEK YIDLRH                  646

SEQ ID NO: 141          moltype = AA  length = 4
FEATURE                 Location/Qualifiers
REGION                  1..4
                        note = CATHEPSIN B SYNTHETIC POLYPEPTIDE FRAGMENT
source                  1..4
                        mol_type = protein
                        organism = synthetic construct
SEQUENCE: 141
GFLG                                                                        4

SEQ ID NO: 142          moltype = AA  length = 4
FEATURE                 Location/Qualifiers
REGION                  1..4
                        note = CATHEPSIN B SYNTHETIC POLYPEPTIDE FRAGMENT
source                  1..4
                        mol_type = protein
                        organism = synthetic construct
SEQUENCE: 142
KKFA                                                                        4

SEQ ID NO: 143          moltype = AA  length = 1210
FEATURE                 Location/Qualifiers
source                  1..1210
```

```
                        mol_type = protein
                        organism = Homo sapiens
SEQUENCE: 143
MRPSGTAGAA LLALLAALCP ASRALEEKKV CQGTSNKLTQ LGTFEDHFLS LQRMFNNCEV    60
VLGNLEITYV QRNYDLSFLK TIQEVAGYVL IALNTVERIP LENLQIIRGN MYYENSYALA   120
VLSNYDANKT GLKELPMRNL QEILHGAVRF SNNPALCNVE SIQWRDIVSS DFLSNMSMDF   180
QNHLGSCQKC DPSCPNGSCW GAGEENCQKL TKIICAQQCS GRCRGKSPSD CCHNQCAAGC   240
TGPRESDCLV CRKFRDEATC KDTCPPLMLY NPTTYQMDVN PEGKYSFGAT CVKKCPRNYV   300
VTDHGSCVRA CGADSYEMEE DGVRKCKKCE GPCRKVCNGI GIGEFKDSLS INATNIKHFK   360
NCTSISGDLH ILPVAFRGDS FTHTPPLDPQ ELDILKTVKE ITGFLLIQAW PENRTDLHAF   420
ENLEIIRGRT KQHGQFSLAV VSLNITSLGL RSLKEISDGD VIISGNKNLC YANTINWKKL   480
FGTSGQKTKI ISNRGENSCK ATGQVCHALC SPEGCWGPEP RDCVSCRNVS RGRECVDKCK   540
LLEGEPREFV ENSECIQCHP ECLPQAMNIT CTGRGPDNCI QCAHYIDGPH CVKTCPAGVM   600
GENNTLVWKY ADAGHVCHLC HPNCTYGCTG PGLEGCPTNG PKIPSIATGM VGALLLLLVV   660
ALGIGLFMRR RHIVRKRTLR RLLQERELVE PLTPSGEAPN QALLRILKET EFKKIKVLGS   720
GAFGTVYKGL WIPEGEKVKI PVAIKELREA TSPKANKEIL DEAYVMASVD NPHVCRLLGI   780
CLTSTVQLIT QLMPFGCLLD YVREHKDNIG SQYLLNWCVQ IAKGMNYLED RRLVHRDLAA   840
RNVLVKTPQH VKITDFGLAK LLGAEEKEYH AEGGKVPIKW MALESILHRI YTHQSDVWSY   900
GVTVWELMTF GSKPYDGIPA SEISSILEKG ERLPQPPICT IDVYMIMVKC WMIDADSRPK   960
FRELIIEFSK MARDPQRYLV IQGDERMHLP SPTDSNFYRA LMDEEDMDDV VDADEYLIPQ  1020
QGFFSSPSTS RTPLLSSLSA TSNNSTVACI DRNGLQSCPI KEDSFLQRYS SDPTGALTED  1080
SIDDTFLPVP EYINQSVPKR PAGSVQNPVY HNQPLNPAPS RDPHYQDPHS TAVGNPEYLN  1140
TVQPTCVNST FDSPAHWAQK GSHQISLDNP DYQQDFFPKE AKPNGIFKGS TAENAEYLRV  1200
APQSSEFIGA                                                        1210

SEQ ID NO: 144          moltype = AA   length = 4
FEATURE                 Location/Qualifiers
REGION                  1..4
                        note = CATHEPSIN B SYNTHETIC POLYPEPTIDE FRAGMENT
source                  1..4
                        mol_type = protein
                        organism = synthetic construct
SEQUENCE: 144
AFKK                                                                 4

SEQ ID NO: 145          moltype = AA   length = 4
FEATURE                 Location/Qualifiers
REGION                  1..4
                        note = CATHEPSIN B SYNTHETIC POLYPEPTIDE FRAGMENT
source                  1..4
                        mol_type = protein
                        organism = synthetic construct
SEQUENCE: 145
GFLG                                                                 4

SEQ ID NO: 146          moltype = AA   length = 9
FEATURE                 Location/Qualifiers
REGION                  1..9
                        note = FAP SYNTHETIC POLYPEPTIDE FRAGMENT
source                  1..9
                        mol_type = protein
                        organism = synthetic construct
SEQUENCE: 146
KQEQNPGST                                                            9

SEQ ID NO: 147          moltype = AA   length = 11
FEATURE                 Location/Qualifiers
REGION                  1..11
                        note = Synthetic polypeptide
source                  1..11
                        mol_type = protein
                        organism = synthetic construct
SEQUENCE: 147
ACDCRGDCFC G                                                        11

SEQ ID NO: 148          moltype = AA   length = 13
FEATURE                 Location/Qualifiers
REGION                  1..13
                        note = Synthetic polypeptide
source                  1..13
                        mol_type = protein
                        organism = synthetic construct
SEQUENCE: 148
DGARYCRGDC FDG                                                      13

SEQ ID NO: 149          moltype = AA   length = 5
FEATURE                 Location/Qualifiers
REGION                  1..5
                        note = Cathepsin B synthetic polypeptide fragment
```

```
                               -continued source                1..5
                      mol_type = protein
                      organism = synthetic construct
SEQUENCE: 149
RGDYK                                                                     5

SEQ ID NO: 150        moltype = AA  length = 5
FEATURE               Location/Qualifiers
source                1..5
                      mol_type = protein
                      organism = Homo sapiens
SEQUENCE: 150
RGDFK                                                                     5

SEQ ID NO: 151        moltype = AA  length = 10
FEATURE               Location/Qualifiers
source                1..10
                      mol_type = protein
                      organism = Homo sapiens
SEQUENCE: 151
RGDYKKYDGR                                                               10

SEQ ID NO: 152        moltype = AA  length = 14
FEATURE               Location/Qualifiers
REGION                1..14
                      note = Cathepsin B synthetic polypeptide fragment
source                1..14
                      mol_type = protein
                      organism = synthetic construct
SEQUENCE: 152
CAGKNFFWKT FTSC                                                          14

SEQ ID NO: 153        moltype = AA  length = 5
FEATURE               Location/Qualifiers
REGION                1..5
                      note = Cathepsin B synthetic polypeptide fragment
SITE                  5
                      note = X - N-methyl valine
source                1..5
                      mol_type = protein
                      organism = synthetic construct
SEQUENCE: 153
RGDFX                                                                     5

SEQ ID NO: 154        moltype = AA  length = 5
FEATURE               Location/Qualifiers
source                1..5
                      mol_type = protein
                      organism = Homo sapiens
SEQUENCE: 154
PHSCN                                                                     5

SEQ ID NO: 155        moltype = AA  length = 5
FEATURE               Location/Qualifiers
SITE                  1
                      note = X - N-acetylproline
SITE                  5
                      note = Z - 2-aminobutanediamide
source                1..5
                      mol_type = protein
                      organism = Homo sapiens
SEQUENCE: 155
XHSCZ                                                                     5

SEQ ID NO: 156        moltype = AA  length = 25
FEATURE               Location/Qualifiers
source                1..25
                      mol_type = protein
                      organism = Homo sapiens
SEQUENCE: 156
TMPFLFCNVN DVCNFASRND YSYWL                                              25

SEQ ID NO: 157        moltype = AA  length = 4
FEATURE               Location/Qualifiers
REGION                1..4
                      note = Cathepsin B synthetic polypeptide fragment
source                1..4
                      mol_type = protein
                      organism = synthetic construct
```

```
SEQUENCE: 157
YSNS                                                                                 4

SEQ ID NO: 158          moltype = AA  length = 5
FEATURE                 Location/Qualifiers
REGION                  1..5
                        note = Cathepsin B synthetic polypeptide fragment
source                  1..5
                        mol_type = protein
                        organism = synthetic construct
SEQUENCE: 158
YSNSG                                                                                5

SEQ ID NO: 159          moltype = AA  length = 20
FEATURE                 Location/Qualifiers
REGION                  1..20
                        note = Cathepsin B synthetic polypeptide fragment
source                  1..20
                        mol_type = protein
                        organism = synthetic construct
SEQUENCE: 159
FLSSRLQDLY SIVRRADRAA                                                               20

SEQ ID NO: 160          moltype = AA  length = 11
FEATURE                 Location/Qualifiers
REGION                  1..11
                        note = Cathepsin B synthetic polypeptide fragment
source                  1..11
                        mol_type = protein
                        organism = synthetic construct
SEQUENCE: 160
IVRRADRAAV P                                                                        11

SEQ ID NO: 161          moltype = AA  length = 13
FEATURE                 Location/Qualifiers
REGION                  1..13
                        note = Cathepsin B synthetic polyipeptide fragment
source                  1..13
                        mol_type = protein
                        organism = synthetic construct
SEQUENCE: 161
RQVFQVAYII IKA                                                                      13

SEQ ID NO: 162          moltype = AA  length = 12
FEATURE                 Location/Qualifiers
REGION                  1..12
                        note = Cathepsin B synthetic polypeptide fragment
source                  1..12
                        mol_type = protein
                        organism = synthetic construct
SEQUENCE: 162
KAFDITYVRL KF                                                                       12

SEQ ID NO: 163          moltype = AA  length = 12
FEATURE                 Location/Qualifiers
REGION                  1..12
                        note = Laminin Synthetic Polypeptide C16S
source                  1..12
                        mol_type = protein
                        organism = synthetic construct
SEQUENCE: 163
DFKLFAVTIK YR                                                                       12

SEQ ID NO: 164          moltype = AA  length = 8
FEATURE                 Location/Qualifiers
REGION                  1..8
                        note = Cathepsin B synthetic polypeptide fragment
source                  1..8
                        mol_type = protein
                        organism = synthetic construct
SEQUENCE: 164
CPQPRPLC                                                                             8

SEQ ID NO: 165          moltype = AA  length = 503
FEATURE                 Location/Qualifiers
source                  1..503
                        mol_type = protein
                        organism = Homo sapiens
SEQUENCE: 165
```

```
MLSQLAMLQG SLLLVVATMS VAQQTRQEAD RGCETLVVQH GHCSYTFLLP KSEPCPPGPE     60
VSRDSNTLQR ESLANPLHLG KLPTQQVKQL EQALQNNTQW LKKLERAIKT ILRSKLEQVQ    120
QQMAQNQTAP MLELGTSLLN QTTAQIRKLT DMEAQLLNQT SRMDAQMPET FLSTNKLENQ    180
LLLQRQKLQQ LQGQNSALEK RLQALETKQQ EELASILSKK AKLLNTLSRQ SAALTNIERG    240
LRGVRHNSSL LQDQQHSLRQ LLVLLRHLVQ ERANASAPAF IMAGEQVFQD CAEIQRSGAS    300
ASGVYTIQVS NATKPRKVFC DLQSSGGRWT LIQRRENGTV NFQRNWKDYK QGFGDPAGEH    360
WLGNEVVHQL TRRAAYSLRV ELQDWEGHEA YAQYEHFHLG SENQLYRLSV VGYSGSAGRQ    420
SSLVLQNTSF STLDSDNDHC LCKCAQVMSG GWWFDACGLS NLNGVYYHAP DNKYKMDGIR    480
WHYFKGPSYS LRASRMMIRP LDI                                            503

SEQ ID NO: 166             moltype = AA  length = 369
FEATURE                    Location/Qualifiers
source                     1..369
                           mol_type = protein
                           organism = Homo sapiens
SEQUENCE: 166
MLKPSLPFTS LLFLQLPLLG VGLNTTILTP NGNEDTTADF FLTTMPTDSL SVSTLPLPEV     60
QCFVFNVEYM NCTWNSSSEP QPTNLTLHYW YKNSDNDKVQ KCSHYLFSEE ITSGCQLQKK    120
EIHLYQTFVV QLQDPREPRR QATQMLKLQN LVIPWAPENL TLHKLSESQL ELNWNNRFLN    180
HCLEHLVQYR TDWDHSWTEQ SVDYRHKFSL PSVDGQKRYT FRVRSRFNPL CGSAQHWSEW    240
SHPIHWGSNT SKENPLFLAL EAVVISVGSM GLIISLLCVY FWLERTMPRI PTLKNLEDLV    300
TEYHGNFSAW SGVSKGLAES LQPDYSERLC LVSEIPPKGG ALGEGPGASP CNQHSPYWAP    360
PCYTLKPET                                                            369

SEQ ID NO: 167             moltype = AA  length = 196
FEATURE                    Location/Qualifiers
source                     1..196
                           mol_type = protein
                           organism = Homo sapiens
SEQUENCE: 167
MRTLACLLLL GCGYLAHVLA EEAEIPREVI ERLARSQIHS IRDLQRLLEI DSVGSEDSLD     60
TSLRAHGVHA TKHVPEKRPL PIRRKRSIEE AVPAVCKTRT VIYEIPRSQV DPTSANFLIW    120
PPCVEVKRCT GCCNTSSVKC QPSRVHHRSV KVAKVEYVRK KPKLKEVQVR LEEHLECACA    180
TTSLNPDYRE EDTDVR                                                    196

SEQ ID NO: 168             moltype = AA  length = 226
FEATURE                    Location/Qualifiers
source                     1..226
                           mol_type = protein
                           organism = Homo sapiens
SEQUENCE: 168
MFIMGLGDPI PEELYEMLSD HSIRSFDDLQ RLLHGDPGEE DGAELDLNMT RSHSGGELES     60
LARGRRSLGS LTIAEPAMIA ECKTRTEVFE ISRRLIDRTN ANFLVWPPCV EVQRCSGCCN    120
NRNVQCRPTQ VQLRPVQVRK IEIVRKKPIF KKATVTLEDH LACKCETVAA ARPVTRSPGG    180
SQEQRAKTPQ TRVTIRTVRV RRPPKGKHRK FKHTHDKTAL KETLGA                   226

SEQ ID NO: 169             moltype = AA  length = 322
FEATURE                    Location/Qualifiers
source                     1..322
                           mol_type = protein
                           organism = Homo sapiens
SEQUENCE: 169
MRTSKCFLKT ASSQRNGVQD PQHERIITVS TNGSIHSPRF PHTYPRNTVL VWRLVAVEEN     60
VWIQLTFDER FGLEDPEDDI CKYDFVEVEE PSDGTILGRW CGSGTVPGKQ ISKGNQIRIR    120
FVSDEYFPSE PGFCIHYNIV MPQFTEAVSP SVLPPSALPL DLLNNAITAF STLEDLIRYL    180
EPERWQLDLE DLYRPTWQLL GKAFVFGRKS RVVDLNLLTE EVRLYSCTPR NFSVSIREEL    240
KRTDTIFWPG CLLVKRCGGN CACCLHNCNE CQCVPSKVTK KYHEVLQLRP KTGVRGLHKS    300
LTDVALEHHE ECDCVCRGST GG                                             322

SEQ ID NO: 170             moltype = AA  length = 364
FEATURE                    Location/Qualifiers
source                     1..364
                           mol_type = protein
                           organism = Homo sapiens
SEQUENCE: 170
MHRLIFVYTL ICANFCSCRD TSATPQSASI KALRNANLRR DDLYRRDETI QVKGNGYVQS     60
PRFPNSYPRN LLLTWRLHSQ ENTRIQLVFD NQFGLEEAEN DICRYDFVEV EDISETSTII    120
RGRWCGHKEV PPRIKSRTNQ IKITFKSDDY FVAKPGFKIY YSLLEDFQPA AASETNWESV    180
TSSISGVSYN SPSVTDPTLI ADALDKKIAE FDTVEDLLKY FNPESWQEDL ENMYLDTPRY    240
RGRSYHDRKS KVDLDRLNDD AKRYSCTPRN YSVNIREELK LANVVFFPRC LLVQRCGGNC    300
GCGTVNWRSC TCNSGKTVKK YHEVLQFEPG HIKRRGRAKT MALVDIQLDH HERCDCICSS    360
RPPR                                                                 364

SEQ ID NO: 171             moltype = AA  length = 6
FEATURE                    Location/Qualifiers
REGION                     1..6
                           note = KALLIKREIN 2 SYNTHETIC POLYPEPTIDE FRAGMENT
source                     1..6
                           mol_type = protein
```

```
                            organism = synthetic construct
SEQUENCE: 171
GKAFRR                                                                   6

SEQ ID NO: 172              moltype = AA  length = 7
FEATURE                     Location/Qualifiers
REGION                      1..7
                            note = MMP-2/-9/ SYNTHETIC POLYPEPTIDE FRAGMENT
SITE                        3
                            note = Z - citrulline (2-Amino-5-(carbamoylamino)pentanoic
                             acid)
SITE                        5
                            note = X - homophenylalanine (2-amino-4-phenylbutanoic acid)
source                      1..7
                            mol_type = protein
                            organism = synthetic construct
SEQUENCE: 172
EPZGXYL                                                                  7

SEQ ID NO: 173              moltype = AA  length = 6
FEATURE                     Location/Qualifiers
REGION                      1..6
                            note = MMP-2/-9/ SYNTHETIC POLYPEPTIDE FRAGMENT
source                      1..6
                            mol_type = protein
                            organism = synthetic construct
SEQUENCE: 173
GILGVP                                                                   6

SEQ ID NO: 174              moltype = AA  length = 8
FEATURE                     Location/Qualifiers
REGION                      1..8
                            note = MMP-2/-9/ SYNTHETIC POLYPEPTIDE FRAGMENT
source                      1..8
                            mol_type = protein
                            organism = synthetic construct
SEQUENCE: 174
GPLGIAGQ                                                                 8

SEQ ID NO: 175              moltype = AA  length = 8
FEATURE                     Location/Qualifiers
REGION                      1..8
                            note = MMP-7 SYNTHETIC POLYPEPTIDE FRAGMENT
source                      1..8
                            mol_type = protein
                            organism = synthetic construct
SEQUENCE: 175
KRALGLPG                                                                 8

SEQ ID NO: 176              moltype = AA  length = 8
FEATURE                     Location/Qualifiers
REGION                      1..8
                            note = MMP-7 SYNTHETIC POLYPEPTIDE FRAGMENT
source                      1..8
                            mol_type = protein
                            organism = synthetic construct
SEQUENCE: 176
RPLALWRS                                                                 8

SEQ ID NO: 177              moltype =   length =
SEQUENCE: 177
000

SEQ ID NO: 178              moltype =   length =
SEQUENCE: 178
000

SEQ ID NO: 179              moltype = AA  length = 4
FEATURE                     Location/Qualifiers
REGION                      1..4
                            note = PLASMIN SYNTHETIC POLYPEPTIDE FRAGMENT
```

```
source               1..4
                     mol_type = protein
                     organism = synthetic construct
SEQUENCE: 179
AFKK                                                                     4

SEQ ID NO: 180       moltype = AA   length = 11
FEATURE              Location/Qualifiers
REGION               1..11
                     note = THROMBIN SYNTHETIC POLYPEPTIDE FRAGMENT
SITE                 1
                     note = X - POLY-L-LYSINE
SITE                 4
                     note = Z - piperidine-4-carboxylic acid
source               1..11
                     mol_type = protein
                     organism = synthetic construct
SEQUENCE: 180
XGFZRSGGGG G                                                            11

SEQ ID NO: 181       moltype = AA   length = 8
FEATURE              Location/Qualifiers
REGION               1..8
                     note = TRYPSIN SYNTHETIC POLYPEPTIDE FRAGMENT
SITE                 1
                     note = X - POLY-L-LYSINE
source               1..8
                     mol_type = protein
                     organism = synthetic construct
SEQUENCE: 181
XGASRFTG                                                                 8
```

The invention claimed is:

1. A compound of the formula:

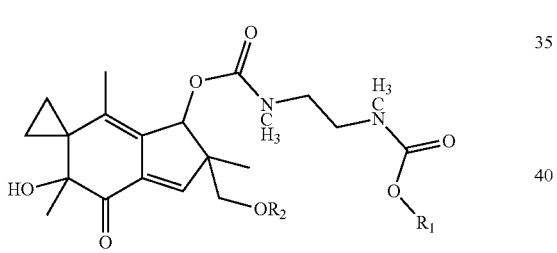

or a pharmaceutically acceptable salt thereof, where $R_1$ and $R_2$ each independently represent —H, -, —OH, —OCH$_3$, —OC(=O)CH$_3$—CH$_3$, —CH$_2$—CH$_3$, —CH—(CH$_3$)$_2$, —C(CH$_3$)$_3$, —CH$_2$—CH$_2$—CH$_3$, —CH$_2$—CH—(CH$_3$)$_2$, —CH—C—(CH$_3$)$_3$, —C(=O)CH$_3$, —CH$_2$OH, and —(C$_1$-C$_4$) alkyl.

2. A composition comprising enantiomers of the compound of claim 1.

3. A composition comprising the composition of claim 2, and a physiologically compatible carrier for treating cancer.

4. A composition comprising the composition of claim 2, in the form of a liposomal particle, a nanoparticle, or a PEGylated compound.

5. A composition comprising racemic mixtures of the compound of claim 1.

6. A composition comprising the composition of claim 5, and a physiologically compatible carrier for treating cancer.

7. A composition comprising the composition of claim 5, in the form of a liposomal particle, a nanoparticle, or a PEGylated compound.

8. A compound of the formula:

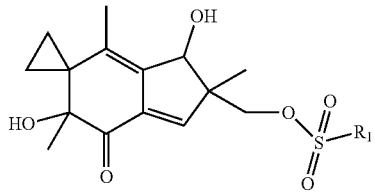

or a pharmaceutically acceptable salt thereof, where $R_1$ represents —H, -, —OH, —OCH$_3$, —OC(=O)CH$_3$—CH$_3$, —CH$_2$—CH$_3$, —CH—(CH$_3$)$_2$, —C(CH$_3$)$_3$, —CH$_2$—CH$_2$—CH$_3$, —CH$_2$—CH—(CH$_3$)$_2$, —CH—C—(CH$_3$)$_3$, C(=O)CH$_3$, CH$_2$OH, and (C$_1$-C$_4$) alkyl.

9. A composition comprising enantiomers of the compound of claim 8.

10. A composition comprising the composition of claim 9, and a physiologically compatible carrier for treating cancer.

11. A composition comprising the composition of claim 9, in the form of a liposomal particle, a nanoparticle, or a PEGylated compound.

12. A composition comprising racemic mixtures of the compound of claim 8.

13. A composition comprising the composition of claim 12, and a physiologically compatible carrier for treating cancer.

14. A composition comprising the composition of claim 12, in the form of a liposomal particle, a nanoparticle, or a PEGylated compound.

15. A compound of the formula:

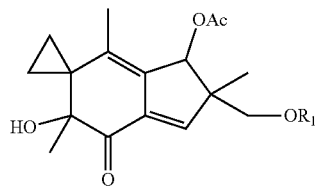

or a pharmaceutically acceptable salt thereof, where $R_1$ represents —H, -, —OH, —OCH$_3$, —OC(=O)CH$_3$—CH$_3$, —CH$_2$—CH$_3$, —CH—(CH$_3$)$_2$, —C(CH$_3$)$_3$, —CH$_2$—CH$_2$—CH$_3$, —CH$_2$—CH—(CH$_3$)$_2$, —CH—C—(CH$_3$)$_3$, C(=O) CH$_3$, CH$_2$OH, and (C$_1$-C$_4$) alkyl.

16. A composition comprising enantiomers of the compound of claim 15.

17. A composition comprising the composition of claim 16, and a physiologically compatible carrier for treating cancer.

18. A composition comprising the composition of claim 16, in the form of a liposomal particle, a nanoparticle, or a PEGylated compound.

19. A composition comprising racemic mixtures of the compound of claim 15.

20. A composition comprising the composition of claim 16, and a physiologically compatible carrier for treating cancer.

* * * * *